(12) United States Patent
Biderman et al.

(10) Patent No.: US 10,166,856 B2
(45) Date of Patent: Jan. 1, 2019

(54) SYSTEMS, METHODS, AND DEVICES FOR ASSESSMENT OF AN OPERATOR OF AN ELECTRICALLY MOTORIZED VEHICLE

(71) Applicant: SUPERPEDESTRIAN, INC., Cambridge, MA (US)

(72) Inventors: Assaf Biderman, Boston, MA (US); Jon Stevens, Manchester, NH (US); Ruben Cagnie, Brighton, MA (US)

(73) Assignee: Superpedestrian, Inc., Cambridge, MA (US)

( * ) Notice: Subject to any disclaimer, the term of this patent is extended or adjusted under 35 U.S.C. 154(b) by 0 days.

(21) Appl. No.: 14/679,721

(22) Filed: Apr. 6, 2015

(65) Prior Publication Data

US 2016/0009293 A1  Jan. 14, 2016

Related U.S. Application Data

(63) Continuation of application No. 14/678,855, filed on Apr. 3, 2015.
(Continued)

(51) Int. Cl.
*B60L 9/00* (2006.01)
*B60K 7/00* (2006.01)
(Continued)

(52) U.S. Cl.
CPC .......... *B60K 7/0007* (2013.01); *A61B 5/0002* (2013.01); *A61B 5/11* (2013.01); *A61B 5/6893* (2013.01); *A61B 5/7275* (2013.01); *A61B 5/7282* (2013.01); *A61G 5/04* (2013.01); *A61G 5/048* (2016.11); *A63B 21/0058* (2013.01); *A63B 21/22* (2013.01); *A63B 22/0605* (2013.01); *A63B 24/0062* (2013.01); *A63B 24/0084* (2013.01); *A63B 24/0087* (2013.01); *B60K 7/00* (2013.01); *B60L 3/0046* (2013.01); *B60L 3/0061* (2013.01); *B60L 3/12* (2013.01); *B60L 7/00* (2013.01); *B60L 7/12* (2013.01);
(Continued)

(58) Field of Classification Search
CPC .......... B60L 15/20; B60L 3/0061; B60L 3/12
USPC ..... 701/2, 22, 29.1, 31.4, 538; 340/988, 439
See application file for complete search history.

(56) References Cited

U.S. PATENT DOCUMENTS

| 3,199,922 A | 8/1965 | Krenz |
| 3,921,741 A | 11/1975 | Garfinkle |

(Continued)

FOREIGN PATENT DOCUMENTS

| CN | 1836969 A | 9/2006 |
| CN | 1944176 A | 4/2007 |

(Continued)

OTHER PUBLICATIONS http://www.greenspeed.us/e%2B_plus_electric_bicycle_battery.htm.
(Continued)

*Primary Examiner* — Gertrude Arthur Jeanglaude
(74) *Attorney, Agent, or Firm* — GTC Law Group PC & Affiliates

(57) ABSTRACT

A system, method, and device for operations of an electrically motorized vehicle. The electrically motorized vehicle can utilize an electrically motorized wheel to convert a non-motorized wheeled vehicle to an electrically motorized wheeled vehicle. A user of the device for the electrically motorized wheel can be profiled by receiving data from a sensor system of the device and creating a profile of the user operating the vehicle from the data.

17 Claims, 63 Drawing Sheets

Related U.S. Application Data

(60) Provisional application No. 62/083,851, filed on Nov. 24, 2014, provisional application No. 62/092,243, filed on Dec. 15, 2014, provisional application No. 61/975,658, filed on Apr. 4, 2014.

(51) Int. Cl.

| | |
|---|---|
| *B60L 11/18* | (2006.01) |
| *B60L 15/20* | (2006.01) |
| *B60Q 5/00* | (2006.01) |
| *B60Q 9/00* | (2006.01) |
| *B60R 16/02* | (2006.01) |
| *B60R 25/04* | (2013.01) |
| *B60R 25/10* | (2013.01) |
| *B60R 25/20* | (2013.01) |
| *B60W 50/08* | (2012.01) |
| *B61L 25/02* | (2006.01) |
| *B62B 3/00* | (2006.01) |
| *B62B 5/00* | (2006.01) |
| *B62M 6/45* | (2010.01) |
| *B62M 6/80* | (2010.01) |
| *B62M 25/08* | (2006.01) |
| *E05B 49/00* | (2006.01) |
| *E05B 81/54* | (2014.01) |
| *G01C 21/36* | (2006.01) |
| *G05D 1/02* | (2006.01) |
| *G06F 8/65* | (2018.01) |
| *G07C 5/00* | (2006.01) |
| *G07C 5/02* | (2006.01) |
| *G07C 5/08* | (2006.01) |
| *G07C 9/00* | (2006.01) |
| *G08G 1/01* | (2006.01) |
| *G08G 1/052* | (2006.01) |
| *G08G 1/123* | (2006.01) |
| *G08G 1/127* | (2006.01) |
| *G08G 1/13* | (2006.01) |
| *G08G 1/00* | (2006.01) |
| *H02P 3/06* | (2006.01) |
| *H02P 6/08* | (2016.01) |
| *H02P 29/20* | (2016.01) |
| *H04L 29/08* | (2006.01) |
| *H04M 1/725* | (2006.01) |
| *A61B 5/00* | (2006.01) |
| *A61B 5/11* | (2006.01) |
| *A61G 5/04* | (2013.01) |
| *A63B 21/005* | (2006.01) |
| *A63B 21/22* | (2006.01) |
| *A63B 22/06* | (2006.01) |
| *A63B 24/00* | (2006.01) |
| *B60L 3/00* | (2006.01) |
| *B60L 3/12* | (2006.01) |
| *B60L 7/00* | (2006.01) |
| *B60L 7/12* | (2006.01) |
| *B60L 11/00* | (2006.01) |
| *H04W 4/60* | (2018.01) |
| *H04W 4/80* | (2018.01) |
| *B60W 50/00* | (2006.01) |
| *E05B 47/00* | (2006.01) |
| *G08G 1/16* | (2006.01) |

(52) U.S. Cl.
CPC .......... *B60L 11/007* (2013.01); *B60L 11/1805* (2013.01); *B60L 11/1809* (2013.01); *B60L 11/1851* (2013.01); *B60L 11/1861* (2013.01); *B60L 11/1864* (2013.01); *B60L 15/20* (2013.01); *B60L 15/2009* (2013.01); *B60L 15/2036* (2013.01); *B60Q 5/005* (2013.01); *B60Q 9/00* (2013.01); *B60R 16/02* (2013.01); *B60R 25/04* (2013.01); *B60R 25/1003* (2013.01); *B60R 25/20* (2013.01); *B60W 50/085* (2013.01); *B61L 25/02* (2013.01); *B62B 3/00* (2013.01); *B62B 5/004* (2013.01); *B62M 6/45* (2013.01); *B62M 6/80* (2013.01); *B62M 25/08* (2013.01); *E05B 49/006* (2013.01); *E05B 81/54* (2013.01); *G01C 21/3632* (2013.01); *G01C 21/3664* (2013.01); *G05D 1/021* (2013.01); *G05D 1/0285* (2013.01); *G05D 1/0287* (2013.01); *G05D 1/0291* (2013.01); *G06F 8/65* (2013.01); *G07C 5/006* (2013.01); *G07C 5/008* (2013.01); *G07C 5/02* (2013.01); *G07C 5/0808* (2013.01); *G07C 9/00007* (2013.01); *G07C 9/00309* (2013.01); *G08G 1/0129* (2013.01); *G08G 1/052* (2013.01); *G08G 1/123* (2013.01); *G08G 1/127* (2013.01); *G08G 1/13* (2013.01); *G08G 1/20* (2013.01); *G08G 1/202* (2013.01); *H02P 3/06* (2013.01); *H02P 6/08* (2013.01); *H02P 29/20* (2016.02); *H04L 67/12* (2013.01); *H04M 1/7253* (2013.01); *H04W 4/60* (2018.02); *H04W 4/80* (2018.02); *B60K 2007/0092* (2013.01); *B60L 2200/12* (2013.01); *B60L 2200/34* (2013.01); *B60L 2200/36* (2013.01); *B60L 2200/40* (2013.01); *B60L 2220/44* (2013.01); *B60L 2220/50* (2013.01); *B60L 2240/12* (2013.01); *B60L 2240/36* (2013.01); *B60L 2240/421* (2013.01); *B60L 2240/423* (2013.01); *B60L 2240/425* (2013.01); *B60L 2240/461* (2013.01); *B60L 2240/463* (2013.01); *B60L 2240/545* (2013.01); *B60L 2240/547* (2013.01); *B60L 2240/549* (2013.01); *B60L 2240/622* (2013.01); *B60L 2240/68* (2013.01); *B60L 2240/70* (2013.01); *B60L 2260/44* (2013.01); *B60W 2050/0014* (2013.01); *B60W 2050/0089* (2013.01); *B60Y 2300/18* (2013.01); *B60Y 2300/1884* (2013.01); *E05B 2047/0088* (2013.01); *G07C 2009/00769* (2013.01); *G08G 1/16* (2013.01); *Y02T 10/641* (2013.01); *Y02T 10/645* (2013.01); *Y02T 10/7005* (2013.01); *Y02T 10/7044* (2013.01); *Y02T 10/7061* (2013.01); *Y02T 10/7275* (2013.01); *Y02T 10/7291* (2013.01); *Y02T 90/16* (2013.01); *Y02T 90/162* (2013.01)

(56) References Cited

U.S. PATENT DOCUMENTS

| | | | |
|---|---|---|---|
| 4,516,647 | A | 5/1985 | Novak |
| 4,721,177 | A | 1/1988 | Qizhen |
| 5,316,101 | A | 5/1994 | Gannon et al. |
| 5,857,537 | A | 1/1999 | Matsumoto et al. |
| 5,937,964 | A | 8/1999 | Mayer et al. |
| 6,024,186 | A | 2/2000 | Suga |
| 6,238,008 | B1 | 5/2001 | Forsythe et al. |
| 6,260,649 | B1 | 7/2001 | Carney |
| 6,278,216 | B1 | 8/2001 | Li |
| 6,286,616 | B1 | 9/2001 | Kutter |
| 6,296,072 | B1 | 10/2001 | Turner |
| 6,347,682 | B1 | 2/2002 | Buchner |
| 6,355,996 | B1 | 3/2002 | Birkestrand |
| 6,516,911 | B1 | 2/2003 | Mayer et al. |
| 6,520,595 | B1 | 2/2003 | Schlanger et al. |
| 6,571,899 | B2 | 6/2003 | Simons |
| 6,580,188 | B2 | 6/2003 | Katagiri et al. |

(56) References Cited

U.S. PATENT DOCUMENTS

| | | |
|---|---|---|
| 6,802,385 B2 | 10/2004 | Pyntikov et al. |
| 6,927,524 B2 | 8/2005 | Pyntikov et al. |
| 6,957,129 B2 | 10/2005 | Hatanaka et al. |
| 6,971,467 B2 | 12/2005 | Katsaros |
| 7,156,196 B2 | 1/2007 | Katsaros et al. |
| 7,275,844 B2 | 10/2007 | Watanabe |
| 7,350,605 B2 | 4/2008 | Mizutani et al. |
| 7,357,209 B2 | 4/2008 | Kokatsu et al. |
| 7,370,720 B2 | 5/2008 | Kokatsu et al. |
| 7,375,450 B2 | 5/2008 | Adachi et al. |
| 7,446,444 B2 | 11/2008 | Iteya et al. |
| 7,495,352 B2 | 2/2009 | Perlo et al. |
| 7,706,935 B2 | 4/2010 | Dube et al. |
| 7,721,835 B2 | 5/2010 | Radtke |
| 7,828,101 B2 | 11/2010 | Radtke et al. |
| 8,056,693 B2 | 11/2011 | Christini et al. |
| 8,131,413 B2 | 3/2012 | Yuan |
| 8,220,578 B2 | 7/2012 | Kerschgens Long |
| 8,245,804 B2 | 8/2012 | Van Rooij |
| 8,405,263 B2 | 3/2013 | Ando et al. |
| 8,449,157 B2 | 5/2013 | Blake et al. |
| 8,616,313 B2 | 12/2013 | Simeray et al. |
| 8,781,736 B2 | 7/2014 | Smith et al. |
| 8,949,022 B1 | 2/2015 | Levitt et al. |
| 8,960,354 B2 | 2/2015 | Yu et al. |
| 9,027,681 B2 | 5/2015 | Biderman et al. |
| 9,108,495 B2 | 8/2015 | Zanfei et al. |
| 9,162,557 B2 | 10/2015 | Lang |
| 9,194,955 B1 | 11/2015 | Fahrner et al. |
| 9,283,804 B2 | 3/2016 | Schlanger |
| 9,290,042 B2 | 3/2016 | Miyamoto |
| 9,290,043 B2 | 3/2016 | Schlanger |
| 9,302,532 B2 | 4/2016 | Chen |
| 9,315,071 B2 | 4/2016 | Webber |
| 9,346,319 B2 | 5/2016 | Schiers |
| 2002/0120382 A1 | 8/2002 | Hatanaka et al. |
| 2002/0177945 A1 | 11/2002 | Davies et al. |
| 2003/0163225 A1 | 8/2003 | Hanson et al. |
| 2004/0002634 A1 | 1/2004 | Nihtila |
| 2004/0098185 A1 | 5/2004 | Wang |
| 2004/0104637 A1 | 6/2004 | Dube et al. |
| 2005/0067207 A1 | 3/2005 | Radtke et al. |
| 2005/0167171 A1 | 8/2005 | Katsaros |
| 2005/0189157 A1 | 9/2005 | Hays et al. |
| 2005/0222933 A1 | 10/2005 | Wesby et al. |
| 2005/0246152 A1 | 11/2005 | Kokatsu et al. |
| 2007/0050157 A1 | 3/2007 | Kahn et al. |
| 2007/0159355 A1 | 7/2007 | Kelly et al. |
| 2007/0188037 A1 | 8/2007 | Lau |
| 2008/0071436 A1 | 3/2008 | Dube et al. |
| 2008/0093913 A1 | 4/2008 | Katsaros |
| 2008/0278302 A1 | 11/2008 | Palmer et al. |
| 2009/0011907 A1 | 1/2009 | Radow et al. |
| 2009/0181826 A1 | 7/2009 | Turner |
| 2009/0192673 A1 | 7/2009 | Song et al. |
| 2010/0180676 A1 | 7/2010 | Braghiroli et al. |
| 2010/0198453 A1 | 8/2010 | Dorogusker et al. |
| 2011/0036671 A1 | 2/2011 | McKay et al. |
| 2011/0130905 A1 | 6/2011 | Mayer et al. |
| 2011/0133542 A1 | 6/2011 | Ratti et al. |
| 2011/0160989 A1 | 6/2011 | Uyeki et al. |
| 2011/0232977 A1 | 9/2011 | Trowell et al. |
| 2012/0129655 A1 | 5/2012 | Zlobinsky et al. |
| 2012/0159978 A1 | 6/2012 | Shih et al. |
| 2012/0173075 A1 | 7/2012 | Mays |
| 2013/0038117 A1 | 2/2013 | Miyamoto et al. |
| 2013/0057117 A1 | 3/2013 | Suzuki et al. |
| 2013/0261862 A1 | 10/2013 | Nishimori et al. |
| 2014/0077584 A1 | 3/2014 | Kim et al. |
| 2014/0162219 A1 | 6/2014 | Stankoulov |
| 2015/0160019 A1 | 6/2015 | Biswal et al. |
| 2015/0210350 A1 | 7/2015 | Biderman et al. |
| 2016/0009169 A1 | 1/2016 | Biderman et al. |
| 2016/0009179 A1 | 1/2016 | Biderman et al. |
| 2016/0009181 A1 | 1/2016 | Biderman et al. |
| 2016/0009223 A1 | 1/2016 | Biderman et al. |
| 2016/0009334 A1 | 1/2016 | Biderman et al. |
| 2016/0009335 A1 | 1/2016 | Biderman et al. |
| 2016/0009336 A1 | 1/2016 | Biderman et al. |
| 2016/0009337 A1 | 1/2016 | Biderman et al. |
| 2016/0009338 A1 | 1/2016 | Biderman |
| 2016/0009339 A1 | 1/2016 | Biderman et al. |
| 2016/0011003 A1 | 1/2016 | Biderman et al. |
| 2016/0011598 A1 | 1/2016 | Biderman et al. |
| 2016/0011599 A1 | 1/2016 | Biderman et al. |
| 2016/0012652 A1 | 1/2016 | Biderman et al. |
| 2016/0012721 A1 | 1/2016 | Biderman et al. |
| 2016/0012723 A1 | 1/2016 | Biderman et al. |
| 2016/0014205 A1 | 1/2016 | Biderman et al. |
| 2016/0014252 A1 | 1/2016 | Biderman et al. |
| 2016/0075175 A1 | 3/2016 | Biderman et al. |
| 2016/0075177 A1 | 3/2016 | Biderman et al. |
| 2016/0075226 A1 | 3/2016 | Biderman et al. |
| 2016/0082772 A1 | 3/2016 | Biderman et al. |
| 2016/0243927 A1 | 8/2016 | Biderman et al. |
| 2016/0304158 A1 | 10/2016 | Biderman et al. |
| 2016/0307376 A1 | 10/2016 | Biderman et al. |
| 2016/0355233 A1 | 12/2016 | Biderman et al. |

FOREIGN PATENT DOCUMENTS

| | | |
|---|---|---|
| CN | 101024379 A | 8/2007 |
| CN | 200979473 Y | 11/2007 |
| EP | 0696537 A2 | 2/1996 |
| EP | 0776818 A1 | 6/1997 |
| EP | 0968911 A1 | 1/2000 |
| EP | 0976649 A2 | 2/2000 |
| EP | 1820727 A1 | 8/2007 |
| EP | 2507123 A2 | 10/2012 |
| FR | 962372 A | 6/1950 |
| FR | 2264676 A1 | 10/1975 |
| GB | 1409379 A | 10/1975 |
| GB | 2336575 A | 10/1999 |
| JP | 01168385 U | 11/1989 |
| JP | 07172372 A | 7/1995 |
| JP | H07172372 A | 7/1995 |
| JP | H08290794 A | 11/1996 |
| JP | 2000006878 A | 1/2000 |
| JP | 2000517051 A | 12/2000 |
| JP | 2001213382 A | 8/2001 |
| JP | 2002082003 A | 3/2002 |
| JP | 2002186116 A | 6/2002 |
| JP | 2002220079 A | 8/2002 |
| JP | 2002255080 A | 9/2002 |
| JP | 2002331987 A | 11/2002 |
| JP | 2003335289 A | 11/2003 |
| JP | 2005531450 A | 10/2005 |
| JP | 2008019843 A | 1/2008 |
| JP | 2008044588 A | 2/2008 |
| JP | 2009006991 A | 1/2009 |
| JP | 2009090938 A | 4/2009 |
| JP | 2009159792 A | 7/2009 |
| JP | 5922583 B2 | 5/2016 |
| KR | 1020140031401 A | 3/2014 |
| WO | 2004073155 A1 | 8/2004 |
| WO | 2011069136 A2 | 6/2011 |
| WO | 2011069136 A3 | 9/2011 |
| WO | 2015/154046 A2 | 10/2015 |
| WO | 2016086057 A1 | 6/2016 |

OTHER PUBLICATIONS http://www.greenspeed.us/e%2B_plus_electric_motor.htm.
http://www.greenspeed.us/e_%2B_plus_electric_bike.htm.
10835238.6, "Application Serial No. 10835238.6, European Extended Search Report Mar. 4, 2015", Massachusetts Institute of Technology, 10 Pages.
PCT/US2010/058999, "International Application Serial No. PCT/US2010/058999, International Preliminary Report on Patentability mailed Jun. 5, 2012", 8 pages.
PCT/US2010/058999, "International Application Serial No. PCT/US2010/058999, International Search Report and Written Opinion mailed Jul. 7, 2011", 13 pages.

(56) References Cited

OTHER PUBLICATIONS

Petron, "A Bicycle Electric Assist Unit", M.S. thesis, Massachusetts Institute of Technology (on file with Massachusetts Institute of Technology Libraries Archives), Sep. 14, 2010, 68 pages.
PCT/US2015/024369, "Application Serial No. PCT/US2015/024369, International Search Report and the Written Opinion", Assaf Biderman, 38 pages.
PCT/US2015/062525, "International Application Serial No. PCT/US2015/062525, International Search Report and Written Opinion mailed Apr. 15, 2016", SUPERPEDESTRIAN, Inc., 23 Pages.
File History of U.S. Appl. No. 90/013,676, filed Jan. 11, 2016, 195 pages.
PCT/US2015/024369, "International Application Serial No. PCT/US2015/024369, International Preliminary Report on Patentability and Written Opinion mailed Oct. 13, 2016", Superpedestrian, Inc., 35 Pages.
U.S. Appl. No. 90/013,676, filed Jan. 11, 2016, SUPERPEDESTRIAN, Inc., file history, 325 pages.

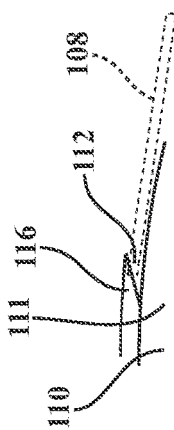
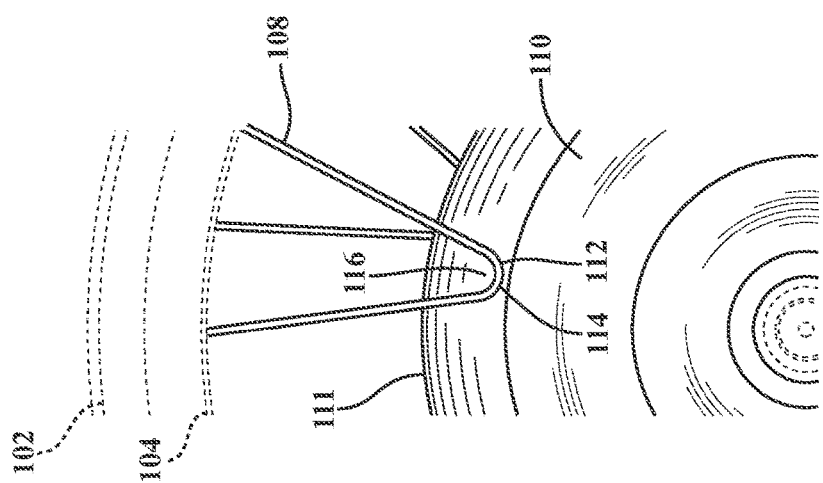
FIG. 1E
FIG. 1D

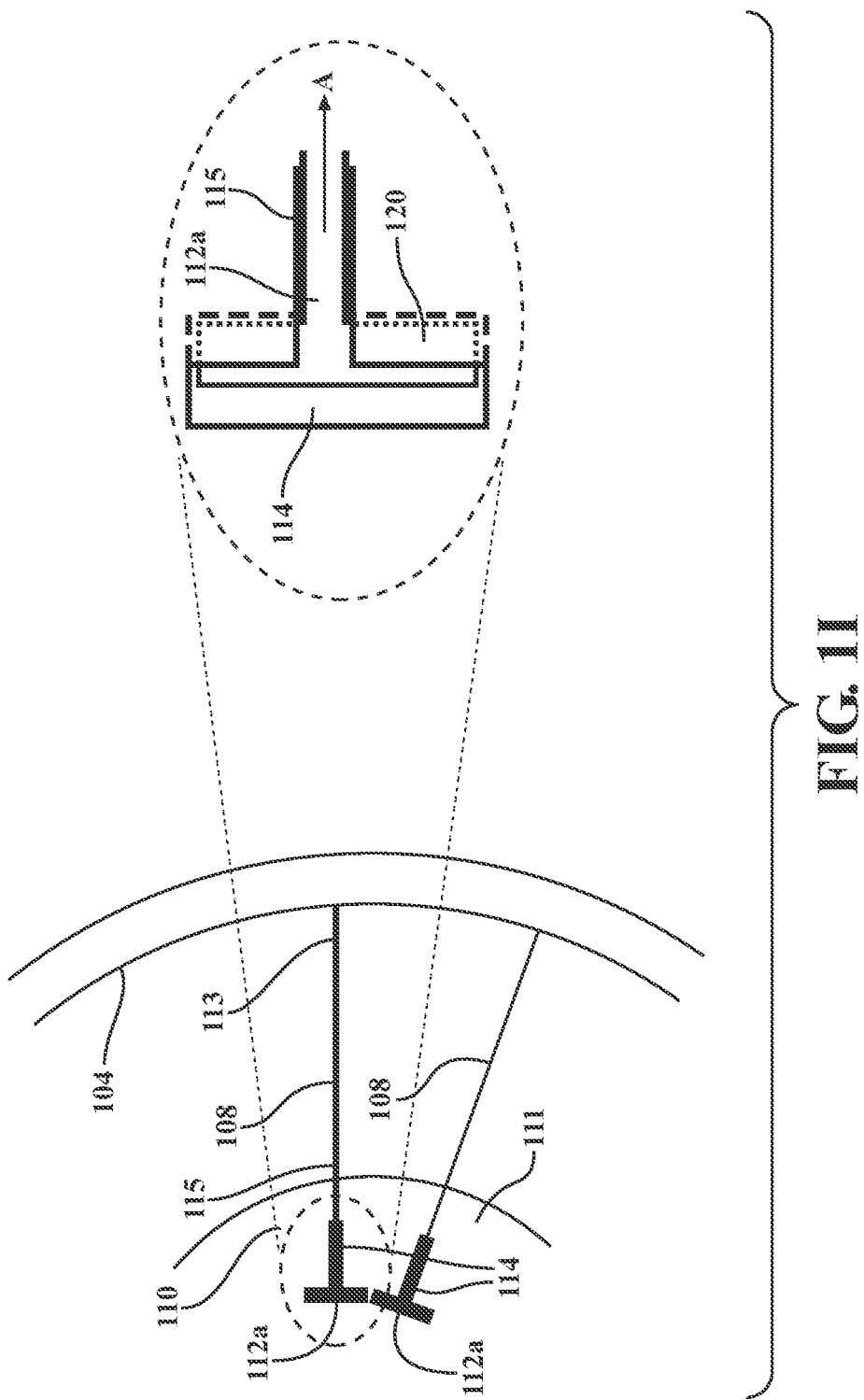

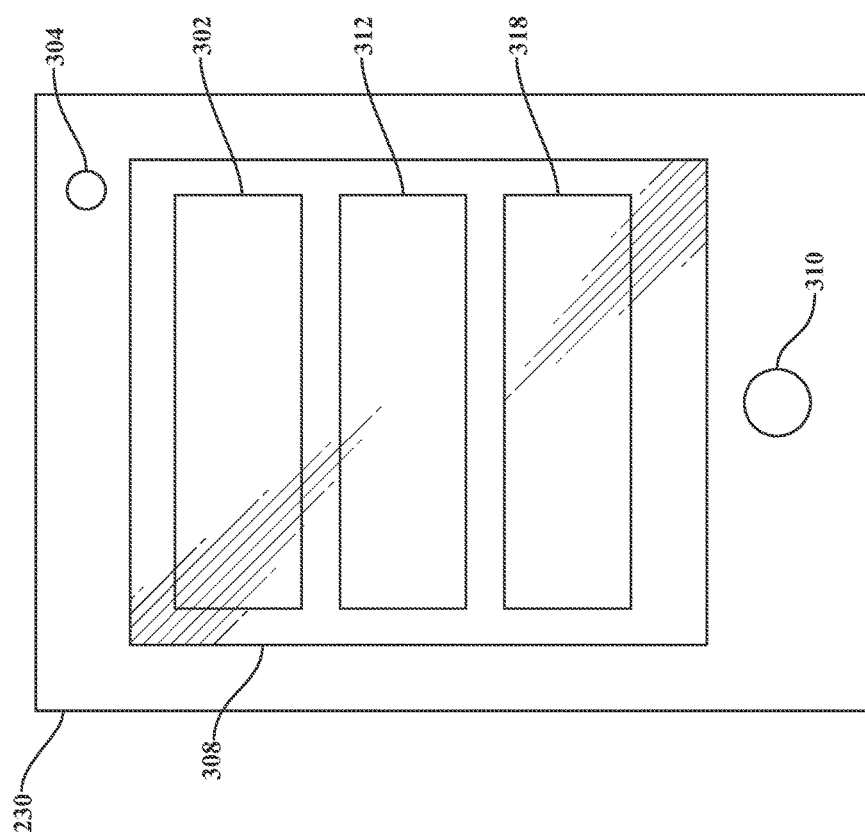

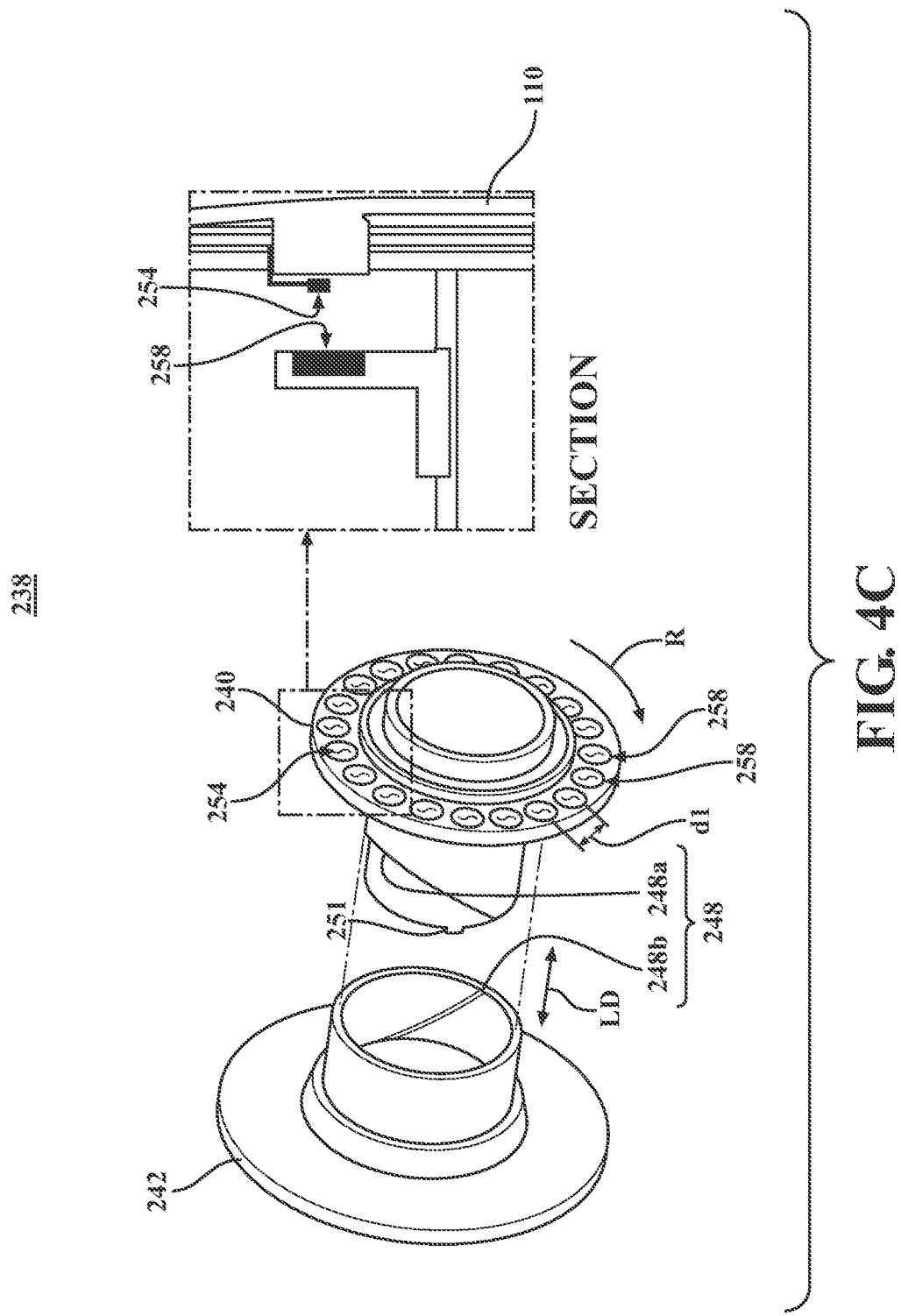

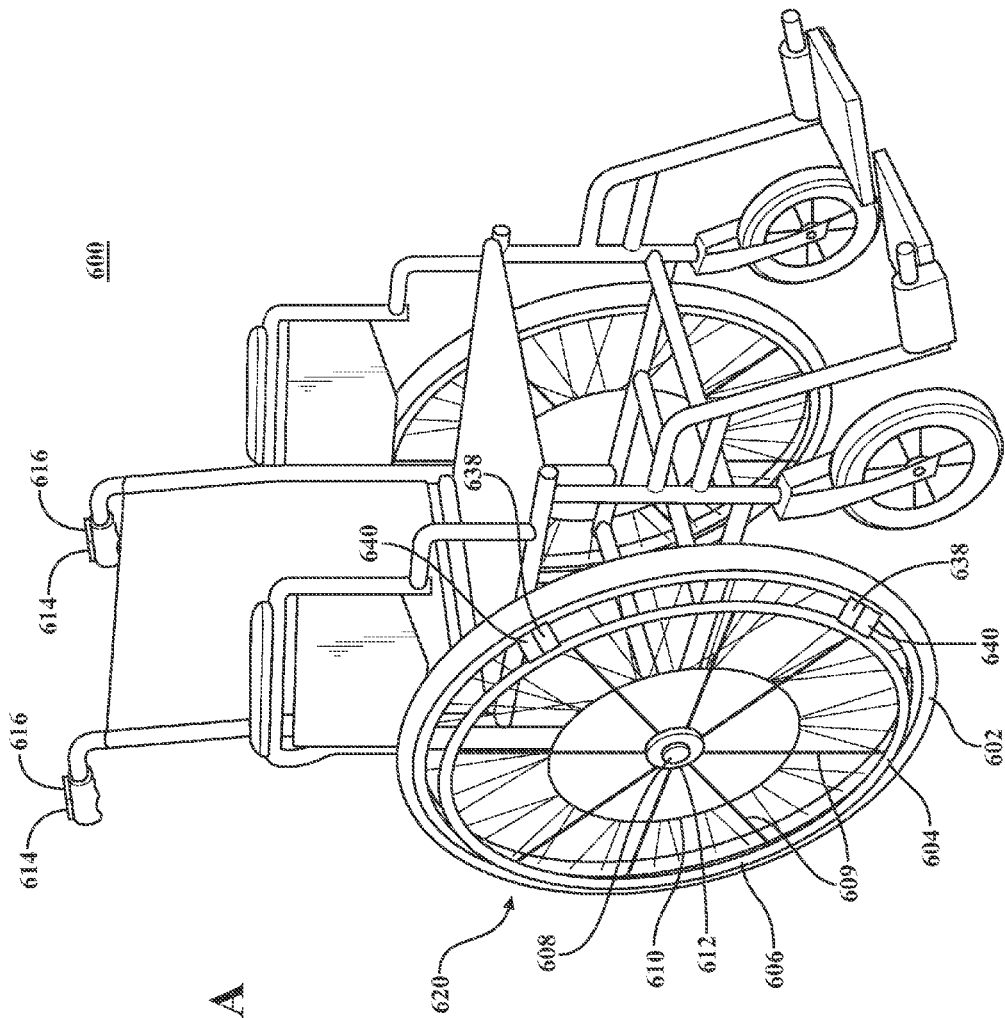

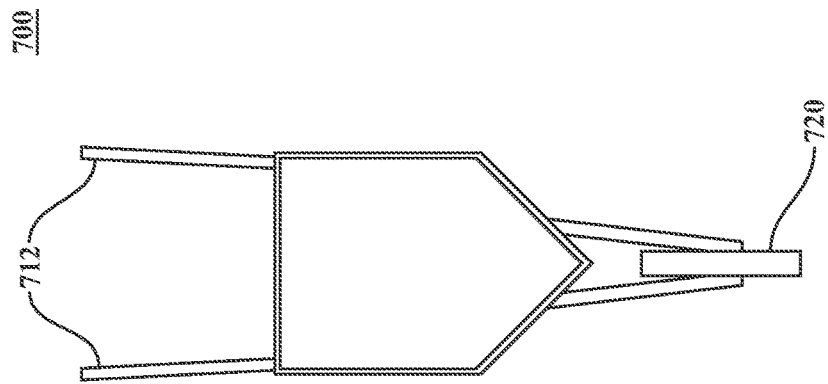
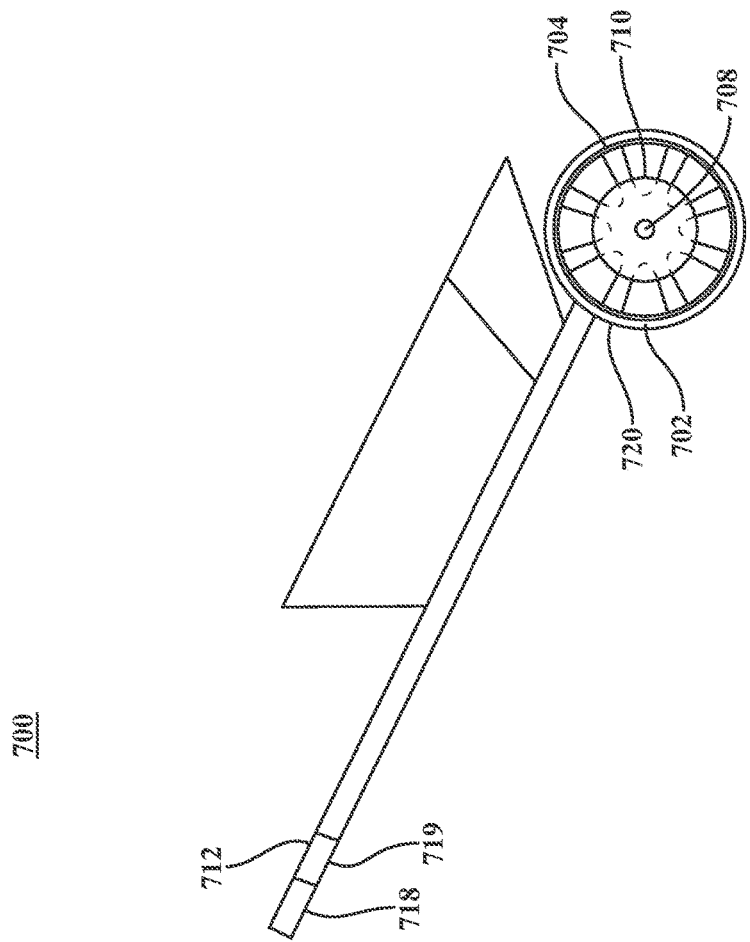
FIG. 7B
FIG. 7A

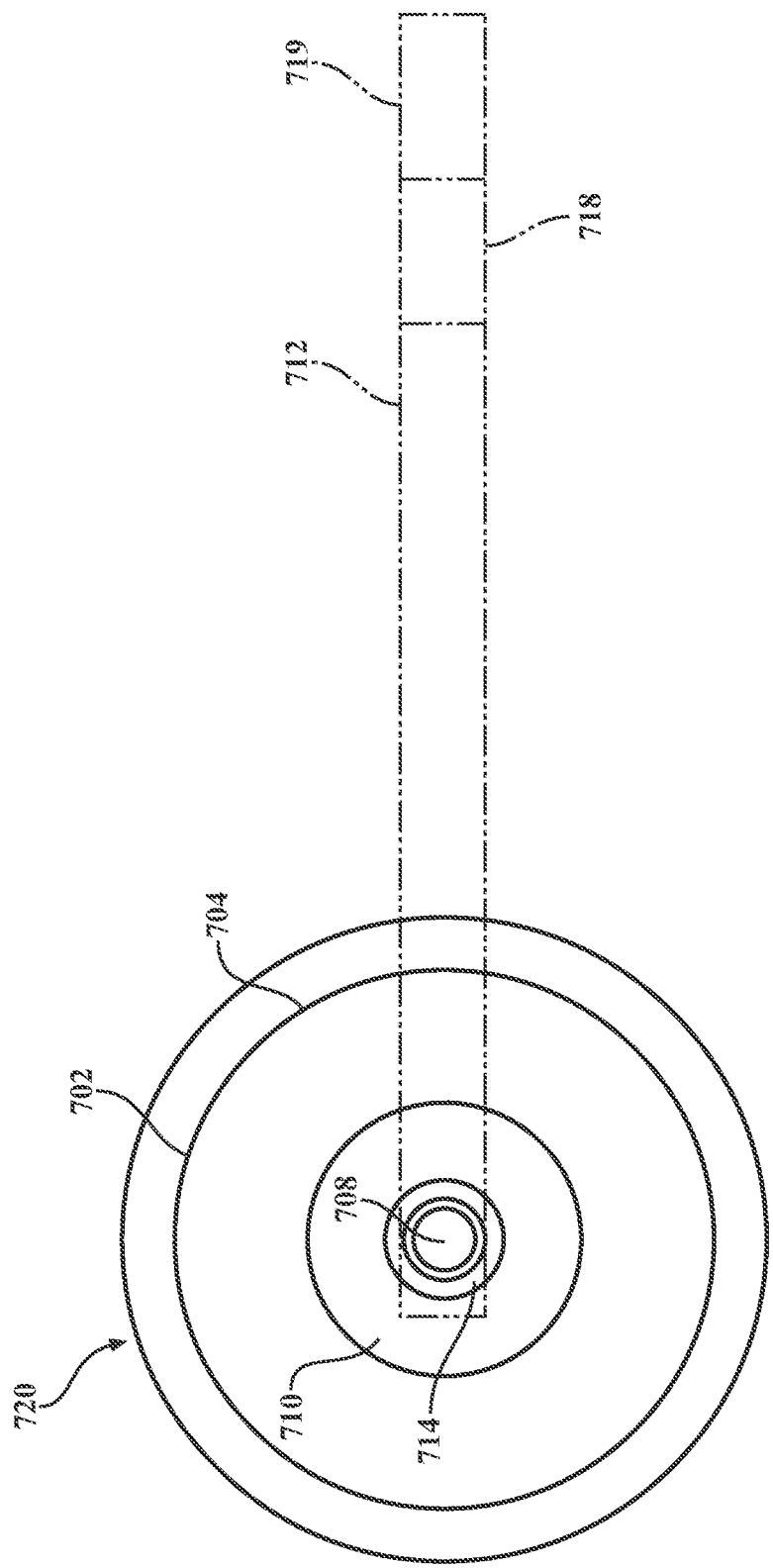

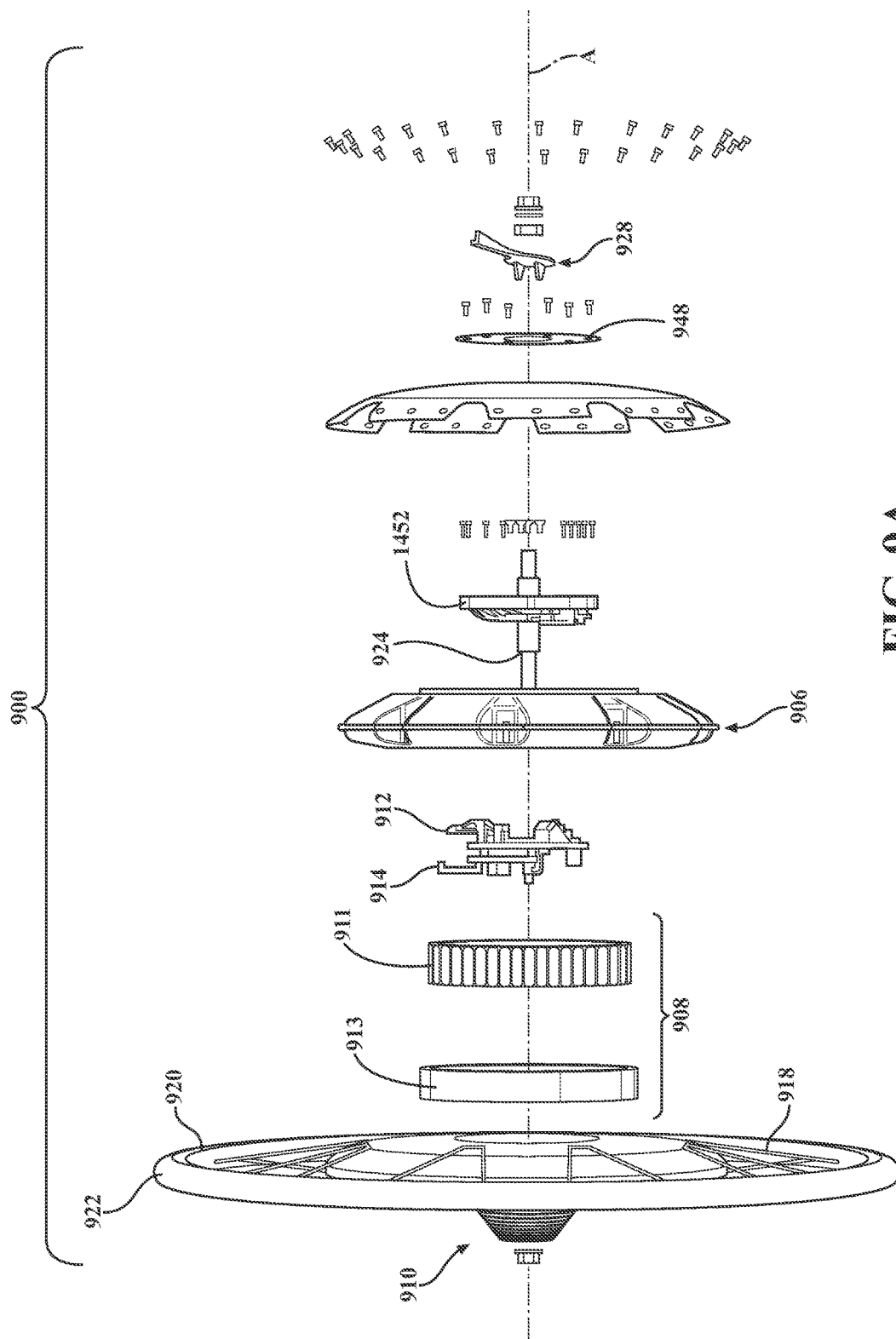

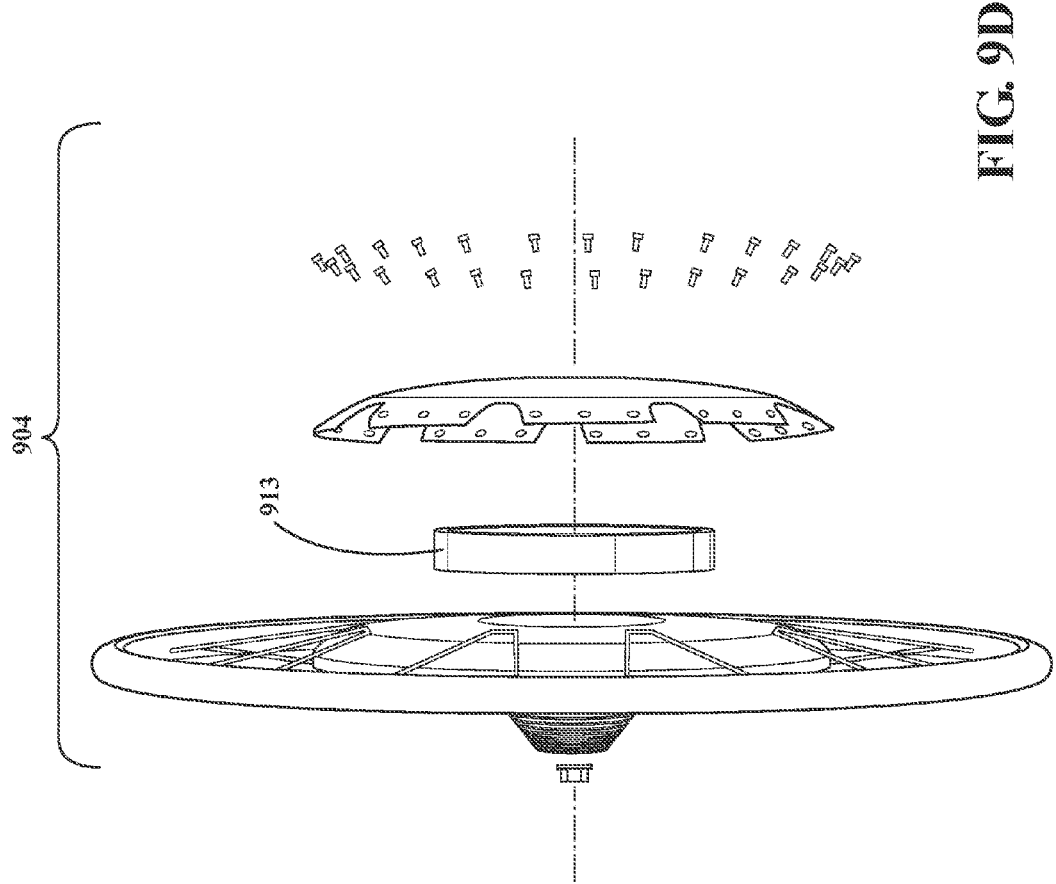

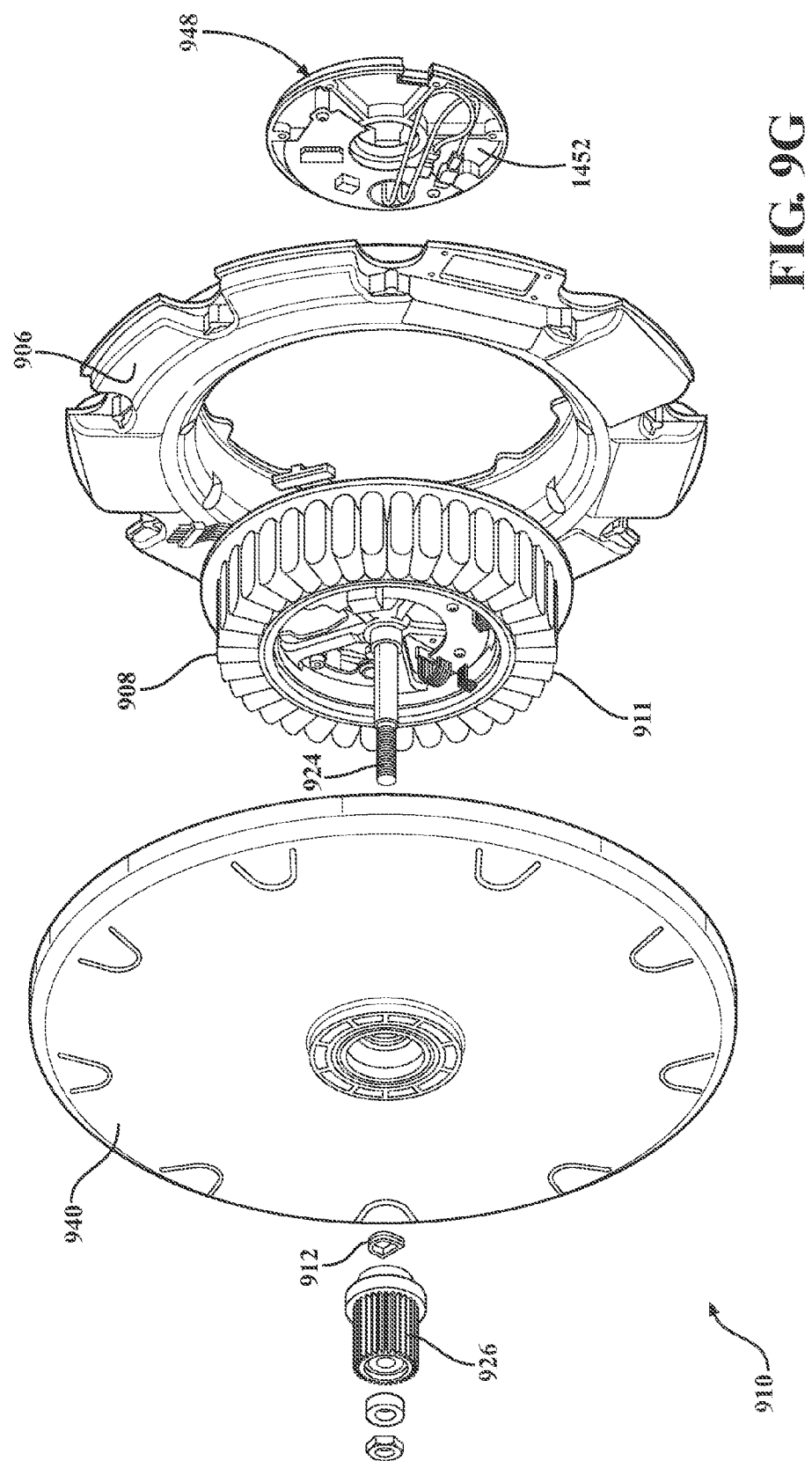

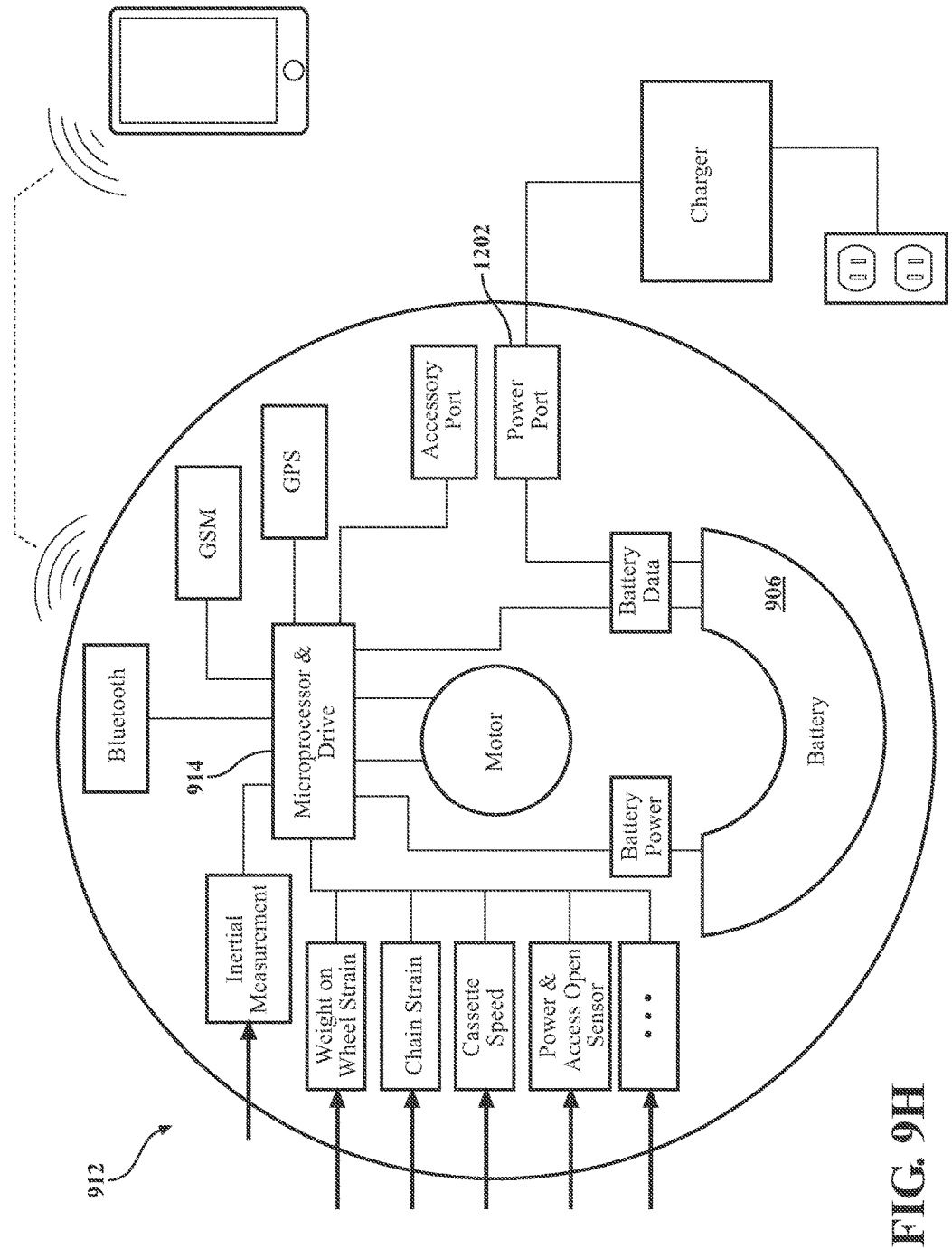

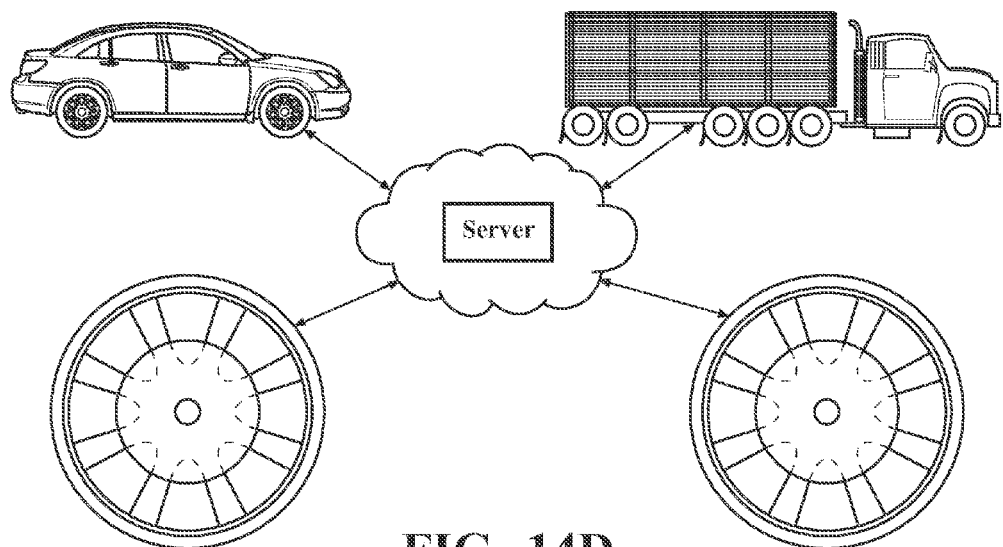
FIG. 14D
FIG. 15A
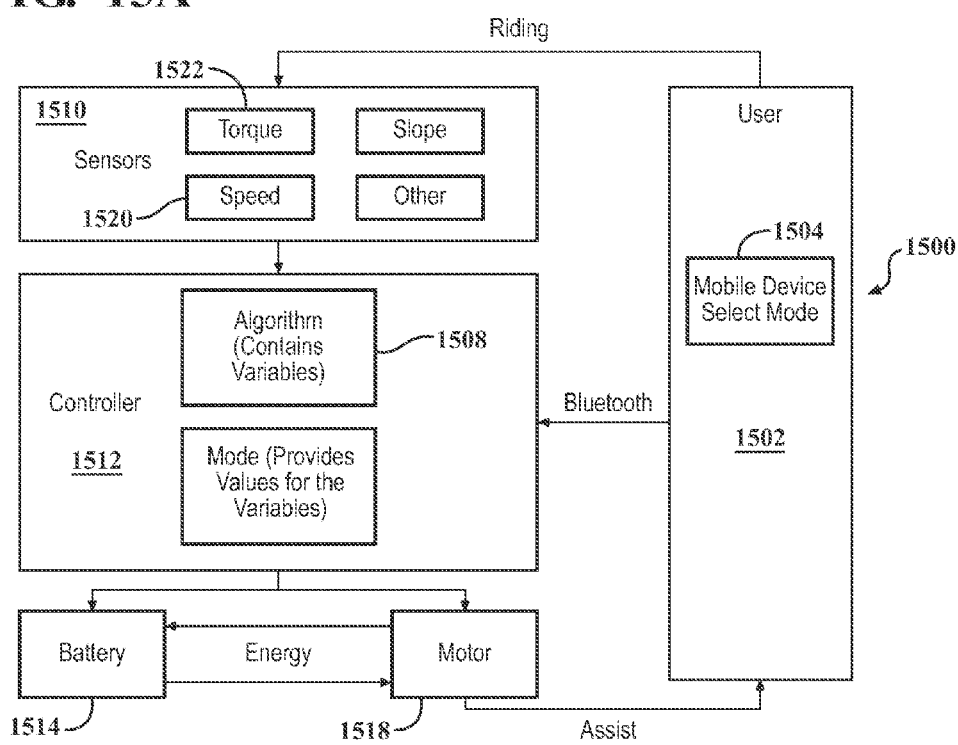

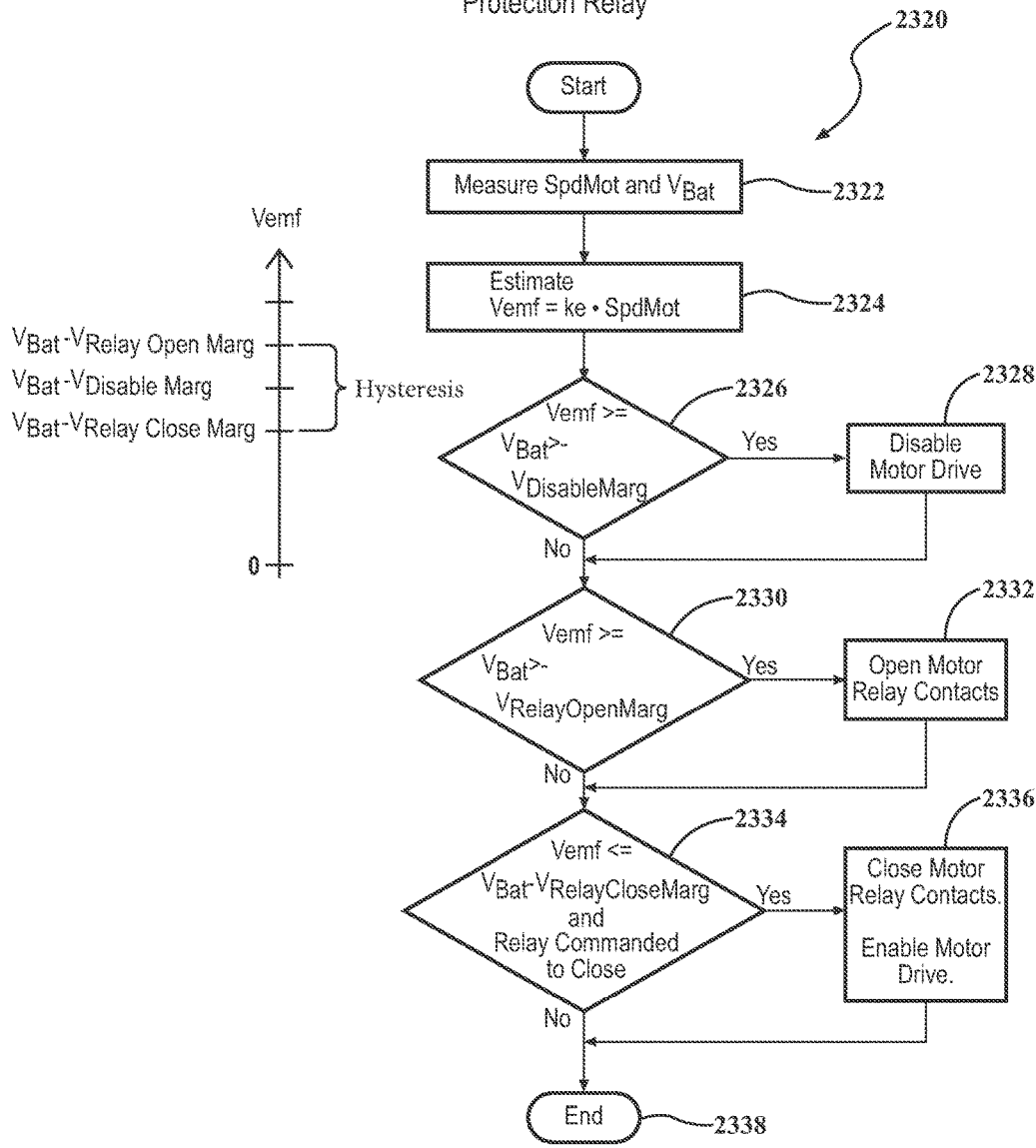
FIG. 23C  Algorithm for Operating Motor Over-Speed Protection Relay

SYSTEMS, METHODS, AND DEVICES FOR ASSESSMENT OF AN OPERATOR OF AN ELECTRICALLY MOTORIZED VEHICLE

This application is a continuation of United States Patent Application having Ser. No. 14/678,855 filed Apr. 3, 2015.

U.S. patent application Ser. No. 14/678,855 filed Apr. 3, 2015 claims priority to United States Provisional Patent Application having Ser. No. 61/975,658 filed Apr. 4, 2014; U.S. Provisional Patent Application Ser. No. 62/083,851 filed Nov. 24, 2014; and U.S. Provisional Patent Application Ser. No. 62/092,243 filed Dec. 15, 2014.

Each of the above applications is hereby incorporated by reference in its entirety.

BACKGROUND

The disclosure relates to electrically motorized wheels, and more particularly to an electrically motorized wheel to convert a non-motorized wheeled vehicle to an electrically motorized wheeled vehicle via installation of the wheel on the vehicle.

There are many wheeled vehicles driven or moved by human power, such as bicycles, wheelchairs, wagons, trailers, carts, rolling tables, push lawnmowers, wheelbarrows, etc. Current electric conversion kits for vehicles such as bicycles generally include a relatively large, bulky battery pack, a control system, and an electric motor that are separately mounted on different parts of the bicycle, such as the frame, the handlebars, and the forks. As the components are separated, a wiring harness provides electrical power from the battery pack to the electric motor and operates as a conduit for signals from the control systems. Installation of such systems may be complex and time consuming, typically requiring a variety of tools and a multi-step process.

SUMMARY

A method of analyzing a fleet of vehicles, each of the vehicles including a device of an electrically motorized wheel for converting the vehicle to an electrically motorized vehicle via installation of the electrically motorized wheel, the method according to one disclosed non-limiting embodiment of the present disclosure can include receiving data from each device of the respective plurality of electrically motorized wheels within a fleet of vehicles; and utilizing the data to facilitate tracking at least one vehicle within the fleet.

A further embodiment of any of the foregoing embodiments of the present disclosure may include, wherein to facilitate operation of each vehicle within the fleet includes optimizing a route for the at least one vehicle in the fleet.

A further embodiment of any of the foregoing embodiments of the present disclosure may include, wherein to facilitate operation of at least one vehicle within the fleet includes optimizing a schedule for the at least one vehicle in the fleet.

A further embodiment of any of the foregoing embodiments of the present disclosure may include, wherein to facilitate operation of at least one vehicle within the fleet includes estimating a delivery time for the at least one vehicle in the fleet.

A further embodiment of any of the foregoing embodiments of the present disclosure may include 1, wherein to facilitate operation of at least one vehicle within the fleet includes optimizing a route for each vehicle in the fleet.

A further embodiment of any of the foregoing embodiments of the present disclosure may include, wherein to facilitate operation of each vehicle within the fleet includes optimizing a schedule for each vehicle in the fleet.

A further embodiment of any of the foregoing embodiments of the present disclosure may include, wherein to facilitate operation of at least one vehicle within the fleet includes estimating a delivery time for each vehicle in the fleet.

A further embodiment of any of the foregoing embodiments of the present disclosure may include analyzing data from each device of each of the plurality of electrically motorized wheels within the fleet includes analyzing at least one of a user fitness level, terrain covered during current excursion, elevation change, level of assistance already provided, remaining battery life, current location, and terrain.

A data analysis system for a fleet of vehicles, each of the vehicles including a device of an electrically motorized wheel for converting a vehicle to an electrically motorized vehicle via installation of the electrically motorized wheel, the data analysis, according to one disclosed non-limiting embodiment of the present disclosure can include a server in communication with each device of each of a plurality of electrically motorized wheels, the server operable to analyze data from each of the devices of the electrically motorized wheels.

A further embodiment of any of the foregoing embodiments of the present disclosure may include, wherein the data includes at least one of a user fitness level, terrain covered during current excursion, elevation change, level of assistance already provided, remaining battery life, current location, and terrain.

A fleet management system for monitoring a plurality of devices each associated with one of a plurality of electrically motorized wheels for converting vehicles to electrically motorized vehicles via installation of the electrically motorized wheels, the fleet management system according to one disclosed non-limiting embodiment of the present disclosure can include a server in communication with each device of each of the plurality of electrically motorized wheels; an electronic data storage structure for storing data communicated from each the plurality of devices; and a fleet management module in communication with the server and the electronic data storage structure.

A further embodiment of any of the foregoing embodiments of the present disclosure may include, wherein the data communicated from each of the plurality of devices includes at least operating version of the electrically motorized wheels wherein the operating version is utilized by the fleet management module to coordinate an application on each of the plurality of devices.

A further embodiment of any of the foregoing embodiments of the present disclosure may include, wherein the data communicated from each of the plurality of devices includes at least one of a user destination, a current location, and available battery life which are utilized by the fleet management module to coordinate route planning for the plurality of electrically motorized wheels.

A further embodiment of any of the foregoing embodiments of the present disclosure may include, wherein the data communicated from each of the plurality of devices includes at least one of wheel speed over time, accelerations, motor assistance and resistance, routing, wheel sensor data, and temperature data which are utilized by the fleet management module to perform a meta-analysis of the provided data to optimize long term fleet routing.

A further embodiment of any of the foregoing embodiments of the present disclosure may include, wherein the fleet management module utilizes the data to evaluate a user efficiency of each user of each of the plurality of electrically motorized wheels.

A further embodiment of any of the foregoing embodiments of the present disclosure may include, wherein the fleet management module utilizes the data to evaluate operation of each of the plurality of electrically motorized wheels.

A further embodiment of any of the foregoing embodiments of the present disclosure may include, wherein the fleet management module utilizes the data to track a location of each of the plurality of electrically motorized wheels.

A further embodiment of any of the foregoing embodiments of the present disclosure may include, wherein the fleet management module utilizes the data to track a battery charge for each of the plurality of electrically motorized wheels.

A further embodiment of any of the foregoing embodiments of the present disclosure may include, wherein the fleet management module is operable to generate aggregated data from the plurality of devices of the plurality of electrically motorized wheels.

A further embodiment of any of the foregoing embodiments of the present disclosure may include, wherein the aggregated data provides a summary associated with the fleet.

A device of an electrically motorized wheel to convert a non-motorized vehicle into a motorized vehicle by installation of the electrically motorized wheel. The device may be configured with control, motor, and energy storage components contained in an aerodynamic hub shell assembly to avoid the heretofore requirements of a separate wiring harness, separate battery pack, and complex installation associated therewith. The device may include a variety of sensing, processing, data collection, networking, and other computing capabilities that facilitate service as an intelligent platform for collecting, processing, and transmitting information about the wheel, its environment, and its user to thereby permit the electrically motorized wheel, its vehicle, its user, and third parties to benefit from a wide range of operational modes, control capabilities, applications, features, and such like.

A control system for a device of an electrically motorized wheel for converting a non-motorized vehicle to an electrically motorized vehicle via installation of the electrically motorized wheel, the system according to one disclosed non-limiting embodiment of the present disclosure can include an application module operable to execute a control algorithm that manages operation of the device; and a boot loader module in communication with the application module, the boot loader module operable to update the application module in response to a validity of the application module.

A further embodiment of any of the foregoing embodiments of the present disclosure may include, wherein the application module and the boot loader module are in communication with a mobile device.

A further embodiment of any of the foregoing embodiments of the present disclosure may include, wherein the communication with the mobile device is wireless.

A further embodiment of any of the foregoing embodiments of the present disclosure may include, wherein the validity of the application module is determined based on the version of the application module currently installed.

A further embodiment of any of the foregoing embodiments of the present disclosure may include, wherein the mobile device is in communication with a remote application data server to determine whether a version number of the application module is the most recent version.

A further embodiment of any of the foregoing embodiments of the present disclosure may include, wherein the mobile device prompts a user in response to the application module not being the most recent version.

A further embodiment of any of the foregoing embodiments of the present disclosure may include, wherein the user is not prompted when at least one of the following conditions is true: battery charge on the mobile device is below a predetermined level, signal strength below a predetermined level, lack of a Wi-Fi connection, device state of charge is below a certain level, and device is not connected to a charger.

A further embodiment of any of the foregoing embodiments of the present disclosure may include, wherein the mobile device downloads the most recent version of the application in response to a positive user response.

A further embodiment of any of the foregoing embodiments of the present disclosure may include, wherein the mobile device will command the boot loader module to execute in response to a successful download of the most recent version of the application.

A method of updating a device of an electrically motorized wheel for converting a non-motorized vehicle to an electrically motorized vehicle via installation of the electrically motorized wheel, the method according to one disclosed non-limiting embodiment of the present disclosure can include updating an application module in response to an indication of the state of validity of the application module in response to start-up of the electrically motorized vehicle, the application module operable to execute a control algorithm that manages operation of the device of the electrically motorized vehicle.

A further embodiment of any of the foregoing embodiments of the present disclosure may include, wherein updating the application module in response to the validity of the application module is initiated by a mobile device.

A further embodiment of any of the foregoing embodiments of the present disclosure may include, wherein updating the application module in response to the validity of the application module is initiated by a user command.

A further embodiment of any of the foregoing embodiments of the present disclosure may include updating via a mobile device.

A further embodiment of any of the foregoing embodiments of the present disclosure may include providing communication between the mobile device and a remote server to determine whether a version number of the application module is the most recent version.

A further embodiment of any of the foregoing embodiments of the present disclosure may include prompting a user via the mobile device in response to the application module not being the most recent version.

A further embodiment of any of the foregoing embodiments of the present disclosure may include, wherein updating the application module includes encrypting the communication thereof.

A method for remote diagnosis of a device of an electrically motorized wheel for converting a non-motorized vehicle to an electrically motorized vehicle via installation of the electrically motorized wheel, the method according to one disclosed non-limiting embodiment of the present disclosure can include receiving operational data from a sensor system of the device; and analyzing the operational data to determine if a diagnostic event has occurred.

A further embodiment of any of the foregoing embodiments of the present disclosure may include, wherein the data includes acceleration data indicative of an impact.

A further embodiment of any of the foregoing embodiments of the present disclosure may include, wherein the data includes temperature data associated with operation of an electric motor of the electrically motorized wheel.

A further embodiment of any of the foregoing embodiments of the present disclosure may include, wherein the data includes temperature data associated with operation of a battery system of the electrically motorized wheel.

A further embodiment of any of the foregoing embodiments of the present disclosure may include receiving the data via a mobile device associated with the electrically motorized wheel.

A further embodiment of any of the foregoing embodiments of the present disclosure may include, communicating the data via the mobile device at a predetermined frequency interval.

A further embodiment of any of the foregoing embodiments of the present disclosure may include, wherein the data includes software and hardware version numbers for the electrically motorized wheel.

A further embodiment of any of the foregoing embodiments of the present disclosure may include, wherein the data includes hazard indicators for the electrically motorized wheel.

A further embodiment of any of the foregoing embodiments of the present disclosure may include, wherein the data includes system response data.

A further embodiment of any of the foregoing embodiments of the present disclosure may include, wherein the data includes system fault data.

A further embodiment of any of the foregoing embodiments of the present disclosure may include, wherein the data includes sensor data that is used for controlling the vehicle.

A method for remote diagnosis of a device for an electrically motorized wheel for converting a non-motorized vehicle to an electrically motorized vehicle via installation of the electrically motorized wheel, the method according to one disclosed non-limiting embodiment of the present disclosure can include receiving operational data from a sensor system of the device; and analyzing the operational data to identify an event associated with operation of the device.

A further embodiment of any of the foregoing embodiments of the present disclosure may include, wherein the data facilitates servicing of the device.

A further embodiment of any of the foregoing embodiments of the present disclosure may include receiving the data via a mobile device associated with the device.

A further embodiment of any of the foregoing embodiments of the present disclosure may include, communicating the data via the mobile device in response to a service call.

A further embodiment of any of the foregoing embodiments of the present disclosure may include, wherein the data includes software and hardware version numbers for the device.

A further embodiment of any of the foregoing embodiments of the present disclosure may include, wherein the data includes hazard indicators for the electrically motorized wheel.

A further embodiment of any of the foregoing embodiments of the present disclosure may include, wherein the data includes system response data.

A further embodiment of any of the foregoing embodiments of the present disclosure may include, wherein the data includes system fault data.

A further embodiment of any of the foregoing embodiments of the present disclosure may include, wherein the data includes sensor data that is used for controlling the vehicle.

A further embodiment of any of the foregoing embodiments of the present disclosure may include, wherein analyzing the operational data to identify the event associated with operation of the electrically motorized wheel includes analyzing the operational data to determine if the event voids a warranty of the electrically motorized wheel.

A further embodiment of any of the foregoing embodiments of the present disclosure may include, wherein analyzing the operational data to determine if the diagnostic event voids a warranty.

A method of controlling a device of an electrically motorized wheel for converting a non-motorized vehicle to an electrically motorized vehicle via installation of the electrically motorized wheel, the method according to one disclosed non-limiting embodiment of the present disclosure can include detecting a fault condition in the device of the electrically motorized wheel; and controlling operation of at least one parameter of the device of the electrically motorized wheel in response to the fault.

A further embodiment of any of the foregoing embodiments of the present disclosure may include, wherein the fault includes a discharge current above a predetermined value.

A further embodiment of any of the foregoing embodiments of the present disclosure may include, wherein the fault includes a regeneration current above a predetermined value.

A further embodiment of any of the foregoing embodiments of the present disclosure may include, wherein the fault includes a voltage above a predetermined value.

A further embodiment of any of the foregoing embodiments of the present disclosure may include, wherein the fault includes a voltage below a predetermined value from motoring.

A further embodiment of any of the foregoing embodiments of the present disclosure may include, wherein the fault includes a temperature above predetermined value.

A further embodiment of any of the foregoing embodiments of the present disclosure may include, wherein detecting the fault includes running a battery current control algorithm and a battery voltage control algorithm.

A further embodiment of any of the foregoing embodiments of the present disclosure may include determining which of a current control gain and a voltage control gain causes a more limiting condition.

A further embodiment of any of the foregoing embodiments of the present disclosure may include determining if the current control gain is less than a voltage control gain, determining an attenuation gain that is equal to the current control gain.

A further embodiment of any of the foregoing embodiments of the present disclosure may include determining if the current control gain is not less than a voltage control gain, determining an attenuation gain that is equal to the voltage control gain.

A further embodiment of any of the foregoing embodiments of the present disclosure may include, wherein the device is an electric motor.

A system, according to another disclosed non-limiting embodiment of the present disclosure can include a device of an electrically motorized wheel, the electrically motorized wheel for converting a non-motorized vehicle to an electrically motorized vehicle via installation of the electrically motorized wheel; a server for executing an application relating to the electrically motorized wheel; and a mobile device in data communication with the device of the electrically motorized wheel and the server for facilitating communication between the device of the electrically motorized vehicle and the server.

A further embodiment of any of the foregoing embodiments of the present disclosure may include a sensor system and a controller mounted to the device, the controller operable to continuously control an electric motor of the device in response to a user input sensed by the sensor system.

A further embodiment of any of the foregoing embodiments of the present disclosure may include, wherein the user input is a rotational input.

A further embodiment of any of the foregoing embodiments of the present disclosure may include, wherein the user input is induced by pedaling.

A further embodiment of any of the foregoing embodiments of the present disclosure may include, wherein the controller controls the device in response to data from the sensor system and from the mobile device.

A further embodiment of any of the foregoing embodiments of the present disclosure may include, wherein the mobile device collects sensor data collected by the electrically motorized wheel and delivered to the mobile device by the data communication facility of the device of the electrically motorized wheel.

A further embodiment of any of the foregoing embodiments of the present disclosure may include, wherein the mobile device collects sensor data associated with an environment external to the electrically motorized wheel.

A further embodiment of any of the foregoing embodiments of the present disclosure may include, wherein the mobile device collects data from at least one peripheral associated with the electrically motorized wheel.

A further embodiment of any of the foregoing embodiments of the present disclosure may include, wherein the server is operable to receive streaming data from the mobile device associated with the device of the electrically motorized wheel.

A further embodiment of any of the foregoing embodiments of the present disclosure may include, wherein the server is operable to aggregate data from a plurality of devices of a respective plurality of electrically motorized wheels.

A further embodiment of any of the foregoing embodiments of the present disclosure may include, wherein the server is operable to analyze routes for a user of the mobile device.

A further embodiment of any of the foregoing embodiments of the present disclosure may include a sensor system mounted to the electrically motorized wheel.

A further embodiment of any of the foregoing embodiments of the present disclosure may include, wherein the sensor system includes a torque sensor that senses power output from a user.

A further embodiment of any of the foregoing embodiments of the present disclosure may include, wherein the sensed power output from a user is associated with a route.

A further embodiment of any of the foregoing embodiments of the present disclosure may include, wherein a location of the route is tagged via a GPS capability of the mobile device.

A further embodiment of any of the foregoing embodiments of the present disclosure may include, wherein the sensed power output and the route location are communicated to the server via the mobile device.

A method of guiding a specific user of an electrically motorized wheel for converting a vehicle to an electrically motorized vehicle via installation of the electrically motorized wheel, the method according to another disclosed non-limiting embodiment of the present disclosure can include receiving data from each of a plurality of electrically motorized wheels; aggregating the data from each of the plurality of electrically motorized wheels; and analyzing the aggregated data to provide the specific user with guidance associated with operation of the electrically motorized wheel of that vehicle.

A further embodiment of any of the foregoing embodiments of the present disclosure may include, wherein guidance associated with operation of the electrically motorized wheel for the specific user is associated with a time efficient route.

A further embodiment of any of the foregoing embodiments of the present disclosure may include, wherein guidance associated with operation of the electrically motorized wheel for the specific user includes suggesting a mode for a route.

A further embodiment of any of the foregoing embodiments of the present disclosure may include, wherein guidance associated with operation of the electrically motorized wheel for the specific user includes profiling the user in comparison to one or more other users.

A system according to another disclosed non-limiting embodiment of the present disclosure can include a server adapted to operate in data communication with a device in each of a plurality of electrically motorized wheels, each of the plurality of electrically motorized wheels for converting a non-motorized vehicle to an electrically motorized vehicle via installation of the electrically motorized wheel; and a data aggregation module in communication with the server operable to take a data set from each of the devices and aggregate the data to transform the data set into an aggregated data set.

A further embodiment of any of the foregoing embodiments of the present disclosure may include, wherein the data from at least one of the plurality of electrically motorized wheels is communicated wirelessly to the server.

A further embodiment of any of the foregoing embodiments of the present disclosure may include, wherein the data is communicated via a wireless telecommunications system in each of the plurality of electrically motorized wheels.

A further embodiment of any of the foregoing embodiments of the present disclosure may include, wherein the data is communicated via a wireless telecommunications system in each of the plurality of electrically motorized wheels to a mobile device associated with each of the plurality of electrically motorized wheels that operates as a data communications gateway to the server.

A further embodiment of any of the foregoing embodiments of the present disclosure may include, wherein the data from at least one of the plurality of electrically motorized wheels is stored on board the electrically motorized wheel.

A further embodiment of any of the foregoing embodiments of the present disclosure may include, wherein the data from each of the electrically motorized wheels is transferred from at least one of the plurality of electrically motorized wheels to a local computer via a removable memory media.

A further embodiment of any of the foregoing embodiments of the present disclosure may include, wherein the data from each of the multiple of electrically motorized wheels are aggregated by the server to provide a spatial and temporal indication of at least one parameter.

A further embodiment of any of the foregoing embodiments of the present disclosure may include, wherein the spatial indication includes a location.

A further embodiment of any of the foregoing embodiments of the present disclosure may include, wherein the temporal indication includes data associated with an environment through which at least one of the multiple of electrically motorized wheels passes.

A further embodiment of any of the foregoing embodiments of the present disclosure may include, wherein the temporal indication includes at least one of temperature, humidity, elevation, atmospheric data and signal strength.

A further embodiment of any of the foregoing embodiments of the present disclosure may include, wherein the temporal indication includes data associated with at least one of the multiple of electrically motorized wheels.

A further embodiment of any of the foregoing embodiments of the present disclosure may include, wherein the temporal indication includes at least one of vehicle speed, battery charge, motor assistance and torque.

A further embodiment of any of the foregoing embodiments of the present disclosure may include, wherein the data from each of the multiple of electrically motorized wheels are aggregated by the server to generate a model constructed from multi-variant data.

A further embodiment of any of the foregoing embodiments of the present disclosure may include, wherein the model is operable to facilitate prediction of future environmental conditions.

A further embodiment of any of the foregoing embodiments of the present disclosure may include, wherein the model is operable to optimize future wheel operation.

A system according to another disclosed non-limiting embodiment of the present disclosure can include a sensor system mounted to an electrically motorized vehicle; a communications module in communication with at least one of the wheel and the sensor system, the communication module operable to communicate data to a server remote from the electrically motorized wheel; and a data integration module in data communication with the server to integrate the data from the sensor system with data from a data source external to the electrically motorized wheel.

A further embodiment of any of the foregoing embodiments of the present disclosure may include, wherein the server correlates the data from the sensor system with at least one data structure of at least one database.

A further embodiment of any of the foregoing embodiments of the present disclosure may include, wherein the data source external to the electrically motorized wheel includes data from a traffic data system.

A further embodiment of any of the foregoing embodiments of the present disclosure may include, wherein the traffic data system includes a traffic camera.

A further embodiment of any of the foregoing embodiments of the present disclosure may include, wherein data source external to the electrically motorized wheel includes map data.

A further embodiment of any of the foregoing embodiments of the present disclosure may include, wherein the map data includes aerial map data.

A further embodiment of any of the foregoing embodiments of the present disclosure may include, wherein the map data includes land use map data.

A further embodiment of any of the foregoing embodiments of the present disclosure may include, wherein the map data includes mobile mapping data.

A further embodiment of any of the foregoing embodiments of the present disclosure may include, wherein the data source external to the electrically motorized wheel includes data from a road traffic sensor.

A further embodiment of any of the foregoing embodiments of the present disclosure may include, wherein the data from at least one of the sensor system and the data source external to the electrically motorized wheel includes image data.

A further embodiment of any of the foregoing embodiments of the present disclosure may include, wherein the data at least one of the sensor system and the data source external to the electrically motorized wheel includes weather data.

A further embodiment of any of the foregoing embodiments of the present disclosure may include, wherein the data at least one of the sensor system and the data source external to the electrically motorized wheel includes temporal data.

A further embodiment of any of the foregoing embodiments of the present disclosure may include, wherein the data at least one of the sensor system and the data source external to the electrically motorized wheel includes spatial data.

A further embodiment of any of the foregoing embodiments of the present disclosure may include, wherein the data from the sensor system includes torque data of the electrically motorized wheel.

A further embodiment of any of the foregoing embodiments of the present disclosure may include, wherein the data at least one of the sensor system and the data source external to the electrically motorized wheel includes speed data of the electrically motorized wheel.

A further embodiment of any of the foregoing embodiments of the present disclosure may include, wherein the data from the sensor system includes "steadiness" of the electrically motorized wheel.

A further embodiment of any of the foregoing embodiments of the present disclosure may include, wherein the data from at least one of the sensor system and the data source external to the electrically motorized wheel includes steadiness of the vehicle.

A further embodiment of any of the foregoing embodiments of the present disclosure may include, wherein the data at least one of the sensor system and the data source external to the electrically motorized wheel includes terrain travelled by the electrically motorized wheel.

A further embodiment of any of the foregoing embodiments of the present disclosure may include, wherein the data from at least one of the sensor system and the data source external to the electrically motorized wheel includes motorized assistance provided by the electrically motorized wheel.

A further embodiment of any of the foregoing embodiments of the present disclosure may include, wherein the data from at least one of the sensor system and the data source external to the electrically motorized wheel includes available battery power of the electrically motorized wheel.

A further embodiment of any of the foregoing embodiments of the present disclosure may include, wherein the data from at least one of the sensor system and the data source external to the electrically motorized wheel includes motor temperature of the electrically motorized wheel.

A system according to another disclosed non-limiting embodiment of the present disclosure can include a server in communication with each of a plurality of electrically motorized wheels and a third party data source, the server operable to integrate the data from each of the electrically motorized wheels and the data from the third party data source, wherein each of the electrically motorized wheels operable to convert a non-motorized wheeled vehicle to an electrically motorized wheeled vehicle via installation of the electrically motorized wheel.

A further embodiment of any of the foregoing embodiments of the present disclosure may include, wherein the data from the third party data source includes data from a traffic camera.

A further embodiment of any of the foregoing embodiments of the present disclosure may include, wherein the data from the third party data source includes data from a road sensor.

A further embodiment of any of the foregoing embodiments of the present disclosure may include, wherein the data from the third party data source includes data from an aerial mapping data source.

A further embodiment of any of the foregoing embodiments of the present disclosure may include, wherein the integrated data provides a spatial and temporal indication of various parameters.

A further embodiment of any of the foregoing embodiments of the present disclosure may include, wherein the spatial indication includes a location.

A further embodiment of any of the foregoing embodiments of the present disclosure may include, wherein the temporal indication includes data associated with an environment through which at least one of the multiple of electrically motorized wheels passes.

A further embodiment of any of the foregoing embodiments of the present disclosure may include, wherein the temporal indication includes at least one of temperature, humidity, elevation, atmospheric data and signal strength.

A further embodiment of any of the foregoing embodiments of the present disclosure may include, wherein the temporal indication includes data associated with at least one of the plurality of electrically motorized wheels.

A further embodiment of any of the foregoing embodiments of the present disclosure may include, wherein the temporal indication includes at least one of vehicle speed, battery charge, motor assistance and torque.

A further embodiment of any of the foregoing embodiments of the present disclosure may include, wherein the integrated data is utilized to generate a model.

A further embodiment of any of the foregoing embodiments of the present disclosure may include, wherein the model is operable to facilitate prediction of future conditions.

A further embodiment of any of the foregoing embodiments of the present disclosure may include, wherein the model is operable to facilitate at least one of bike lane placement, urban planning, cell tower placement, pollution reduction initiatives.

A further embodiment of any of the foregoing embodiments of the present disclosure may include, wherein the model is operable to facilitate analysis of real time conditions.

A system according to another disclosed non-limiting embodiment of the present disclosure can include a server in communication with each of a plurality of electrically motorized wheels, the server operable to integrate movement data from each of the electrically motorized wheels, wherein each of the electrically motorized wheels operable to convert a non-motorized wheeled vehicle to an electrically motorized wheeled vehicle via installation of the electrically motorized wheel.

A further embodiment of any of the foregoing embodiments of the present disclosure may include, wherein the server is operable to integrate the movement data to facilitate public health analysis.

A further embodiment of any of the foregoing embodiments of the present disclosure may include, wherein the server is operable to integrate the movement data to facilitate bike path location determinations.

A further embodiment of any of the foregoing embodiments of the present disclosure may include, wherein the server is operable to integrate the movement data to facilitate fleet management.

A further embodiment of any of the foregoing embodiments of the present disclosure may include, wherein the server is operable to integrate the movement data to facilitate traffic analysis.

A method of analyzing a fleet of vehicles, each of the vehicles including a device of an electrically motorized wheel for converting the vehicle to an electrically motorized vehicle via installation of the electrically motorized wheel, the method according to one disclosed non-limiting embodiment of the present disclosure can include receiving data from each device of the respective plurality of electrically motorized wheels within a fleet of vehicles; and utilizing the data to facilitate tracking at least one vehicle within the fleet.

A further embodiment of any of the foregoing embodiments of the present disclosure may include, wherein to facilitate operation of each vehicle within the fleet includes optimizing a route for the at least one vehicle in the fleet.

A further embodiment of any of the foregoing embodiments of the present disclosure may include, wherein to facilitate operation of at least one vehicle within the fleet includes optimizing a schedule for the at least one vehicle in the fleet.

A further embodiment of any of the foregoing embodiments of the present disclosure may include, wherein to facilitate operation of at least one vehicle within the fleet includes estimating a delivery time for the at least one vehicle in the fleet.

A further embodiment of any of the foregoing embodiments of the present disclosure may include 1, wherein to facilitate operation of at least one vehicle within the fleet includes optimizing a route for each vehicle in the fleet.

A further embodiment of any of the foregoing embodiments of the present disclosure may include, wherein to facilitate operation of each vehicle within the fleet includes optimizing a schedule for each vehicle in the fleet.

A further embodiment of any of the foregoing embodiments of the present disclosure may include, wherein to facilitate operation of at least one vehicle within the fleet includes estimating a delivery time for each vehicle in the fleet.

A further embodiment of any of the foregoing embodiments of the present disclosure may include analyzing data from each device of each of the plurality of electrically motorized wheels within the fleet includes analyzing at least one of a user fitness level, terrain covered during current excursion, elevation change, level of assistance already provided, remaining battery life, current location, and terrain.

A data analysis system for a fleet of vehicles, each of the vehicles including a device of an electrically motorized wheel for converting a vehicle to an electrically motorized vehicle via installation of the electrically motorized wheel, the data analysis, according to one disclosed non-limiting embodiment of the present disclosure can include a server in communication with each device of each of a plurality of electrically motorized wheels, the server operable to analyze data from each of the devices of the electrically motorized wheels.

A further embodiment of any of the foregoing embodiments of the present disclosure may include, wherein the data includes at least one of a user fitness level, terrain covered during current excursion, elevation change, level of assistance already provided, remaining battery life, current location, and terrain.

A fleet management system for monitoring a plurality of devices each associated with one of a plurality of electrically motorized wheels for converting vehicles to electrically motorized vehicles via installation of the electrically motorized wheels, the fleet management system according to one disclosed non-limiting embodiment of the present disclosure can include a server in communication with each device of each of the plurality of electrically motorized wheels; an electronic data storage structure for storing data communicated from each the plurality of devices; and a fleet management module in communication with the server and the electronic data storage structure.

A further embodiment of any of the foregoing embodiments of the present disclosure may include, wherein the data communicated from each of the plurality of devices includes at least operating version of the electrically motorized wheels wherein the operating version is utilized by the fleet management module to coordinate an application on each of the plurality of devices.

A further embodiment of any of the foregoing embodiments of the present disclosure may include, wherein the data communicated from each of the plurality of devices includes at least one of a user destination, a current location, and available battery life which are utilized by the fleet management module to coordinate route planning for the plurality of electrically motorized wheels.

A further embodiment of any of the foregoing embodiments of the present disclosure may include, wherein the data communicated from each of the plurality of devices includes at least one of wheel speed over time, accelerations, motor assistance and resistance, routing, wheel sensor data, and temperature data which are utilized by the fleet management module to perform a meta-analysis of the provided data to optimize long term fleet routing.

A further embodiment of any of the foregoing embodiments of the present disclosure may include, wherein the fleet management module utilizes the data to evaluate a user efficiency of each user of each of the plurality of electrically motorized wheels.

A further embodiment of any of the foregoing embodiments of the present disclosure may include, wherein the fleet management module utilizes the data to evaluate operation of each of the plurality of electrically motorized wheels.

A further embodiment of any of the foregoing embodiments of the present disclosure may include, wherein the fleet management module utilizes the data to track a location of each of the plurality of electrically motorized wheels.

A further embodiment of any of the foregoing embodiments of the present disclosure may include, wherein the fleet management module utilizes the data to track a battery charge for each of the plurality of electrically motorized wheels.

A further embodiment of any of the foregoing embodiments of the present disclosure may include, wherein the fleet management module is operable to generate aggregated data from the plurality of devices of the plurality of electrically motorized wheels.

A further embodiment of any of the foregoing embodiments of the present disclosure may include, wherein the aggregated data provides a summary associated with the fleet.

A method of profiling a user of a device for an electrically motorized wheel, the electrically motorized wheel for converting a non-motorized vehicle to an electrically motorized vehicle via installation of the electrically motorized wheel, the method according to another disclosed non-limiting embodiment of the present disclosure can include receiving data from a sensor system of the device; and creating a profile of a user operating the vehicle from the data.

A further embodiment of any of the foregoing embodiments of the present disclosure may include identifying trends in the profile of the user over time.

A further embodiment of any of the foregoing embodiments of the present disclosure may include detecting changes in mobility patterns of the user from the profile.

A further embodiment of any of the foregoing embodiments of the present disclosure may include detecting long-term, slowly developing diseases from the profile.

A further embodiment of any of the foregoing embodiments of the present disclosure may include communicating the data into an electronic medical record (EMR) of the user.

A further embodiment of any of the foregoing embodiments of the present disclosure may include aggregating the user data with data from a plurality of other users of electrically motorized wheels to provide data sets for public health analysis.

A device of an electrically motorized wheel to convert a non-motorized wheeled vehicle to an electrically motorized wheeled vehicle via installation of the device, the device, according to another disclosed non-limiting embodiment of the present disclosure can include a control system mounted to the device, the control system operable to continuously control the device in response to a user input; and a sensor system mounted to the device, the sensor system operable to sense data that may be used to profile a user operating the vehicle.

A further embodiment of any of the foregoing embodiments of the present disclosure may include, wherein the sensor system is operable to sense a state of the user.

A further embodiment of any of the foregoing embodiments of the present disclosure may include, wherein the sensor system is operable to monitor a user's physical capabilities over time to facilitate identification of trends.

A further embodiment of any of the foregoing embodiments of the present disclosure may include, wherein the sensor system is operable to sense mobility patterns of the user.

A system, according to another disclosed non-limiting embodiment of the present disclosure can include a server adapted to operate in data communication with a plurality of electrically motorized wheels, each of the plurality of electrically motorized wheels being of a type adapted for converting a non-motorized vehicle to an electrically motorized vehicle via installation of the electrically motorized wheel;

and a data aggregation module in communication with the server operable to take a data set from each of the electrically motorized wheels and aggregate the data set to transform the data sets into an aggregated data set to generate a recommended setting to a user of one of the plurality of electrically motorized wheels based on the aggregated data set.

A further embodiment of any of the foregoing embodiments of the present disclosure may include, wherein the recommended setting includes an operational profile.

A further embodiment of any of the foregoing embodiments of the present disclosure may include, wherein the recommended setting includes a route.

A further embodiment of any of the foregoing embodiments of the present disclosure may include, wherein the recommended setting is based at least in part on demographics.

A further embodiment of any of the foregoing embodiments of the present disclosure may include, wherein the recommended setting is based at least in part on fitness.

A further embodiment of any of the foregoing embodiments of the present disclosure may include, wherein the recommended setting is based at least in part on a similarity to one or more of a user of the other of the plurality of electrically motorized wheels.

A method of controlling operation of an electrically motorized wheel for converting a non-motorized vehicle to an electrically motorized vehicle via installation of the electrically motorized wheel, the method according to another disclosed non-limiting embodiment of the present disclosure can include receiving a recommended setting for the electrically motorized wheel from aggregated data collected from a plurality of electrically motorized wheels.

A further embodiment of any of the foregoing embodiments of the present disclosure may include, wherein the recommended setting is received in a control system of the electrically motorized wheel.

A further embodiment of any of the foregoing embodiments of the present disclosure may include, wherein the recommended setting is received at a mobile device in communication with the electrically motorized wheel.

A system, according to one disclosed non-limiting embodiment of the present disclosure can include a server in communication with a device of each of a plurality of electrically motorized wheels, each of the electrically motorized wheels operable to convert a non-motorized wheeled vehicle to an electrically motorized wheeled vehicle via installation of the electrically motorized wheel, the server operable to track a position of each of the electrically motorized wheels and communicate the position thereof to a transportation network.

A further embodiment of any of the foregoing embodiments of the present disclosure may include, wherein the transportation network is accessible by a remote user.

A further embodiment of any of the foregoing embodiments of the present disclosure may include, wherein the remote user is a car.

A further embodiment of any of the foregoing embodiments of the present disclosure may include, wherein the remote user is one of the plurality of electrically motorized wheels.

A system according to one disclosed non-limiting embodiment of the present disclosure can include a server in communication with each of a device of each of a plurality of electrically motorized wheels, each of the plurality of electrically motorized wheels operable to convert a non-motorized wheeled vehicle to an electrically motorized wheeled vehicle via installation of the electrically motorized wheel, the server operable to integrate the data from each of the devices; and a display module in communication with the server to overlay the integrated data on a map to provide an overlaid map.

A further embodiment of any of the foregoing embodiments of the present disclosure may include, wherein the overlaid map is at least one of a street pattern, a land use map, a topographical map, a population density map, and an open space map.

A further embodiment of any of the foregoing embodiments of the present disclosure may include, wherein the overlaid map is accessible on a mobile device.

A further embodiment of any of the foregoing embodiments of the present disclosure may include, wherein the overlaid map provides an overview of environmental conditions.

A further embodiment of any of the foregoing embodiments of the present disclosure may include, wherein the overlaid map provides an overview of environmental conditions in real time.

A further embodiment of any of the foregoing embodiments of the present disclosure may include, wherein the overlaid map provides historical data of past environmental conditions.

A further embodiment of any of the foregoing embodiments of the present disclosure may include, wherein the overlaid map provides a prediction of future environmental conditions.

A further embodiment of any of the foregoing embodiments of the present disclosure may include, wherein the overlaid map provides an overview of environmental conditions, the environmental conditions including at least one of a temperature, a humidity, an air quality metric, a wind speed and a wind direction.

A further embodiment of any of the foregoing embodiments of the present disclosure may include, wherein the overlaid map provides an overview of environmental conditions, the environmental conditions including a temperature.

A further embodiment of any of the foregoing embodiments of the present disclosure may include 5, wherein the overlaid map provides an overview of environmental conditions, the environmental conditions including a traffic pattern.

A further embodiment of any of the foregoing embodiments of the present disclosure may include, wherein the integrated data provides a spatial and temporal indication of various parameters.

A further embodiment of any of the foregoing embodiments of the present disclosure may include, wherein the spatial indication includes a location.

A further embodiment of any of the foregoing embodiments of the present disclosure may include, wherein the temporal indication includes data associated with an environment through which at least one of the multiple of electrically motorized wheels passes.

A further embodiment of any of the foregoing embodiments of the present disclosure may include, wherein the temporal indication includes at least one of temperature, humidity, elevation, atmospheric data and signal strength.

A further embodiment of any of the foregoing embodiments of the present disclosure may include, wherein the temporal indication includes data associated with at least one of the multiple of electrically motorized wheels.

A further embodiment of any of the foregoing embodiments of the present disclosure may include, wherein the temporal indication includes at least one of vehicle speed, battery charge, motor assistance and torque.

A method to integrate data, according to one disclosed non-limiting embodiment of the present disclosure can include receiving data from a device of each of a plurality of electrically motorized wheels, each of the multiple of electrically motorized wheels operable to convert a non-motorized wheeled vehicle to an electrically motorized wheeled vehicle via installation of the electrically motorized wheel; and integrating the data from each of the devices via a server, the integrated data being adapted to be overlaid on a map.

A further embodiment of any of the foregoing embodiments of the present disclosure may include, wherein the data is integrated with a location on the map based on spatial data associated with each data point.

A further embodiment of any of the foregoing embodiments of the present disclosure may include, wherein the integrated data overlaid on the map provides an overview of environmental conditions.

A further embodiment of any of the foregoing embodiments of the present disclosure may include, wherein the integrated data overlaid on the map provides an overview of environmental conditions in real time.

A further embodiment of any of the foregoing embodiments of the present disclosure may include, wherein the integrated data overlaid on the map provides historical data of past environmental conditions.

A further embodiment of any of the foregoing embodiments of the present disclosure may include, wherein the integrated data overlaid on the map provides a prediction of future environmental conditions.

A further embodiment of any of the foregoing embodiments of the present disclosure may include, wherein the integrated data overlaid on the map provides an overview of environmental conditions, the environmental conditions include a traffic pattern.

A method for controlling operation over a prescribed route of a vehicle with an electrically motorized wheel, the electrically motorized wheel for converting the vehicle to an electrically motorized vehicle via installation of the electrically motorized wheel, the method according to one disclosed non-limiting embodiment of the present disclosure can include adjusting a control parameter for an electrically motorized wheel operating along a particular route such that operation of the electrically motorized wheel is managed with respect to the particular route.

A further embodiment of any of the foregoing embodiments of the present disclosure may include, wherein the adjusting the control parameter is performed in response to a mode selected by a user.

A further embodiment of any of the foregoing embodiments of the present disclosure may include, wherein the mode includes maintaining a predefined battery reserve with respect to the particular route.

A further embodiment of any of the foregoing embodiments of the present disclosure may include, wherein the mode includes maintaining a user selected battery reserve.

A further embodiment of any of the foregoing embodiments of the present disclosure may include, wherein the mode accommodates traffic data associated with the particular route.

A further embodiment of any of the foregoing embodiments of the present disclosure may include, wherein the mode accommodates user capability data associated with the particular route.

A further embodiment of any of the foregoing embodiments of the present disclosure may include, wherein the mode accommodates user preference data associated with the particular route.

A further embodiment of any of the foregoing embodiments of the present disclosure may include, wherein the mode accommodates road data associated with the particular route.

A further embodiment of any of the foregoing embodiments of the present disclosure may include, wherein the adjusting the control parameter includes adjusting a motor assistance and a motor resistance along the particular route.

A further embodiment of any of the foregoing embodiments of the present disclosure may include storing a data set from each of a plurality of electrically motorized wheels in an electronic data structure; analyzing a subset of the plurality of data sets, the subset associated with a particular route; and communication data associated with the subset to the electrically motorized wheel traversing the particular route.

A method for controlling battery usage over a prescribed route of a vehicle with an electrically motorized wheel, the electrically motorized wheel for converting the vehicle to an electrically motorized vehicle via installation of the electrically motorized wheel, the method according to one disclosed non-limiting embodiment of the present disclosure can include adjusting a control parameter for an electrically motorized wheel operating along the particular route such that a battery life parameter is managed over the particular route.

A further embodiment of any of the foregoing embodiments of the present disclosure may include, wherein adjusting the control parameter include selection of at least one mode.

A further embodiment of any of the foregoing embodiments of the present disclosure may include, wherein the battery life parameter is managed to maintain a predefined battery reserve with respect to the particular route.

A further embodiment of any of the foregoing embodiments of the present disclosure may include, wherein adjusting the control parameter includes adjusting an assistance from the electrically motorized wheel along the particular route such that the battery life parameter is managed to complete the particular route.

A further embodiment of any of the foregoing embodiments of the present disclosure may include, wherein adjusting the control parameter includes adjusting a motor assistance and a motor resistance.

An electrically motorized wheeled vehicle according to one disclosed non-limiting embodiment of the present disclosure can include a plurality of electrically motorized wheels to convert a non-motorized wheeled vehicle to an electrically motorized wheeled vehicle via installation of the electrically motorized wheel, each of the plurality of electrically motorized wheels in communication with at least one other of the plurality of electrically motorized wheels to coordinate operation of the plurality of electrically motorized wheels to coordinate operation of the vehicle.

A further embodiment of any of the foregoing embodiments of the present disclosure may include, wherein at least one of the electrically motorized wheels includes a ring handle.

A further embodiment of any of the foregoing embodiments of the present disclosure may include, wherein each wheel has a ring handle, and user input to the respective ring handles in differing rotational directions results in steering of the vehicle.

A further embodiment of any of the foregoing embodiments of the present disclosure may include, wherein each wheel has a ring handle, and user input to the respective ring handles in differing rotational directions results in pivoting of the vehicle.

A further embodiment of any of the foregoing embodiments of the present disclosure may include, wherein each wheel has a ring handle, and user input to at least one of the respective ring handles results in braking of the respective wheel.

A further embodiment of any of the foregoing embodiments of the present disclosure may include, wherein forward user input to ring handles of the plurality of wheels results in forward movement of the vehicle.

A further embodiment of any of the foregoing embodiments of the present disclosure may include, wherein backward user input to the ring handles of the plurality of wheels results in aft movement of the vehicle.

A further embodiment of any of the foregoing embodiments of the present disclosure may include, wherein the wheels are mounted to an undercarriage.

A further embodiment of any of the foregoing embodiments of the present disclosure may include, wherein the undercarriage is mounted to a pull handle.

A further embodiment of any of the foregoing embodiments of the present disclosure may include, wherein the wheels are mounted to a shopping cart.

A further embodiment of any of the foregoing embodiments of the present disclosure may include, wherein the wheels are mounted to a wagon.

A further embodiment of any of the foregoing embodiments of the present disclosure may include, wherein the wheels are mounted to a wheelchair.

A device of an electrically motorized wheel that is adapted to convert a non-motorized wheeled vehicle to an electrically motorized wheeled vehicle via installation of the device, the device according to one disclosed non-limiting embodiment of the present disclosure can include a first control system mounted to a first device, the control system operable to continuously control the first device in response to a user input, the control system including a protocol for coordinating with a second control system of a second device of a second electrically motorized wheel.

A further embodiment of any of the foregoing embodiments of the present disclosure may include, wherein the user input to the device also results in an output from the second device of the second electrically motorized wheel.

A further embodiment of any of the foregoing embodiments of the present disclosure may include, wherein the user input to the first device and a second user input to the second device results in an equivalent output from the respective electrically motorized wheels.

A further embodiment of any of the foregoing embodiments of the present disclosure may include, wherein the user input to the first device and a second user input to the second device results in a coordinated output.

A method for controlling operation of a plurality of devices of respective electrically motorized wheels adapted to convert a non-motorized wheeled vehicle to an electrically motorized wheeled vehicle via installation of the plurality of electrically motorized wheels, the method according to one disclosed non-limiting embodiment of the present disclosure can include receiving a user input at a first device of a first electrically motorized wheel, the user input operable to control an amount of assistance or resistance from the first device of the first electrically motorized wheel and an amount of assistance or resistance from a second device of a second electrically motorized wheel daisy chained to the first device of the first electrically motorized wheel.

A further embodiment of any of the foregoing embodiments of the present disclosure may include, wherein the user input is a rotational input.

A further embodiment of any of the foregoing embodiments of the present disclosure may include, further comprising receiving the rotational input via a ring handle of a wheelchair.

A further embodiment of any of the foregoing embodiments of the present disclosure may include, wherein the user input to the first device of the first electrically motorized wheel results in a first output from the first device of the first electrically motorized wheel and a second output from the second device of the second electrically motorized wheel.

A method for controlling operation of a plurality of devices of respective electrically motorized wheels adapted to convert a non-motorized wheeled vehicle to an electrically motorized wheeled vehicle via installation of the plurality of electrically motorized wheels, the method according to one disclosed non-limiting embodiment of the present disclosure can include daisy chaining a plurality of devices of a respective plurality of electrically motorized wheels to coordinate operation of the vehicle.

A further embodiment of any of the foregoing embodiments of the present disclosure may include communicating a user input through each of the plurality of devices.

A further embodiment of any of the foregoing embodiments of the present disclosure may include coordinating a user input through each of the plurality of devices.

A further embodiment of any of the foregoing embodiments of the present disclosure may include communicating a user input from at least one of the plurality of devices to each of the plurality of devices.

A further embodiment of any of the foregoing embodiments of the present disclosure may include, wherein daisy chaining includes communicating between each of the plurality of devices.

A further embodiment of any of the foregoing embodiments of the present disclosure may include, wherein daisy chaining includes wirelessly communicating between each of the plurality of devices.

A further embodiment of any of the foregoing embodiments of the present disclosure may include, wherein daisy chaining includes communicating between each of the plurality of devices via a cable.

A further embodiment of any of the foregoing embodiments of the present disclosure may include, wherein the cable connects to CAN interface on each of the each of the plurality of devices.

A further embodiment of any of the foregoing embodiments of the present disclosure may include, wherein the cable connects to a charging port on each of the plurality of devices.

A further embodiment of any of the foregoing embodiments of the present disclosure may include, wherein daisy chaining includes wirelessly communicating from one of the plurality of devices to the other of the plurality of devices.

A further embodiment of any of the foregoing embodiments of the present disclosure may include, wherein the one of the plurality of devices is in communicates with a mobile device.

A further embodiment of any of the foregoing embodiments of the present disclosure may include a control system in communication with the plurality of devices.

A method for controlling a device of an electrically motorized wheel for converting a vehicle to an electrically motorized vehicle via installation of the electrically motorized wheel, the method according to one disclosed non-limiting embodiment of the present disclosure can include calculating a set of parameters associated with a fitness level of the user for use in determining an amount of assistance a user will receive from the electrically motorized wheel.

A further embodiment of any of the foregoing embodiments of the present disclosure may include, wherein the user input is performed remotely.

A further embodiment of any of the foregoing embodiments of the present disclosure may include, wherein the user input is performed via a remote device.

A further embodiment of any of the foregoing embodiments of the present disclosure may include, wherein the user input includes an amount of calories to be burned.

A further embodiment of any of the foregoing embodiments of the present disclosure may include, wherein the user input includes a maximum not to exceed torque.

A further embodiment of any of the foregoing embodiments of the present disclosure may include, wherein the user input includes a heart rate.

A further embodiment of any of the foregoing embodiments of the present disclosure may include, wherein the user input includes a time period.

A further embodiment of any of the foregoing embodiments of the present disclosure may include, wherein the user input includes a destination.

A further embodiment of any of the foregoing embodiments of the present disclosure may include, wherein the user input includes a route.

A further embodiment of any of the foregoing embodiments of the present disclosure may include, wherein the route simulates a particular bicycle race.

A further embodiment of any of the foregoing embodiments of the present disclosure may include, wherein the user input includes a desired terrain.

A device of an electrically motorized wheel to convert a non-motorized wheeled vehicle to an electrically motorized wheeled vehicle via installation of the device, the device according to one disclosed non-limiting embodiment of the present disclosure can include a control system mounted to the electrically motorized wheel, the control system operable to control an amount of assistance from the electrically motorized wheel while travelling uphill and an amount of resistance from the electrically motorized wheel while traveling downhill to result in a user input requirement about equivalent to that required by a user in the specified environment.

A further embodiment of any of the foregoing embodiments of the present disclosure may include, wherein the specified environment is a type of terrain.

A further embodiment of any of the foregoing embodiments of the present disclosure may include, wherein the specified environment is a particular route.

A method for controlling a device of an electrically motorized wheel for converting a vehicle to an electrically motorized vehicle via installation of the electrically motorized wheel, the method according to one disclosed non-limiting embodiment of the present disclosure can include calculating a set of parameters associated with a fitness level of the user for use in determining an amount of resistance a user will receive from the device of the electrically motorized wheel.

A further embodiment of any of the foregoing embodiments of the present disclosure may include, wherein the user input is performed remotely.

A further embodiment of any of the foregoing embodiments of the present disclosure may include, wherein the user input is performed via a remote device.

A further embodiment of any of the foregoing embodiments of the present disclosure may include, wherein the user input includes an amount of calories to be burned.

A further embodiment of any of the foregoing embodiments of the present disclosure may include, wherein the user input includes a maximum not to exceed torque.

A further embodiment of any of the foregoing embodiments of the present disclosure may include, wherein the user input includes a heart rate.

A further embodiment of any of the foregoing embodiments of the present disclosure may include, wherein the user input includes a time period.

A further embodiment of any of the foregoing embodiments of the present disclosure may include, wherein the user input includes a destination.

A further embodiment of any of the foregoing embodiments of the present disclosure may include, wherein the user input includes a route.

A further embodiment of any of the foregoing embodiments of the present disclosure may include, wherein the route simulates a particular bicycle race.

A further embodiment of any of the foregoing embodiments of the present disclosure may include, wherein the user input includes a desired terrain.

A further embodiment of any of the foregoing embodiments of the present disclosure may include charging a device from the user input to the electrically motorized wheel.

A further embodiment of any of the foregoing embodiments of the present disclosure may include generating power from the user input to the electrically motorized wheel.

A further embodiment of any of the foregoing embodiments of the present disclosure may include generating power to a power grid from the user input to the electrically motorized wheel.

A further embodiment of any of the foregoing embodiments of the present disclosure may include storing power generated from the user input to the electrically motorized wheel.

A further embodiment of any of the foregoing embodiments of the present disclosure may include charging a mobile device from the user input to electrically motorized wheel, the mobile device operable to communicate the user input to the electrically motorized wheel.

A further embodiment of any of the foregoing embodiments of the present disclosure may include discarding power generated from the user input to the electrically motorized wheel.

A further embodiment of any of the foregoing embodiments of the present disclosure may include discarding power generated from the user input to the electrically motorized wheel through heat production.

A further embodiment of any of the foregoing embodiments of the present disclosure may include determining the amount of resistance the user will receive from the device of the electrically motorized wheel, the amount of resistance determined based on a particular distance.

A further embodiment of any of the foregoing embodiments of the present disclosure may include determining the amount of resistance the user will receive from the device of the electrically motorized wheel, the amount of resistance determined based on a particular time.

A method of controlling a device of an electrically motorized wheel for converting a non-motorized vehicle to an electrically motorized vehicle via installation of the electrically motorized wheel, the method according to one disclosed non-limiting embodiment of the present disclosure can include receiving a first input indicative of a quantity of energy a user wishes to expend operating the electrically motorized vehicle; receiving a second input indicative of a destination; and controlling operation of the device of the electrically motorized wheel in response to the first input and the second input to achieve the use of the desired quantity of user expended energy over a route to the destination.

A further embodiment of any of the foregoing embodiments of the present disclosure may include, wherein the first input is in Calories.

A further embodiment of any of the foregoing embodiments of the present disclosure may include calculating an amount of energy based on the terrain between the destination and an initial point.

A further embodiment of any of the foregoing embodiments of the present disclosure may include, wherein the controlling includes adjusting at least one of the assistance and the resistance provided by the electrically motorized wheel to a user input of a user.

A further embodiment of any of the foregoing embodiments of the present disclosure may include, wherein the user input is a pedaling input.

A further embodiment of any of the foregoing embodiments of the present disclosure may include, wherein the second input is one of an address and a GPS location.

A device of an electrically motorized wheel that is adapted to convert a non-motorized wheeled vehicle to an electrically motorized wheeled vehicle via installation of the device, the device according to one disclosed non-limiting embodiment of the present disclosure can include a control system mounted to the electrically motorized wheel, the control system operable to control a amount of assistance and resistance from the electrically motorized wheel to burn a desired quantity of energy a user wishes to expend operating the electrically motorized vehicle.

A further embodiment of any of the foregoing embodiments of the present disclosure may include, wherein the desired quantity of energy is input to the control system via a mobile device.

A further embodiment of any of the foregoing embodiments of the present disclosure may include, wherein the desired quantity of energy is input as Calories.

A method for controlling a device of an electrically motorized wheel for converting a vehicle to an electrically motorized vehicle via installation of the electrically motorized wheel, the method according to one disclosed non-limiting embodiment of the present disclosure can include controlling an amount of assistance from the device of the electrically motorized wheel while travelling uphill and an amount of resistance from the electrically motorized wheel while traveling downhill to result in a user input requirement about equivalent to that required to propel the vehicle on a level surface.

A further embodiment of any of the foregoing embodiments of the present disclosure may include, wherein the controlling the amount of assistance while travelling uphill and the amount of resistance while traveling downhill is based on a user selection.

A further embodiment of any of the foregoing embodiments of the present disclosure may include, wherein the controlling includes adjusting a user adjustable parameter.

A further embodiment of any of the foregoing embodiments of the present disclosure may include 3, wherein the user adjustable parameter includes a minimum incline of the hill.

A further embodiment of any of the foregoing embodiments of the present disclosure may include, wherein the user adjustable parameter includes a desired user input limit.

A further embodiment of any of the foregoing embodiments of the present disclosure may include, wherein the amount of resistance while traveling downhill includes braking.

A further embodiment of any of the foregoing embodiments of the present disclosure may include, wherein the user adjustable parameter includes a maximum downhill speed.

A further embodiment of any of the foregoing embodiments of the present disclosure may include, wherein the controlling includes a mode selection from a plurality of operational modes.

A further embodiment of any of the foregoing embodiments of the present disclosure may include, wherein one of the plurality of operational modes includes a maximum power storage mode.

A further embodiment of any of the foregoing embodiments of the present disclosure may include wherein the amount of assistance and resistance is based in part on data from sensors on the wheel.

A further embodiment of any of the foregoing embodiments of the present disclosure may include, wherein the sensors on the wheel include at least one of speed, altitude, temperature, humidity, voltage, battery amount, incline and electrical current amount.

A further embodiment of any of the foregoing embodiments of the present disclosure may include wherein the amount of assistance and resistance is based in part on calculations based on sensor data.

A further embodiment of any of the foregoing embodiments of the present disclosure may include, wherein the calculation based on sensor data includes an estimate of gear ratio.

A device of an electrically motorized wheel that is adapted to convert a non-motorized wheeled vehicle to an electrically motorized wheeled vehicle via installation of the device, the device according to one disclosed non-limiting embodiment of the present disclosure can include a control system of the device of the electrically motorized wheel, the control system operable to control an amount of assistance from the electrically motorized wheel while travelling uphill and an amount of resistance from the electrically motorized wheel while traveling downhill to result in a user input requirement about equivalent to that required to propel the vehicle on a level surface.

A further embodiment of any of the foregoing embodiments of the present disclosure may include, wherein the amount of assistance from the electrically motorized wheel while travelling uphill and the amount of resistance from the electrically motorized wheel while traveling downhill is effectuated via a mobile device.

A further embodiment of any of the foregoing embodiments of the present disclosure may include, wherein the amount of assistance from the electrically motorized wheel while travelling uphill and the amount of resistance from the electrically motorized wheel while traveling downhill is selected from one of a multiple of modes.

A further embodiment of any of the foregoing embodiments of the present disclosure may include, wherein the mode is selectable while the electrically motorized wheel is in motion.

A device of an electrically motorized wheel that is adapted to convert a non-motorized wheeled vehicle to an electrically motorized wheeled vehicle via installation of the device, the device according to one disclosed non-limiting embodiment of the present disclosure can include a control system of the device of the electrically motorized wheel, the control system operable to control an amount of assistance from the electrically motorized wheel while travelling uphill to result in a user input requirement about equivalent to that required to propel the vehicle on a level surface.

A further embodiment of any of the foregoing embodiments of the present disclosure may include, wherein the amount of assistance from the electrically motorized wheel while travelling uphill is effectuated via a mobile device.

A further embodiment of any of the foregoing embodiments of the present disclosure may include, wherein the amount of assistance from the electrically motorized wheel while travelling uphill is selected from one of a multiple of modes.

A further embodiment of any of the foregoing embodiments of the present disclosure may include wherein the mode is selectable while the electrically motorized wheel is in motion.

A device of an electrically motorized wheel that is adapted to convert a non-motorized wheeled vehicle to an electrically motorized wheeled vehicle via installation of the device, the device according to one disclosed non-limiting embodiment of the present disclosure can include a control system mounted to the electrically motorized wheel, the control system operable to continuously control the electrically motorized wheel in response to a user input; and a wireless communication system mounted to the electrically motorized wheel, the wireless communication system in communication with the control system, the wireless communication system operable to receive an input to remotely configure operation of the electrically motorized wheel.

A further embodiment of any of the foregoing embodiments of the present disclosure may include, wherein the remotely configuring is effectuated via a mobile device.

A further embodiment of any of the foregoing embodiments of the present disclosure may include, wherein the remotely configuring is performable while the electrically motorized wheel is in motion.

A further embodiment of any of the foregoing embodiments of the present disclosure may include, wherein the remotely configuring is effectuated via selection of one of a plurality of operational modes.

A further embodiment of any of the foregoing embodiments of the present disclosure may include, wherein each of the plurality of operational modes includes particular values for a control equation effecting an amount of assistance or resistance generated by the electrically motorized wheel in response user input.

A further embodiment of any of the foregoing embodiments of the present disclosure may include, wherein each of the plurality of operational modes includes particular values for a control equation effecting an amount of assistance or resistance generated by the electrically motorized wheel in response to an environmental input.

A further embodiment of any of the foregoing embodiments of the present disclosure may include, wherein selection of an operation mode includes transmitting particular values for a control operation to the control system mounted to the electrically motorized wheel.

A further embodiment of any of the foregoing embodiments of the present disclosure may include, wherein each of the particular values is fixed.

A further embodiment of any of the foregoing embodiments of the present disclosure may include, wherein each of the particular values is calculated in near real time.

A further embodiment of any of the foregoing embodiments of the present disclosure may include, wherein selection of one of the plurality of operational modes is a standard mode with default values for the control equation.

A further embodiment of any of the foregoing embodiments of the present disclosure may include, wherein the plurality of operational modes includes a flatten city mode that provides assistance on at least one hill climb.

A device of an electrically motorized wheel that is adapted to convert a non-motorized wheeled vehicle to an electrically motorized wheeled vehicle via installation of the device, the device according to one disclosed non-limiting embodiment of the present disclosure can include an electric motor selectively operable to rotate a rotating system relative to a static system; a mechanical drive system coupled to the rotational unit, the mechanical drive system operable to rotate the rotational unit in response to a user input applied by the user; a sensor system mounted to the device of the electrically motorized wheel, the sensor system operable to identify parameters indicative of the user input; a control system mounted to the electrically motorized wheel, the control system in communication with the sensor system to continuously control the electric motor in response to the user input; a power source mounted to the device of the electrically motorized wheel, the power source electrically connected to the control system and the electric motor; and a wireless communication system mounted to the device of the electrically motorized wheel in communication with the control system, the wireless communication system operable to receive an input from a mobile device to adjust a control equation effecting an amount of assistance or resistance generated by the electrically motorized wheel in response to the user input.

A further embodiment of any of the foregoing embodiments of the present disclosure may include, wherein the input from the mobile device includes selection of an operational mode.

A further embodiment of any of the foregoing embodiments of the present disclosure may include, wherein the input from the mobile device is operable to adjust the control equation.

A further embodiment of any of the foregoing embodiments of the present disclosure may include, wherein to configure operation of the electrically motorized wheel includes wirelessly communicating the input while the electrically motorized wheel is in motion.

A method of controlling a device of an electrically motorized wheel that is adapted to convert a non-motorized wheeled vehicle to an electrically motorized wheeled vehicle via installation thereof, the method according to one disclosed non-limiting embodiment of the present disclosure can include remotely configuring the device to control an amount of assistance or resistance generated by the electrically motorized wheel in response to at least one of a user input and an environmental input.

A further embodiment of any of the foregoing embodiments of the present disclosure may include, wherein the remotely configuring is effectuated via a mobile device.

A further embodiment of any of the foregoing embodiments of the present disclosure may include, wherein the remotely configuring is performable while the electrically motorized wheel is in motion.

A further embodiment of any of the foregoing embodiments of the present disclosure may include, wherein the remotely configuring is effectuated via selection of one of a plurality of operational modes.

A further embodiment of any of the foregoing embodiments of the present disclosure may include, wherein each of the plurality of operational modes includes particular values for a control equation.

A further embodiment of any of the foregoing embodiments of the present disclosure may include, wherein each of the particular values is fixed.

A further embodiment of any of the foregoing embodiments of the present disclosure may include, wherein each of the particular values is calculated in essentially real time.

A further embodiment of any of the foregoing embodiments of the present disclosure may include, wherein selection of one of the plurality of operational modes is a standard mode in response to no communication with a mobile device.

A further embodiment of any of the foregoing embodiments of the present disclosure may include, wherein a set of default values is used for the control equation in response to no communication with a mobile device.

A further embodiment of any of the foregoing embodiments of the present disclosure may include, wherein the plurality of operational modes includes a flatten city mode that provides assistance on at least one hill climb.

A further embodiment of any of the foregoing embodiments of the present disclosure may include, wherein the at least one of the plurality of operational modes includes adjustable parameters to tune the at least one mode.

A further embodiment of any of the foregoing embodiments of the present disclosure may include, wherein the last values sent by the mobile device are stored and used for a control equation in response to no communication with a mobile device.

A further embodiment of any of the foregoing embodiments of the present disclosure may include, wherein the environmental input is external to the electrically motorized wheeled vehicle.

A method of controlling a device of an electrically motorized wheel for converting a non-motorized vehicle to an electrically motorized vehicle via installation of the electrically motorized wheel, the method according to one disclosed non-limiting embodiment of the present disclosure can include detecting a parameter indicative of a user input applied to the device of the electrically motorized wheel to obtain user input data; detecting a parameter indicative of an operational state of the electrically motorized wheel to obtain operational state data; processing the user input data and the operational state data to obtain a blended control data structure that scales the importance of the user input data based on the operational state data; and controlling operation of an electric motor of the electrically motorized wheel in response to the blended control data structure.

A further embodiment of any of the foregoing embodiments of the present disclosure may include, wherein the blended control data structure is scaled to respond more strongly to the user input data at a relatively low speed.

A further embodiment of any of the foregoing embodiments of the present disclosure may include, wherein the blended control data structure is scaled to respond less strongly to the user input data at a relatively high speed.

A further embodiment of any of the foregoing embodiments of the present disclosure may include, wherein the blended control structure is scaled to respond strongly to the user input data at a relatively low speed and is scaled to respond less strongly to the user input data at relatively high speed.

A further embodiment of any of the foregoing embodiments of the present disclosure may include, wherein the user input data includes a torque.

A further embodiment of any of the foregoing embodiments of the present disclosure may include, wherein the operational state data includes a speed.

A device of an electrically motorized wheel that is adapted to convert a non-motorized wheeled vehicle to an electrically motorized wheeled vehicle via installation of the device, the device according to one disclosed non-limiting embodiment of the present disclosure can include a control system operable to control an amount of assistance and resistance provided by the device in response to a blended control data structure.

A further embodiment of any of the foregoing embodiments of the present disclosure may include, wherein the blended control data structure is scaled to respond more strongly to the measured torque at a relatively low speed.

A further embodiment of any of the foregoing embodiments of the present disclosure may include, wherein the blended control data structure is scaled to respond less strongly to the measured torque at a relatively high speed.

A further embodiment of any of the foregoing embodiments of the present disclosure may include, wherein the blended control data is scaled to respond strongly to measured torque at a relatively low speed and is scaled to respond less strongly to measured torque at relatively high speed.

A further embodiment of any of the foregoing embodiments of the present disclosure may include, wherein the blended control data relies upon data from a torque sensor at relatively low speeds and one of a speed sensor and a measure of power at relatively high speed.

A further embodiment of any of the foregoing embodiments of the present disclosure may include, wherein the blended control structure scales the importance of a sensor based on speed.

A further embodiment of any of the foregoing embodiments of the present disclosure may include, wherein the sensor is a torque sensor.

A further embodiment of any of the foregoing embodiments of the present disclosure may include, wherein the sensor is a speed sensor.

A further embodiment of any of the foregoing embodiments of the present disclosure may include, wherein the amount of assistance and resistance provided by the electrically motorized wheel is transitioned from one setting to another by the blended control data structure.

A further embodiment of any of the foregoing embodiments of the present disclosure may include, wherein the amount of assistance and resistance provided by the electrically motorized wheel is transitioned via a step progression.

A method of controlling a device of an electrically motorized wheel for converting a vehicle to an electrically motorized vehicle via installation of the electrically motorized wheel, the method according to another disclosed non-limiting embodiment of the present disclosure can include detecting a temperature of an electric motor of the electrically motorized wheel; and controlling operation of the electric motor to maintain the detected temperature within a desired range.

A further embodiment of any of the foregoing embodiments of the present disclosure may include, wherein the controlling operation includes controlling assistance to a pedaling input transmitted to electrically motorized wheel.

A further embodiment of any of the foregoing embodiments of the present disclosure may include, wherein the controlling operation includes controlling resistance to a pedaling input transmitted to electrically motorized wheel.

A further embodiment of any of the foregoing embodiments of the present disclosure may include, wherein the controlling operation includes at least one of reducing and stopping assistance to a pedaling input transmitted to electrically motorized wheel in response to the temperature being outside a predetermined temperature.

A further embodiment of any of the foregoing embodiments of the present disclosure may include, wherein the controlling operation includes at least one of reducing and stopping resistance to a pedaling input transmitted to electrically motorized wheel in response to the temperature being outside a desired temperature range.

A further embodiment of any of the foregoing embodiments of the present disclosure may include, wherein the electric motor is mounted within a hub shell assembly of the electrically motorized wheel.

A further embodiment of any of the foregoing embodiments of the present disclosure may include, wherein the controlling operation includes controlling assistance to a user input transmitted to electrically motorized wheel.

A further embodiment of any of the foregoing embodiments of the present disclosure may include, wherein the controlling operation includes controlling resistance to a user input transmitted to electrically motorized wheel.

A method of controlling a device of an electrically motorized wheel for converting a vehicle to an electrically motorized vehicle via installation of the electrically motorized wheel, the method according to another disclosed non-limiting embodiment of the present disclosure can include detecting a temperature within a hub shell assembly of the device of the electrically motorized wheel; and controlling operation of an electric motor of the device of the electrically motorized wheel to maintain the detected temperature within a desired range.

A further embodiment of any of the foregoing embodiments of the present disclosure may include, wherein the controlling operation includes controlling assistance to a user input transmitted to electrically motorized wheel.

A further embodiment of any of the foregoing embodiments of the present disclosure may include, wherein the controlling operation includes controlling resistance to a user input transmitted to electrically motorized wheel.

A further embodiment of any of the foregoing embodiments of the present disclosure may include, wherein the controlling operation includes at least one of reducing and stopping assistance to a pedaling input transmitted to electrically motorized wheel in response to the temperature being outside a predetermined temperature.

A further embodiment of any of the foregoing embodiments of the present disclosure may include, wherein the controlling operation includes at least one of reducing and stopping resistance to a pedaling input transmitted to electrically motorized wheel in response to the temperature being outside a desired temperature range.

A device of an electrically motorized wheel that is adapted to convert a non-motorized wheeled vehicle to an electrically motorized wheeled vehicle via installation of the device, the device according to another disclosed non-limiting embodiment of the present disclosure can include a heat generating component within a hub shell assembly of the device of the electrically motorized wheel; a sensor system operable to detect a temperature of the heat generating component; and a control system in communication with the sensor system, the control system operable to control an electric motor within the hub shell assembly to maintain the detected temperature of the heat generating component within a desired range.

A further embodiment of any of the foregoing embodiments of the present disclosure may include, wherein the heat generating component is the electric motor.

A further embodiment of any of the foregoing embodiments of the present disclosure may include, wherein the heat generating component is a battery system in communication with the electric motor.

A further embodiment of any of the foregoing embodiments of the present disclosure may include, wherein the heat generating component is a control board.

A method of calculating a gear ratio, the method according to another disclosed non-limiting embodiment of the present disclosure can include detecting a frequency content of a rider effort operable to control a device of an electrically motorized wheel; detecting a speed of the device of the electrically motorized wheel; and calculating a gear ratio based on the user input and the frequency content of the rider effort.

A further embodiment of any of the foregoing embodiments of the present disclosure may include, wherein the gear ratio is utilized to control the device of an electrically motorized wheel for converting a non-motorized vehicle to an electrically motorized vehicle via installation of the electrically motorized wheel.

A further embodiment of any of the foregoing embodiments of the present disclosure may include, wherein detecting the frequency content of a rider effort occurs at the device of the electrically motorized wheel.

A further embodiment of any of the foregoing embodiments of the present disclosure may include, wherein detecting the speed occurs at the device of the electrically motorized wheel.

A method of controlling a device of an electrically motorized wheel for converting a vehicle to an electrically motorized vehicle via installation of the electrically motorized wheel, the method according to another disclosed non-limiting embodiment of the present disclosure can include detecting a rotational velocity of a cassette of an electrically motorized wheel; detecting a user input to the electrically motorized wheel; and calculating a gear ratio from the rotation velocity and the user input.

A further embodiment of any of the foregoing embodiments of the present disclosure may include, wherein the user input is determined as a pedal cadence.

A further embodiment of any of the foregoing embodiments of the present disclosure may include, wherein the user input is a pedaling input.

A further embodiment of any of the foregoing embodiments of the present disclosure may include, wherein detecting the rotation velocity of the electrically motorized wheel and detecting the user input to the electrically motorized wheel occurs at the electrically motorized wheel via at least a speed sensor and a torque sensor.

A further embodiment of any of the foregoing embodiments of the present disclosure may include, wherein the speed sensor and the torque sensor are mounted within a free wheel unit.

A method of controlling a device of an electrically motorized wheel for converting a non-motorized vehicle to an electrically motorized vehicle via installation of the electrically motorized wheel, the method according to another disclosed non-limiting embodiment of the present disclosure can include measuring a speed of an electric motor of the device of the electrically motorized wheel that is in electrical connection to a direct mechanical drive; measuring a voltage of a battery that powers the device of the electric motor; estimating terminal-to-terminal EMF voltage (VEMF); determining if VEMF is greater or equal to a voltage limit; and if the VEMF is above the limit, disconnecting an electrical connection between the motor drive and the electric motor.

A further embodiment of any of the foregoing embodiments of the present disclosure may include upon determining that VEMF is greater than a limit, opening a motor relay contact to the electric motor.

A further embodiment of any of the foregoing embodiments of the present disclosure may include upon determining that VEMF is less than an amount that is a specified margin lower than the limit, closing the motor relay contact.

A further embodiment of any of the foregoing embodiments of the present disclosure may include utilizing a motor resistance from the electric motor to dissipate braking energy.

A device of an electrically motorized wheel that is adapted to convert a non-motorized wheeled vehicle to an electrically motorized wheeled vehicle via installation of the device, the device according to another disclosed non-limiting embodiment of the present disclosure can include a control system mounted to the device of the electrically motorized wheel, the control system operable to continuously control the electrically motorized wheel in response to a user input; and a sensor system mounted to the device of the electrically motorized wheel, the sensor system in communication with the control system to control the electrically motorized wheel at least in part based on data sensed by the sensor system.

A further embodiment of any of the foregoing embodiments of the present disclosure may include, wherein the data sensed by the sensor system includes torque.

A further embodiment of any of the foregoing embodiments of the present disclosure may include, wherein the data sensed by the sensor system includes speed.

A further embodiment of any of the foregoing embodiments of the present disclosure may include, wherein the data sensed by the sensor system includes acceleration.

A further embodiment of any of the foregoing embodiments of the present disclosure may include, wherein the data sensed by the sensor system includes an angular rate measure.

A further embodiment of any of the foregoing embodiments of the present disclosure may include, wherein the data sensed by the sensor system includes environmental conditions.

A further embodiment of any of the foregoing embodiments of the present disclosure may include, where in the data sensed by the sensor system includes wind speed.

A further embodiment of any of the foregoing embodiments of the present disclosure may include, wherein the data sensed by the sensor system includes a temperature within a hub shell assembly of the electrically motorized wheel.

A further embodiment of any of the foregoing embodiments of the present disclosure may include, wherein the data sensed by the sensor system includes a battery current.

A further embodiment of any of the foregoing embodiments of the present disclosure may include, wherein the data sensed by the sensor system includes a battery level.

A further embodiment of any of the foregoing embodiments of the present disclosure may include, wherein the data sensed by the sensor system includes a surface condition upon which the electrically motorized wheel is operating.

A further embodiment of any of the foregoing embodiments of the present disclosure may include, wherein the data sensed by the sensor system includes a slope upon which the electrically motorized wheel is operating.

A physical therapy system according to another disclosed non-limiting embodiment of the present disclosure can include a device of an electrically motorized wheel to supply at least one of assistance and resistance to a user, the amount of the at least one of assistance and resistance is modified in response to a set of control parameters; a prescription module to prescribe a physical therapy prescription for operation of the device of the electrically motorized wheel; and a rehabilitation application in communication with the prescription module to calculate the set of control parameters based on the physical therapy prescription.

A further embodiment of any of the foregoing embodiments of the present disclosure may include, wherein the rehabilitation application is operable on a mobile device that communicates between the device of the electrically motorized wheel and the prescription module.

A further embodiment of any of the foregoing embodiments of the present disclosure may include, wherein the rehabilitation application is operable to communicate user compliance with at least one of prescribed exertion, time and frequency to the prescription system via communication with the prescription module.

A further embodiment of any of the foregoing embodiments of the present disclosure may include, wherein the rehabilitation application is operable to communicate user compliance with physical therapy prescription via communication with the prescription module.

A further embodiment of any of the foregoing embodiments of the present disclosure may include, wherein the physical therapy prescription prescribes at least one of an amount of exertion, time, and frequency of a rehabilitation exercise.

A method of providing physical therapy according to another disclosed non-limiting embodiment of the present disclosure can include prescribing a prescribed amount of exertion for a user; calculating a set of control parameters for a device of an electrically motorized wheel based on the prescribed amount of exertion; and communicating the calculated control parameters to an electrically motorized wheel.

A further embodiment of any of the foregoing embodiments of the present disclosure may include controlling at least one of an assistance and resistance provided by the device of the electrically motorized wheel for the user in response to the calculated control parameters.

A further embodiment of any of the foregoing embodiments of the present disclosure may include, wherein the prescribed amount of exertion includes at least one of a time of exertion and a frequency of exertion.

A further embodiment of any of the foregoing embodiments of the present disclosure may include communicating at least one of the actual amounts of exertion by the user, the time of exertion, and the frequency of exertion relative to prescribed.

A further embodiment of any of the foregoing embodiments of the present disclosure may include, wherein the prescribed amount is controlled remotely in essentially real time.

A physical training system according to another disclosed non-limiting embodiment of the present disclosure can include a device of an electrically motorized wheel to supply at least one of assistance and resistance to a user wherein the amount of the at least one of assistance and resistance is modified in response to a set of control parameters; a user interface to facilitate a user goal specification; and a control module operable to calculate the set of control parameters based on the user goal specification and communicate the set of control parameters to the device of the electrically motorized wheel.

A further embodiment of any of the foregoing embodiments of the present disclosure may include, wherein the user goal specification includes at least one of target total calories burned, rate of calorie expenditure, exercise time, exercise frequency, and target increase is energy expenditure.

A further embodiment of any of the foregoing embodiments of the present disclosure may include, wherein the device of the electrically motorized wheel communicates at least one of amount of assistance provided, amount of resistance provided, total calories burned during exercise period, rate of calories burned, torque applied by the user to the training application.

A further embodiment of any of the foregoing embodiments of the present disclosure may include, wherein the control module is effectuated by a training application on a mobile device.

A method for controlling an electrically motorized vehicle, the method according to another disclosed non-limiting embodiment of the present disclosure can include calculating a set of parameters to control an amount of assistance or resistance generated by the device of the electrically motorized wheel in response to a user input the set of parameters calculated in response to a user selecting one of a plurality of operational modes.

A further embodiment of any of the foregoing embodiments of the present disclosure may include, wherein the plurality of operational modes include a "flattening city" mode that provides assistance on at least one hill climb.

A further embodiment of any of the foregoing embodiments of the present disclosure may include, wherein the plurality of operational modes include an exercise mode that is associated with a user entering a targeted amount of calories to be burned.

A further embodiment of any of the foregoing embodiments of the present disclosure may include, wherein the exercise mode includes limiting resistance generated by the electrically motorized wheel in response to a maximum value input by the user.

A further embodiment of any of the foregoing embodiments of the present disclosure may include, wherein the one of the plurality of operational modes is associated with a user-entered limit.

A further embodiment of any of the foregoing embodiments of the present disclosure may include, wherein the user-entered limit includes an amount of calories to be burned.

A further embodiment of any of the foregoing embodiments of the present disclosure may include, wherein the user entered limit includes a heart rate.

A further embodiment of any of the foregoing embodiments of the present disclosure may include, wherein the user entered limit includes a time.

A further embodiment of any of the foregoing embodiments of the present disclosure may include, wherein the user entered limit includes a speed of the electrically motorized wheel.

A further embodiment of any of the foregoing embodiments of the present disclosure may include, wherein at least one of the set of parameters are associated with a limit based on an operational condition of the electrically motorized wheel.

A further embodiment of any of the foregoing embodiments of the present disclosure may include, wherein at least one of the set of parameters are associated with a limit based on preexisting data.

A further embodiment of any of the foregoing embodiments of the present disclosure may include, wherein the preexisting data includes a local regulation.

A further embodiment of any of the foregoing embodiments of the present disclosure may include, wherein the preexisting data includes a location.

A further embodiment of any of the foregoing embodiments of the present disclosure may include, wherein the limit is a maximum speed based on location and local speed regulations.

A further embodiment of any of the foregoing embodiments of the present disclosure may include, wherein the location is at least one of on-road and off-road.

A further embodiment of any of the foregoing embodiments of the present disclosure may include, wherein the user selecting is performed via a mobile device.

A further embodiment of any of the foregoing embodiments of the present disclosure may include, wherein the mobile device provides a user interface.

A further embodiment of any of the foregoing embodiments of the present disclosure may include, wherein the user interface includes at least one button that occupies a minimum of 1 inch by 1 inch of display space.

A further embodiment of any of the foregoing embodiments of the present disclosure may include, wherein the user interface includes a gesture identifiable by the mobile device.

A device of an electrically motorized wheel that is adapted to convert a non-motorized wheeled vehicle to an electrically motorized wheeled vehicle via installation of the device, the device according to another disclosed non-limiting embodiment of the present disclosure can include a control system mounted to the device of the electrically motorized wheel, the control system operable to calculate a set of parameters to control an amount of assistance or resistance generated by the device in response to at least one of a user input, a wheel operating condition, and an environmental factor; and a wireless communication system mounted to the device of the electrically motorized wheel, the wireless communication system in communication with the control system, the wireless communication system operable to receive an operational mode that at least partially defines the set of parameters.

A further embodiment of any of the foregoing embodiments of the present disclosure may include, wherein the operational mode is effectuated via a selection on a mobile device.

A further embodiment of any of the foregoing embodiments of the present disclosure may include, wherein the remotely configuring is performable while the electrically motorized wheel is in motion.

A user interface for controlling a device of an electrically motorized wheel for converting a vehicle to an electrically motorized vehicle via installation of the electrically motorized wheel, the user interface according to one disclosed non-limiting embodiment of the present disclosure can include at least one button displayable by the user interface to control a function associated with the device.

A further embodiment of any of the foregoing embodiments of the present disclosure may include, wherein the at least one button is operable to select an operational mode of the device.

A further embodiment of any of the foregoing embodiments of the present disclosure may include, wherein the at least one button is related to navigation of the device.

A further embodiment of any of the foregoing embodiments of the present disclosure may include 1, wherein the at least one button is related to locking and unlocking the electrically motorized wheel.

A further embodiment of any of the foregoing embodiments of the present disclosure may include, wherein the at least one button is related to an identification of an obstacle.

A further embodiment of any of the foregoing embodiments of the present disclosure may include, wherein the button occupies a minimum of 1 inch by 1 inch of display space.

A further embodiment of any of the foregoing embodiments of the present disclosure may include, wherein the user interface is a user interface of a touch screen-enabled mobile device.

A method of navigating an electrically motorized wheel that is adapted for converting a vehicle to an electrically motorized vehicle via installation of the electrically motorized wheel, the method according to one disclosed non-limiting embodiment of the present disclosure can include displaying a directional arrow for guidance of the vehicle on which the electrically motorized wheel is installed along a route; and pointing the directional arrow in the direction of a next stage of a route to a destination with respect to a present position of the electrically motorized wheel.

A further embodiment of any of the foregoing embodiments of the present disclosure may include, wherein the directional arrow is displayed without a map.

A further embodiment of any of the foregoing embodiments of the present disclosure may include determining the route at least in part from third party data.

A further embodiment of any of the foregoing embodiments of the present disclosure may include occupying a minimum of 1 inch by 1 inch of display space with the directional arrow.

A further embodiment of any of the foregoing embodiments of the present disclosure may include aggregating a plurality of routes similar to the route and optimizing the aggregated plurality of routes to determine the route guided by the directional arrow.

A method of navigating a vehicle, the method according to one disclosed non-limiting embodiment of the present disclosure can include displaying a directional arrow on a mobile device mountable to the vehicle, the directional arrow operable to provide guidance of the vehicle along a route; and pointing the directional arrow in the direction of a next stage of the route to a destination with respect to a present position of the mobile device.

A further embodiment of any of the foregoing embodiments of the present disclosure may include, wherein the directional arrow is displayed without a map.

A further embodiment of any of the foregoing embodiments of the present disclosure may include, wherein the route is indifferent to roads.

A further embodiment of any of the foregoing embodiments of the present disclosure may include occupying a minimum of 1 inch by 1 inch of display space with the directional arrow.

A method of protecting an electrically motorized wheel to convert a non-motorized wheeled vehicle to an electrically motorized wheeled vehicle via installation thereof, the method according to another disclosed non-limiting embodiment of the present disclosure can include unlocking at least one feature of the electrically motorized wheel in response to receiving an indicator that a mobile device of the user of the electrically motorized wheel is within a predetermined proximity of the electrically motorized wheel.

A further embodiment of any of the foregoing embodiments of the present disclosure may include, wherein the indicator is a signal that includes a unique identifier of the mobile device.

A further embodiment of any of the foregoing embodiments of the present disclosure may include, wherein the mobile device is a smartphone.

A further embodiment of any of the foregoing embodiments of the present disclosure may include, wherein the proximity is determined via a wireless communication.

A further embodiment of any of the foregoing embodiments of the present disclosure may include, wherein the wireless communication is a local wireless communication from the mobile device to the electrically motorized wheel.

A further embodiment of any of the foregoing embodiments of the present disclosure may include, wherein the wireless communication is through a communications network.

A further embodiment of any of the foregoing embodiments of the present disclosure may include, wherein the location of at least one of the mobile device and the wheel is based on a global positioning system.

A further embodiment of any of the foregoing embodiments of the present disclosure may include, wherein the location of at least one of the mobile device and the wheel is based on a cellular network triangulation system.

A further embodiment of any of the foregoing embodiments of the present disclosure may include requiring a security input to the mobile device as a condition to unlocking the wheel.

A further embodiment of any of the foregoing embodiments of the present disclosure may include, wherein the security input includes at least one of entry of a code, entry of a password, a facial recognition, recognition of a secure token, and a fingerprint scan.

A further embodiment of any of the foregoing embodiments of the present disclosure may include, wherein the security input includes a secure token, wherein the secure token is an electronic key.

A further embodiment of any of the foregoing embodiments of the present disclosure may include, wherein the electronic key for another vehicle is a car key.

A further embodiment of any of the foregoing embodiments of the present disclosure may include locking the electrically motorized wheel in response to the mobile device being beyond the proximity.

A further embodiment of any of the foregoing embodiments of the present disclosure may include, wherein locking the wheel is further conditioned on the wheel not being in motion.

A further embodiment of any of the foregoing embodiments of the present disclosure may include locking the electrically motorized wheel in response to the mobile device not being within a predetermined proximity.

A further embodiment of any of the foregoing embodiments of the present disclosure may include, wherein locking the wheel is further conditioned on the wheel not being in motion.

A further embodiment of any of the foregoing embodiments of the present disclosure may include locking the electrically motorized wheel in response to a user not being seated on the vehicle.

A further embodiment of any of the foregoing embodiments of the present disclosure may include locking the electrically motorized wheel in response to the electrically motorized wheel being stationary for a predetermined time period.

A further embodiment of any of the foregoing embodiments of the present disclosure may include, wherein the unlocking includes exiting a high-impedance state.

A further embodiment of any of the foregoing embodiments of the present disclosure may include, wherein the locking includes configuring a motor controller to enter a high-impedance state resisting rotation of electrically motorized wheel.

A further embodiment of any of the foregoing embodiments of the present disclosure may include, wherein the mobile device is an electronic car key.

A further embodiment of any of the foregoing embodiments of the present disclosure may include, wherein the mobile device is a key.

A further embodiment of any of the foregoing embodiments of the present disclosure may include, wherein the mobile device is a fob.

A system according to another disclosed non-limiting embodiment of the present disclosure can include a motor controller mounted to a device of an electrically motorized wheel that is adapted for converting a non-motorized vehicle to an electrically motorized vehicle via installation of the electrically motorized wheel, the motor controller operable to continuously control the device in response to a user input; and a wireless control system in communication with the motor controller, the wireless control system operable to selectively manage the state of a locking mode of the electrically motorized wheel.

A further embodiment of any of the foregoing embodiments of the present disclosure may include, wherein the locking mode is operable to trigger an alarm in response to movement of the electrically motorized wheel.

A further embodiment of any of the foregoing embodiments of the present disclosure may include, wherein the locking mode is operable to report GPS coordinates and a time stamp in response to the alarm being triggered.

A further embodiment of any of the foregoing embodiments of the present disclosure may include, wherein the device is selectively unlocked.

A further embodiment of any of the foregoing embodiments of the present disclosure may include, wherein the device is selectively unlocked in response to the wireless control system being within a predetermined proximity with the device.

A further embodiment of any of the foregoing embodiments of the present disclosure may include, wherein the device is selectively unlocked in response to a user sitting on the vehicle.

A further embodiment of any of the foregoing embodiments of the present disclosure may include communicated at least one of an email message and a text message to the wireless control system in response to movement of the device while in the locked mode.

A method according to another disclosed non-limiting embodiment of the present disclosure can include locking a device of an electrically motorized wheel, the electrically motorized wheel for converting a non-motorized vehicle to an electrically motorized vehicle via installation of the electrically motorized wheel; and triggering an alarm in response to movement of the locked electrically motorized wheel.

A further embodiment of any of the foregoing embodiments of the present disclosure may include reporting GPS coordinates of the device to a wireless control system in response to the alarm being triggered.

A further embodiment of any of the foregoing embodiments of the present disclosure may include, reporting a time stamp of the device to a wireless control system in response to the alarm being triggered.

A method according to another disclosed non-limiting embodiment of the present disclosure can include locking a device of an electrically motorized wheel, the electrically motorized wheel being adapted for converting a non-motorized vehicle to an electrically motorized vehicle via installation of the electrically motorized wheel; and awaiting a request to unlock the device.

A further embodiment of any of the foregoing embodiments of the present disclosure may include, wherein awaiting the request includes awaiting a wireless signal.

A further embodiment of any of the foregoing embodiments of the present disclosure may include, wherein the wireless signal is generated by a mobile device.

A further embodiment of any of the foregoing embodiments of the present disclosure may include, wherein the mobile device is a smartphone.

A further embodiment of any of the foregoing embodiments of the present disclosure may include, wherein the mobile device is an electronic car key.

A further embodiment of any of the foregoing embodiments of the present disclosure may include, wherein the wireless signal is generated by a mobile device associated with an owner of the device.

A further embodiment of any of the foregoing embodiments of the present disclosure may include, wherein the wireless signal is generated by a mobile device associated with a guest authorized by the mobile device associated with the owner of the device.

A further embodiment of any of the foregoing embodiments of the present disclosure may include, wherein awaiting the request includes awaiting plugging in of a device into the electrically motorized wheel.

A further embodiment of any of the foregoing embodiments of the present disclosure may include, wherein the mobile device is a key.

A further embodiment of any of the foregoing embodiments of the present disclosure may include, wherein the mobile device is a fob.

A device of an electrically motorized wheel that is adapted to convert a non-motorized wheeled vehicle to an electrically motorized wheeled vehicle via installation of the device, the device according to one disclosed non-limiting embodiment of the present disclosure can include an accessory port of the device of the electrically motorized wheel, the accessory port configured with a hardware interface to provide an accessory device with power and communication with a control system of the device.

A further embodiment of any of the foregoing embodiments of the present disclosure may include, wherein the accessory device is mountable to the electrically motorized wheel.

A further embodiment of any of the foregoing embodiments of the present disclosure may include, wherein the accessory device is a mobile device.

A further embodiment of any of the foregoing embodiments of the present disclosure may include, wherein the power is provided to an electrical grid through the accessory port.

A further embodiment of any of the foregoing embodiments of the present disclosure may include, wherein the accessory port is provided on a user interface of the electrically motorized wheel.

A further embodiment of any of the foregoing embodiments of the present disclosure may include, wherein the accessory device includes a light.

A further embodiment of any of the foregoing embodiments of the present disclosure may include, wherein the accessory device includes a speaker.

A further embodiment of any of the foregoing embodiments of the present disclosure may include, wherein the accessory device includes an inertial measurement sensor including at least one of the following: accelerometer, gyroscopic sensor, inclinometer.

A further embodiment of any of the foregoing embodiments of the present disclosure may include, wherein the wherein the accessory device includes a gyroscopic sensor operable to identify a user operation of the vehicle.

A further embodiment of any of the foregoing embodiments of the present disclosure may include 9, wherein the gyroscopic sensor facilitates stability of the vehicle.

A device of an electrically motorized wheel to convert a non-motorized wheeled vehicle to an electrically motorized wheeled vehicle via installation of the device, the device according to one disclosed non-limiting embodiment of the present disclosure can include a static system and a rotating system around an axis of rotation, the static system coupled to the non-motorized wheel vehicle; an electric motor selectively operable to rotate the rotating system relative to the static system; a mechanical drive system coupled to the rotational unit, the mechanical drive system operable to rotate the rotational unit in response to a rotational input applied by the user; a sensor system mounted to the electrically motorized wheel, the sensor system operable to identify parameters indicative of the rotational input; a control system mounted to the electrically motorized wheel, the control system in communication with the sensor system to continuously control the electric motor in response to the rotational input; a power source mounted to the electrically motorized wheel, the power source electrically connected to the control system and the electric motor; and a hardware interface in communication with the control system, the hardware interface operable to provide communication and power interchange between the electrically motorized wheel and an accessory device.

A further embodiment of any of the foregoing embodiments of the present disclosure may include, wherein the hardware interface includes at least one of as USB, USB 2.0, Thunderbolt, Dicom, PCI Express, CAN.

A further embodiment of any of the foregoing embodiments of the present disclosure may include, wherein the accessory device includes a light.

A further embodiment of any of the foregoing embodiments of the present disclosure may include, wherein the accessory device includes a speaker.

A further embodiment of any of the foregoing embodiments of the present disclosure may include, wherein the accessory device includes a gyroscopic sensor.

A further embodiment of any of the foregoing embodiments of the present disclosure may include, wherein the gyroscopic sensor facilitates performance of the vehicle.

A further embodiment of any of the foregoing embodiments of the present disclosure may include, wherein the gyroscope facilitates stability of the vehicle.

A further embodiment of any of the foregoing embodiments of the present disclosure may include, wherein the accessory device includes a proximity sensor.

A further embodiment of any of the foregoing embodiments of the present disclosure may include, wherein the accessory device includes an interface to a power grid.

A further embodiment of any of the foregoing embodiments of the present disclosure may include, wherein the accessory device includes a power storage device.

A further embodiment of any of the foregoing embodiments of the present disclosure may include, wherein the accessory device includes a memory storage device.

A further embodiment of any of the foregoing embodiments of the present disclosure may include, wherein the accessory device includes a stand to lock the electrically motorized wheel.

A further embodiment of any of the foregoing embodiments of the present disclosure may include, wherein the accessory device includes a dock to charge the electrically motorized wheel.

A device of an electrically motorized wheel to convert a non-motorized wheeled vehicle to an electrically motorized wheeled vehicle via installation of the device, the device according to one disclosed non-limiting embodiment of the present disclosure can include a control system of the device, the control system operable to continuously control the electrically motorized wheel in response to a user input; and a hardware interface in communication with the control system, the hardware interface operable to provide communication and power interchange between the control system and an accessory device.

A further embodiment of any of the foregoing embodiments of the present disclosure may include, wherein the accessory device includes a light.

A further embodiment of any of the foregoing embodiments of the present disclosure may include, wherein the accessory device includes a battery.

A further embodiment of any of the foregoing embodiments of the present disclosure may include, wherein the accessory device includes a proximity sensor.

A further embodiment of any of the foregoing embodiments of the present disclosure may include, wherein the accessory device includes a gyroscopic sensor.

A further embodiment of any of the foregoing embodiments of the present disclosure may include, wherein the gyroscopic sensor facilitates performance of the vehicle.

A further embodiment of any of the foregoing embodiments of the present disclosure may include, wherein the gyroscope facilitates stability of the vehicle.

A further embodiment of any of the foregoing embodiments of the present disclosure may include, wherein the hardware interface is mountable within a hub shell assembly that contains the control system.

A further embodiment of any of the foregoing embodiments of the present disclosure may include, wherein the accessory device is mountable within the hub shell assembly.

A further embodiment of any of the foregoing embodiments of the present disclosure may include, wherein the hardware interface is mountable external to a hub shell assembly that contains the control system.

A device of an electrically motorized wheel to convert a non-motorized wheeled vehicle to an electrically motorized wheeled vehicle via installation of the device, the device according to one disclosed non-limiting embodiment of the present disclosure can include a modular systems package of the device of the electrically motorized wheel, the modular systems package including a control system operable to continuously control the device of the electrically motorized wheel in response to a user input.

A further embodiment of any of the foregoing embodiments of the present disclosure may include, wherein the modular systems package includes a communications system.

A further embodiment of any of the foregoing embodiments of the present disclosure may include, wherein the modular systems package includes a global positioning system (GPS).

A further embodiment of any of the foregoing embodiments of the present disclosure may include, wherein the modular systems package is in communication with a sensor operable to provide data regarding the user.

A further embodiment of any of the foregoing embodiments of the present disclosure may include, wherein the sensor is wearable by the user.

A further embodiment of any of the foregoing embodiments of the present disclosure may include, wherein the modular systems package includes a sensor operable to sample an environmental condition.

A further embodiment of any of the foregoing embodiments of the present disclosure may include, wherein the environmental condition includes at least one of temperature, humidity, wind direction, wind speed, $CO_2$, $NO_x$.

A further embodiment of any of the foregoing embodiments of the present disclosure may include, wherein the environmental condition includes a terrain condition.

A further embodiment of any of the foregoing embodiments of the present disclosure may include, wherein the modular systems package is in communication with a sensor operable to provide data regarding the wheel operation conditions.

A further embodiment of any of the foregoing embodiments of the present disclosure may include, wherein the wheel operation conditions include at least one of motor temperature, battery voltage, battery current, cassette rotation speed, battery temperature, electronics temperature, and motor relay status.

A further embodiment of any of the foregoing embodiments of the present disclosure may include, wherein the modular systems package includes a communication system for communication with a server that correlates data from the modular systems package with a database.

A further embodiment of any of the foregoing embodiments of the present disclosure may include, wherein the modular systems package is mounted within a hub shell assembly.

A modular systems package for a device of an electrically motorized wheel to convert a non-motorized wheeled vehicle to an electrically motorized wheeled vehicle via installation of the device, the modular systems package according to one disclosed non-limiting embodiment of the present disclosure can include an electric motor selectively operable to rotate a rotating system relative to a static system; a sensor system operable to identify parameters indicative of a user input; and a control system in communication with the sensor system to continuously control the electric motor in response to the user input.

A further embodiment of any of the foregoing embodiments of the present disclosure may include, wherein the modular systems package includes a communications system.

A further embodiment of any of the foregoing embodiments of the present disclosure may include, wherein the modular systems package includes a global positioning system (GPS) unit.

A further embodiment of any of the foregoing embodiments of the present disclosure may include, wherein the modular systems package includes a cellular communications system.

A further embodiment of any of the foregoing embodiments of the present disclosure may include a power source mounted to the electrically motorized wheel, the power source electrically connected to the control system and the electric motor.

A further embodiment of any of the foregoing embodiments of the present disclosure may include, wherein the sensor system is further enabled to identify parameters indicative of wheel operations.

A further embodiment of any of the foregoing embodiments of the present disclosure may include, wherein parameters indicative of wheel operations include at least one of motor temperature, battery voltage, battery current, battery charge, cassette rotation speed, and motor rely status.

A system to facilitate user safety when using an electrically motorized wheel that is adapted for converting a vehicle to an electrically motorized vehicle via installation of the electrically motorized wheel, the system according to another disclosed non-limiting embodiment of the present disclosure can include a proximity sensor on the electrically motorized wheel in communication with a user mobile device; and a proximity alert module on the mobile device enabled to alert a user when a sensed proximity crosses a threshold.

A further embodiment of any of the foregoing embodiments of the present disclosure may include, wherein the alert is at least one of an audible alert, a visual alert, and a tactile alert.

A further embodiment of any of the foregoing embodiments of the present disclosure may include, wherein the alert includes a "jitter" in performance.

A further embodiment of any of the foregoing embodiments of the present disclosure may include, wherein the alert includes an operational command to the electrically motorized wheel.

A system to facilitate user safety when using an electrically motorized wheel for converting a vehicle to an electrically motorized vehicle via installation of the electrically motorized wheel, the system according to another disclosed non-limiting embodiment of the present disclosure can include a proximity sensor mounted to the electrically motorized wheel; a proximity alert module on a mobile device in communication with the proximity sensor.

A further embodiment of any of the foregoing embodiments of the present disclosure may include, wherein the proximity alert module is operable to notify a user of an object within a predetermined proximity of the electrically motorized vehicle.

A further embodiment of any of the foregoing embodiments of the present disclosure may include, wherein the proximity alert module is operable to notify other vehicles of the electrically motorized vehicle's geographic position when a sensed proximity crosses a threshold.

A further embodiment of any of the foregoing embodiments of the present disclosure may include, wherein the proximity sensor is at least one of a LIDAR, RADAR, SONAR, and imagery device.

A system to facilitate user safety when using an electrically motorized wheel for converting a vehicle to an electrically motorized vehicle via installation of the electrically motorized wheel, the system according to another disclosed non-limiting embodiment of the present disclosure can include a proximity sensor on the electrically motorized wheel; a geographic positioning system; and a proximity alert module on a mobile device in communication with the proximity sensor and the geographic positioning system.

A further embodiment of any of the foregoing embodiments of the present disclosure may include, wherein the proximity alert module is operable to notify a user of an object within a predetermined.

A further embodiment of any of the foregoing embodiments of the present disclosure may include, wherein the proximity alert module is operable to notify other vehicles of the electrically motorized vehicle's geographic position when a sensed proximity crosses a threshold.

A further embodiment of any of the foregoing embodiments of the present disclosure may include, wherein the proximity sensor is at least one of a LIDAR, RADAR, SONAR, and imagery device.

These and other systems, methods, objects, features, and advantages of the present disclosure will be apparent to those skilled in the art from the following detailed description of the other embodiment and the drawings. All documents mentioned herein are hereby incorporated in their entirety by reference.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE FIGURES

Various features will become apparent to those skilled in the art from the following detailed description of the disclosed non-limiting embodiment. The drawings that accompany the detailed description can be briefly described as follows:

Various features will become apparent to those skilled in the art from the following detailed description of the disclosed non-limiting embodiment. The drawings that accompany the detailed description can be briefly described as follows:

FIG. 1D schematically represents a side view of a hub and spoke interface.

FIG. 1E schematically represents a sectional view of a hub and spoke interface.

FIG. 1I schematically represents an enlarged plan view of embodiments of an attachment end of a spoke, showing how the attachment end seats into the pocket.

FIG. 3 is a simplified schematic of the mobile device.

FIG. 4C schematically represents details of embodiments of a torque sensor system.

FIG. 6A schematically represents embodiments of the electrically motorized wheel installed on a wheelchair.

FIG. 7A schematically represents a side view of a wheelbarrow retrofitted with the electrically motorized wheel of FIG. 1A.

FIG. 7B schematically represents a top down view of electrically motorized wheelbarrow of FIG. 7A.

FIG. 7C schematically represents details of the force sensing connection between the electrically motorized wheel and electrically motorized wheelbarrow.

FIG. 9A is an exploded view of a single speed electrically motorized wheel.

FIG. 9D is an exploded view of a rotational system of the electrically motorized wheel.

FIG. 9G is an exploded view of a mechanical drive system of the electrically motorized wheel.

FIG. 9H is a schematic view of a system of the electrically motorized vehicle.

FIG. 14D is a schematic view of a global traffic net system for the electrically motorized vehicle.

FIG. 15A is a schematic view of a system for the electrically motorized vehicle.

FIG. 23C is a flow chart for operation of the electrically motorized vehicle.

DETAILED DESCRIPTION

Figure 1A:
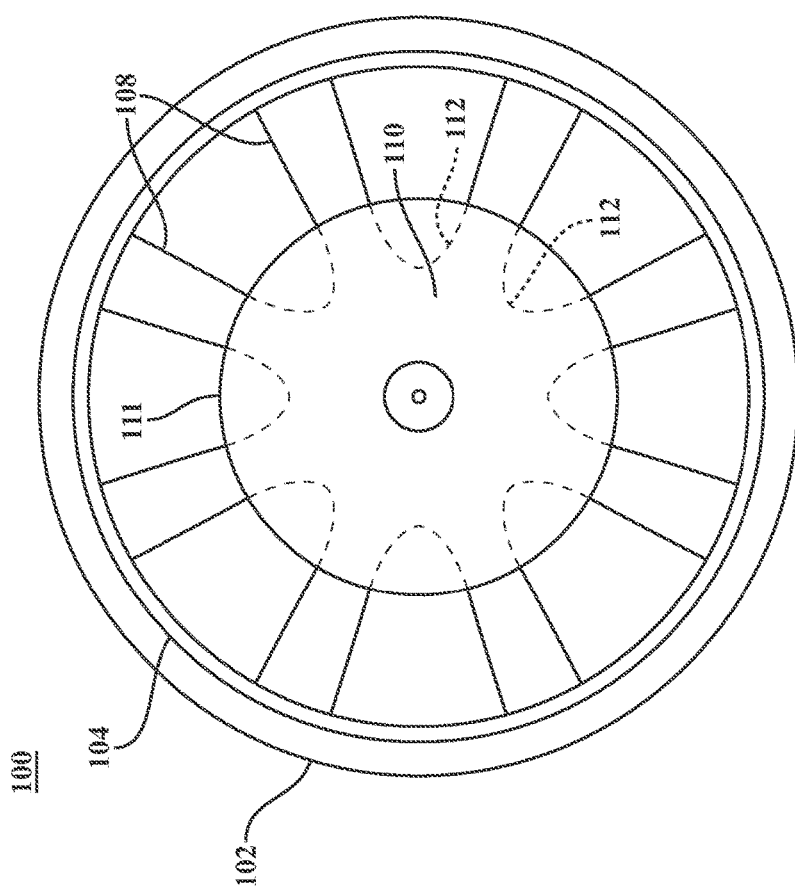
FIG. 1A schematically represents a side view of an electrically motorized wheel.

FIG. 1A schematically illustrates an electrically motorized wheel 100 to convert a non-motorized vehicle, such as a bicycle, into a motorized vehicle, by installation of the electrically motorized wheel onto the vehicle. Disclosure that is not specifically limited to bicycles should be understood to apply to other wheeled vehicles except where context precludes such application. It should be further understood that although particular systems are separately defined, each or any of the systems can be otherwise combined or separated via hardware and/or software.

While many of the components, modules, systems, subsystems, uses, methods and applications disclosed herein are described in connection with embodiments of an electrically motorized wheel, or a device of an electrically motorized wheel, it should be understood that many of the descriptions herein in connection with an electrically motorized wheel are exemplary and that many of the inventive concepts may be applied more generally (that is not necessarily in connection with a wheel), such as to electrically motorized vehicles generally, electrically motorized bikes, electric bikes, e-bikes, pedelec bikes, electric assist bikes, scooters, battery powered vehicles, and other vehicles that are powered by mechanisms other than an electrically motorized wheel or device thereof. For example, inventive concepts relating to data collection by or control of an electrically motorized wheel (including involving an associated user device like a smart phone) may apply in the context of another vehicle, such as an electrically motorized or hybrid vehicle, or to a sub-system or component thereof, such as a battery management system, any energy storage and delivery system, any drive system, or the like. Similarly, inventive concepts being described in connection to an electrically motorized wheel, or device thereof, as a platform having various interfaces, including accessory interfaces for connection to and interfacing with a wide range of other devices and systems, may in many cases apply to other vehicles, or components or sub-systems thereof, that do not use an electrically motorized wheel. Further, concepts relating to mechanical and thermal structures may apply more generally, such as to components of other vehicles, to motor systems, and the like. Further, skilled artisans will appreciate, where applicable, that embodiments described herein in connection with the mounting to or otherwise containment on a wheel or device of a wheel may be applied to a vehicle in other spatial arrangements or configurations outside of or off (either partially or wholly), a wheel or device on/off a wheel. Except where otherwise indicated, the disclosure herein is not intended to be limited to an electrically motorized wheel, and various other such embodiments as disclosed throughout this disclosure are intended to be encompassed, as limited only by the claims.

The electrically motorized wheel 100 can include a tire 102, a wheel rim 104, a plurality of spokes 108, and a motorized wheel hub 110. References in this disclosure to a device of an electrically motorized wheel should be understood to encompass any of these elements, as well as components or sub-systems of any of them, except where context indicates otherwise. Also, references throughout this disclosure to the electrically motorized wheel 100 should be understood to encompass any such devices of the wheel, components, or sub-systems, except where context indicates otherwise. For example, a reference to a use of an electrically motorized wheel 100 (such as for data collection, as a platform for connection of accessories, or the like) and/or a reference to an input, operational state, control parameter, or the like of an electrically motorized wheel 100 should be understood to include and apply to uses, inputs, operational states, control parameters, and the like of a device, component of sub-system of the wheel (e.g., using or controlling the motorized wheel hub 110 or some other sub-system inside the hub 110), whether or not the entire set of components is present (e.g., spokes, rim, tire, etc.) in a particular embodiment. The descriptions and corresponding figures are intended to be illustrative only and are in no way to limit the type of vehicles, or the specific details of how a user input is transmitted to and interpreted by the electrically motorized wheel 100.

The motorized wheel hub 110 can include a hub shell assembly 111 that completely encloses components and systems to power the wheel 100, including inducing or resisting movements such as rotation, of the rim 104, spokes 108 and tire 102. The enclosed components and systems may include various modules, components, and sub-systems and may be referred to as a modular systems package. That is, the modular systems package describes the various elements that are contained within the hub shell assembly 111. In embodiments, the wheel rim 104 is connected to the self-contained motorized wheel hub 110 via a plurality of spokes 108 that are under tension. Further, although this embodiment has specific illustrated components in a bicycle embodiment, the embodiments of this disclosure are not limited to those particular combinations and it is possible to use some of the components or features from any of the embodiments in combination with features or components from any of the other embodiments.

In embodiments, each of the plurality of spokes 108 that connect the wheel rim 104 to the motorized wheel hub 110 may have a first end and a second end that extend at an angle to each other, and an intermediate attachment portion 112 formed such that the first and second ends extend at an acute angle with respect to each other such that the first and second ends attach to the wheel rim 104.

Figure 1C:
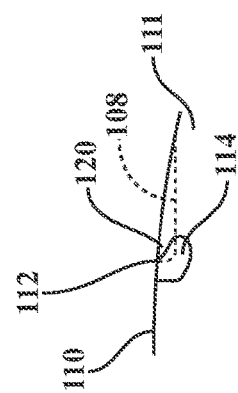
FIG. 1C schematically represents a sectional view of a hub and spoke interface.
Figure 1B:
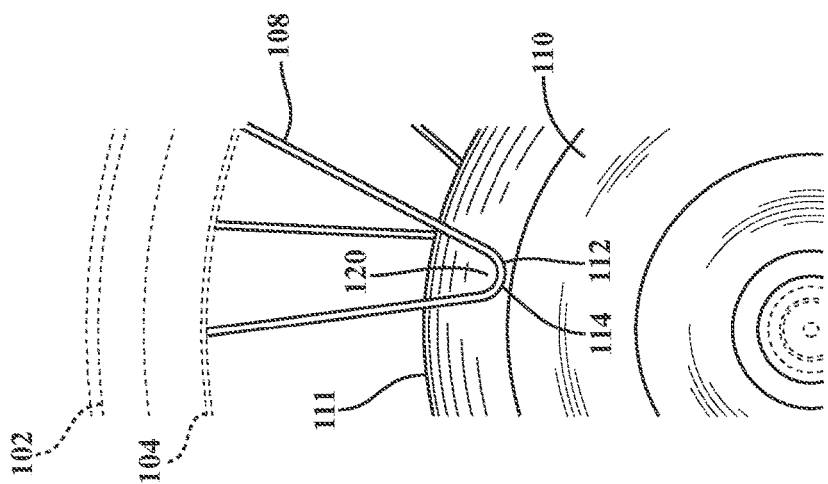
FIG. 1B schematically represents a side view of a hub and spoke interface.

FIGS. 1B-1C illustrate embodiments in which the attachment portion 112 may fit into a recess 114 in the surface of the motorized wheel hub 110 to secure the motorized wheel hub 110 to the attachment portions 112 of the plurality of spokes 108. The recess 114 may have a shape to receive and secure a curved or angled attachment portion 112. The internal portion of the recess 114 extends slightly closer to the wheel rim 104 in a radial direction to form a lip 120. As the spoke 108 is tightened, it pulls attachment portion 112 radially toward electrically motorized wheel rim. This causes the attachment portion to slide along the lip 120 and into the pocket 114. The attachment portion 112 becomes trapped in the recess 114 thereby securing the spoke attachment portion 112 to the motorized wheel hub 110.

With reference to FIGS. 1D and 1E, the attachment portion 112 is secured at least partially under an overhang 116 in the surface of the motorized wheel hub 110 to thereby secure the motorized wheel hub 110 between the attachment portions 112 of the plurality of spokes 108. The overhang 116 may be shaped to receive and secure under compression the attachment portion 112 of the respective wheel spoke 108. The attachment portion 112 may also be directionally oriented such that the attachment portion 112 is inserted at a particular angle then rotated to be locked into the recess 114. The attachment portion 112 thereby remains secured within the recess 114 even if the proper tension no longer remains on the spoke 108.

Figure 1F:
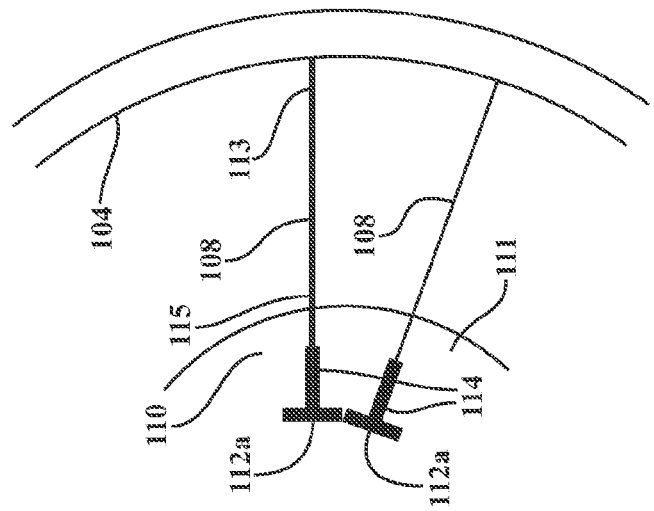
FIG. 1F schematically represents a side view of a hub and spoke interface.
Figure 1G:
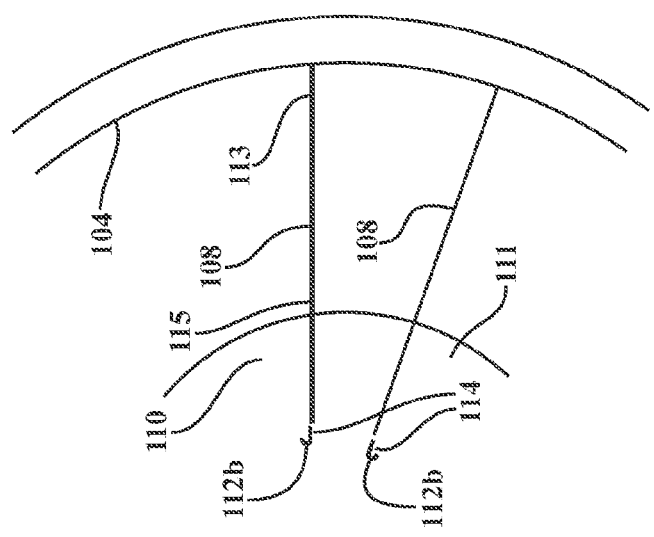
FIG. 1G schematically represents a side view showing a hub and spoke interface.
Figure 1H:
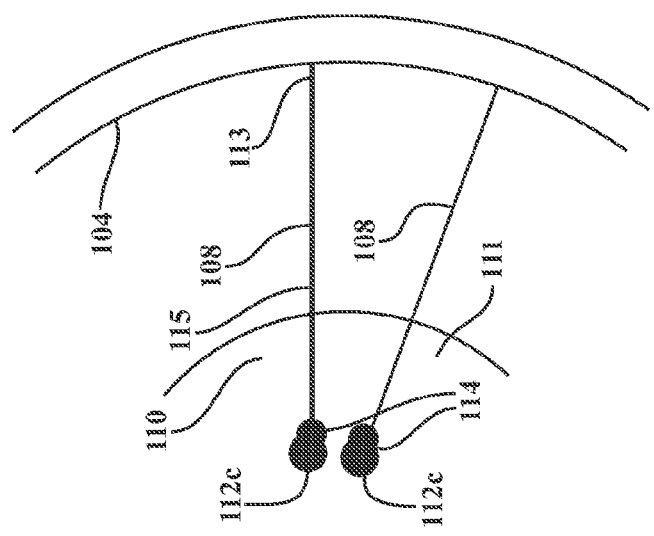
FIG. 1H schematically represents a side view showing a hub and spoke interface.

With reference to FIGS. 1F-1H alternative embodiments of connections between the wheel rim 104 and the motorized wheel hub 110 are schematically illustrated. The spokes 108 may have first ends, referred to as the rim ends 113, that extend from the wheel rim 104, and the second ends that attach to the motorized wheel hub 110, being an attachment end 112a, 112b, 112c. The attachment ends 112a, 112b, 112c may be shaped in the form of a 'T' (FIG. 1F), 'J' (FIG. 1G), 'L,', rounded, or otherwise enlarged head shape (FIG. 1H), relative to the diameter of a neck 115 of the spoke.

The attachment ends 112a, 112b, 112c fit into a recess 114 in the surface of the motorized wheel hub 110 wherein the recess 114 has the complementary shape to receive the respective attachment ends, to thereby secure the motorized wheel hub 110 to the plurality of spokes 108. The internal portion of each recess 114 extends toward the wheel rim 104 in a radial direction, to thereby form a lip 120. The lip 120 and the recess 114 trap and secure the respective attachment ends 112a, 112b, 112c in the recess 114 as the plurality of spokes 108, under tension, are pulled toward the wheel rim 104.

With reference to FIG. 1I, embodiments of an attachment end of the spoke illustrates the attachment end 112a being seated in the pocket 114. The attachment end 112a is received into the "T-shaped" pocket 114—generally downward into the plane of the page. After fitting into the pocket 114, the spoke is tightened and the neck 115 is pulled toward the rim (indicated schematically by arrow "A".) This results in the attachment end being seated within the deepest portion of pocket 114.

The plurality of spokes 108 may include a first set of spokes and a second set of spokes. The attachment sections of a first set of spokes 108 connect to a first side of the motorized wheel hub 110 and the attachment sections of the second set of spokes 108 connect to the surface of a second side of the motorized wheel hub 110. The ends of the plurality of spokes 108 of the first set may be interleaved with the ends of the plurality of spokes 108 of the second set and the interleaved sets alternately connected around an inner circumference of the wheel rim 104 such that the spokes are interlaced, i.e, woven around each other.

In embodiments, the motorized wheel hub 110 is connected to the wheel rim 104 via a mesh material.

In embodiments, the motorized wheel hub 110 is connected to the wheel rim 104 via a disk, or other solid structure.

In embodiments, the wheel rim 104 and motorized wheel hub 110 can alternately be connected according to conventional straight wheel spoking parameters.

Figure 2A:
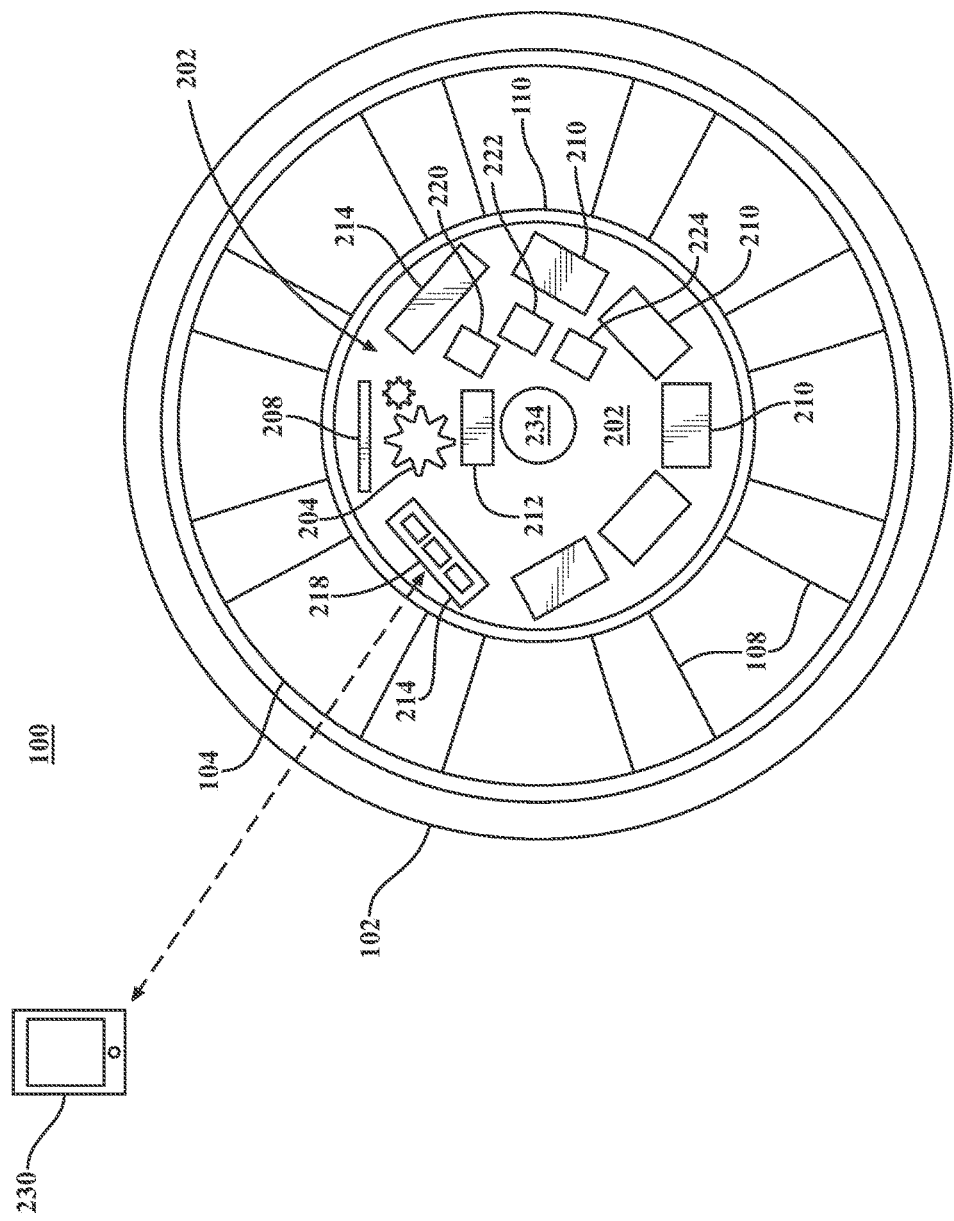
FIG. 2A is a side view of electrically motorized wheel of FIG. 1A with its side cover removed showing internal elements.

With reference to FIG. 2A, the motorized wheel hub 110 can include a modular systems package 202 packaged within a hub shell assembly 111 (FIG. 1A) to enclose elements of the electrically motorized wheel 100. As such, the modular systems package 202 may be completely contained within the hub shell assembly 111 and protected from external environmental conditions. In embodiments, components of the modular systems package may include sub-assemblies, sub-systems, components, modules and the like that may be adapted to be removed and replaced, while other sub-systems, components and modules remain in place. For example, interfaces between the various elements may be adapted to facilitate ease of connection and disconnection of the elements during assembly of the modular systems package 202 or in the field. These interfaces may include various conventional electrical, mechanical and data connectors, ports, adaptors, gateways, buses, conduits, cables, and the like. References in this disclosure to the components of the modular systems package 202 should be understood to include any of the referenced items, except where context indicates otherwise.

In embodiments, a coating material may be applied to the modular systems package 202 and/or its components to protect against environmental conditions, such as moisture, dust, dirt and debris that may penetrate the hub shell assembly 111. The coating material may conform to the hub shell assembly and/or to individual components to encase or otherwise coat the coated components. The coating material may also protect the internal components from impact.

The modular system package 202 may include a motor 204, a motor control system 208, an electrical storage system, such as a battery system 210, a mechanical drive system 212, a control system 214, and accessory port 218, which may include a hardware interface 232, such as a port (e.g., a USB port) to provide support for an accessory device, such as providing electrical power and/or a data connection to the accessory device. The accessory port 218 may be in communication with the battery system 210 to receive power and be in communication with the control system 214. The accessory port 218 may include a short range wireless communications system 220, a telecommunications system 222, a global positioning system 224, an interface for a removable data storage device 228 (such as a USB storage device), and/or other components.

The mechanical drive system 212 may include a pulley, chain, drive shaft or other interface to transmit a rotational input by a user. It should be understood that various interfaces may be provided. If the electrically motorized wheeled vehicle is a bicycle, it may also include a wheel hub gear system 234, or sprocket, connected to the motor 204.

The control system 214 may include one or more processing systems such as micro-processors, CPUs, application specific integrated circuits, field programmable gate arrays, computers (including operating system, CPU, storage and other components, possibly include a hypervisor or other component for virtualization of functions. The processing systems may be configured to communicate with and control the motor control system 208 and the battery system 210, as described in detail elsewhere herein, such as to implement various operational modes, features and the like. The control system 214, may be referred to in some cases as a computing system or as a control system, may further be configured to provide and manage various communications and networking functions communicate with and control the telecommunications system 222, the short range wireless communications system 220, the global positioning system 224, the removable data storage device 228, various networking systems (e.g., cellular, satellite and internet protocol-based networks) and others.

The telecommunications system 222 and the global positioning system 224 may include a global positioning system (GPS) unit 224 or other location positioning technologies (e.g., using triangulation by cellular tower locations, accessing a database of locations of installed devices, such as wireless access points or infrastructure elements 252 (e.g., call boxes and traffic lights), or the like) that provide location and time data. The telecommunications system 222 can provide access to mobile, cellular, Wi-Fi data networks and others. In embodiments, the telecommunications system 222 includes a general packet radio service (GPRS) unit or other wireless technology that can provide access to 2 G, 3 G, LTE and other cellular communications systems or other modes of wireless communications. In embodiments, the telecommunications system 222 and the global positioning system 224 may be integrated within the control system 214.

The control system 214 may include processing capabilities for handling the collection of data from various sources, such as sensors, external data sources, external systems (e.g., traffic, weather, and other systems that provide data about the environment of the user and systems that provide data about other wheels, such as fleet management or other aggregate-based information), user input to user interfaces, and others. Processing data may include receiving, translating, transforming, storing, extracting, loading, and otherwise performing operations on the data. Processing may include performing computations and calculations, executing algorithms based on inputs, and providing results, such as to other processing elements of the wheel, to users, to external systems, and the like. Processing may include modules for handling storage systems that are local to the wheel or that are remote, such as cloud storage or storage on a mobile device. Processing may also include handling various interfaces, including managing data and electrical interfaces, such as interfaces with a user interface on the wheel, a user interface of a device, such as a mobile device, that is used to control the wheel, interfaces to storage systems, interfaces to databases, and interfaces to external systems. The interfaces may include application-programming interfaces, including ones that enable machine-to-machine connections to external systems, to control devices, and to other wheels.

The battery system 210 can include one or more rechargeable batteries, one or more bulk capacitors (optionally including one or more super-capacitors), and/or a combination thereof. The battery system 210 can be configured as a single, removable contoured battery assembly 1352. The battery system 210 may have, or be associated with, a battery management system 254, which may be part of, or in data communication with, the control system 214, to collect data related to the operating state of the battery system 210 (e.g., temperature, state of charge, voltage levels, current levels and the like) and to enable management of the wheel, including operating modes of the battery system 210. The battery system 210 may be configured as multiple, removable battery assemblies, which can be controlled from individual battery management systems, or a central battery management system. It should be understood that the battery system 210 may be of various forms such as fuel cells, capacitors, etc.

The accessory port 218 may include various hardware interfaces 232, such as ports that support devices that use such protocols as USB, USB 2.0, Thunderbolt, Dicom, PCI Express, NVMe, NFC, Bluetooth, Wifi, etc. Software, firmware, or the like may be handled by the control system 214 to enable communication according to such protocols. The plurality of accessory ports 218 may, for example, accommodate a respective plurality of sensors. In various embodiments the sensors may be in direct data and/or electrical communication with the control system 214 or may be connected through a facility such as a gateway (such as enabled by a mobile device), network interface, switch, router, or other communications network facility. That is, sensors may be local to the wheel 100, vehicle or may be remote sensors in data communication with the wheel, such as associated with a mobile device that is used to control the wheel or an entirely external system.

The plurality of sensors may include environmental sensors 246 that are operable to measure environmental attributes such as temperature, humidity, wind speed and direction, barometric pressure, elevation, air quality (including particulate levels and levels of specific pollutants, among others), the presence of chemicals, molecules, compounds, and the like (such as carbon dioxide, nitrogen, ozone, oxygen, sulfur and others), radiation levels, noise levels, signal levels (e.g., GPS signal strength, wireless network signal levels, radio frequency signals, and the like), and many others. Sensors may thus sense various physical, chemical, electrical, and other parameters.

The plurality of sensors may also include sensors operable to measure various properties and parameters related to the wheel and elements of the wheel, such as wheel rotation velocity, angular momentum, speed and direction (forward and backward), acceleration, sensors to measure force applied to mechanical components and structures of the vehicle (such as handles, pedals, the frame, the handlebars, the fork, the seat), such as to sense forces, weight, strain, stress, sources and direction of force, increases and reductions in force, and others.

In embodiments, forces are sensed with respect to user input, such as the strength and direction of pedaling or braking by a bicycle user, using a hand brake or throttle on various kinds of vehicle, pushing one or more ring handles of a wheelchair, pushing on handles of a wheelbarrow, pulling on a handle of a wagon, or the like. For example, a torque sensor 238 may sense torque from pedaling input by a bicycle user, data from which may be related to the control unit 214, which may control the motor control system 208 of the wheel, such as moving the wheel faster as the user pedals faster. The plurality of sensors can include sensors for sensing fields and signals, such as radio frequency (RF), RADAR, SONAR, IR, Bluetooth, RFID, cellular, Wi-Fi, electrical fields, magnetic fields, and others. For example, such sensors can provide functions to a vehicle that is provided with a sensor-enabled wheel 100, such as RADAR detection, communications detection, proximity detection, object detection, collision detection, detection of humans or animals, and others. The accessory port 218 may also support supplemental hardware 248 such as the introduction of one or more accessory devices such as a gyroscope, lighting systems (including headlights, taillights, brake lights, and the like), audio systems (e.g., with speakers), supplemental memory systems, USB-based accessories (e.g., charging systems for mobile devices), security or anti-theft devices, and many others.

Figure 2B:
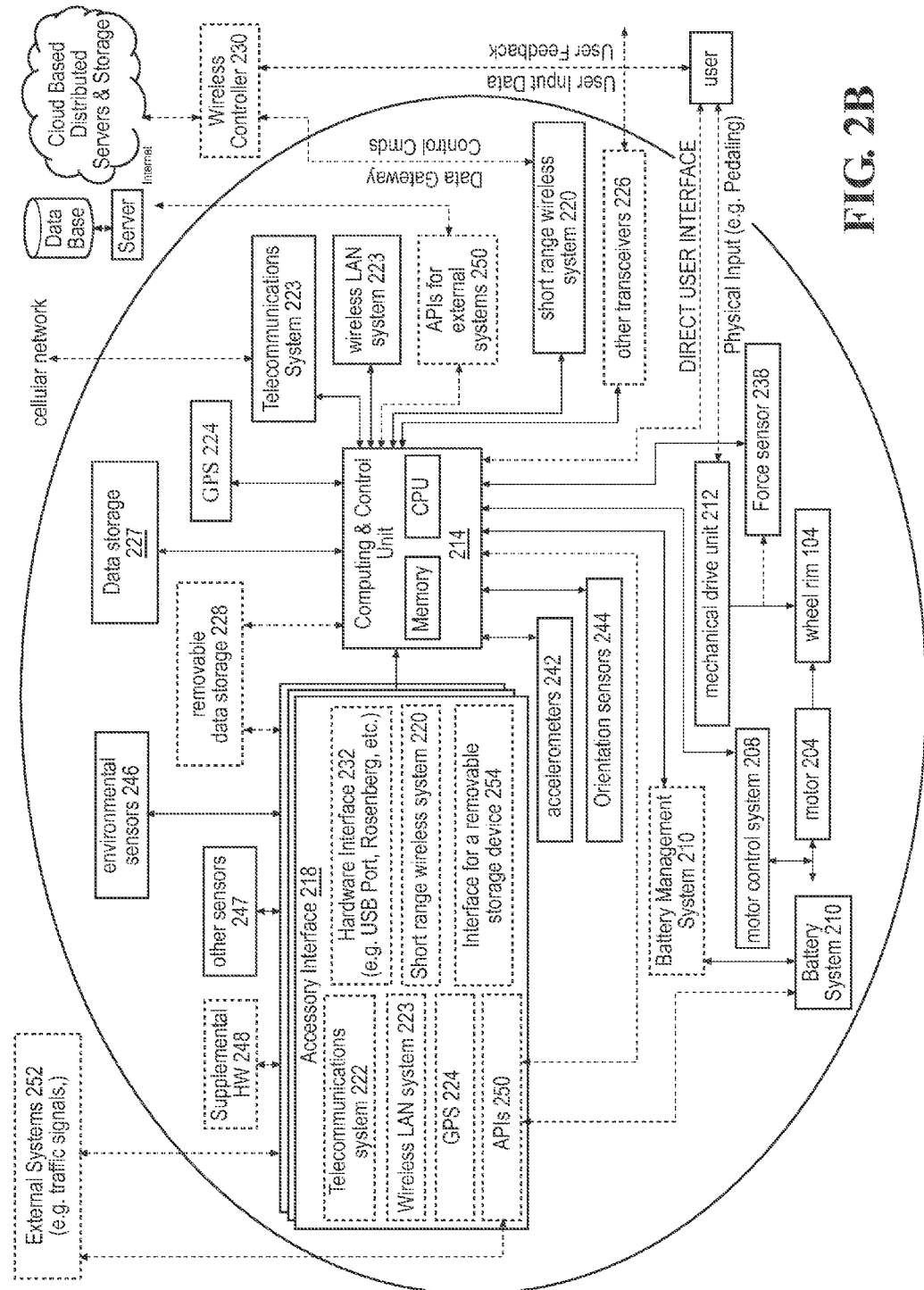
FIG. 2B is a schematic diagram of an embodiments of the electrically motorized vehicle including the electrically motorized wheel of FIG. 1A.

With reference to FIG. 2B, a schematic of embodiments of the motorized vehicle, in embodiments, includes elements of the motorized wheel hub 110 enclosed in the hub shell assembly 111. In operation, a user provides an input force delivered to a physical interface of the mechanical drive system 212 (such as a pedal, handle, or the like). In a bicycle type vehicle environment, a pedal and chain or belt drive the mechanical drive system 212. Other embodiments are described in connection with FIGS. 6-8.

The sensor system may include a force sensor 238, such as a torque sensor, that senses a force, such as the torque applied by the user to the mechanical drive system 212 for subsequent communication to the control system 214. As described later, this torque or other force may be sensed in other connected structures. The control system 214 may be or include a microprocessor, CPU, general computing device, or any other device that is capable of executing instructions on a computer readable medium.

The control system 214 may also receive data from other sources, such as an accelerometer 242, an orientation sensor 244 and/or other such sensors, either directly (such as through a direct connection to a sensor), or through a network connection or gateway, an API, or through an accessory port 218 (such as enabling access to the sensors of accessories, peripherals or external systems that connect to the wheel through the accessory port 218). Based on the calculation of, for example, sensed torque, acceleration, motion, orientation, etc., the control system 214 determines if power should be applied to a motor 204 through a motor control system 208 to cause acceleration or deceleration of the wheel rim 104. Deceleration may be effectuated by application of power to the motor to generate a rotational force opposite that of the current rotation, or by reducing the level of rotational force in the same direction, such as in cases where the effects of gravity, friction, wind resistance, or the like are enough to induce deceleration on the vehicle in the absence of continued levels of rotational force.

The control system 214 may include one or more accessory devices, peripherals, or external systems in communication therewith. Such accessory devices may include, various sensors, such as environmental sensors 246, and other sensors 247 which may sense various physical parameters of the environment, in connection with the description of supplemental hardware 248 and infrastructure elements 232. The control system 214 may process data collected and received from the various sources and channels described throughout this disclosure, such as from the environmental sensors 246, other sensors 247, external devices, a mobile device, a supplemental hardware device 248, one or more APIs for external systems 250, through various networking channels, such as from servers, distributed storage systems, and the cloud, from force sensors, from user interface elements on the wheel, etc. The control system 214 may store data, such as in local memory associated with the CPU of the control system 214, a separate data storage system, a removable data storage system 228, a server-based data storage system, and a cloud-based storage system. The control system 214 may communicate the data as required to the motor controller, and to the various other systems with respect to which it is in data communication as noted above (e.g., the accessories, sensors, peripherals, servers, storage systems, mobile devices and the like). In embodiments, and as described in more detail below, this may include communication of messages to the user through tactile input, such as a vibration, resistance, or the like, delivered to the user via the mechanical drive system 212. Data may include location data, such as from a GPS unit 224.

The motorized wheel hub 110 may also communicate wirelessly with other elements outside of the hub shell assembly 111 via a communication system such as a telecommunication system 222, a wireless LAN system 223, and/or a short range wireless system 220 that, for example, may be a Bluetooth system, an RFID system, an IR system, or the like. Also, other transceivers 226 may be used to communicate with any elements outside of housing 11. Communications may be undertaken using various networking protocols (e.g., IP, TCP/IP, and the like), by application programming interfaces, by machine-to-machine interfaces, and the like.

The telecommunication system 222 may be a cellular mobile communication transceiver, which can communicate with mobile devices, servers, or other processing devices that communicate via a cellular network.

The wireless LAN transceiver 223 can communicate with various hosts, servers and other processing equipment through the Internet, such as to servers and cloud computing resources, such as when the motorized wheel hub 110 is within a wireless LAN area, such as near an access point, switch, router, base station, Wifi hot spot, or the like. This may facilitate the upload and download of data, such as new software or firmware to any of the modular components to update the various capabilities of the wheel.

The short-range wireless system 220 may facilitate communication of the motorized wheel hub 110 either directly to an external system, a server, a cloud resource, or the like, or may facilitate communication via a mobile device 230 not mounted to the motorized wheel hub 110, which may serve as a gateway or bridge for communications between the motorized wheel hub 110 and such external systems, servers, cloud resources, or the like. The mobile device 230 may comprise any element or system external to the motorized wheel hub 110 that can include a data communication interface to the motorized wheel hub 110, such as a smart mobile device, tablet, wireless appliance or the like. The mobile device 230 may include an application, menu, user interface, or the like that is adapted to control the wheel, or one or more functions or features of the wheel, such as displaying data from the wheel, data from sensors, or the like, selecting modes of control or operation of the wheel, providing navigation and other instructions in connection with use of the wheel, and many other capabilities described in more detail throughout this disclosure.

With reference to FIG. 3, the electrically motorized wheel 100 may be configured and/or controlled via the mobile device 230 which may include a microprocessor 302 a low battery light 304, a display 308 which may include a touchscreen, a physical button 310, a short range wireless communications system 312 such as wireless USB, Bluetooth, IEEE 802.11 and others, and a connection status light 314, a telecommunications system unit 318 such as a general packet radio service (GPRS) unit that can provide access to 2 G and 3 G cellular communications systems or other types of 2 G, 3 G and 4 G telecommunications systems, an audio speaker 320, an warning light 322 and others.

The mobile device 230 is operable to wirelessly communicate with the electrically motorized wheel 100, such as via the short-range wireless communications systems 312, 220. The mobile device 230 may be operable to access, receive and display various types of data collected by sensors such as delivered through the accessory port 218 of the electrically motorized wheel 100 or by other data collection capabilities described herein, and in embodiments may be used to configure the data collection processes. For example, the mobile device 230 can be utilized to remotely configure the control system 214 and sensor systems of the electrically motorized wheel 100 to collect various types of data, such as environmental, location and wheel status data.

The mobile device 230 can also be utilized as an authentication key to unlock at least one feature of the wheel. For instance, as an owner of the wheel, the mobile device can be authenticated with the owner certificate of the wheel, which would enable that owner to modify wheel settings. Mobile devices owned by non-owners can be used to unlock the same, or different features of the wheel. That is, a non-owner may be restricted from certain features.

The mobile device 230 can also be utilized to select and/or control operational modes of the electrically motorized wheel 100. For example, a user can remotely configure the electrically motorized wheel 100 via the mobile device 230 to operate according to one of a multiple of predefined modes. Alternatively, or in addition thereto, the mobile device 230 may be utilized as an interface to set or modify operational parameters of a control algorithm during operation of the electrically motorized wheel 100, thereby creating "new," e.g., user tailored operational modes.

The mobile device 230 may also be configured to download new operational modes, applications and behaviors to control the electrically motorized wheel 100. The mobile device 230 may also be configured as a game console for gaming applications, provide a display for data updates from the electrically motorized wheel 100, operate as an interface to a fleet management system, and others.

In embodiments the electrically motorized wheel may have a sensor system to sense applied force, vehicle movement, and other data. Sensors may include ones for sensing torque applied to electrically motorized wheel, sensors for measuring wheel rotation velocity, speed and direction (forward or backward), sensors to measure force applied to vehicle handles, sensors on wheel fork to sense source/direction of force reduction, and others. The detected forces and torque may be used to manage energy generation, capture, storage and delivery based on torque detected. User input may be applied to the electrically motorized wheel using pedals on a bicycle or tricycle or a ring handle for a wheelchair.

Figure 4A:
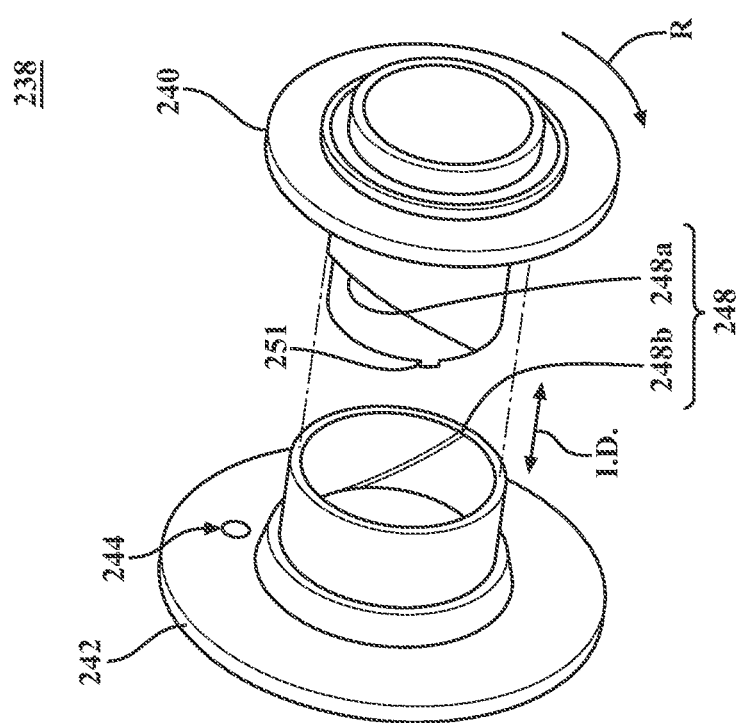
FIG. 4A schematically represents details of an embodiment of a torque sensor system.

With reference to FIG. 4A, a torque sensor system 238 for an electrically motorized wheel 100 is constructed and arranged to measure a user torque applied to electrically motorized wheel hub gear system 234. In embodiments, the torque sensor system 238 is constructed and arranged to measure a rotational velocity of electrically motorized wheel hub gear system 234. The torque sensor system 238 includes an inner sleeve secured to electrically motorized wheel hub gear system such as via welding such that the inner sleeve 240 rotates with the electrically motorized wheel hub gear system 234.

In embodiments, the torque sensor system 234 further includes a proximity sensor 244 on the inner or outer sleeve

240, 242 so that the lateral displacement LD between the inner and outer sleeve 240, 242 can be measured.

In embodiments, an interaction between the inner sleeve 240 and the outer sleeve 242 results in a lateral displacement of the inner sleeve 240 with respect to the outer sleeve 242 such that a torque applied by a user is obtained from the lateral displacement such as via a proximity sensor 244. In other embodiments, the torque sensor system 238 includes a displacement sensor 248 with a spring/elastomer and a pressure sensor located on the outer sleeve 242.

In embodiments, the rotation of the inner sleeve 240 causes a ramp of the inner sleeve to ride up or down a ramp of the outer sleeve 242. The inner and outer sleeves 240, 242 include opposing ramps 248a, 248b, which can affect a lateral displacement ("LD") between the inner sleeve 240 and the outer sleeve 242. For example, when a torque is applied to one of the inner sleeve 240 and outer sleeve 242, the inner sleeve 240 can rotate R in a clockwise or counterclockwise direction with respect to the outer sleeve 242. The rotation R of the inner sleeve 240 causes the ramp 248a of the inner sleeve 240 to ride up or down the ramp 248b of the outer sleeve 240. Accordingly, the rotation R of the inner sleeve 240 can affect the lateral displacement LD between the inner sleeve 240 and the outer sleeve 242. That is, as the ramp 248a of the inner sleeve 240 rides up the ramp 242b of the outer sleeve 242, the lateral displacement LD between the inner and outer sleeves 240, 242 increases, and as the ramp 248a of the inner sleeve 240 rides down the ramp 248b of the outer sleeve 242, the lateral displacement LD between the inner and outer sleeves 240, 242 decreases.

In other embodiments a velocity sensor 250 includes a plurality of magnets provided in an alternating magnetic pole configuration on an outer surface of the inner sleeve 240 and a Hall Effect sensor. In embodiments, the spring/elastomer mechanism being provided in a cylindrical housing of the outer sleeve 242, and configured to provide a gap region so that a notch of the inner sleeve 240 can be positioned in the gap region.

Figure 4B:
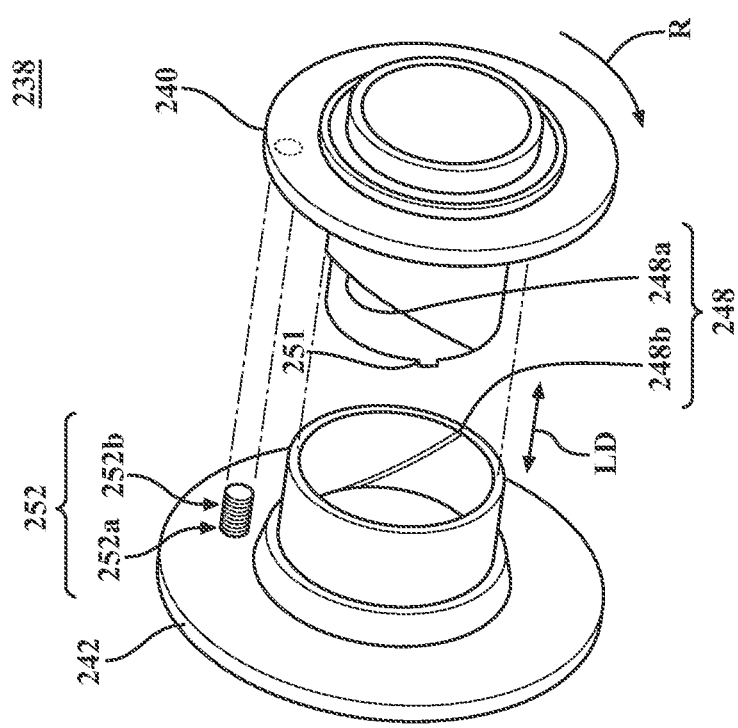
FIG. 4B schematically represents details of embodiments of a torque sensor system.
Figure 4D:
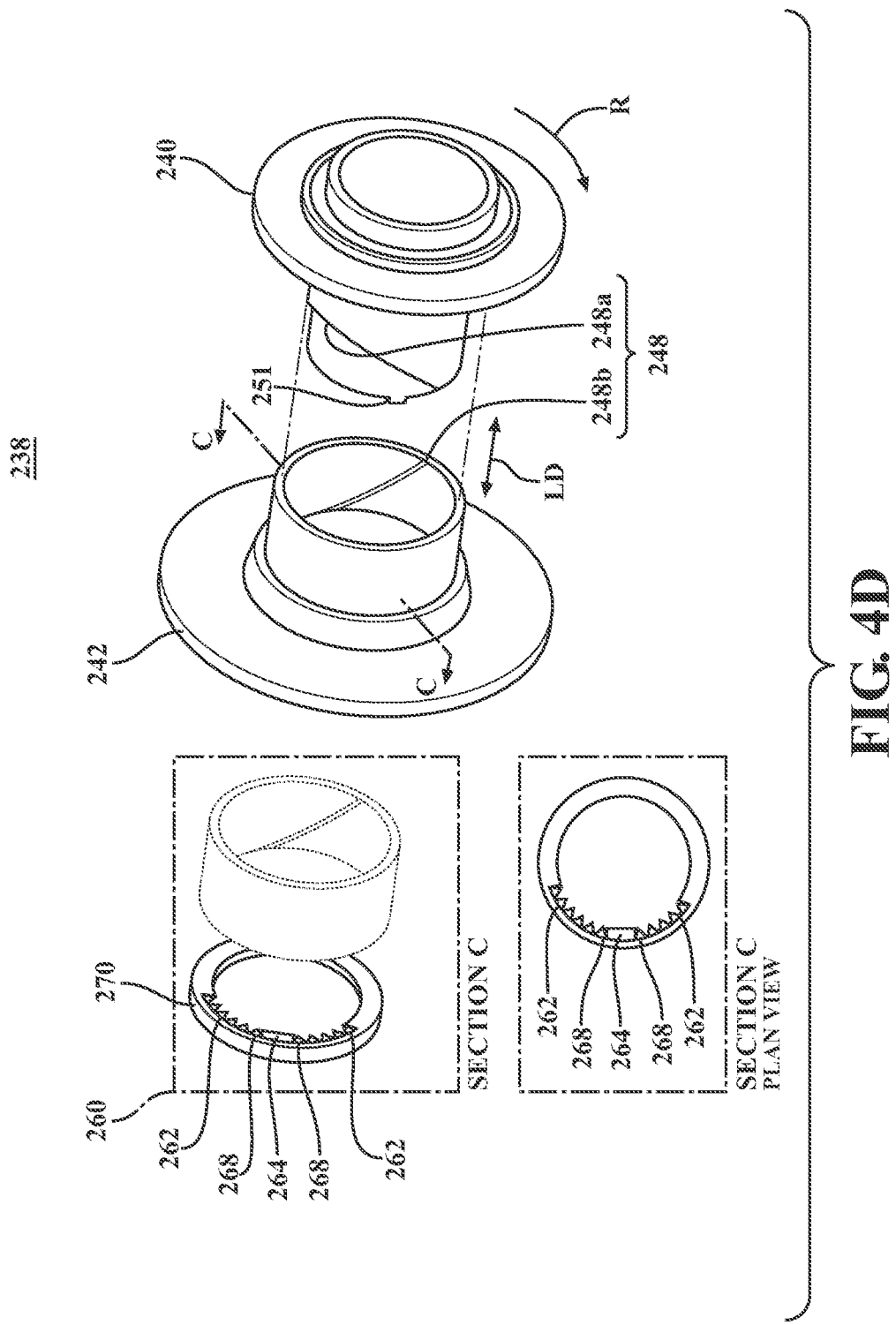
FIG. 4D schematically represents details of embodiments of a torque sensor system.

The inner sleeve 240 can be provided with a notch 251 that can interface with a spring/elastomer mechanism 260 (FIG. 4D). The spring/elastomer mechanism 260 applies a known force (i.e., by way of a known spring constant) on the inner sleeve 240 via the notch 251 of the inner sleeve 240. Accordingly, a torque applied to one of the inner and outer sleeves 240, 242 can be calculated from a combination of a measured lateral displacement LD and a known force applied to the notch of the inner sleeve 240.

The torque sensor system 238 illustrated in FIG. 4B operates in a similar manner as the torque sensor system 238 illustrated in FIG. 4A; however, the proximity sensor 244 of the torque sensor system 238 illustrated in FIG. 4A is replaced with a displacement sensor 252 with a spring/elastomer 252a and pressure sensor 252b, or other technologies for measuring distance such as resistive, capacitive, or other types of distance measurement technologies.

With reference to FIG. 4C, a torque sensor system 238 can alternatively or additionally include a velocity sensor system including one or more Hall Effect sensors 254 and a plurality of magnets 258. In embodiments, the magnets 258 are provided in an alternating configuration on an outer surface of the inner sleeve 240, and spaced apart by a predetermined distance dl. That is, the magnets 258 provided on the outer surface of the inner sleeve alternate magnetic poles (e.g., N-S-N-S-N-S). In this manner, a velocity measurement can be calculated based using a variety of methods such as, number of magnetic poles measured per unit time, or time elapsed between magnetic poles, and other principles using a time-distance relationship.

With reference to FIG. 4D the spring/elastomer mechanism 260 of a torque sensor system 150 can include first and second springs/elastomers 262 and pressure sensors 268. The first and springs/elastomers 262 are provided in a cylindrical housing 270 of the outer sleeve 242, and are configured to provide a gap region 264 so that the notch 251 of the inner sleeve 240 can provided in the gap region 264. As described above, the spring/elastomer mechanism 260 can apply a known force (i.e., by way of a known spring constant) on the inner sleeve 240 via the notch 251.

The electrically motorized wheel 100 described above in connection with FIGS. 1A, 2A and 2B may be used to assist in powering a variety of human-powered wheeled vehicles such as bicycles, tricycles, wagons, trailers, wheel barrows, push carts (e.g., medical carts, carts used in food preparation, food service and others, delivery carts, carts use to move goods around warehouses and industrial facilities, etc.), carts used in moving (e.g., to move furniture, pianos, appliances, and large items), riding toys, wheeled stretchers, rolling furniture, wheeled appliances, wheelchairs, strollers, baby carriages, shopping carts and others.

In embodiments, such as for bicycles and tricycles, the electrically motorized wheel 100 may be readily installed by a customer for converting a vehicle to an electrically motorized vehicle via installation of the electrically motorized wheel. In these embodiments the electrically motorized wheel 100 may be attached to a vehicle using the existing attachment mechanisms. Embodiments may include a developer kit for adapting the electrically motorized wheel 100 to the hardware environment of a specific non-electric vehicle such as a wheelchair, wheelbarrow, wagon and others.

The hardware developer kit facilitates attachment of sensor/peripheral devices to an open serial port of the electrically motorized wheel 100. This data can then be transmitted to the mobile device and subsequently to the server for access by the API. Since the API is accessible, developers may take readings from the sensor/peripheral devices to thereby expand the sensing/functionality/features of the electrically motorized wheel 100. Power for the sensor/peripheral devices may be their own power source or supplied by the electrically motorized wheel 100 either through a power connection internal to the electrically motorized wheel 100 or though the power port that permits power to flow in either direction—in from a charger or out to an external device if desired.

The electrically motorized wheel 100 may be used to provide additional motive force and braking to various types of otherwise human only powered vehicles. Thus, an entire vehicle may be sold as an integrated product, including an appropriately designed electrically motorized wheel 100.

Figure 5:
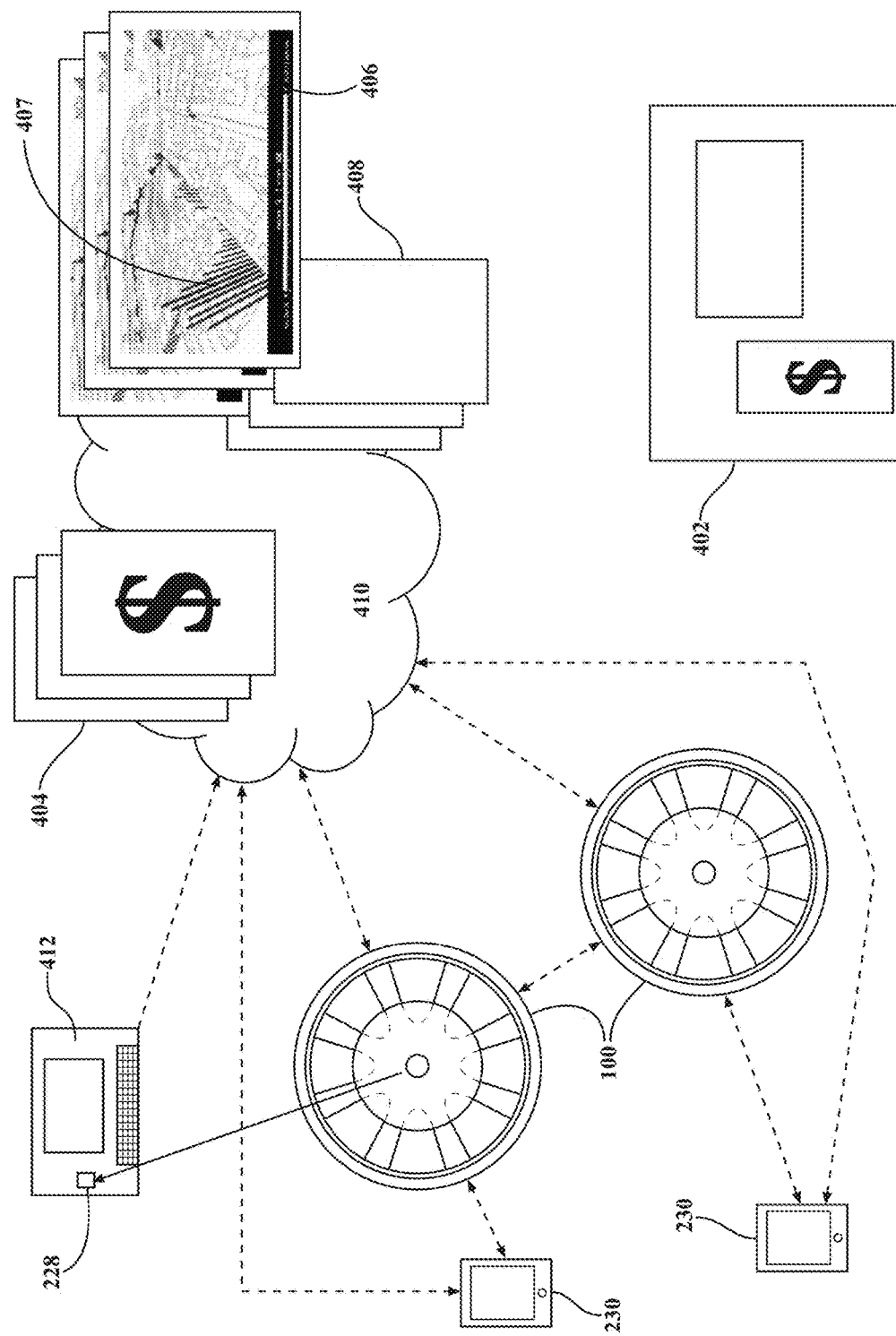
FIG. 5 schematically represents the environment of the mobile device.

With reference to FIG. 5 the electrically motorized wheel 100 may be purchased and serviced at a traditional brick and mortar store 402 such as a bicycle store, a hardware store, a store specializing in the vehicle to which electrically motorized wheel 100 is attached and others, or by electronic commerce. Thus, an electrically motorized wheel 100 may be provided as an individual element that can be attached to any generic vehicle, or it may be adapted for use with a wheel of a particular vehicle. For example, many bicycles have unique design features, colors, branding elements, or the like that can be matched, or complemented, by providing a electrically motorized wheel 100 that has appropriately related aesthetic features.

In embodiments, additional hardware and software accessories, applications, and other features may be purchased either at traditional brick and mortar stores 402, online stores 404, mobile app stores, and others. For example, a electrically motorized wheel 100 may be provided with a unique identifier, such as a serial number stored in memory, which can be used as an identifier of the electrically motorized wheel 100, the user, or the vehicle on which the electrically motorized wheel 100 is installed, for purposes of various applications, including navigation applications, applications measuring exercise, traffic reporting applications, pollution-sensing applications, and others. Such applications may be provided, for example, on a mobile device that presents user interface elements that include, or that are derived from, data inputs from electrically motorized wheel.

In embodiments, data from the electrically motorized wheel may be uploaded to one or more application data servers 408 on the server 410 via a wireless communications system 318 in the motorized wheel hub 110. The communication may include a relatively short-range wireless system 220 to transmit the data to the mobile device 230 and thence from the mobile device 230 to the server 410 via the wireless telecommunications system 318. Data may alternatively or additionally be physically transferred from the electrically motorized wheel 100 to a local computer 412 via removable storage media 228 and from the local computer 412 to the one or more application data servers 408.

In embodiments a standard interfaces may be provided for both the software and hardware systems. An accessory port 218 (FIG. 2B) may support standard protocols such as USB, USB 2.0, Thunderbolt, Dicom, PCI Express and others. These interfaces may facilitate the support of accessory devices and peripherals such as environmental sensors, gyroscopes, supplemental memory and others by providing power to operate the accessory device and an interface for data transfer between the accessory device and data storage in the motorized wheel hub 110.

In embodiments, data exchange may occur using a short-range wireless system 220 such as wireless USB, Bluetooth, IEEE 802.11 and others. Data exchange may alternatively or additionally be performed over long-range wireless or telecommunications system 222 such as 2 G, 3 G, and 4 G networks.

In embodiments an API and/or software development kit facilitates access to data storage and transfer of data over a wireless network to a computer on a network, integration of sensor data with other data collected simultaneously, use of processing and reporting functions of the sensor-enabled wheel (e.g., reporting energy used, charge status, miles traveled, data from environmental sensors, user-entered data, or other data), and others.

In embodiments, the API and/or software development kit facilitates software and/or hardware access to the motor control system 208 of the electrically motorized wheel 100 such as when power is applied to electrically motorized wheel, when resistance is applied to electrically motorized wheel, energy regeneration, power management, access to the sensor data collected, and others.

In embodiments, the electrically motorized wheel 100 may be purchased through a variety of channels including online, specialty bicycle shops, and others. Further, online stores 404 may provide for purchase of "applications" or "behaviors" that leverage the hardware and software APIs to provide unique user experiences. These behaviors may be purchased online and downloaded to the electrically motorized wheel 100 through a short-range wireless connection 220 or via a standard hardware interface such as a cable that plugs into an appropriate port. Applications may include gaming, fleet management, rental management, environmental sensing and management, fitness, traffic management, navigation and mapping, social interface, health management, and others.

Many vehicles, either individually or those within a common fleet, may employ the electrically motorized wheel. As the vehicles are moving around various locations, the electrically motorized wheel may be utilized to sample the environment. The data collected can thus be utilized to provide a spatial and temporal indication of various parameters that are sampled.

In one example, current temperature data is sampled over the area covered by the vehicles at the location of each of the vehicles. As the vehicles move from location to location, a collection of such data is a representation at different locations over time. This may be expanded to numerous parameters sampled by numerous vehicles over time to monitor multi-dimensional phenomena to facilitate the generation of models that contain multivariate data, and other scientific uses such as for predicting future environmental conditions.

In another example, data may be collected and processed to profile the user. That is, as the vehicles move from location to location, a collection of data is generated to indicate how specific users operate the vehicle. Such data may facilitate generation of a feedback loop that may be utilized to improve infrastructure development, (e.g., traffic lights and municipal networks). The data may also be utilized to indicate to the user, for example, more efficient operations of the vehicle, e.g., recommended mode utilization.

The data may also be utilized to interact with a transportation to alert other vehicles such as smart cars to the presence of the vehicle with the electrically motorized wheel 100 as well as alert the user of the electrically motorized wheel 100 to the presence of the other vehicles.

The electrically motorized wheel 100 may additionally support a plurality of sensors that collect and process attributes related to the vehicle and the electrically motorized wheel 100 itself such as torque applied, velocity, "steadiness" of the vehicle, acceleration of the vehicle, usage of vehicle including time, distance, and terrain travelled, motorized assistance provided, available battery power, motor temperature, etc.

The electrically motorized wheel 100 may also include a data collection platform for integrating and analyzing the data collected by the plurality of sensors. In embodiments, the collected data may be integrated with data from a plurality of other electrically motorized wheels 100 as well as data from $3^{rd}$ party sources such as traffic data systems, geographical information systems (GIS) databases, traffic cameras, road sensors, air quality monitoring systems, emergency response systems, mapping systems, aerial mapping data, satellite systems, weather systems, and many others.

This combined data may then be integrated and analyzed onboard the electrically motorized wheel 100, off board the electrically motorized wheel 100, or a combination thereof. Such combined data leverages the sensor data collected by the plurality of vehicles traversing a relatively large geographic area and correlates the terrain traversed to time. This readily facilitates determination of a variety of insights as the plurality of electrically motorized wheels 100 essentially operate as distributed sensor network to provide sensor data for aggregation and interpretation. For example, the plurality of wheels, or a specific subset thereof, may be viewed in the aggregate to determine the best bicycling routes through a city, to promote the collective health of users (such as by routing away from areas with low air quality), and the like.

In embodiments, the telecommunications system and the global positional system may transmit data and/or communicate with infrastructure, other vehicles, or non-infrastructure entities in the surrounding environment. This data transfer or communication can alert the vehicles of a potential collision, cause traffic lights to switch, etc.

The data collected from the plurality of electrically motorized wheels 100 and viewed in the aggregate to may facilitate the generation of detailed analyses and maps 406. The maps 406 may be utilized to depict, for example, environmental phenomena that vary over space and time. This data can be overlaid on existing street patterns, land use maps, topographical maps, population density maps and open space maps creating layered maps which may be accessed through mobile devices or a webpage and which provide an overview of environmental conditions in real time, as well as historical data detailing past conditions or predictions of future conditions.

These layered maps may be used as a tool with which cities, businesses, and/or individuals may, for example, monitor environmental conditions; facilitate determination of future environmental and traffic policy decisions such as the planning of new roads and paths; planning of commercial real-estate development; positioning of new cell towers and network repeaters; real time traffic analysis; the study of phenomena like urban heat islands, emergency preparedness; noise and environmental pollution; and when planning the least polluted routes through cities.

For example, data collected relative to wind speed and direction may be used to understand airflow through a city and used to map the impact of a dirty bomb and how it might disperse through a city. Data collected relative to signal strength and traffic patterns may be utilized to facilitate wireless companies in decisions regarding the placement of new cell towers. Temperature data collected over time may lead to the creation of urban gardens to ameliorate urban heat islands. Data related to global position and elevation may be used to provide ground truth for existing maps. Data related to traffic patterns may be used in planning of new commercial locations and store layouts. For example, bar graphs 407 may be overlaid onto a street map 406 to indicate high traffic areas, slow commute areas, high pollutant conditions, etc.

Aggregated data may also be used to facilitate improved real-time navigation, adjust real-time traffic patterns, divert bicycle traffic to other areas of the city, etc.

In embodiments, a multi-user game system permits users of vehicles having one or more electrically motorized wheels 100 to exchange data such as location, distance, torque applied, effort expended, distance travelled, total change in elevation, calories burned, heart rate elevation, environmental data collected and others.

In one example, a remote racing game may leverage the control systems of the individual electrically motorized wheels 100 and the local environmental data to modify the electrically motorized wheel 100 behavior in conjunction with the local terrain in such a way that players in different locations experienced a common effort of attempting to bicycle up a hill while riding across terrain that varied among players based on location. In embodiments the ability to modify the electrically motorized wheel 100 behaviors might be used to handicap users of difference skill levels.

Embodiments may include achievements, which may be unlocked after users surpass certain thresholds. For instance, a user could get a medal after riding 1000 miles. Achievements may include other distance thresholds, calorie thresholds, number of trips, number of cities, number of friends, power generated, and others.

Embodiments may include a system for targeting commercial opportunities to users wherein the offer is partially based on the location of the electrically motorized wheel 100. Embodiments may include a variant on geo-caching where the users visit specified geographic locations. The data collection system would be collecting data location and time and users would be able to compare locations visited and when.

In embodiments, profiling a user of the electrically motorized wheel may include assessing a user's current physical capabilities and monitoring the user's physical capabilities over time to facilitate identification of trends. Data collected may include torque applied, distance traversed over time, stability of electrically motorized wheel 100 and others. It should be understood that various sensors including heart rate sensors may be utilized to profile a user operating the electrically motorized wheel.

Analysis may be performed to sense changes in mobility patterns such as frequency, force applied, distance travelled, steadiness, times of day system accessed and others. Small changes in these measurements may be used to sense long-term, slowly developing diseases, such as Parkinson's syndrome, which are typically difficult to sense because the change in user capabilities is gradual over an extended period of time. This data may be provided directly from this system into an electronic medical record, EMR, or associated with an individual's healthcare data. The data may be aggregated with data from a plurality of other electrically motorized wheels 100 to provide data sets for public health analysis.

An example, data gathered from the electrically motorized wheel that facilitates physical therapy is the direct power the person's legs can output as compared to conventional sensors which may only measure steps taken and heart rate. The data gathered from the electrically motorized wheel may thereby be utilized to detect how the person's leg muscles are changing over time because torque is directly detected through the torque sensor.

In embodiments techniques such as collaborative filtering may be used to sort through different options, then suggest to one user options used by other users that are determined to be most similar to that user. Statistical techniques for sensing similarity may be performed, based on correlations, e.g., based on matrices of the "distances" between users with respect to various defined attributes that can be measured or derived based on the data collected by electrically motorized wheel or entered by the user. Thus, users who are similar to each other may be presented with similar applications, user interfaces, drive modes, navigation options, and others. For example, two users who regularly ride similar routes may be utilized to identify that one route is substantially faster given similar exertion/less hilly/fewer stops/intersections, etc. Such route comparison may be utilized to suggest a different route to the user of the slower route.

In an embodiment, data may be collected from a fleet of vehicles such as delivery vehicles, messenger services and others. Data collected may be analyzed and synthesized to facilitate a dispatcher in optimizing routes, schedules, estimating deliver times and others based on user fitness levels, terrain covered during current excursion including mileage, elevation change, level of assistance already provided, remaining battery life, current location, and terrain along proposed routes and others.

Data aggregated from public or private fleets may be analyzed to determine when bicycles need to be taken in for service, where bike racks should be located, where charging stations should be located, how many bicycles are in service at any given time, and other useful scenarios.

In embodiments, the electrically motorized wheel 100 may be installed on store shopping carts. The electrically motorized wheel 100 may assistance shopper shoppers needing additional assistance, for specialized large, heavier carts such as those adapted for shopping with children, as the cart increases in weight, and others. The data collected may include aisles traversed, time spent in which aisles, where along the aisle vehicle stop, and other such data. This data may be used to map the traffic flow through a store to facilitate planning for product placement, improved store layout and others.

In embodiments, the hardware API may facilitate hardware plug-ins to further modify the performance of the vehicle on which the electrically motorized wheel 100 is mounted. That is, the hardware plug-ins may include options, upgrades or other selectable accessory devices that each particular user may select and readily install, i.e., "plug-in" to their electrically motorized wheel 100.

In embodiments, the hardware plug-in may be a gyroscopic sensor that plugs into an electrically motorized wheel 100 on a bicycle to facilitate the performance of "wheelies" or other tricks. The gyroscopic sensor may be used to determine the orientation of electrically motorized wheeled vehicle. Several gyroscopic sensors may be used to determine the orientation of the vehicle in several dimensions. If these are monitored over a period of time, the stability of the vehicle may be determined.

Data from the hardware interface may be processed by the mobile device 230 (FIG. 3), and/or transmitted via the mobile device 230 to a server for processing. Data from the hardware interface may alternatively or additionally communicate directly from the electrically motorized wheel to a server using long-range wireless or telecommunications system such as 2 G, 3 G, and 4 G networks. Further, the processed data may be communicated back to the electrically motorized wheeled vehicle to form a feedback loop to facilitate operation of the electrically motorized wheeled vehicle, each vehicle within a fleet, and/or other electrically motorized wheeled vehicles that may benefit from the collected data.

The accessory port 218 may support one or more sensors that are operable to measure environmental attributes such as temperature, humidity, wind speed and direction, barometric pressure, elevation, air quality, the presence of chemicals such as carbon dioxide, nitrogen, ozone, sulfur and others, radiation levels, noise levels, GPS signal strength, wireless network signal levels and others. The data collected by the sensors may be stored locally on the electrically motorized wheel or transmitted wirelessly to a remote system such as a network computer. Data stored locally on the electrically motorized wheel may later be transmitted wirelessly or otherwise transferred from the electrically motorized wheel to one or more application data servers 408. The data collected by the sensors may be stored in conjunction with additional contextual data such as the date and time data was collected, the GPS location associated with particular data, other data collected at the same time, date, location and others.

In embodiments the electrically motorized wheel 100 may be equipped with a system to alert users of objects in close proximity, thus enhancing user safety. In embodiments, the system may utilize the accessory port 218 to support a proximity sensor such as an optical sensor, an electromagnetic proximity-sensing detector, or the like. The proximity sensors facilitate detection of objects that approach the vehicle on which the electrically motorized wheel 100 is mounted, such as from behind or from the side, then display data or warnings on the mobile device 230.

The proximity of an object which is detected by the proximity sensor may be used to trigger automated actions as well, including decreasing speed, electronic braking, increasing speed, or triggering actions to connected peripheral devices, such as headlights, blinkers, hazard lights, personal electronic devices, bells, alarms, protective equipment, and others.

Proximity sensors may be mounted within the motorized wheel hub 110 adjacent to a window that allows an optical beam, an electromagnetic beam, or such transmission to pass through a static portion of the hub shell assembly 111. Alternatively, RADAR, SONAR or other beams may pass directly through the hub shell assembly 111.

The proximity sensors may communicate with the mobile device 230 to provide an alert to the user when an object is detected within a certain threshold distance. This alert may be conveyed using one or more of audible, visible, and tactile methods. This alert may be incorporated into the electrically motorized wheel 100 such as by shaking the vehicle or communicated to another device mounted elsewhere on the vehicle such as the mobile device 230, a GPS unit, a smart mobile device, tablet or the like. The proximity data may be transmitted using short-range wireless technologies such as wireless USB, BlueTooth, IEEE 802.11 and others.

With reference to FIG. 6A, another disclosed embodiment of an electrically motorized wheel is illustrated herein as a wheelchair 600 retrofitted with at least two electrically motorized wheels 620 that are daisy chained one to another. Although this embodiment has specific illustrated components in a wheelchair embodiment, the embodiments of this disclosure are not limited to those particular combinations and it is possible to use some of the components or features from any of the embodiments in combination with features or components from any of the other embodiments.

The electrically motorized wheel 620 includes a multiple of motorized wheel hubs 610 comparable to those described above but these electrically motorized wheels 620 are daisy changed together. "Daisy chained," as described herein, indicates operation of the plurality of electrically motorized wheel 620 in concert, serial, parallel or other coordination. That is, the multiple of motorized wheel hubs 610 may communicate one to another in a "daisy chain" or other distributed interparty communication, and/or may be individually controlled directly but with regard to others.

A plurality of electrically motorized wheels 620 may be daisy changed together via a daisy chain protocol operable on the control system 214. The daisy chain protocol may be software resident on the control system 214 or may be effectuated via a hardware device that plugs into each of the plurality of electrically motorized wheels 620 to coordinate operation of the plurality of electrically motorized wheels 620 and thereby facilitate operation of the vehicle. For example, should a user input be communicated to one electrically motorized wheel 620 the other electrically motorized wheel 620 daisy chained thereto may rotate in an opposite direction to perform a pivot-in-place of the vehicle to which the daisy chained wheels are installed. It should be understood that although a wheelchair is illustrated, various other vehicles may utilize daisy chained electrically motorized wheels.

For example, power can be shared between daisy chained wheels through a wired interconnection. Adjustments may be performed locally on each wheel but may be compensated appropriately and smoothly in another daisy chained wheel. Alternatively, adjustments could also be made in parallel.

For example, wheels may be daisy-chained by different firmware and a cable that ties all the CAN interfaces together. The firmware could have one of the wheels be a central controller communicating with all the other wheels. Alternatively, control could be distributed, each wheel determining its own command but in-part based on the commands of the other wheels. It is also possible to add an external controller that performs coordination of the wheel command. For example, a plug may be connected to an accessory port in each of the wheels to be daisy chained.

Power may flow either in or out of the power port. The direction of flow is based upon what is connected, e.g., a charger will push current in, and a load will draw current out. The battery management system controls when the power port is open. For example, the power port opens when it detects a charge or when directed by the main wheel electronics, which thereby permits an external device to be powered. For example, a rider may connect an external device that needs power, and use an app to command the power port to turn on.

Figure 6B:
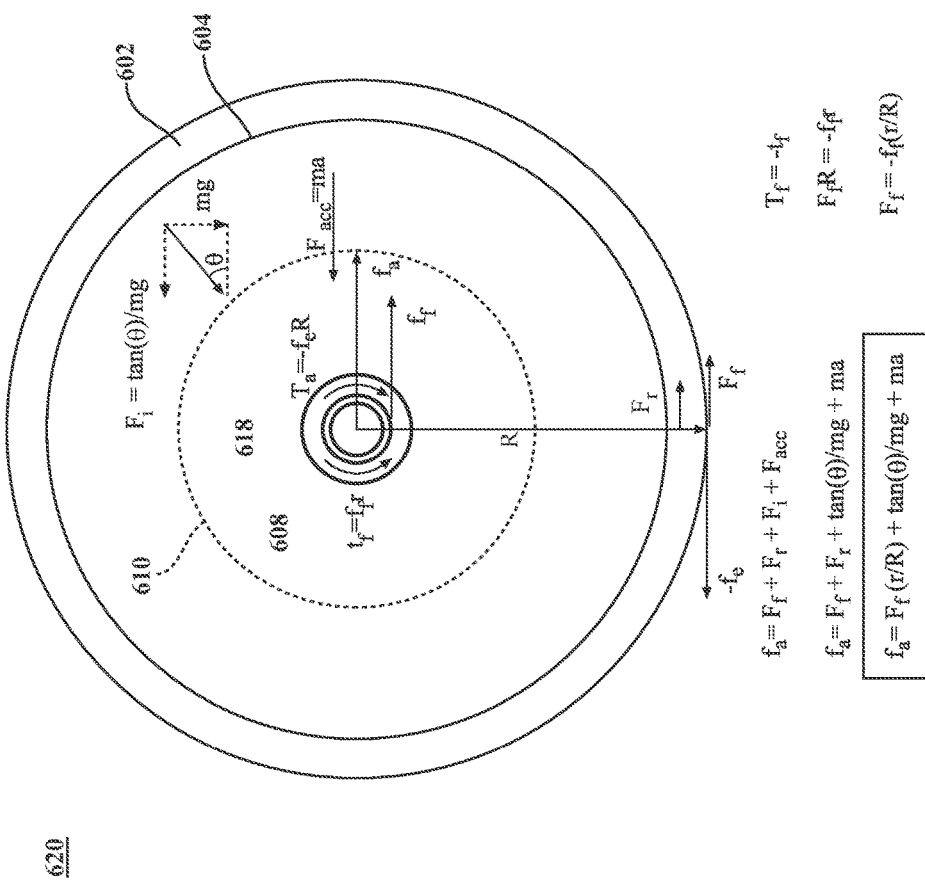
FIG. 6B schematically represents forces and torques associated with the electrically motorized vehicle.

With reference to FIG. 6B, one or more forces are applied ($f_a$) to electrically motorized wheeled vehicle that pass through the rigid body to a axles 608 upon which the electrically motorized wheels 620 are mounted. The forces provided to the vehicle ($f_a$) should be absorbed into the translational motion of the vehicle and the rotational motion of the electrically motorized wheel 620.

For force analyses purposes, the electrically motorized wheelchair 600 is assumed to be a rigid body. The force of earth ($f_e$) presents an equal and opposite reactionary force where the tire 602 meets the ground. This reactionary force is exerted onto electrically motorized wheel tangentially at a distance R equal to the radius of the electrically motorized wheel 620 from the axle 608 causing a rotational applied torque ($T_a$) on electrically motorized wheel in a forward rotational direction equal to $T_a = f_e R$. There is a frictional force ($f_f$) exerted between the axle 608 and bearings 618 that resists motion. (This represents the frictional force for all wheels on the vehicle.) The frictional force ($f_f$) at the bearings 618 causes a frictional torque of $t_f = f_f r$ resisting rotation. This torque ($t_f$) can be replaced by an equivalent torque of a force ($F_f$) applied at a radius R. Therefore, $F_f = -f_f(r/R)$. Electrically motorized wheels rotate when the force provided by the user $f_a$ exceeds the frictional, gravitational (incline) forces, and aerodynamic forces which are often negligible at wheel chair speeds.

The rolling force $F_r$ resisting rotation of the tire 602 is small and may be ignored for these calculations, (as are other small forces).

$F_i$ is the amount of force required to push the vehicle up an inclined angle q.

The excess force over and above those described above, is expressed in acceleration of the vehicle, a. The force causing acceleration of the vehicle is described by the mass of the vehicle multiplied by the acceleration of the vehicle.

$$F_{acc} = ma.$$

Therefore, the total force applied to the vehicle fa is used to overcome the force of friction $F_f$, the force required to rolling of the tires $F_r$, the force to move up an incline $F_i$ and the force for acceleration $F_{acc}$.

$$f_a = F_f + F_r + F_i + F_{acc}$$

$$f_a = F_f + F_r + \tan(q)/mg + ma$$

(where q is the angle of incline.)

Since the force required to roll the tires is assumed negligible, this term drops out.

$$f_a = -f_f(r/R) + \tan(q)/mg + ma$$

When the applied force ($f_a$) exceeds the force of friction ($F_f$), the force of tire rotation ($F_r$) the force due to moving up an incline ($F_i$) it causes acceleration of the electrically motorized wheel 620 in a forward direction. Therefore, by knowing the force of friction $f_f$ due to electrically motorized wheel bearings, the radius r of the bearings, the radius R of electrically motorized wheel, the mass m of the vehicle and sensing the angle of incline q and the acceleration a, one may approximate the user input force $f_a$. This may then be used as an input to determine electric power to be provided to the electric motor in embodiments. Therefore, sensors are required to measure acceleration, and incline of the vehicle. An estimate is required for the frictional force and possibly the tire rolling force (to be more exact). Weight (and therefore mass) could be an initial given parameter, or it can be a measured parameter.

The electrically motorized wheel 620 is accelerated when the user force $f_a$ is applied to the axle 608. This force is applied to the ends of the axle as the electrically motorized wheel is mounted between the ends of the axles. If the axle is accelerated in a forward direction, the translational inertia of electrically motorized wheel causes electrically motorized wheel to resist a change in velocity, causing a force on the axle between the ends opposite the direction of acceleration. This may cause a slight flexing, bending or displacement of the axle 608 proportional to the force being exerted upon the axle 608. Pressure may be measured between the axle and the electrically motorized wheel 620 as an input. A forward acceleration on the ends of the axle 608 causes electrically motorized wheel to exert a rearward force of the middle of the axle 608 causing it to flex or bend slightly to cause the spacing between the axle 608 and electrically motorized wheel structures to change. Sensing these changes will assistance the motorized wheel hub 610 in sensing that a user intends to move electrically motorized wheelchair 600 forward. This may be used in embodiments for sensing input force applied to the vehicle $f_a$. Similarly, stopping the electrically motorized wheelchair 600 moving at a given speed causes the opposite forces on the axle 608 indicating that the user intends to slow or stop electrically motorized wheelchair 600.

The friction of the bearings ($f_f$) of a rotating wheel cause torsion of the axle 608. This torsion may be measured and used to signal that the user is trying to accelerate forward. A reduction in this torque, or an opposite torque sensed at the axle 608 would cause the indication that a moving wheelchair 600 should be slowed or stopped. If the force on electrically motorized wheelchair 600 is sensed to be in a reverse direction and electrically motorized wheelchair 600 is moving in a reverse direction (determined by sensors) then the motorized wheel hub 610 determines that the user intends to accelerate in the reverse direction. Therefore, the force applied to the vehicle may be determined.

By monitoring various motion and acceleration parameters and the forces/torque applied, outside forces applied to the vehicle (both positive and negative) may be estimated. The estimated outside forces are then used to power the electric motor in a direction in which the vehicle is moving or in a direction opposite the direction the vehicle is moving, causing a braking effect or acceleration in a reverse direction.

In embodiments, the user may also operate the electrically motorized wheelchair 600 by rotating the electrically motorized wheels. A ring handle 606 is attached to the motorized wheel hub 610. Typically, a user rotates ring handle 606 to cause electrically motorized wheelchair to move in one direction or rotates the ring handle 606 of each wheel in an opposite direction to cause the electrically motorized wheelchair 600 to pivot. It should be understood that in this vehicle embodiment, the ring handle 606 is the user input and, in contrast to a bicycle embodiment, is typically rotationally fixed rather than mounted via a freewheel typical of a bicycle. That is, the ring handle 606 is the mechanical drive system 612 for the electrically motorized wheel 620.

In embodiments, the torque sensors 638 are attached between the electrically motorized wheel 620 and the ring handle 606 to measure the user input such as a rotation, torque or other input. Since the ring handle 606 does not freewheel, the user input may be related to an applied torque. For example, a rim torque transceiver 640 transmits the sensed torque to the motorized wheel hub 610. The motorized wheel hub 610 then determines which direction the user is attempting to move and assist in that direction. If the torque sensors 638 sense that the user is attempting to slow using the ring handle 606, the motorized wheel hub 610 determines that a braking force is necessary.

By causing power to be provided urging the electrically motorized wheel 620 to drive in a direction opposite that of the direction currently moving, a braking effect is effectuated. Various other types of vehicles may provide power in a manner similar to a wheelchair, such as various types of push carts used in medical, food service, moving, warehouse and similar applications, various riding toys, and other applications where wheeled devices or vehicles are pushed or pulled by human power.

With reference to FIGS. 7A and 7B, an example wheelbarrow 700 is retrofitted with an electrically motorized wheel 720. Although this embodiment has specific illustrated components in for a wheelbarrow, the embodiments of this disclosure are not limited to those particular combinations and it is possible to use some of the components or features from any of the embodiments in combination with features or components from any of the other embodiments.

The electrically motorized wheel 720 includes a multiple of motorized wheel hubs 710 comparable to those described above but that are daisy changed together. That is, the plurality of electrically motorized wheels 720 operate in concert. The motorized wheel hub 710 rotates around an axle 708 that is fixed relative to a handle 712 (FIG. 7C).

The electrically motorized wheelbarrow 700 may have comparable functionality to that described above with the exception that the attitude may be determined differently as the electrically motorized wheelbarrow is typically designed to be tilted when in operation and level when not being used. Therefore, additional sensors may be used to determine the tilt relative to the ground and the inclination of the ground relative to a vertical line (representing direction of gravity). This can be done by measuring the distance from the front of the hub to the ground and the back of the hub to the ground and sensing a difference in distance between these. The vertical line may be determined by various known means, such as using gravity. Together these can be used to determine the incline angle of a hill up which electrically motorized wheelbarrow is travelling.

In embodiments, an axle transceiver 715 is utilized to transmit data from the handle 712 via axle force sensors 714 in communication with the control system 214. The handle 712 may alternatively include handle sensors 718 adjacent to the handles 712 to facilitate differentiating whether differential forces between the axle 708 and wheel hubs 710 is the result of force applied to one or both handles 712, or, for example, a change in terrain elevation. Data sensed by handle sensors 718 may be transmitted via a handle transceiver 719 to the control system 214 which may then determine which direction the user is trying to move and assistance in that direction.

For example, were the electrically motorized wheelbarrow 700 be moving while the input from the axle force sensors 714 and the handle sensors 718 are interpreted to be an attempt to slow the electrically motorized wheelbarrow 700, the control system 214 may determine that a braking force is required. Power is then provided to the motorized wheel hub 710 urging the motorized wheel hub 710 to drive in a direction opposite the direction of movement to cause a braking effect. This braking effect will facilitate stopping of the electrically motorized wheelbarrow 700.

Figure 8:
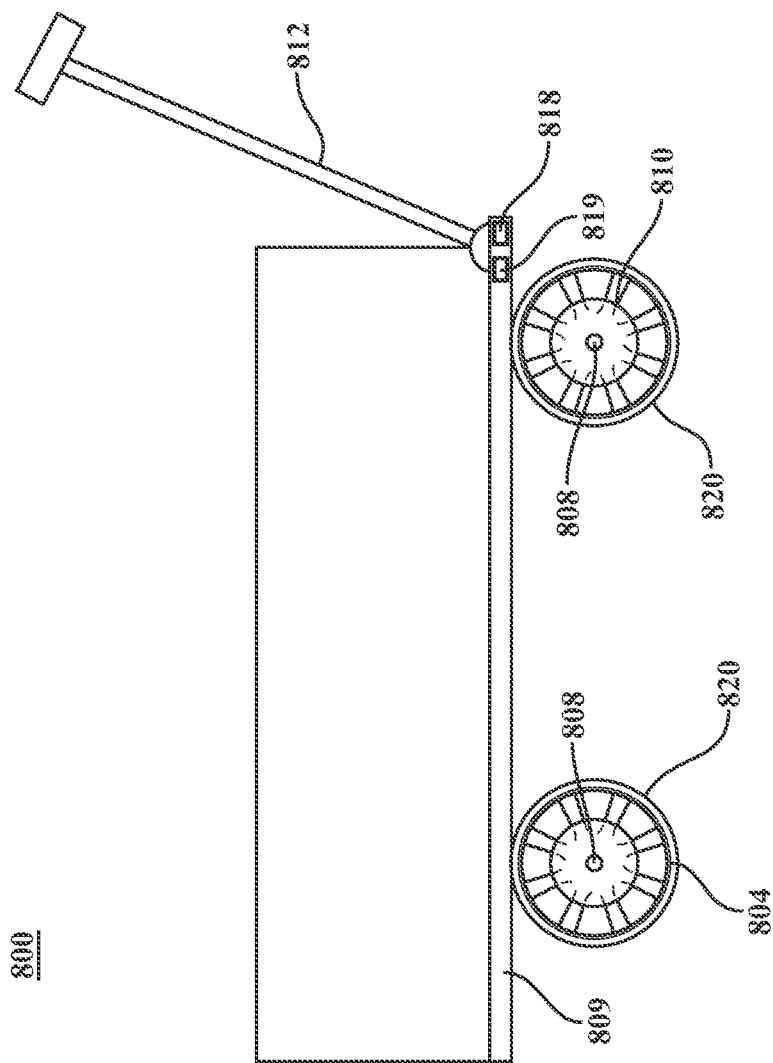
FIG. 8 schematically represents a side view of a wagon retrofitted with the sensor enabled electrically motorized wheel of FIG. 1A.

With reference to FIG. 8, in embodiments, a wagon 800 has installed thereon one or more electrically motorized wheels 820 with a motorized wheel hub 810 comparable to those described above. Although this embodiment has specific illustrated components in a wagon embodiment, the embodiments of this disclosure are not limited to those particular combinations and it is possible to use some of the components or features from any of the embodiments in combination with features or components from any of the other embodiments.

A user pulls a handle 812 of the wagon 800, which transmits the pulling force to an undercarriage 809 of the wagon 800 to which the electrically motorized wheels 820 are mounted.

Again, the wagon 800 is assumed to be a rigid body, such that the pulling force applied to the handle 812 is also applied through the wagon 800 and to axles 808. Each axle 808 and electrically motorized wheel 820 mounted thereto interact in a manner comparable to that of the electrically motorized wheelbarrow 700. As indicated, the determination of the force being applied on the wagon is based upon one or more inputs provided to the control system of the motorized hub.

In embodiments, a handle sensor 818 that measures magnitude, applied direction and applied force at the juncture of the handle 812 and the undercarriage 809. A transceiver 819 coupled to the handle sensor 818 transmits the force data to a control system 214 of the electrically motorized wheel 820. Based on the received data, the control system 214 operates to assist, for example, application of a positive force in the directions of motion, a braking force applied opposite the direction of motion, and relative motion such as to facilitate turning.

Even though the electrically motorized wheel has been described in connection with retrofitting a wagon, other vehicles such as a trailer or other wheeled vehicle that are pulled may be retrofitted in a comparable manner.

Figure 9B:
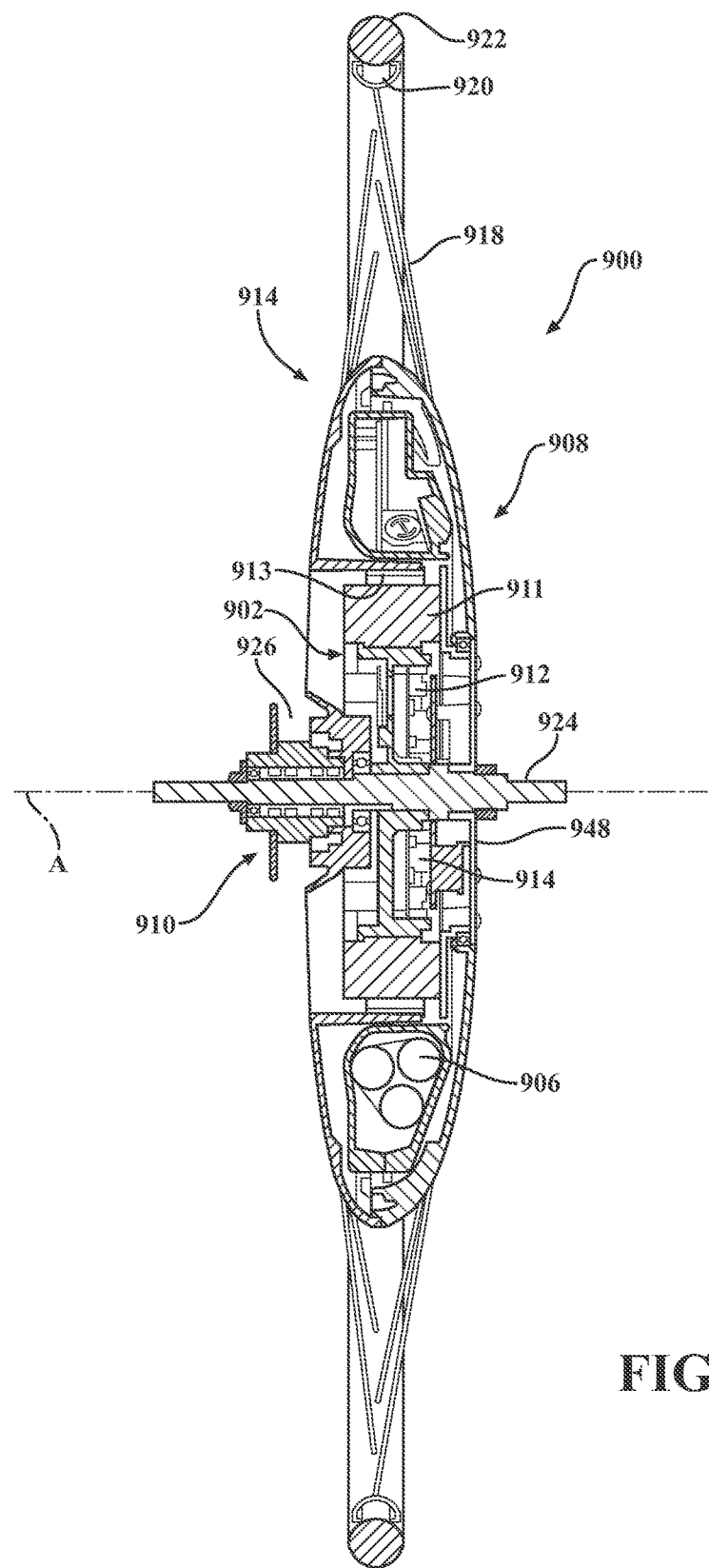
FIG. 9B is a sectional view of a single speed electrically motorized wheel.
Figure 9C:
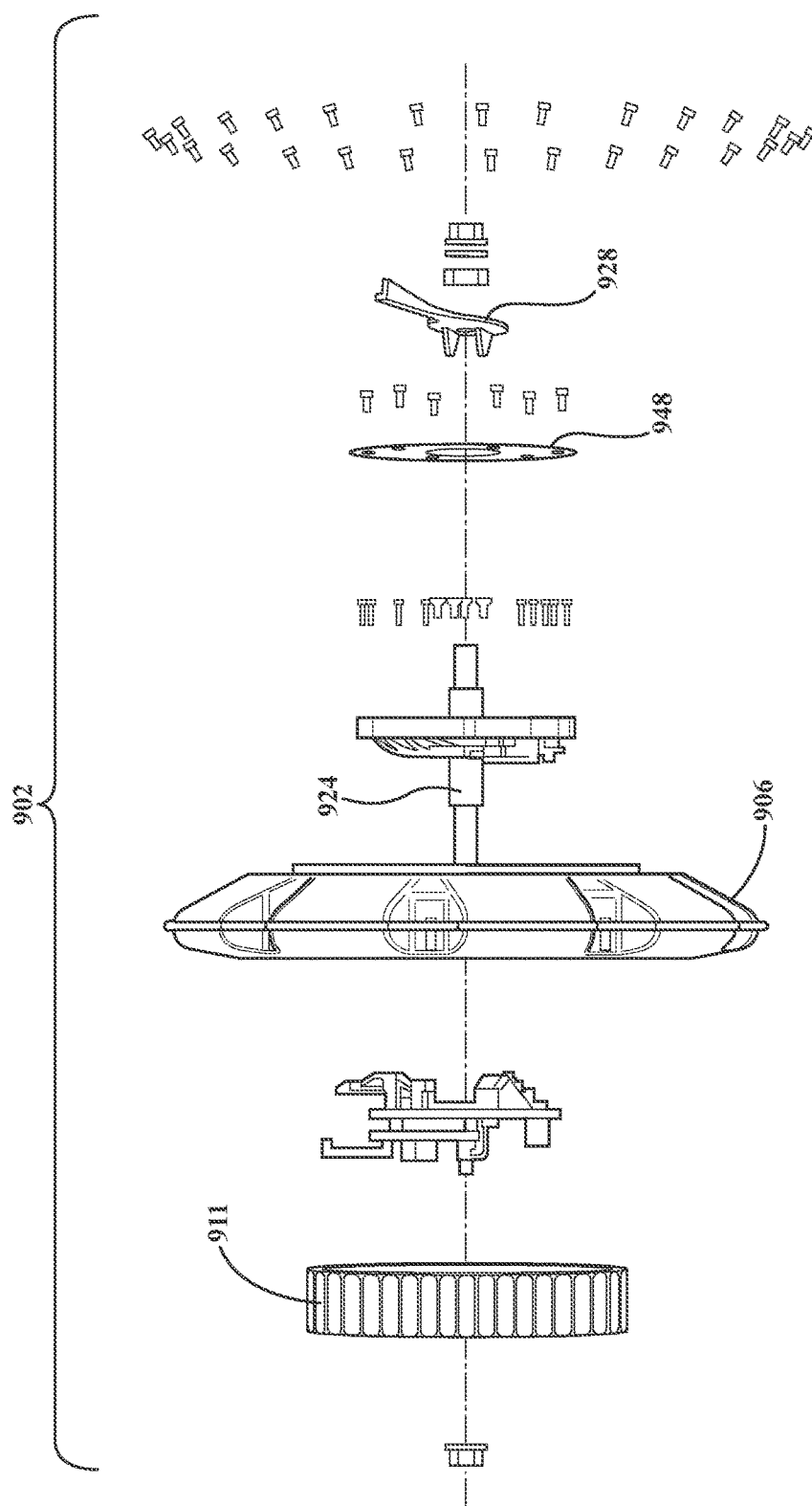
FIG. 9C is an exploded view of a static system of the electrically motorized wheel.
Figure 9E:
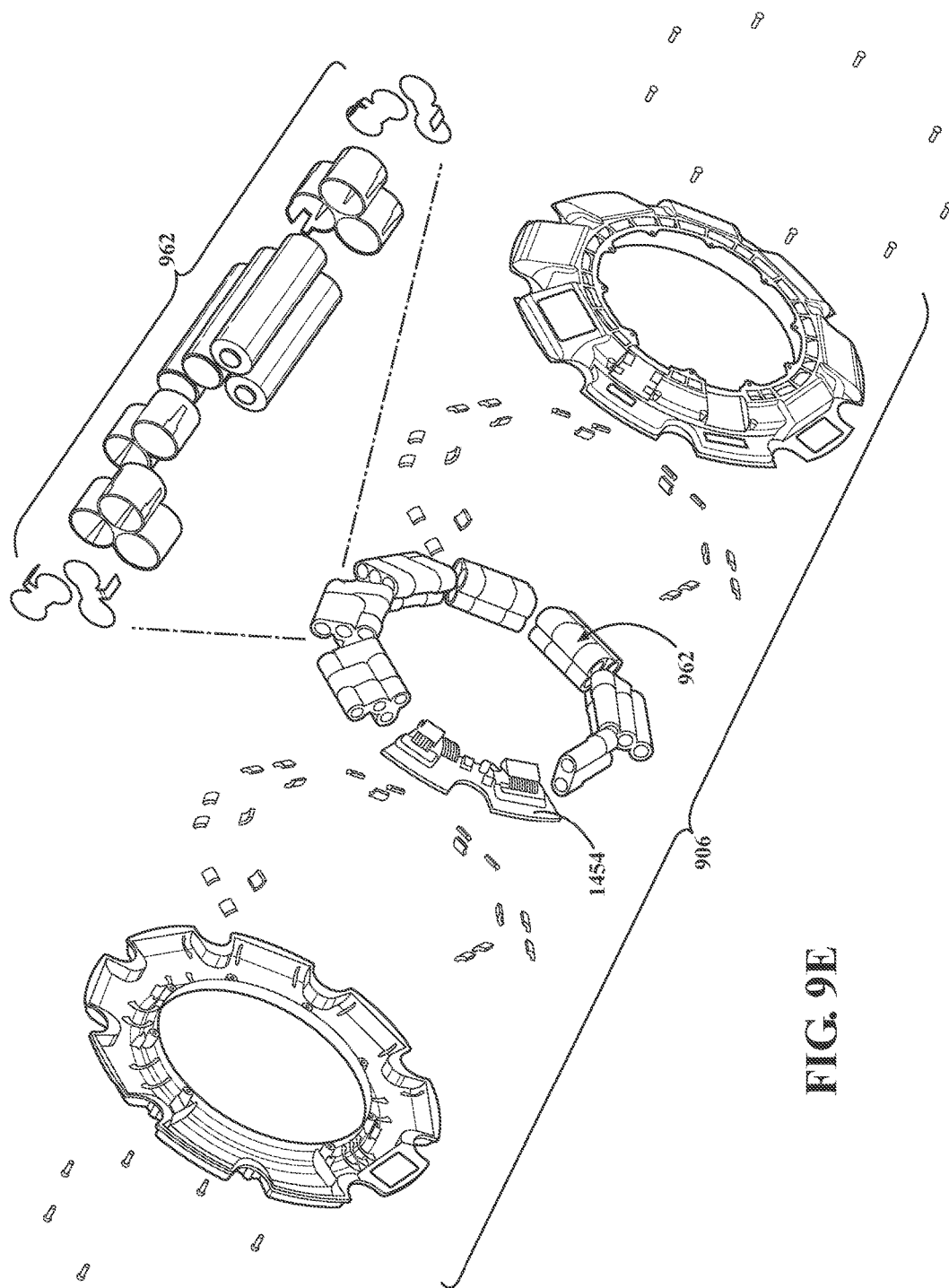
FIG. 9E is an exploded view of a system of the electrically motorized wheel.
Figure 9F:
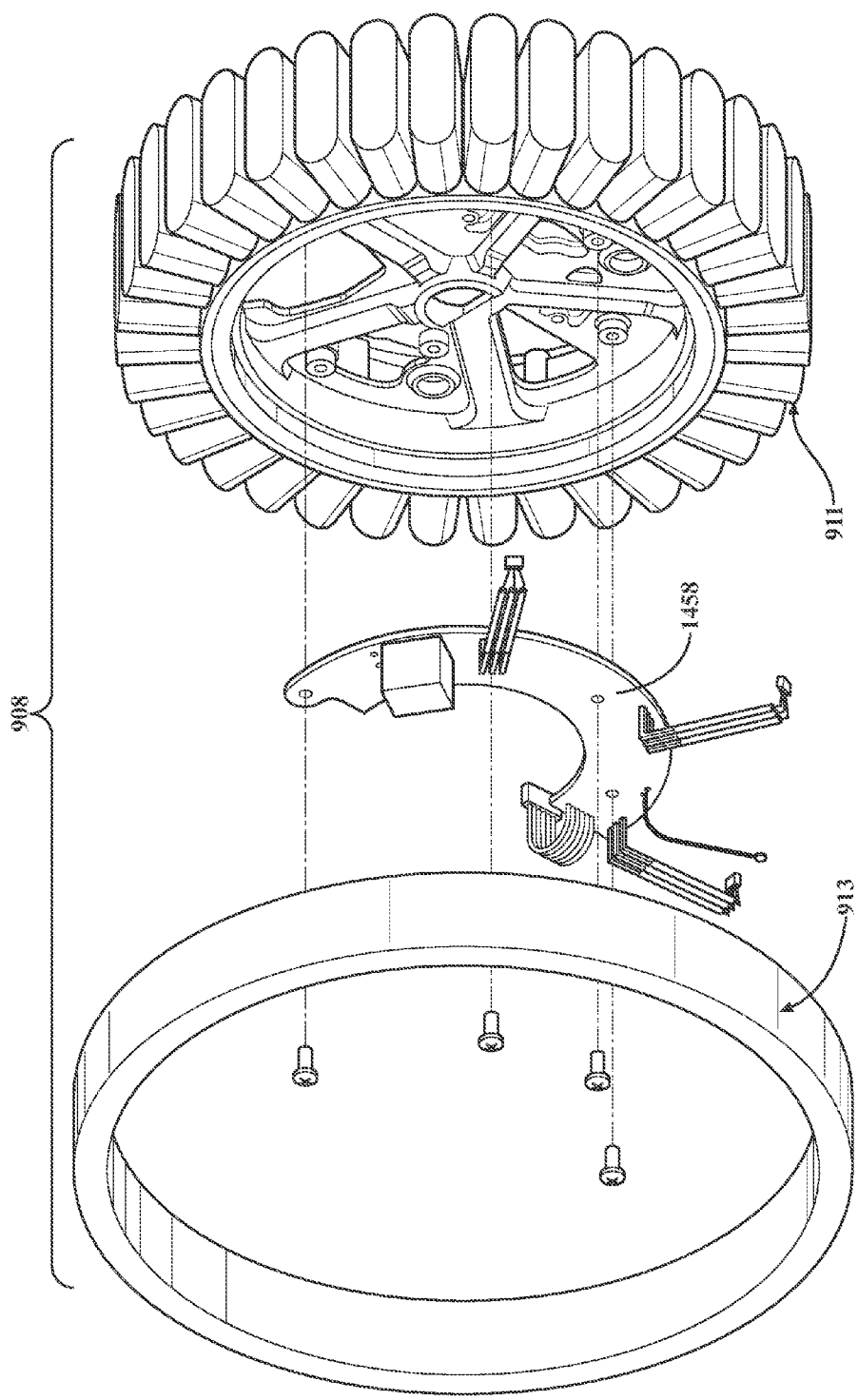
FIG. 9F is an exploded view of an electric motor of the electrically motorized wheel.

With reference to FIG. 9A, embodiments of an electrically motorized wheel 900 (FIG. 9B) generally includes a static system 902 (FIG. 9C), a rotating system 904 (FIG. 9D), a battery system 906 (FIG. 9E), an electric motor 908 (FIG. 9F), a mechanical drive system 910 (FIG. 9G), a sensor system 912 (FIG. 9H), a control system 914 (FIG. 9H), a hub shell assembly 916 (FIG. 9I), a multiple of spokes 918, a rim 920, a tire 922, a shaft 924, and a free hub torque assembly 926 (FIG. 9G). It should be understood that, although particular systems and components are separately defined, each, or any, may be otherwise combined or separated via hardware and/or software except where context indicates otherwise. Further, although this embodiment has specific illustrated components in a bicycle embodiment, the embodiments of this disclosure are not limited to those particular combinations and it is possible to use some of the components or features from any of the embodiments in combination with features or components from any of the other embodiments.

The static system 902 and the rotating system 904 are arranged around an axis of rotation A of the electrically motorized wheel 900, and the static system 902 is coupled to the non-motorized wheeled vehicle via a torque arm assembly (or via torque transmitting features designed into the axle) 928 (FIG. 9I) such that the rotating system 904 is rotatable relate to the static system 902. The electric motor 908 is selectively operable to rotate the rotating system 904 relative to the static system 902 to drive the spokes 918, the rim 920, and tire 922 thereof.

The mechanical drive system 910 is coupled to the rotational system 904 to rotate the rotational system 904 in response to an input applied by the user such as a pedaling input, ring handle of a wheelchair, pushing of a handle, pulling of a handle, etc. In a bicycle embodiment, the mechanical drive system 910 may include a multiple of sprockets for a multi-speed wheel 900A (FIG. 9A, 9B, 10A), often referred to as a "cassette," or a single sprocket for a single speed wheel 900B (FIG. 10B) that receive a rotational input from a pedaling input via a chain or belt.

The sensor system 912 may be operable to identify parameters indicative of the rotational input, such that the control system 914 in communication with the sensor system 912 is operable to continuously control the electric motor 908 in response to the input, such as that induced by a user pedaling. That is, the control system 914 is in communication with the sensor system 912 to continuously control the electric motor 908 even if the control momentarily results in no power being exerted by the electric motor 908. The battery system 906 is electrically connected to the control system 914 and the electric motor 908.

Figure 9I:
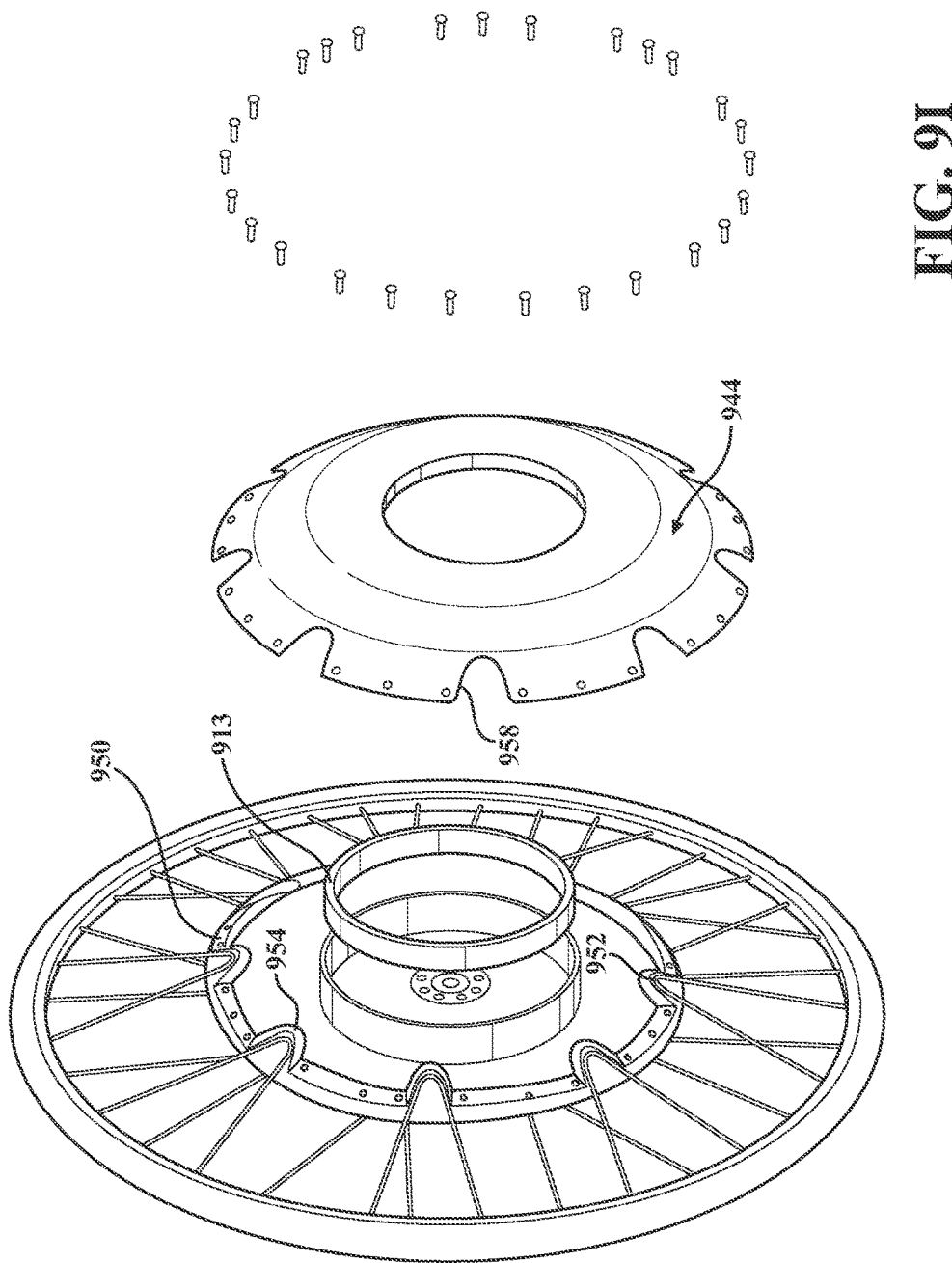
FIG. 9I is an exploded view of a system of the electrically motorized wheel.

In embodiments, the battery system 906, the electric motor 908, the mechanical drive system 910, the sensor system 912, and the control system 914, are contained with the hub shell assembly 916 (FIG. 9I). The hub shell assembly 916 may thereby be a device readily installed into a non-motorized wheeled vehicle through, for example, installation onto the spokes or rim of the electrically motorized wheel to provide an electrically motorized wheeled vehicle. Alternatively, the hub shell assembly 916 with the enclosed battery system 906, electric motor 908, mechanical drive system 910, sensor system 912, and control system 914 may be preinstalled on the electrically motorized wheel 900 to provide a self-contained device inclusive of the spokes 918, the rim 920, and the tire 922, such that an entire wheel of the vehicle is replaced by the electrically motorized wheel 900. That is, all operable componentry is on the electrically motorized wheel 900 itself and is installed as a self-contained device that does not require further modification of the vehicle.

With reference to FIG. 9I, the hub shell assembly 916, according to embodiments, generally includes a drive side shell 940, a non-drive side ring 942, a removable access door 944, a user interface system 948, and the torque arm assembly 928. The hub shell assembly 916 is defined around the axis of rotation A defined by a shaft 924.

In embodiments, the hub shell assembly 916 contains a contoured battery assembly 1016 of the battery system 906 that contains a multiple of battery packs 962 (FIG. 9E) defined as a ring around the axis "A." The battery system 906 in embodiments is rotationally stationary, however, the battery system 906 may, alternatively rotate within the hub shell assembly 916. It should be understood that various shaped battery packs, e.g., linear, arced, circular, cylindrical, "L," "T," etc., may be combined or otherwise assembled to achieve a desired configuration, such as an essentially scalloped shaped contoured battery assembly 1016 that is passable through a contoured inner periphery 954 of the non-drive side ring 942.

Figure 10A:
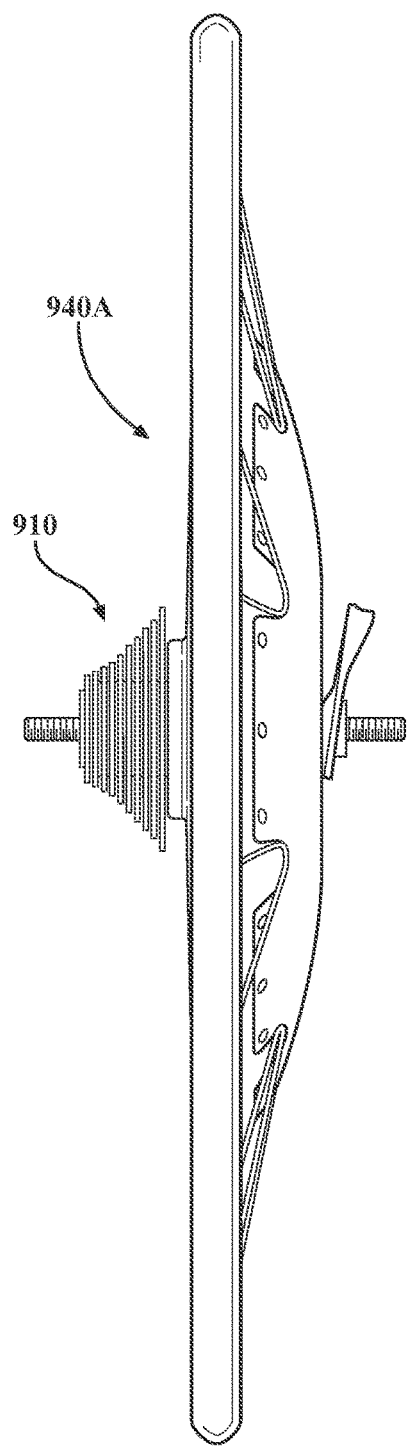
FIG. 10A is a sectional view of a single speed electrically motorized wheel.
Figure 10B:
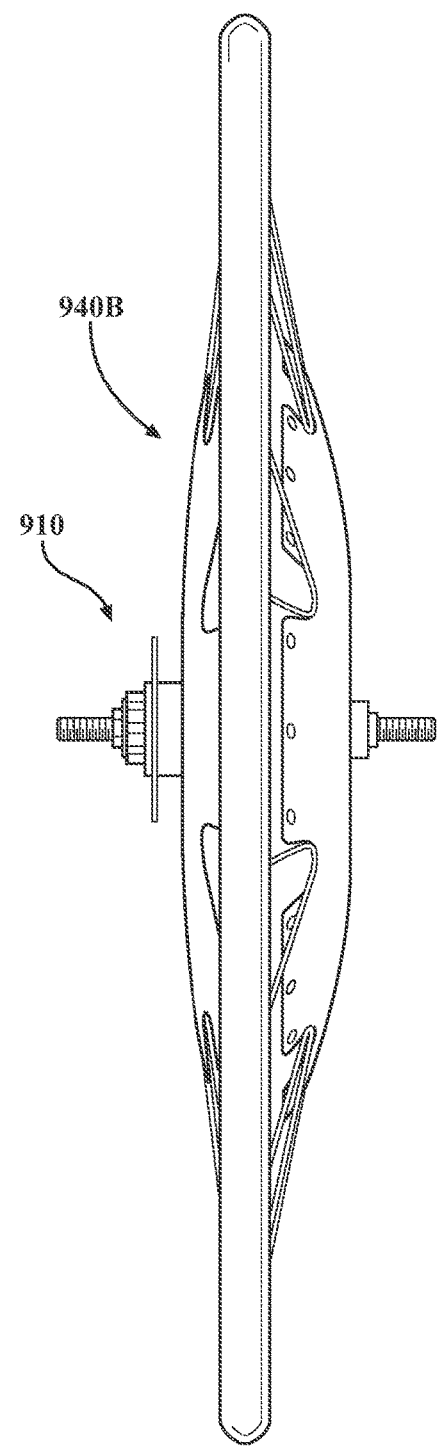
FIG. 10B is a sectional view of a multiple speed electrically motorized wheel.

The drive side shell 940 is a generally circular, lens-shaped shell chassis that supports the mechanical drive system 910. The mechanical drive system 910 may include a free hub torque assembly 926 and the free hub sensor system 912 (FIG. 9G). The convex contour of the drive side shell 940 may be defined to specifically accommodate the mechanical drive system 910. For example, the multi-speed hub 940A may be relatively flatter than the single speed hub 940B (FIGS. 10A, 10B).

With continued reference to FIG. 9I, the non-drive side ring 942 typically includes a multiple of spoke interfaces 952 such as arcuate grooves to receive the spokes 918. The non-drive side ring 942 is held in contact with the drive side shell 940 via the tension of the spokes 918, fasteners, or a combination thereof. A contoured inner periphery 954 of the non-drive side ring 942 matches an outer contoured periphery 958 of the door 944 such that the door 944 is readily removed without despoking or delacing to access the contoured battery assembly 1016 that contains the multiple of batteries packs 962 of the battery system 906.

In one example, the contoured inner periphery 954 may be scalloped and the contoured battery assembly 960 may be formed of a multiple of circumferential segments to facilitate removal. An inner periphery 970 of the removable access door 944 may be circular to receive the user interface system 948. As will be further described, the user interface system 948 is mounted to the static system 902 and may include, for example, a power port, on/off switch, status lights, etc.

Figure 11A:
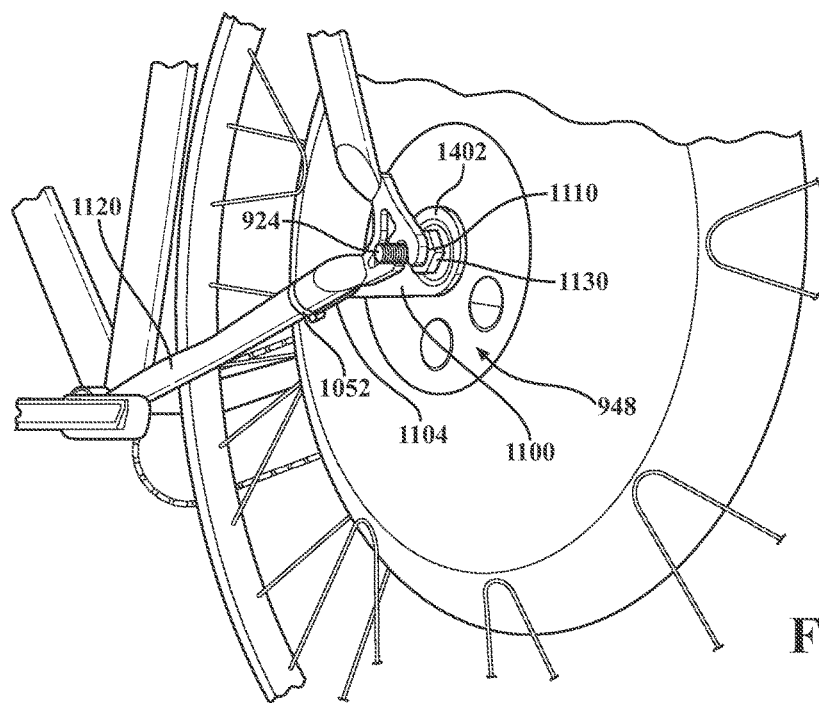
FIG. 11A is a perspective view of a multiple speed electrically motorized wheel.

With reference to FIG. 11A, a torque arm 1100 provides a substantially rigid mechanical connection between the stationary portion of the hub assembly and the frame of the vehicle on which the electrically motorized wheel is mounted, thereby maintaining the stationary portion in a fixed position relative to the frame of the vehicle. As various bicycle frames have various rear drop-outs (where the axle fits the frame) one challenge is how to transfer the torque to the frame as in a non-motorized vehicle, the frame of reference is the pedal, and forward force is resisted.

Figure 11B:
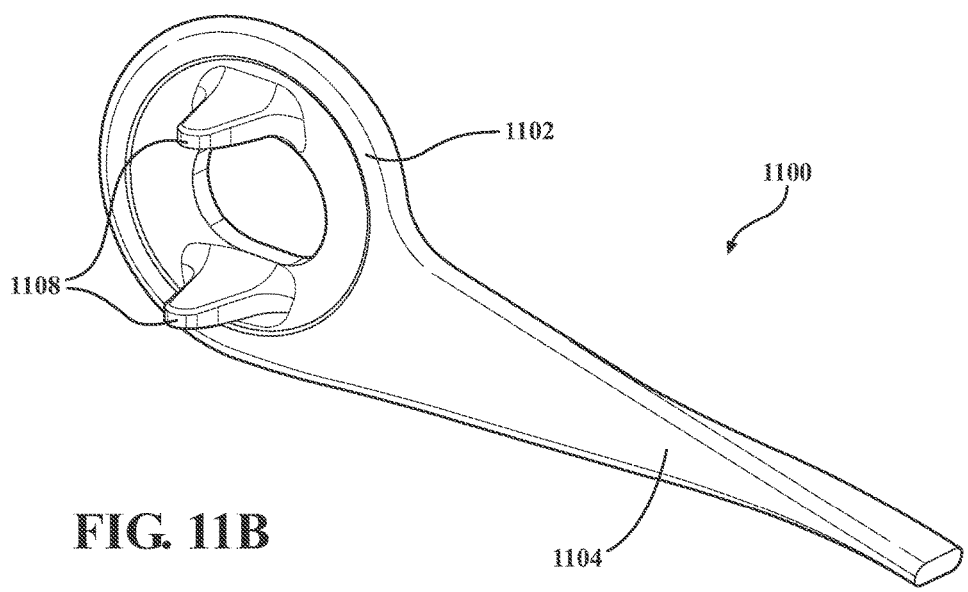
FIG. 11B is a perspective view of a torque arm for the electrically motorized wheel.
Figure 11C:
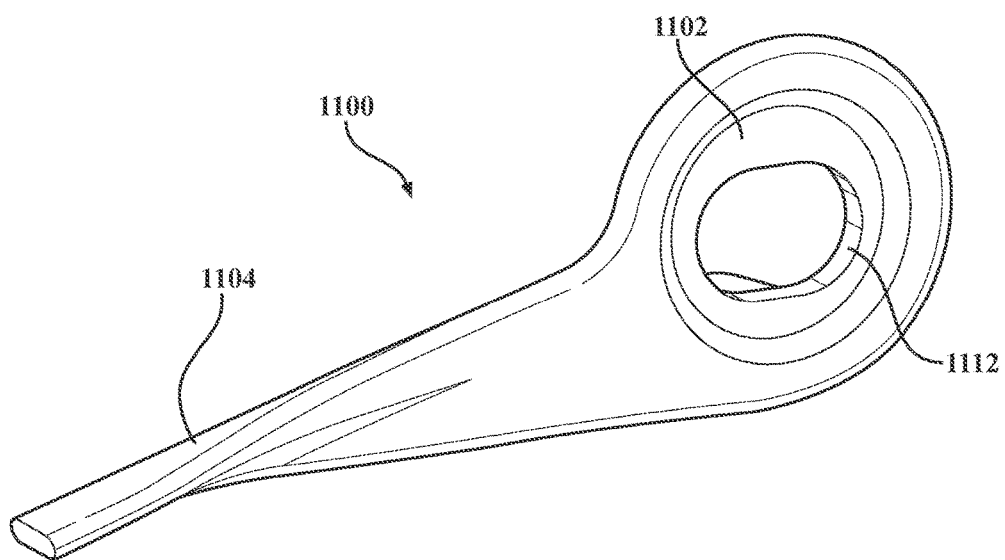
FIG. 11C is a perspective view of a torque arm for the electrically motorized wheel.

The torque arm 1100 generally includes a ring portion 1102, an arm portion 1104, and a hinge portion 1108 (FIG. 11B) that extends from the ring portion 1102. An inner periphery 1112 (FIG. 11C) of the ring portion 1102, and an increased diameter shaft section, may be non-circular, e.g., oval or polygonal to rotationally key the torque arm 1100 to the shaft 924, yet permit the torque arm 1100 to pivot relative thereto.

Figure 11E:
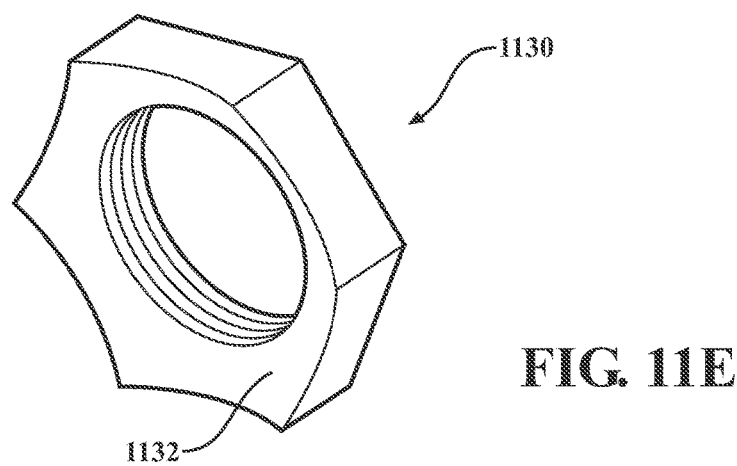
FIG. 11E is a perspective view of a nut for the torque arm for the electrically motorized wheel.
Figure 11D:
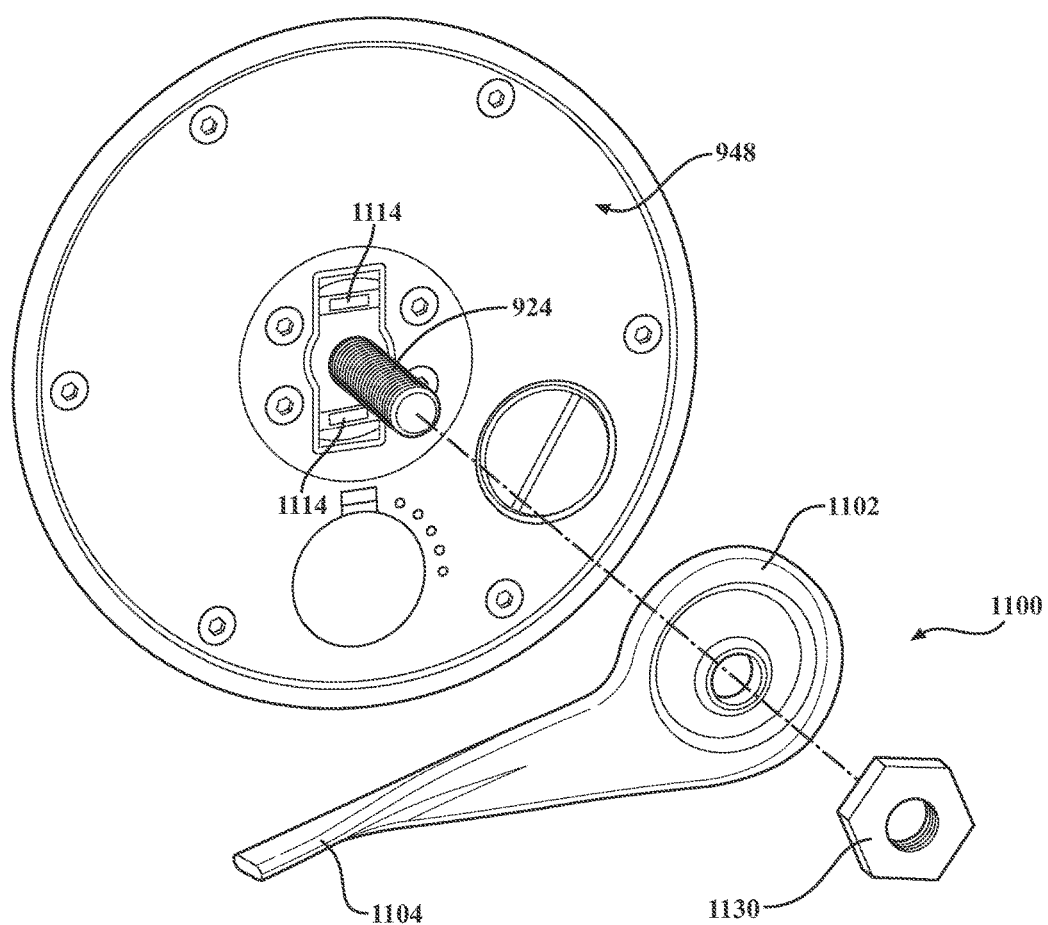
FIG. 11D is a perspective view of a torque arm for the electrically motorized wheel.

The hinge portions 1108 extend from the ring portion 1102 to interface with respective indentations 1114 in the user interface system 948 (FIG. 11D). The hinge portion 1108 defines a pivot for the torque arm 1100 such that the arm portion 1104 may interface with a frame member 1120, and alternatively, may be secured thereto via a clamp 1052. It should be understood that various clamps and other interfaces may be utilized to secure the arm to the frame member 1120 as well as positional relationships that do not require a clamp such as that which locates the arm portion 1104 to rotationally ground the static system to the frame member 1120.

The hinge portions 1108 further permit the design of other torque resisting interfaces other than the illustrated torque arm 1100 design that couples the non-rotating parts to a bike frame. For example a manufacturing tester might have a complete differently shaped reaction torque mount that utilizes the same mating features.

A lock nut 1130 may include a non-planar surface 1132 (FIG. 11E) such as a concave, conical, arcuate, or semi-spherical surface to interface with a related convex, conical, arcuate, or semi-spherical surface 1015 (FIG. 11C) to accommodate any angle of the torque arm 1100 with respect to the shaft 924 to interface with the frame member 1120 (FIG. 11A).

The torque arm 1100 facilitates accommodation of different bicycle frames, is rotatable when aligning the electrically motorized wheel to the bicycle frame during install, then pivot outwards or inwards with respect to the electrically motorized wheel, such that the torque arm 1100 remains directly under the frame member 1120 onto which the electrically motorized wheel is installed. This facilitates effective torque transfer and uncomplicated installation of the electrically motorized wheel. Further, although this torque arm embodiment has specific illustrated components in a bicycle embodiment, the embodiments of this disclosure are not limited to those particular combinations and it is possible to use some of the components or features from any of the embodiments in combination with features or components from any of the other embodiments.

Figure 12A:
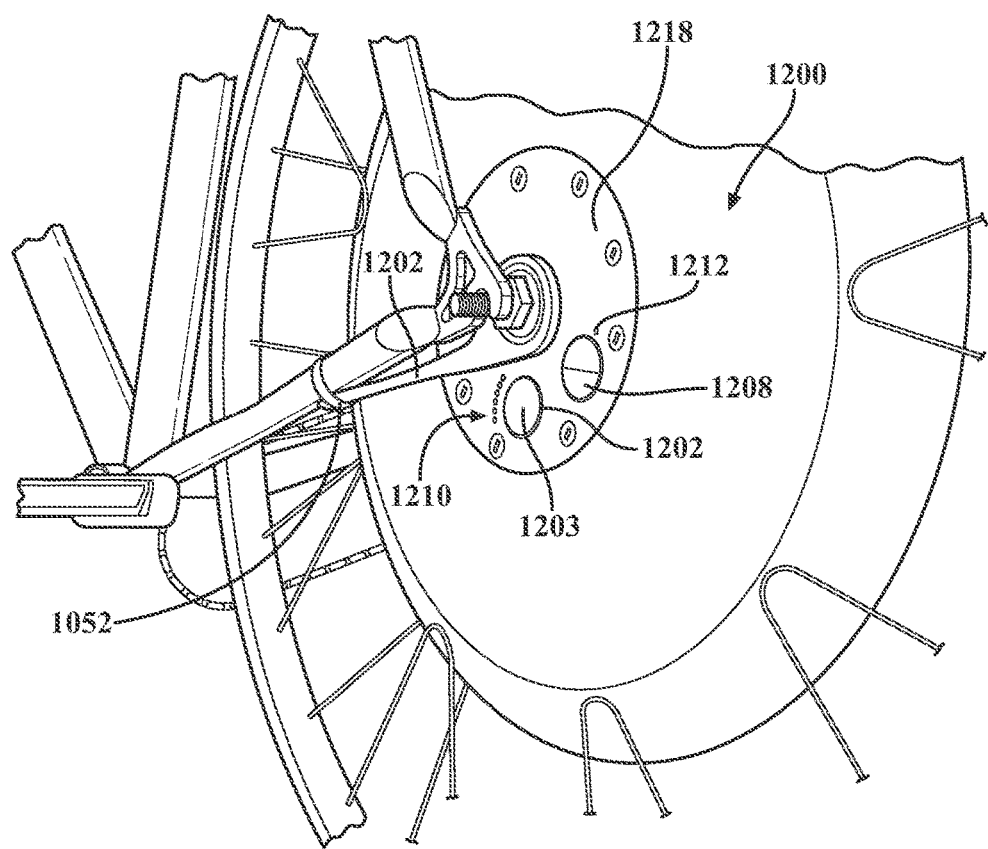
FIG. 12A is a perspective view of a user interface for the electrically motorized vehicle.

With reference to FIG. 12A, the user interface system 948 include a user interface 1200 that is located on the non-drive side to support the torque arm 1100 (FIG. 11A) yet remain clear of the mechanical drive system, chain, sprocket, etc. that are located on the drive-side. This permits an accessible user interface 1200 as well as an effective support for the torque arm 1100 with respect to the bicycle frame. In other embodiments, the user interface 1200 may include a display screen.

The user interface 1200 may include a power port 1202 (FIG. 12B) such as a Rosenberger connection under a removable cover 1203, an on/off switch 1208, an arrangement of battery power status lights 1210, and a power indicator light 1212. In one example, the arrangement of battery power status lights 1210 is arcuate to at least partially surround the removable cover 1203, and the power indicator light 1212 may be located adjacent to the rotary on/off switch 1208. The battery power status lights 1210 and the power indicator light 1212 are visible through respective windows 1214, 1216 in a user interface cover plate 1218. In this example, the rotary on/off switch 1208 is generally flush with the interface cover plate 1218 to facilitate, for example minimal aerodynamic resistance. It should be understood that various ports, hardware interfaces, and other user interfaces may alternatively or additionally be provided.

Figure 12B:
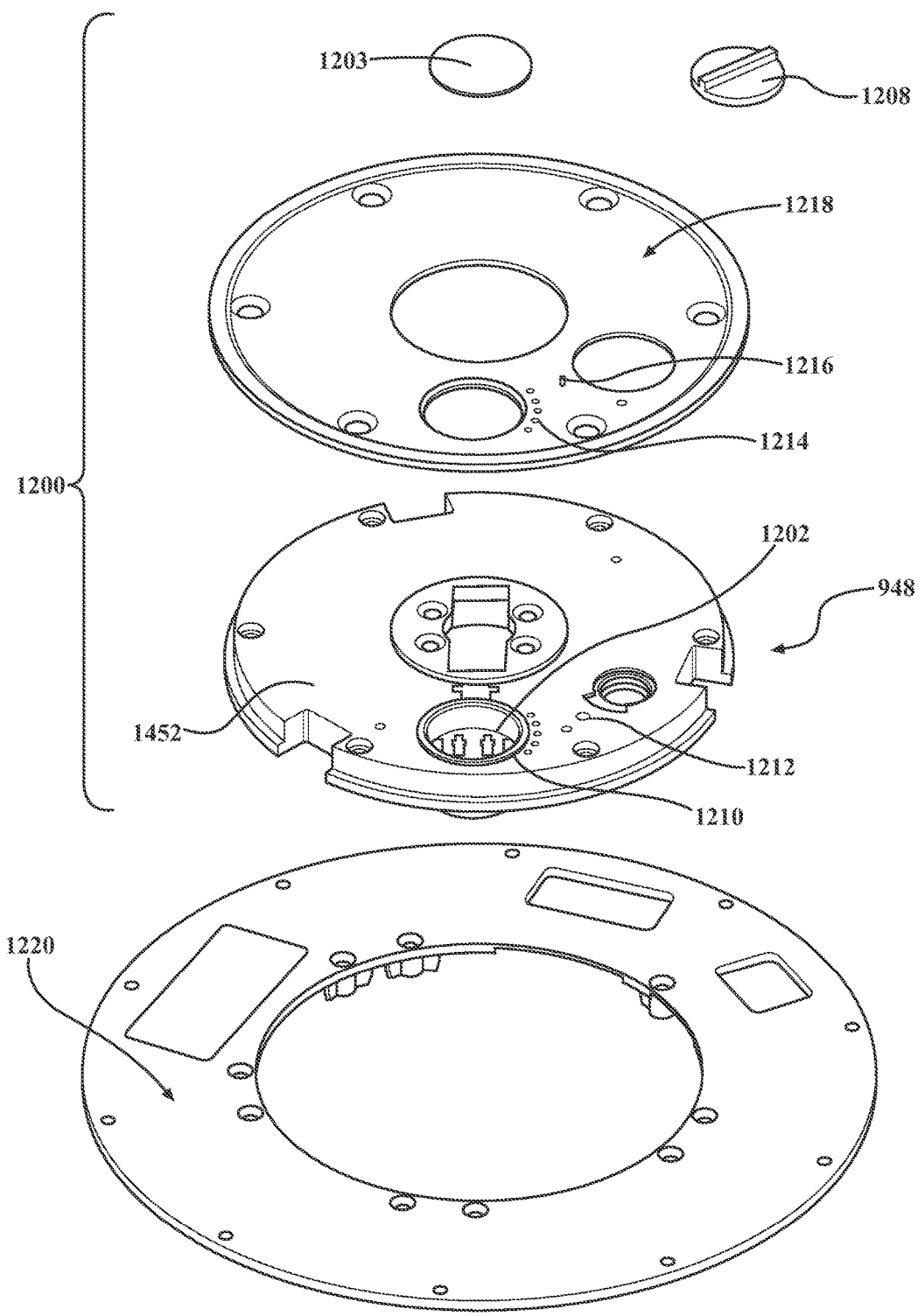
FIG. 12B is a perspective view of a plug for the user interface for the electrically motorized vehicle.

With reference to FIG. 12B, the user interface system 948 may be mounted to a battery mount plate 1220 that supports the battery system 906 in rotationally static manner. That is, the user interface system 948 is a portion of the static system that is at least partially supported by the battery mount plate 1220 about which the rotating system rotates.

Normal operations of the electrically motorized wheel may result in the heating of various components, including motor components, various electrical components, mechanical components, and energy storage components. The generated heat may eventually affect performance of such components; impose stress as a result of thermal expansion and contraction of materials; affect the stability or working lifetime of components; or the like. For example, semiconductor components in processors can be sensitive to heat, batteries can be rendered inoperable, and motors can provide reduced output or be damaged when overheated.

Figure 13A:
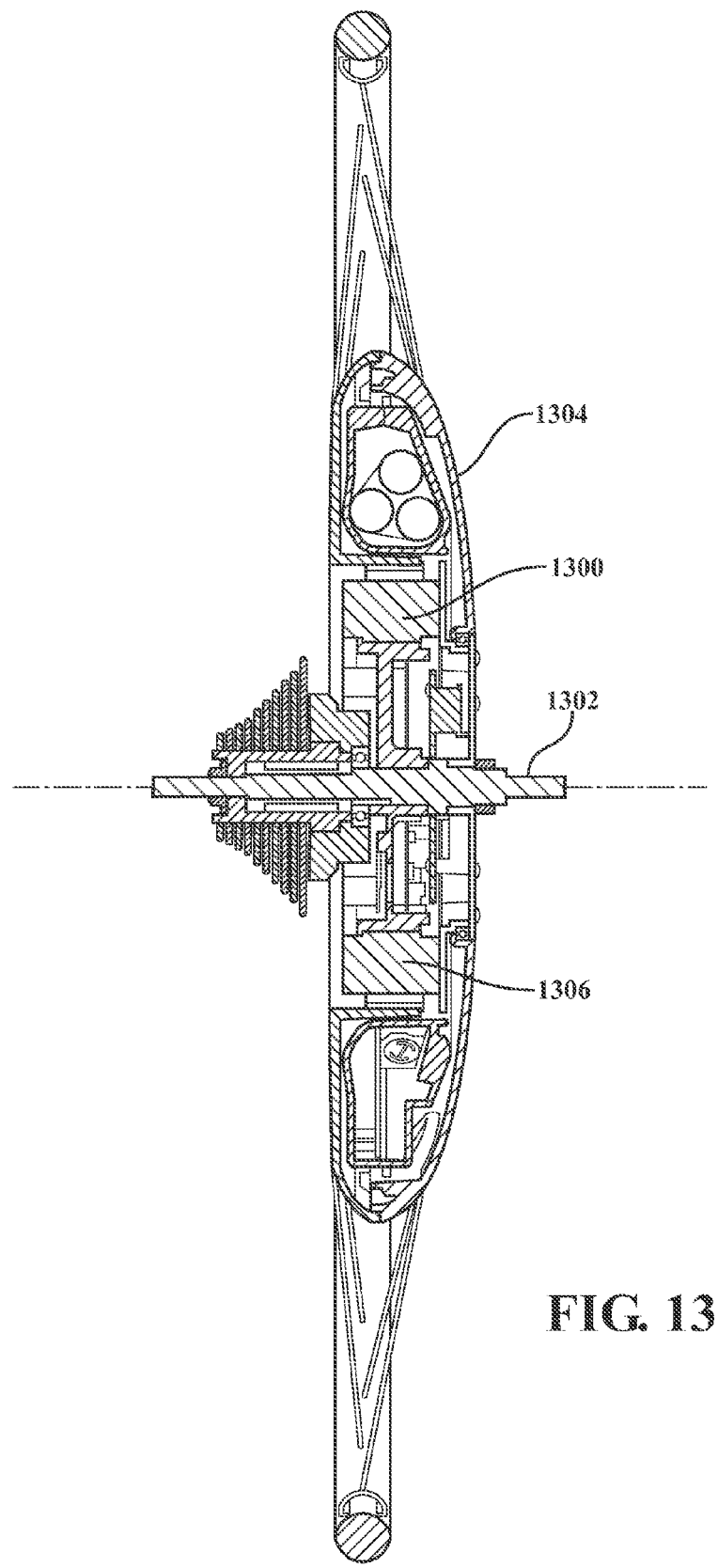
FIG. 13A is a sectional view for a thermal path within the electrically motorized wheel.
Figure 13B:
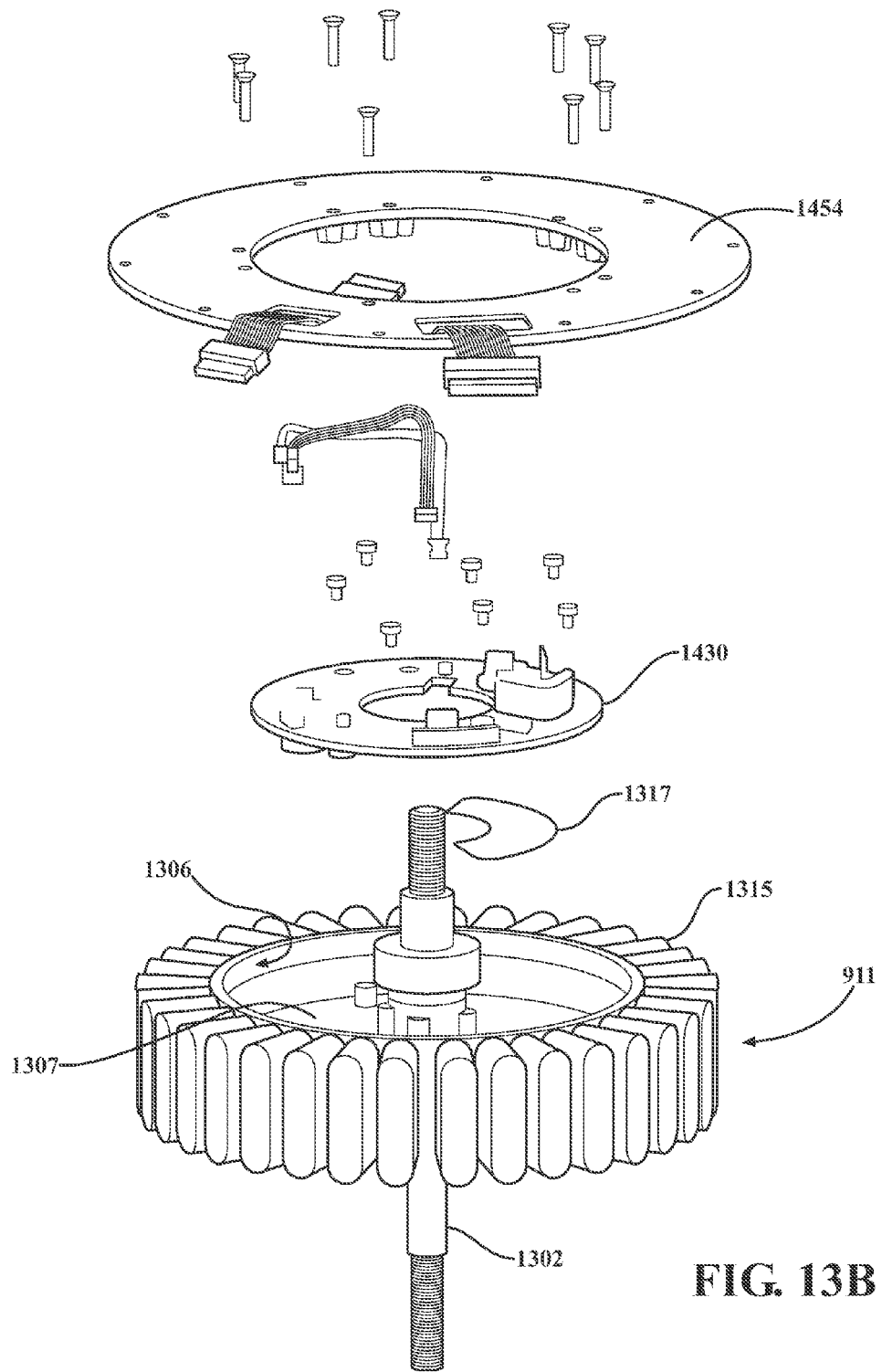
FIG. 13B is a perspective view for a thermal path within the electrically motorized wheel.

With reference to FIGS. 13A and 13B, passive thermal management is performed through the conduction of heat along a conductive thermal path 1300 to the shaft 1302, thence into and/or through the hub shell assembly 1304. Both the electric motor windings 1315 of the stator 911, and the main control board 1430 of the control system are non-moving in embodiments.

In embodiments, the motor windings 1315 surround a hub 1306 of the stator 911, while a heat generating electronic board, such as the main control board 1430 is mounted directly thereto. The control system thus utilizes a web 1307 of the hub of the stator 911 as a heat sink for the main control board 1430 (FIG. 13B). A thermally conductive, yet electronically insulated pad 1317 may also be utilized between the board 1430 and the stator 911.

The stator 911 is mounted to the shaft 1302 that is attached to the frame of the bicycle. Some of the heat from, for example, the control board 1430 and the motor windings 1315, thus ultimately flows through the stator 911 to the shaft 1302, thence to the bicycle frame along the conductive thermal path 1300. The bicycle frame thus operates as a heat sink of significant volume.

Figure 13C:
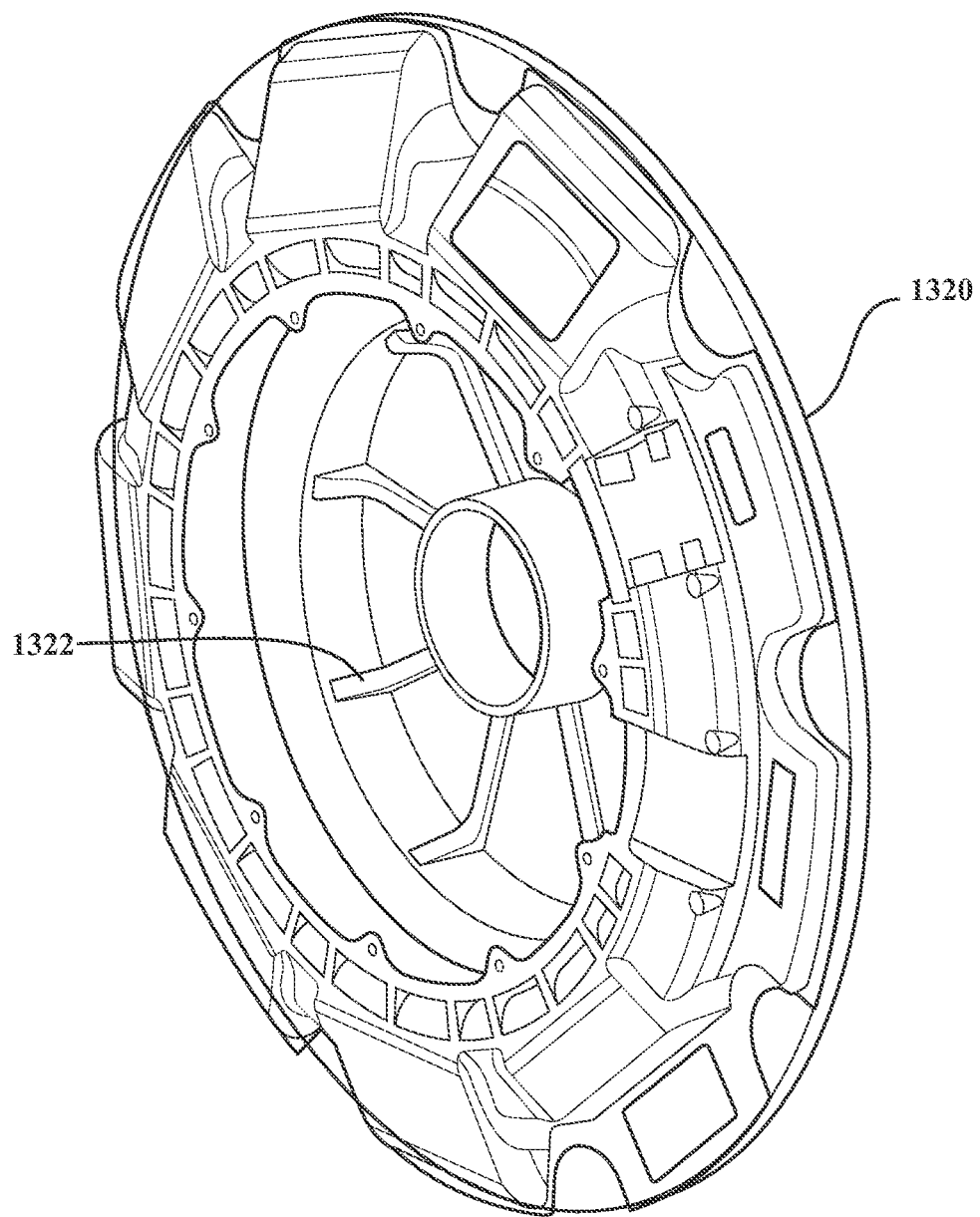
FIG. 13C is an outer side view for a thermal path within the electrically motorized wheel.

With reference to FIG. 13C, a drive side shell 1320 may include internal convection elements 1322. The convection elements 1322 may be fins of various thermally radiative shapes that are located, for example, on the interior surface of the drive side shell 1320 to maximize airflow such as within and/or along gaps through which air may inherently flow. The convection elements 1322 may be otherwise positioned to facilitate direction of airflow. That is, the convection elements 1322 may guide free stream airflow as well as that airflow which is generated from the rotation of the rotating hub shell assembly 1304.

The drive side shell 1320 may also be manufactured of a lightweight material such as aluminum, magnesium, titanium, and other alloys for heat transfer without air exchange. Some of the heat from, for example, the battery system 906, the main control board 1430, and/or the motor stator 911, heats the air inside the spinning hub shell assembly components 1304 1320 and the air transfers the heat to the full internal surface area of the spinning hub shell assembly components 1304 1320 which, in turn, transfer the heat through conduction to the external surface and through convection to the ambient air around the exterior of these hub shell assembly components.

In other embodiments, an active cooling system communicates air through or over the heat generating components to conduct heat therefrom. The air may be introduced through a passage 1324 (illustrated schematically) such as a vent, valve, and/or pump may be actively controlled to open and close so as to initiate, moderate, and control, the airflow.

In one example, airflow may be selectively induced by opening the passages 1324 to the ambient environment to provide passive cooling. Alternatively, one or more heat exchangers within the hub shell assembly 1304 may be utilized to actively cool the airflow. For example, the vent, valve and/or pump may induce airflow in response to a sensor that identifies a temperature above a predetermined or calculated threshold. Such selective operation may be performed so as to minimize aerodynamic interference. That is, drag is typically greater when the passage 1324 or air scoop is open than when closed. Alternatively, the vent may be operated by centripetal force, opening under the force of rotation and closing when the wheel is stopped. This would facilitate water resistance yet provide ventilation.

Figure 13D:
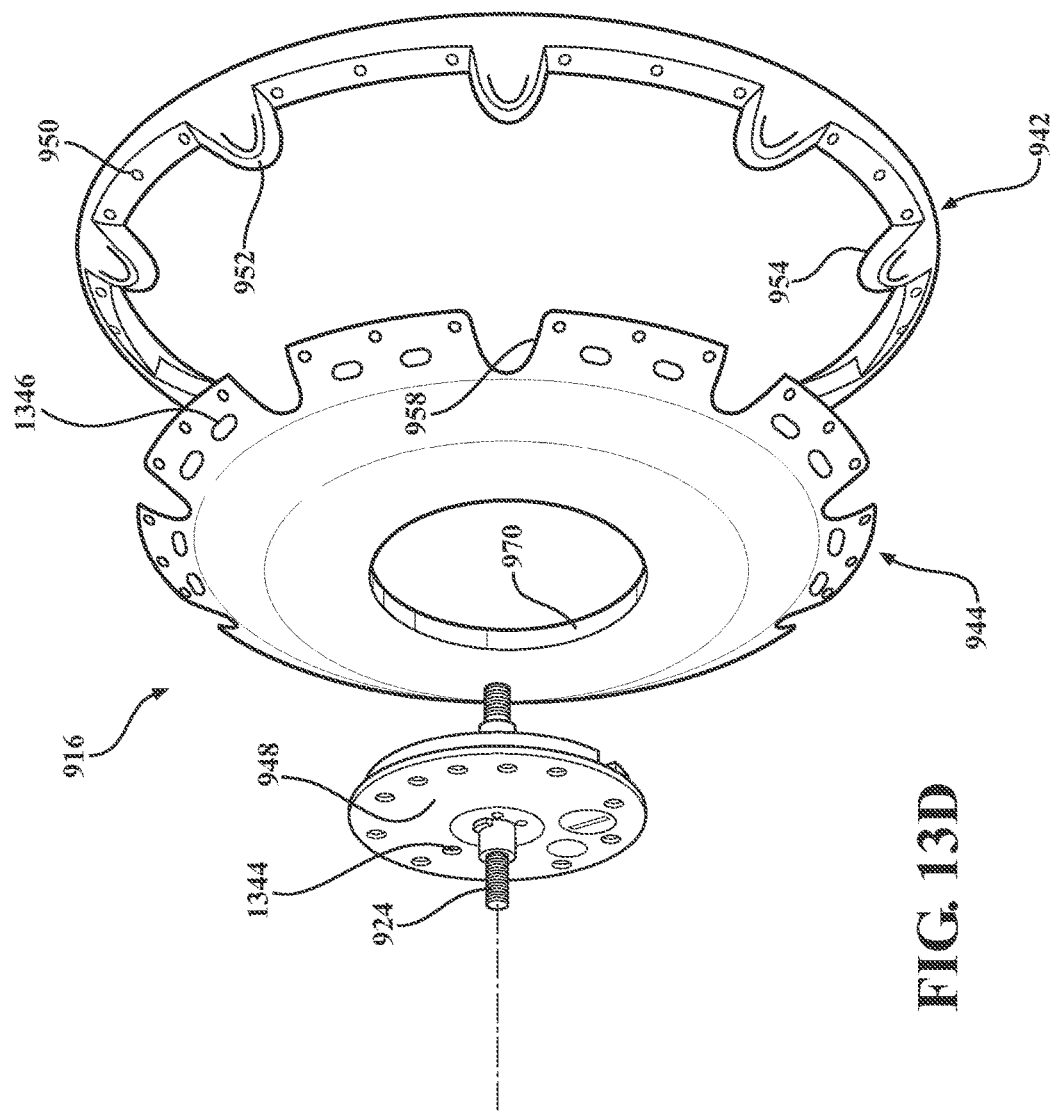
FIG. 13D is an inner side view of an airflow path through the electrically motorized wheel.

In another example, the passage 1324 is generally the internal cavity of the hub shell assembly such that intakes 1344, which may be located in the rotationally fixed UI panel 948, intake air which is then essentially flung radially outward through outlets 1346 in the shell 944 (FIG. 13D).

In embodiments, another fluid such as a gas, vapor, or liquid, may be used. The fluid cooling system may include one or more pumps, valves, or the like, as well as sealed fluid channels that pass the fluid over parts that benefit from conductive cooling. For example, a fluid may be passed over or through one or more of the heat generating components. Alternatively, the fluid may be passed over or through the hub shell assembly 1304 to provide a chilled environment for the components therein. The fluid system may be under control of the control system, which may be responsive to inputs, such as from a user or based on a temperature sensor.

Figure 13E:
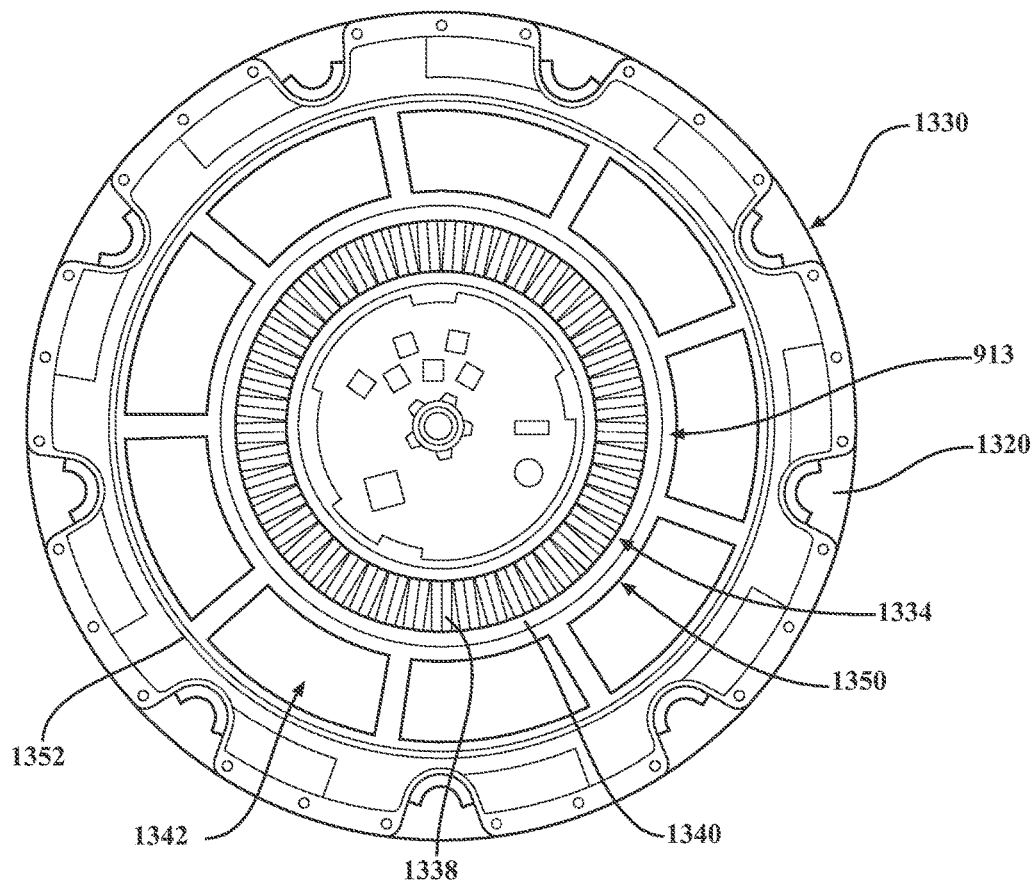
FIG. 13E is a side view of an airflow path through the electrically motorized wheel.

With reference to FIG. 13E, a rotating system 1330 and a static system 1322 may form a gap 1334 of, for example, about 2 mm between a stationary motor winding 1338 and a magnetic ring rotor 913 that is fixed to, and rotates with, the shell 1320. When power is supplied to the motor winding 1338, a magnetic current is induced from the electrical wires wound on the stator 911 causing the magnetic ring rotor 913 and the shell 1320 to rotate. In embodiments, the magnetic ring rotor 913 is arranged between a battery housing 1342 and the motor windings 1338—both of which are stationary—but are organized such that the magnetic ring rotor 1340, located therebetween, rotates with the shell 1320.

A gap 1350 may also be located between the shell 1320 and the contoured battery assembly 1352 as the shell 1320 rotates relative to the rotationally stationary contoured battery assembly 1352. These gaps operate as a thermal insulator. To avoid this insulation effect and induce airflow for cooling, the gap widths may be optimized for passive thermal cooling, mechanical operation, and combinations thereof. Convection elements 1322 of thermal radiative shapes may be positioned to maximize airflow direction such as within and/or along gaps to facilitate passive thermal cooling.

Figure 13F:
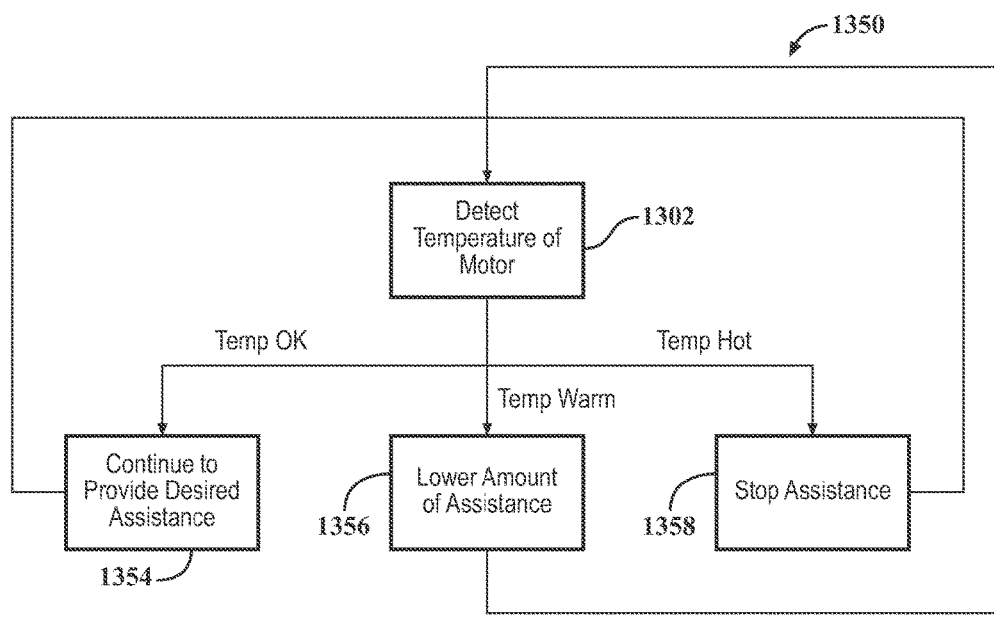
FIG. 13F is a schematic view of a power system for the electrically motorized vehicle.
Figure 13G:
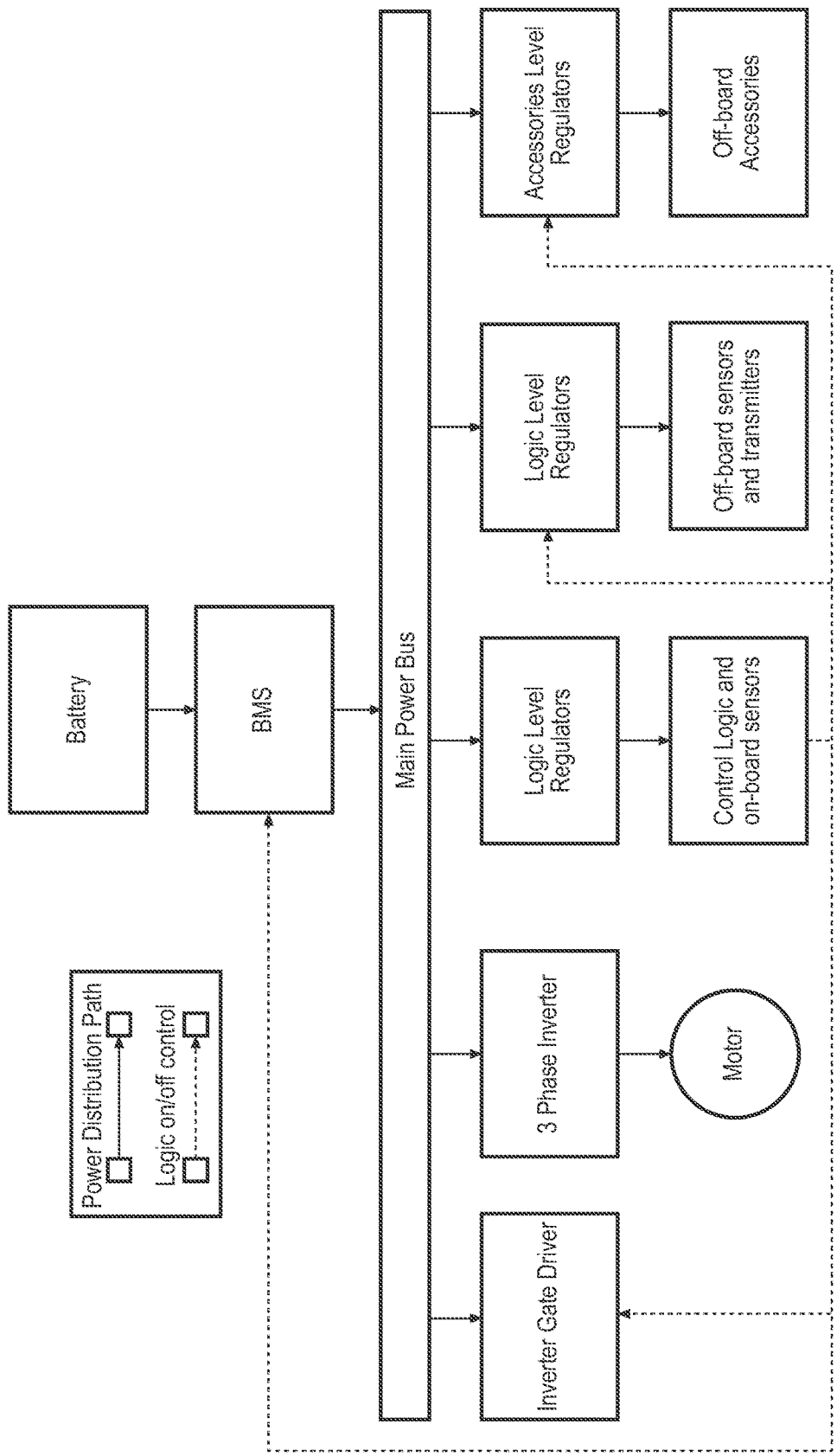
FIG. 13G is a schematic view of a power system for the electrically motorized vehicle.

With reference to FIG. 13F, active thermal management according to embodiments, is performed through control of the electric motor to limit temperatures below a desired maximum. Such active thermal management may be performed through control of power usage within the power distribution system 1360 of the electrically motorized wheel (FIG. 13G).

In embodiments, active thermal control algorithms 1350 generally include sensing temperatures of the electric motor, the main control board and energy stage components, electronic controllers, battery, or other heat sensitive components then attenuating operation of the electric motor, the primary heat source, to limit these sensed temperatures below a desired maximums by selectively attenuating an assistance/resistance 1354, 1356, 1358.

Figure 14A:
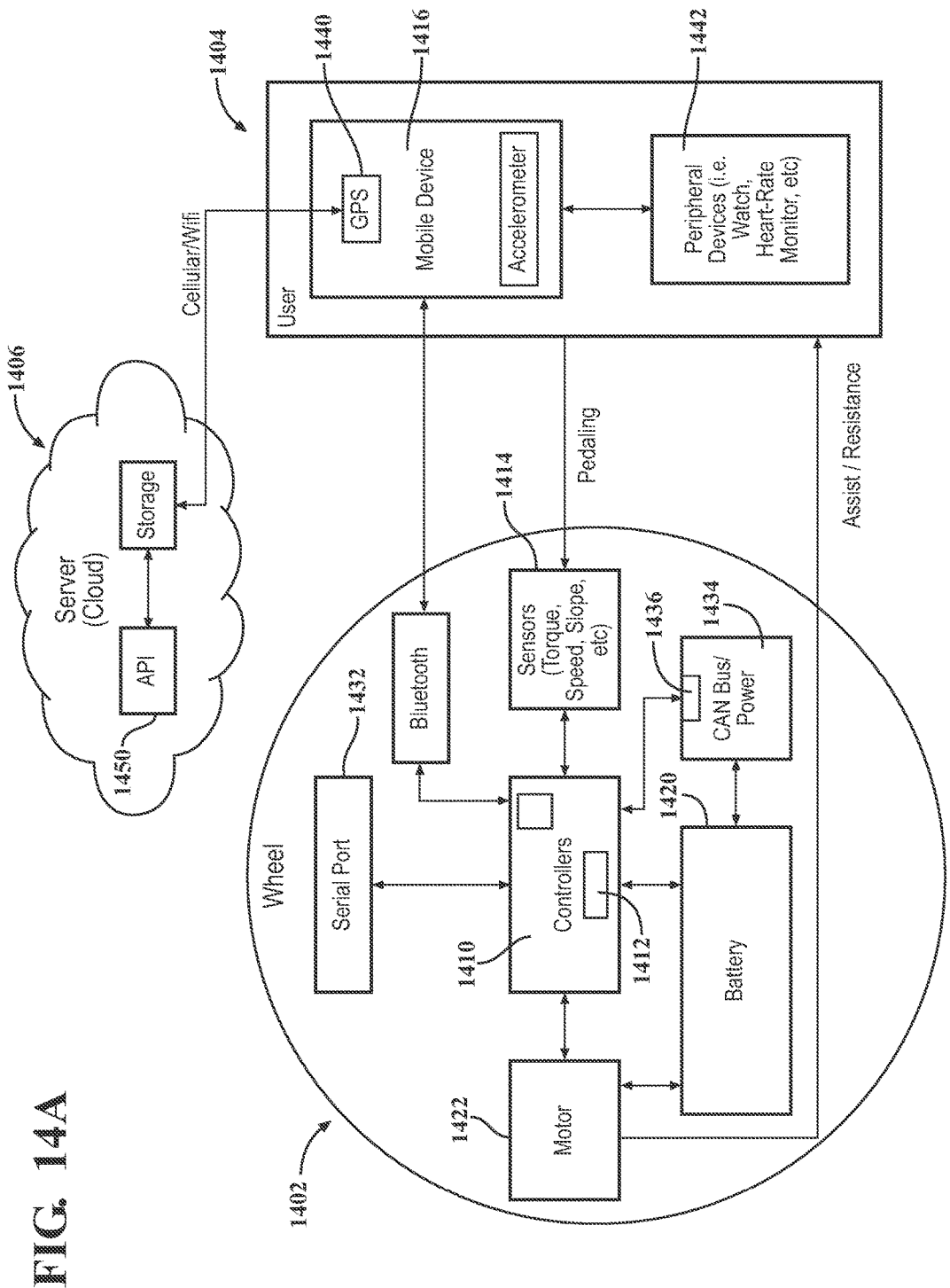
FIG. 14A is a schematic view of a system for the electrically motorized vehicle.

With reference to FIG. 14A, a data flow 1400 can be provided between the electrically motorized wheel 1402, the user 1404, and a server 1406 such as a cloud-based server/API or other remote server, module, or system. Various communication and data links may be provided between the electrically motorized wheel 1402, the user 1404, and the server 1406 such as a mobile device 1416 which serves as an interface therebetween for relatively long range cellular and satellite type communication. That is, a smart phone of the user associated with the electrically motorized wheel 1402 operates as a data link between the electrically motorized wheel 1402 and the server 1406. The electrically motorized wheel 1402 is operable to calculate the assistance and resistance required at any given time, i.e., essentially instantaneously.

The control system 1410 utilizes an algorithm 1412 that applies data from a sensor system 1414 and, if available, the mobile device 1416, to determine an essentially instantaneous energy transfers between a battery system 1420 and an electric motor 1422. The control system 1410 may also regulate and monitor the sensors 1414 and connected components for faults and hazards for communication to the mobile device 1416.

Figure 14B:
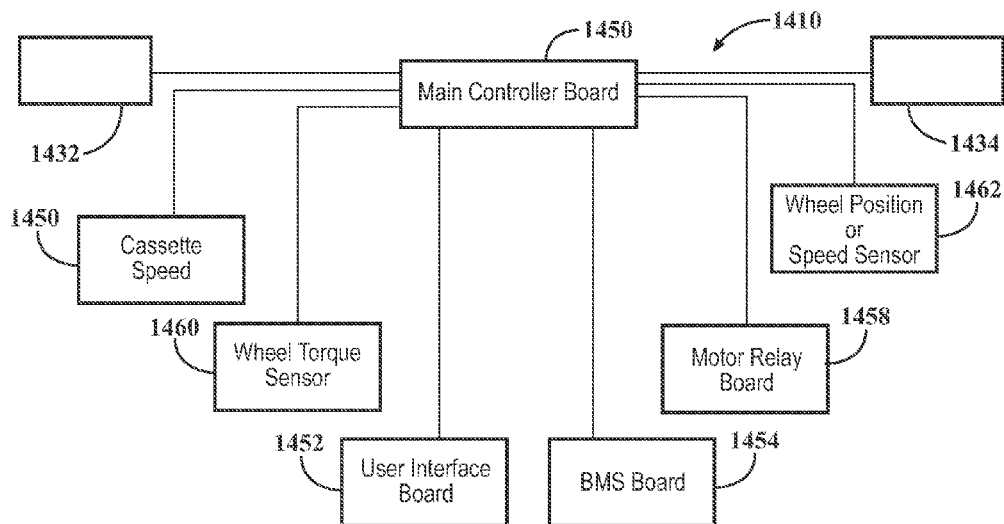
FIG. 14B is a schematic view of a system for the electrically motorized vehicle.

With reference to FIG. 14B, the control system 1410 may include a multiple of printed circuit boards to distribute control, facilitate maintenance, and thermal management thereof. In this example, the control system 1410 includes a main control board 1450, a User Interface board 1452, a Battery Management System (BMS) board 1454 (FIG. 12B), a motor interface board 1458, and a sensor system, here disclosed as a wheel torque sensor 1460, and a wheel speed sensor 1462. It should be understood that the boards may be otherwise combined or distributed. It should also be understood that other sensors such as a GSM, GPS, inertial measurement sensors, weight on wheel strain sensors, chain strain sensors, cassette speed sensors, environmental sensors, and other sensors may be provided and integrated into the one or more of the boards. Further, various ports and hardware interface may additionally be provided, to include, but not be limited to, a diagnostic connector, a charger connector, and/or others.

The User Interface board 1452, in one example, may include relatively short-range wireless systems such as Bluetooth, IEEE 802.11, etc., for communication with the user interface 1200.

In one example, the motor interface board 1458 hosts the motor relay, the motor commutation hall sensors and the motor temperature sensor. The motor interface board 1458 collects those signals to one connector for connection to the main control board 1450.

The Battery Management System (BMS) board 1454 (FIG. 9E) may, in one example, be mounted to the contoured battery assembly 1352. The motor relay board 1458 may be mounted to the stator 911 (FIG. 9F) such that the stator 911 operates as a heat sink.

The control system 1410 may further include a hardware interface 1432, e.g. input ports, data ports, charging ports, device slots, and other interfaces, that permit the plug in of other sensors, hardware devices, and/or peripherals to provide communication with the main control board 1450 and associated boards. Alternatively or in addition, each board may have one or more hardware interface 1432 such as a power port for the Battery Management System (BMS) board 1454.

Additionally, a charging port 1434 that, similar to a USB connector, provides not only power, but also data transfer. This may be performed through, for example, a controller area network (CAN bus) interface 1436 integrated into the connection. Between the hardware interface 1432 and CAN bus interface implementation of additional sensors or external plugin hardware components is readily enabled, e.g., extended battery, lights, humidity sensors, proximity sensors, speakers, anti-theft devices, charging racks, etc.

Data from the hardware interface 1432 may be communicated to the mobile device 1416 via short-range wireless systems. The data may be processed by the mobile device 1416, and/or further transmitted via the mobile device 1416 to a server for processing. Data may be communicated directly from the electrically motorized wheel to the server using relatively long-range wireless communications systems such as cellular, satellite, etc.

Feedback to the user, alterations to control parameters, and/or other data may be communicated to the electrically motorized wheel on the basis of the processed data. In one example, distance sensor data, e.g. RADAR, SONAR, LIDAR, imagery, etc., that provide for identification of an approaching object, may feedback such identification to the user in the form of an audible, visual or tactile sensation. For example, a rear directed camera might communicate imagery to the mobile device 1416 so that a user may be readily apprised of traffic approaching from the rear. Alternatively, identification of an approaching object by the rear directed camera may result in a tactile output from the electrically motorized wheel, e.g., a shaking or jitter, to gain the attention of the user.

In another example, environmental data indicating high humidity levels, altitude, and/or other environmental factors may be utilized to adjust the control parameters for a given mode such that additional motor assistance is provided under such conditions. For example, as the vehicle traverses a mountain, additional assistance may be provided at higher altitudes.

The mobile device 1416 may collect data at a rate of, for example, about 1 data point per second. Each data point may include time and location data stamps from, for example, a GPS module 1440 or the inertia navigation system. Applications to interface with the electrically motorized wheel 1402 may thus perform minimal calculations. Other peripheral devices 1442 such as a wearable health monitor may also be utilized with, or as a replacement for, the mobile device 1416 to provide data collection and/or communication with the electrically motorized wheel.

The electrically motorized wheel may also communicate with a server via the mobile device 1416. The server enables reception and/or streaming of data collected by one or more electrically motorized wheels for communication and display essentially in real time from the mobile device 1416 to the electrically motorized wheel, another electrically motorized wheel, and/or a fleet of electrically motorized wheels such as a delivery service, shopping cart fleet of a store, etc.

The collected data may include direction of travel, faults associated with the fleet vehicle, and other data. Aggregated data collected from a single electrically motorized wheel, or multiple electrically motorized wheels, may then be utilized to, for example, analyze routes and modes, provide different analyses of the data, customize a user experience, and/or generate suggestions for a more efficient commute.

In embodiments, the hardware interface 1432 may be utilized to charge devices such as a mobile device 1502. That is, the mobile device 1502 such as a smart phone may be utilized as a user interface to the electrically motorized wheel as well as being charged therefrom.

With reference to FIG. 15A, a mobile device user interface 1500 for a mobile device 1502 may provide selection among various operational modes 1504. The mobile device user interface 1500 may be a downloadable application or other software interface to provide, for example, selection among the operational modes 1504, data communication, and/or data transfer to and from the electrically motorized wheel. In alternative embodiments, the operational mode may be selected for the user, such as based on user inputs, a user profile, information about user history, environmental factors, information about a route, inputs of third parties (e.g., a doctor or trainer) or many other factors disclosed throughout this disclosure. Selection of an operational mode may occur at the wheel 100, on the user mobile device, or remotely, such as on a server or other external system.

In embodiments, an algorithm 1508 that governs a control regime for a device of the wheel 100 such as to control operation of the electrically motorized wheel or device thereof typically includes a set of parameters in which each parameter is a placeholder for a multiplier, or gain, in the algorithm 1508. The selected mode 1504 provides values for the set of parameters, one of which may optionally select which algorithm or control regime to use. These values may be input into the selected algorithm 1508 to provide an associated level of assistance or resistance the user will experience in response inputs, such as from to the sensor data from the sensor system 1510, data from external systems (e.g., information systems containing terrain information, weather systems, traffic systems, and the like), and further input from the user. It should be understood that each parameter, multiplier, and/or term may correlate to some control relationship such as exponential, a linear function, a step function, or a separate calculation, that relates a control input to a specified level of motor control output.

The system may transition among various operational modes, such as based on user selection or other determination of the appropriate operational mode. Alternatively, in embodiments where the wheel itself does not automatically select an operational mode based on sensor or similar inputs, if no mobile device 1502 or other selection facility is in present communication with the control system 1512, a standard mode may be automatically set as a default operational mode, or the wheel may use the most recently used past mode, if a mobile device or other selection facility was previously connected. Generally, in bicycle embodiments, the user need only ride the bicycle, and the wheel sensor system 1510 will sense various input data such as torque, slope, speed, etc., that is then communicated to the control system 1512 that employs the algorithm 1508. The operational mode selected by the user via the mobile device, or otherwise selected, essentially provides values for the parameters in the algorithm 1508. When the parameters, having the appropriate values for the selected operational model, are applied to the present set of inputs (such as sensed by the sensor system 1510 or otherwise obtained, such as by a data collection facility of the wheel 100), the algorithm produces an output. The output determines the current control command for the wheel, which in embodiments is essentially a specification of the nature and extent of the energy exchange between a battery system 1514 and an electric motor 1518. The output of the electric motor 1518 is the level of assistance or resistance that the user experiences when operating the wheel 100, which varies for a particular situation, based on the selected mode.

For some operational modes, the value for a single parameter may be supplied to the algorithm 1508. This value may represent an overall gain for the assistance provided. For example, a standard mode may provide an overall gain value of one (1) to the algorithm 1508, in contrast to a "turbo" mode that may result in an overall gain value greater than one (>1) being supplied to the algorithm 1508. Conversely, a selection of an "economy" mode may result in an overall gain value less than one (<1) being supplied to the algorithm 1508. Alternatively, the overall gain may be used to adjust the algorithm based upon the total payload weight the wheel is propelling, compensate other environmental conditions such as a head wind, or other conditions.

For some operational modes, a plurality of parameter values may be supplied to the algorithm 1508. These values may be associated with parameters representing multipliers or gains for different portions of the algorithm 1508 to control various components that contribute to the overall ride, such as wheel data, user input data (such as torque or cadence), environmental factors (such as slope or wind resistance), "gestures" or command motions, such as sensed at the user inputs (such as backpedaling to control braking), etc. The parameters may alternatively or additionally represent multipliers for different sensor values and/or calculated values representative of various components that contribute to the overall ride.

In embodiments, the algorithm 1508 can have a general form that relates control inputs to outputs. The control inputs may fall generally into a set of categories such as inputs that relate to inputs from the rider or another individual, either sensed (e.g., as rider torque) or entered data (e.g., as a riders weight or age, a training goal entered by a physical therapist for the rider, a work constraint entered by a physician of a rider, or the like); inputs that relate to the operational state of the electrically motorized wheel (e.g., wheel speed); inputs that relate to the conditions of the environment or operational context of the wheel (e.g., slope, temperature, wind, etc.); and inputs collected from various data sources (e.g., other vehicles, other wheels, traffic networks, infrastructure elements, and many others). These inputs may be combined with other parameters such as gains, or passed through other conditioning functions such as a filter. The output of these combinations of inputs may be the "terms" of the algorithm 1508. These terms may be linear, non-linear, discrete, continuous, time-dependent, or time-invariant.

These terms may then be summed, multiplied, divided, or otherwise combined (such as taking the maximum or minimum of some or all of the terms) to provide one or more outputs. In some embodiments, it may be advantageous to provide a multitude of terms in the control system that isolate or separate conditions under which a user would receive assistance or resistance. For example it may be advantageous to be able to have a separate terms for the amount of effort that a rider puts in and for aerodynamic forces such as riding against the wind.

This beneficially allows each term to have a form that is suited to the input and underlying phenomenon. For example in the case of the rider effort, it may be a linear or proportional response, and in the case of aerodynamic forces it may be proportional to the square of the wheel or vehicle speed at lower speeds and a cube or other function at higher speeds. The rider, or one specifying the response of the wheel to inputs, such as a provider of wheels, may thereby readily adjust the gains independently to customize the response of the control to the conditions that they care about, e.g. hills, wind, power, or the like.

Additionally, multipliers on some or all of the terms allow the gains for each term to be scaled together in response to another input. For example, increasing the overall responsiveness to rider inputs with environmental temperature could provide the rider with more assistance when operating in high temperatures and thus prevent a user from excessive exertion or perspiration.

In embodiments, the algorithm 1508 uses a combination of terms (or types of terms). For example, a mechanical drive unit input torque and a wheel operational state (such as wheel speed) may be summed to construct a motor command with the sum including a term proportional to rider input torque and a term proportional to wheel speed. In other examples, terms such as ones based on environmental inputs or data collected by the wheel may similarly be combined with any of the other input types noted in this disclosure.

In another example, the algorithm 1508 use a summation of a series of input terms, each multiplied by gains (which may be adjusted as noted above based on the selected operational mode of the wheel) to yield a command, such as a current command for the motor.

In embodiments, given the various inputs (e.g. rider inputs such as: mechanical drive unit input torque; mechanical drive unit input speed; and rider weight; various wheel operational states, such as wheel speed and angle of the device with respect to gravity; data inputs such as safety information from a traffic system or other vehicle; and environmental inputs such as ambient temperature) a motor command equation may be constructed such as by creating terms proportional to various inputs. For example, the equation may include a term proportional to rider input torque; a term proportional to the square of wheel speed; a term proportional to the angle of the device with respect to gravity; a multiplier that is proportional to ambient temperature; a multiplier that is zero when input speed in zero and increases as input speed approaches wheel speed; and a multiplier that is proportional to the rider's weight (optionally normalized to a base weight). The terms may then be summed, and where applicable the sum may be multiplied by a multiplier.

In an embodiment, the gains may be independent and variable over time. This allows the rider, provider, or other user to adjust the response to a desired preference. Additionally, multipliers may allow some overall multiplication of the response to factors that in general may warrant an overall increase in assistance, such as a hot ambient temperature.

Alternatively, or in addition, the algorithm 1508 can be constructed in a manner that allows switching between different forms, such as among the examples given above. In this case, one parameter of the equation may be an identifier for which form of equation to use (i.e., which terms, gain parameters and multipliers are to be used, such as for a selected operational mode).

Figure 15B:
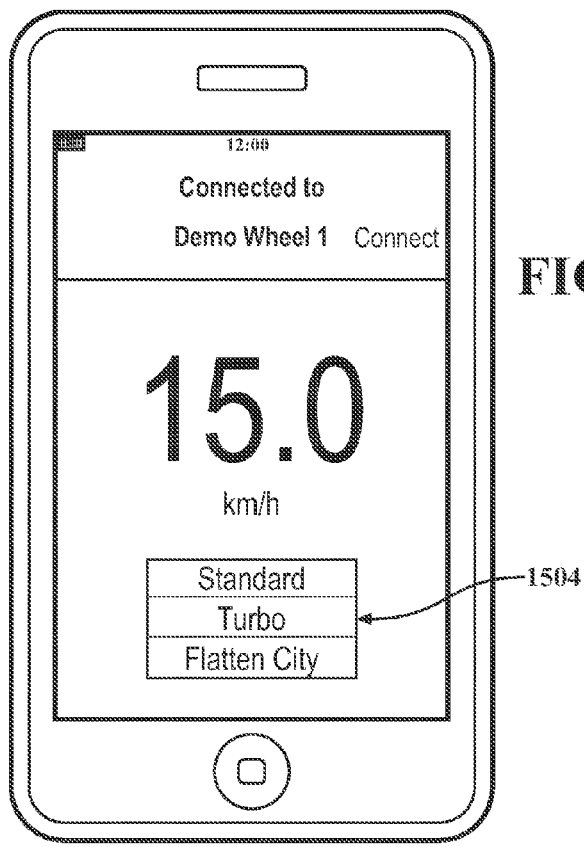
FIG. 15B is a page of a mobile device in communication with the electrically motorized vehicle.

With reference to FIG. 15B, the user may select an operational mode from a multiple of operational modes that alters the behavior of the electrically motorized wheel. Each mode may include one or more parameter settings, and/or combinations thereof to change the operational behavior of the electrically motorized wheel. Example operational modes 1504, as will be further described, may include a "turbo" mode for maximum assistance; a "flatten city" mode; "fitness challenge" mode; a "maximum power storage" mode a "standard" mode; a "exercise" mode; a "rehabilitation" mode; a "training" mode, a "commuter" mode, a "maximum help" mode etc. The "flatten city" mode may provide motor assistance on ascents and hill climbs, with braking on descents to thereby "flatten" the terrain. The "commuter" mode may allow a user to enter a "not-to-be-exceeded" torque or exertion level to modulate the assistance. The exercise mode may allow a user to enter a total number of Calories to be burned, a desired rate of Calorie burn, a maximum level of exertion or torque, etc. Each mode may also include adjustable parameters to automatically modulate the assistance provided over the duration of the ride by the electrically motorized wheel such as a minimum time that the assistance must be available, maximum speed, and/or others.

The mobile device user interface 1500 may present the multiple of operational modes 1504 in an order that allows a user to browse different control parameters, such as Eco-Mode; Maximum Assistance Mode; Target Energy Mode, Maximum Energy Storage, etc. That is, a user can essentially scroll through a multiple of operational modes.

Alternatively, the mobile device user interface 1500 may provide an "automatic mode" that selects the desired mode automatically without user input. That is, the automatic mode may be speed based to select between modes during a trip so that the vehicle obtains the shortest time. Alternately, the automatic mode may be time based to select between modes during a trip so that the vehicle reaches a destination at a desired time. Such selections may be made based completely on sensor data determined by the electrically motorized wheel, or alternatively or in addition with data from a server or from other data devices that a user may be using such as a health monitoring device such as a heart rate monitor.

The "flatten city" mode provides assistance or resistance on non-level terrain. Adjustable parameters may include data about the level of assistance, minimum incline of the hill before rendering assistance, and others. That is, the amount of assistance while travelling uphill and the amount of resistance while traveling downhill may be controlled to require user input about equivalent to a user input required on a level surface.

The "maximum speed control" mode introduces braking on hills to limit the maximum speed of the vehicle. Such a "maximum speed control" may also determine the maximum permitted speed to particular legal jurisdictions as determined by a global Positioning Unit.

The "maximum energy storage" mode maximizes the power storage achieved. Such "maximum energy storage" mode may also be related to energy conservation or energy recovery.

The "fitness challenge" mode might include applying resistance to the electrically motorized wheel to require additional effort by the user and thus provide a work-out to the user.

The "fitness challenge" mode may provide parameter assistance and resistance to, for example, simulate intermittent uphill climbs, an uphill climb of a desired duration, height or other parameter. Such parameter assistance and resistance may be associated with a user's performance or preset conditions, work-outs, heart rate, etc. The "fitness challenge" mode may also provide visual/audible encouragement to user via a mobile device. The encouragement may indicate upcoming challenges and an expected output by the user and may be presented on the mobile device user interface 1500.

Adjustable parameters for each mode may include data about the desired destination, a maximum desired exertion for the user, the maximum desired speed, current location, and others. Data such as destination may be used together with data on current geospatial location, possible routes to a destination and associated road modes, traffic data, user preferences, user capability/fitness level, together with data related to wheel capacity such as energy storage data and others. The combination of data may be used to suggest possible routes, manage power utilization over the selected or anticipated commute route, estimate remaining battery life based on available energy, user fitness level, topography of proposed route, etc.

Figure 15C:
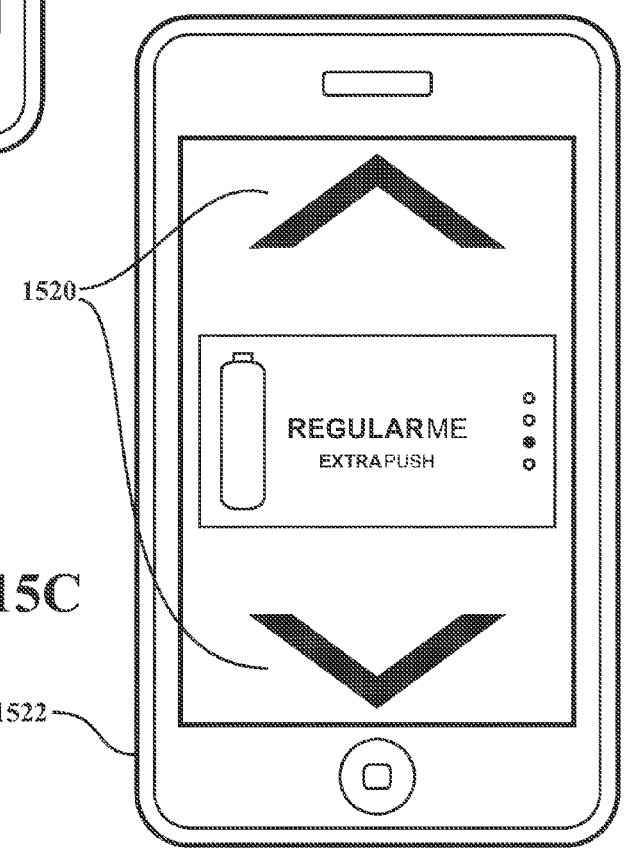
FIG. 15C is a page of a mobile device in communication with the electrically motorized vehicle.

With reference to FIG. 15C, the user interface may include relatively large buttons 1520 and/or icons for navigation functions such as scrolling through the different modes as well as other actions which may be performed while the vehicle is in motion, or idle during a trip (e.g. at a stop light). The use of the large buttons 1520 facilitates visibility and selection while riding. The large button 1520 may occupy a significant portion of the available screen area so as to enable easy selection by a user, for example, the buttons 1520 on the mobile device 1522 may each occupy a minimum of 1 inch by 1 inch of display space.

Figure 15E:
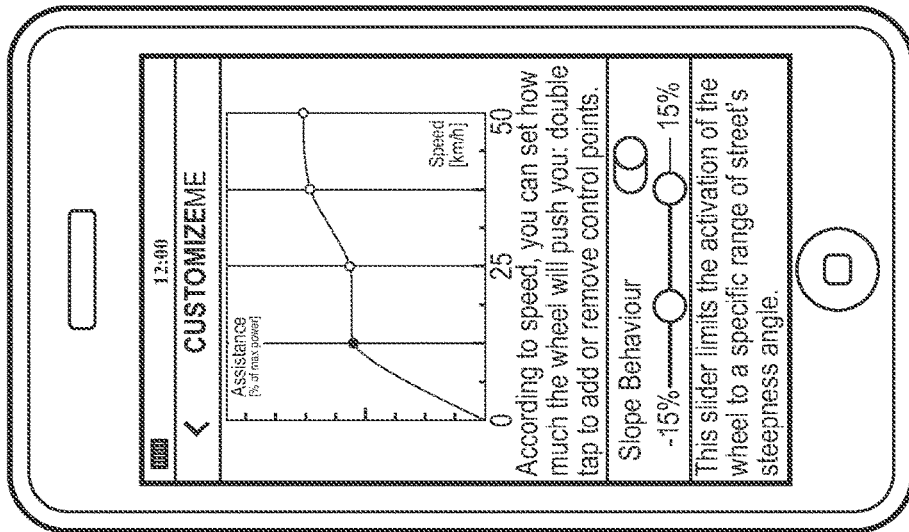
FIG. 15E is a page of a mobile device in communication with the electrically motorized vehicle.
Figure 15D:
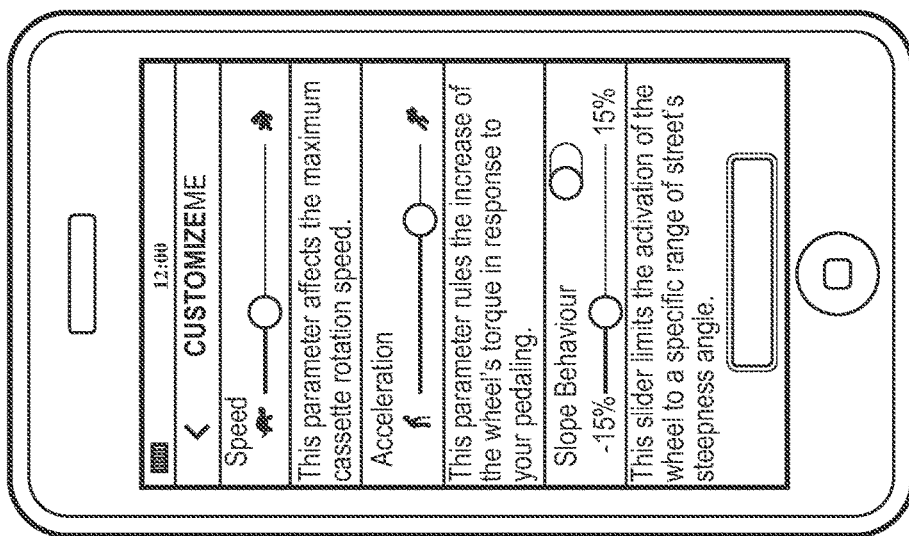
FIG. 15D is a page of a mobile device in communication with the electrically motorized vehicle.

Similar to creating custom sound settings with an equalizer, the user can create custom assistance modes from within the mobile application, or by logging into their account online. With reference to FIG. 15D, upon selection of an operational mode, the mobile user interface may permit the input of parameters 1530 such as a maximum speed of the cassette, an acceleration in response to pedaling, slope behavior and/or other inputs. In one example, the inputs may be provided via a slider. Once the parameters have been entered, the user mobile interface may transition to a progress screen 1538 (FIG. 15E) that highlights progress to the goal such as the destination and specified calorie burn.

Figure 16B:
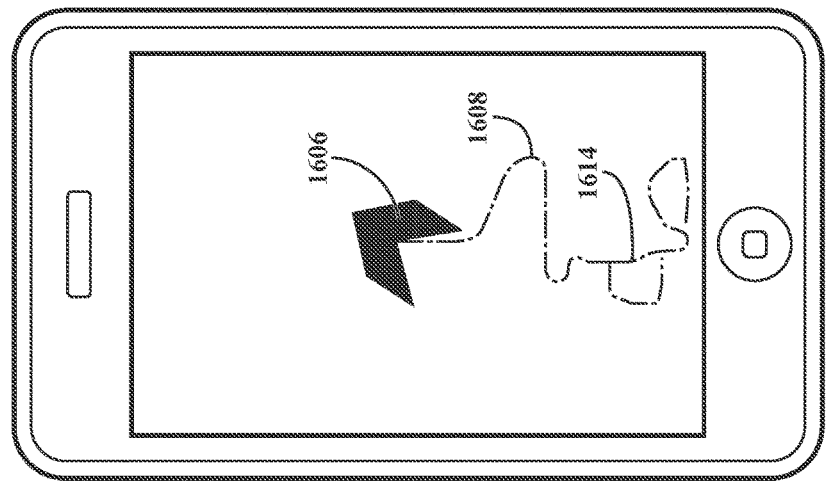
FIG. 16B is a mobile device page of a system for the electrically motorized vehicle.
Figure 16A:
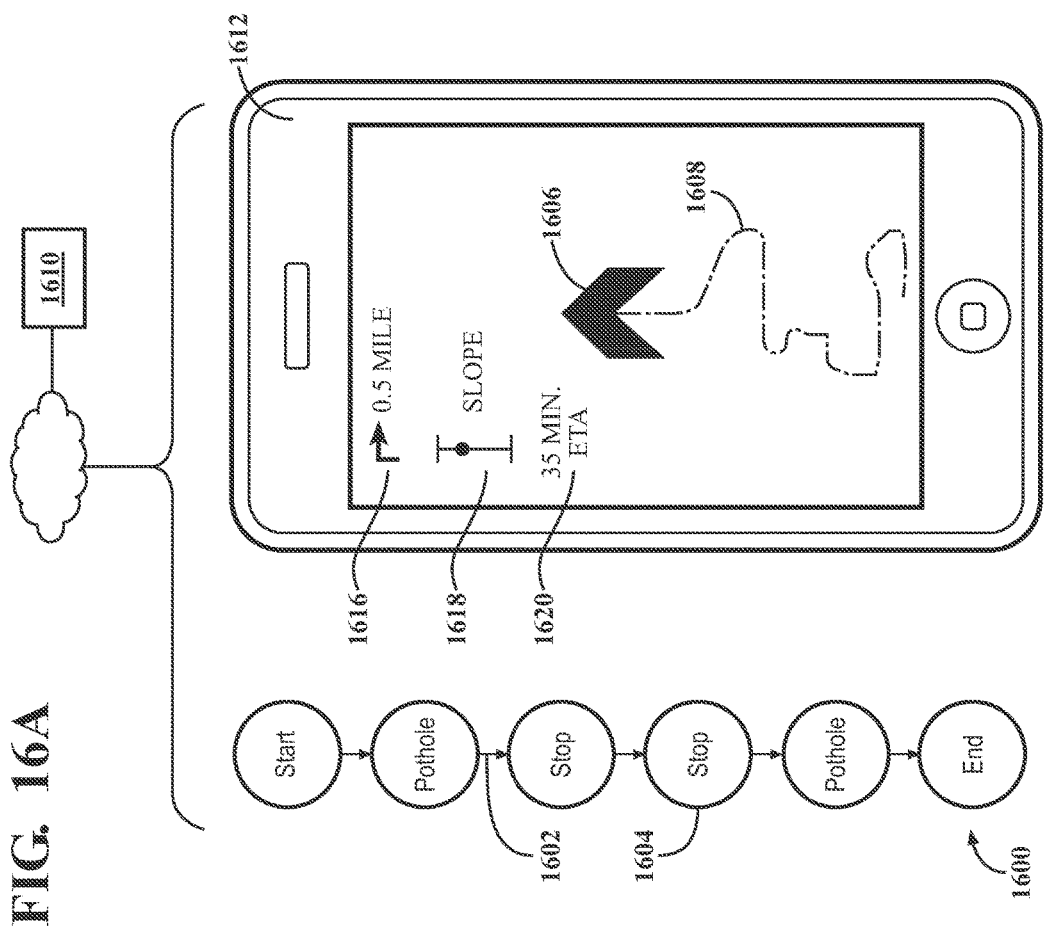
FIG. 16A is a schematic view of a system for the electrically motorized vehicle.

With reference to FIG. 16A, a trip 1600 may be represented as, a line 1602 with one or more events 1604 there-along. The mobile device or other application may calculate the trip 1600. A directional arrow 1606 may also be provided for guidance along a calculated route 1608 to navigate without a map, and without turn-by-turn directions. Instead, the directional arrow 1606 points in the direction of the destination which may be advantageous as bicycles need not be necessarily restricted to motor roadways.

The route 1608 may be accompanied by other symbology such as, for example, distance notation 1616 to indicate how far to the next turn. Further, the view may be presented to account for the vehicle direction of travel such that the current direction is, for example, straight up to facilitate orientation. Other symbology such as an elevation graph 1618 may be provided to indicate upcoming hills, a time such as ETA 1620, and other such navigation and trip related data.

In embodiments, the route 1608 may be enhanced for a particular user through a slight alternation 1614 in the route 1608 (FIG. 16B). For example, various third party data sources such as demographic data of an area may be utilized to determine the route 1608 so as to avoid areas based on various parameters in response to a user selection.

The data from each trip 1600 may be communicated either directly to a server 1610 using a wireless or cellular technology, or from the control system of the electrically motorized wheel to the connected mobile device 1612 thence to the server or stored on the mobile device to be communicated to the server at a later time according to a set of rules that may include, for example, battery charge on the mobile device, signal strength, the presence of a Wi-Fi connection, and others.

Alternatively, aggregated data from a multiple of other electrically motorized wheels may be searched to select, for example, a more efficient, faster, or more scenic route. Data from the server may be associated with the specific electrically motorized wheel that generated the trip data then aggregated with trip data from other electrically motorized wheels. The aggregated data may then be subjected to statistical techniques for sensing similarity, based on correlations, e.g., based on common segments of the trip data, destinations, origins, etc. The aggregated data may then be provided to the user to, for example, make recommendations for routes, mode selection, and other guidance that will benefit the user.

The electrically motorized wheel and the mobile device 1502 may be utilized to catalogue potholes, road conditions, and other obstacles from, for example, GPS data and accelerometer data along the route. The GPS data and/or other sensors, can be utilize to facilitate such cataloging in an automated manner. For example, start/stops, uneven terrain, and other obstacles can be directly indicated from the electrically motorized wheel via the speed sensor, the torque sensor, and the inertial sensors (accelerometers and gyroscopes) of the sensor system. The torque sensor also directly measures power output from the user for association and catalogue with the route location and conditions.

In embodiments, obstacle detection may be catalogued in response to sudden changes in elevation or acceleration that are detected by the sensor system. That is, the cataloging is essentially automatic. For example, a sudden swerve, detection that the user is standing on the pedal, or other such indices may be utilized to catalog a pothole to a particular GPS position.

Figure 16D:
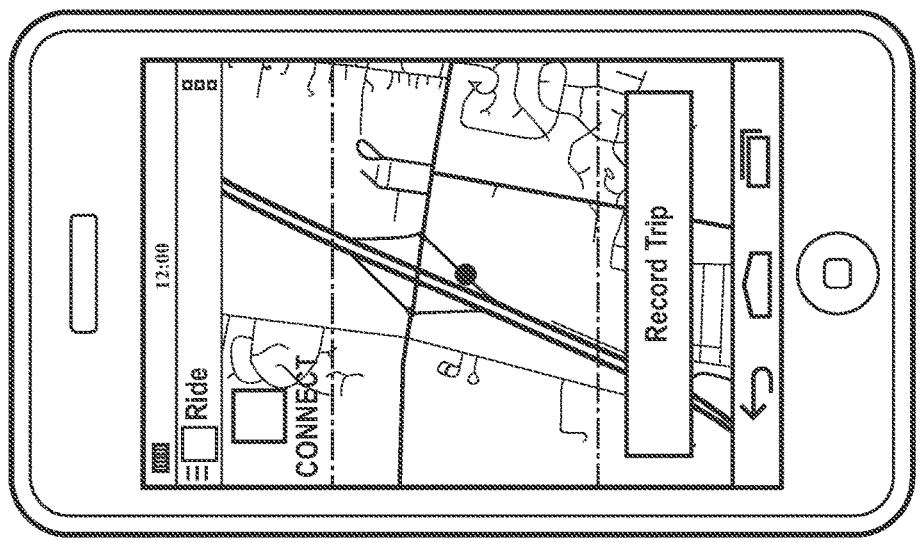
FIG. 16D is a mobile device page of a system for the electrically motorized vehicle.
Figure 16C:
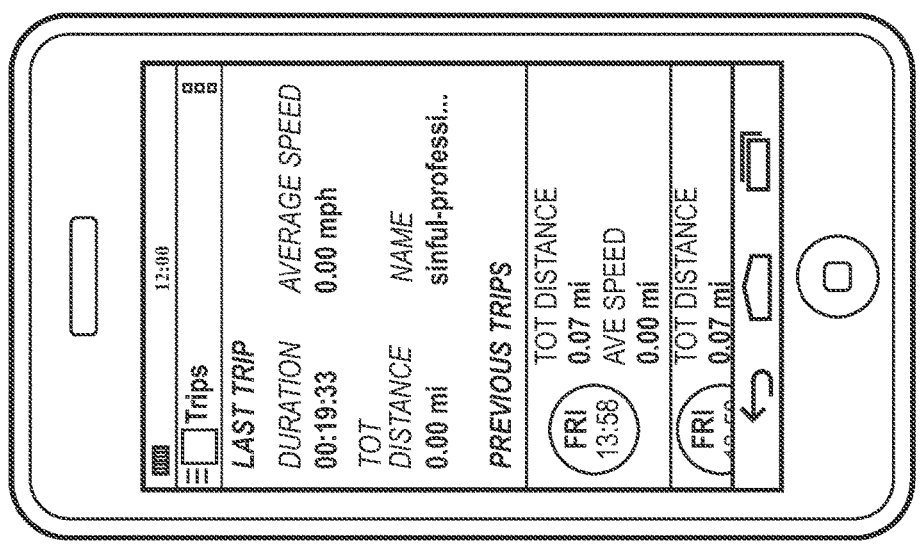
FIG. 16C is a mobile device page of a system for the electrically motorized vehicle.
Figure 16F:
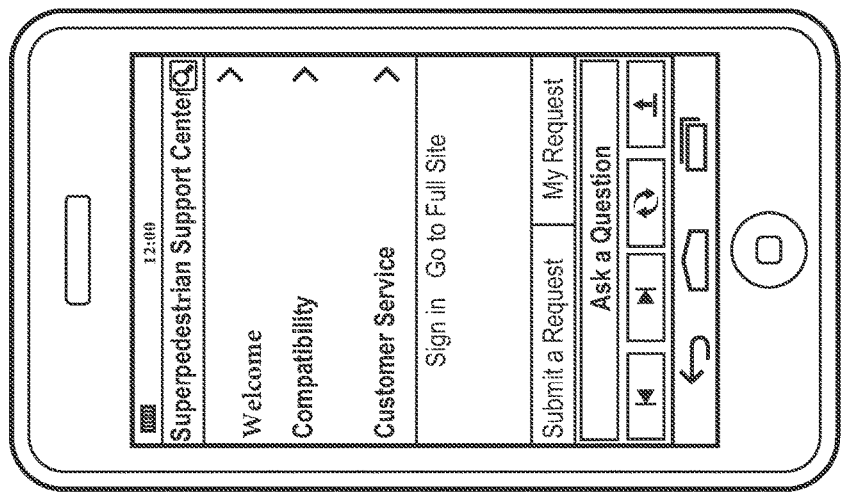
FIG. 16F is a mobile device page of a system for the electrically motorized vehicle.
Figure 16E:
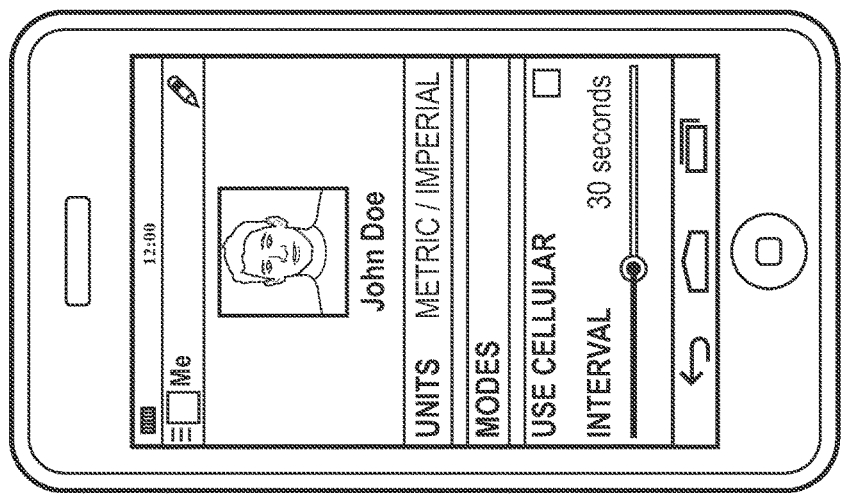
FIG. 16E is a mobile device page of a system for the electrically motorized vehicle.
Figure 16G:
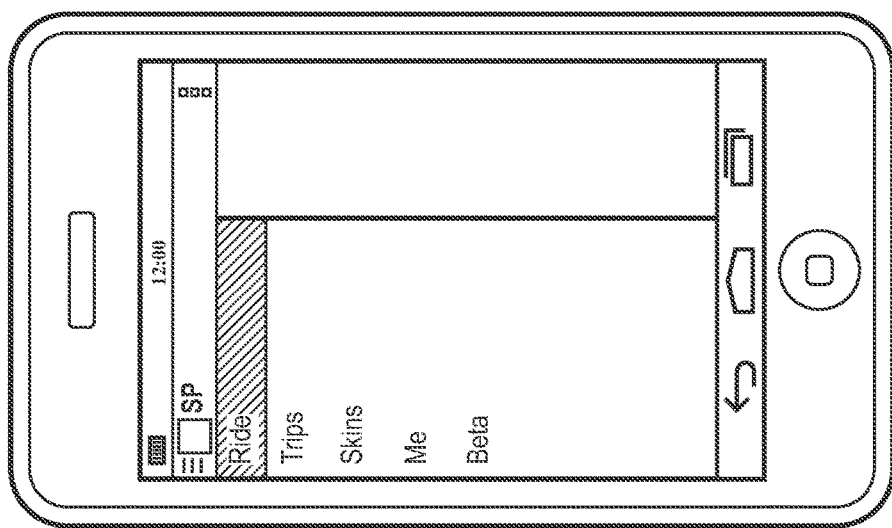
FIG. 16G is a mobile device page of a system for the electrically motorized vehicle.

Alternately, or in addition, the mobile device 1502 may be utilized to accept user input, such as pothole detection, along a route. That is, the cataloging is essentially manual. For example, should the user identify a pothole, the user may touch a button on the mobile device 1502 which is then catalogued via GPS. Other represented pages may include last trip (FIG. 16C), record trip (FIG. 16D), user settings (FIG. 16E), support (FIG. 16F), and others (FIG. 16G). It should be understood that the illustrated pages are merely representative, and various other pages may be alternatively or additionally provided.

Figure 17A:
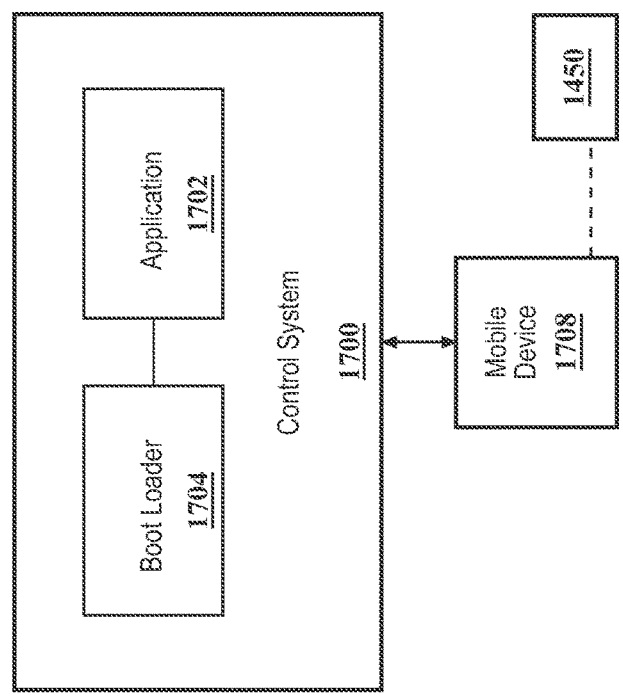
FIG. 17A is a schematic view of a system for the electrically motorized vehicle.

With reference to FIG. 17A, the control system 1700 of the electrically motorized wheel may include an application module 1702 that executes various functions, to include, for example, operation of control algorithms that manage the operation of the electrically motorized wheel. A boot loader module 1704 is in communication with the application module 1702 to facilitate loading and updating thereof. It should be understood that various hardware, software, and combinations thereof may be used to implement the modules.

In embodiments, upon start-up of the control system 1700, the electrically motorized wheel verifies that the version of the application module 1702 currently installed on the control system 1700 is valid and current. It should be understood that 'start-up" may include connection by various user interfaces that communicate with the electrically motorized wheel as well as various security and other communications. If, for example, the application module 1702 is valid and up to date, system initialization occurs. If the application module 1702 is not valid, the control system 1700 may initiate the boot loader module 1704 to update the application module 1702.

In embodiments, when a mobile device 1708 connects with the control system 1700, the control system 1700 may upload firmware version numbers for the application module 1702, the boot loader module 1704, and other elements, such as a Bluetooth (BT) radio and the battery management system. The mobile device 1708 may check with a source, such as a server operating such an application program interface (API) of a cloud-based server, to determine whether the uploaded version number of the application module 1702 is the most recent version.

In embodiments, non-mobile devices such as a desktop computer may connect locally with the control system 1700 such as via a Bluetooth connection.

If a newer version is available, the user may, based on a rule set, be prompted via the mobile device 1708 to update the electrically motorized wheel. That is, updated firmware for updated operation of the electrically motorized wheel. If the user elects to update the electrically motorized wheel, the mobile device 1708 may direct the control system 1700 to enter the boot loader module 1704. The rule set for updates may permit updates only under certain defined conditions such as when there is a minimum battery life on the electrically motorized wheel, a minimum battery life on the mobile device 1708, a minimum signal strength for the mobile device 1708, availability of direct power for electrically motorized wheel and mobile device, and others.

Upon downloading the updated version of the application module 1702, the mobile device 1708 may command the boot loader module 1704 to download the new version of the application module 1702 and, if download is successful, to erase the current application module 1702 from the control system 1700. Alternatively, the new version of the application module 1702 may be downloaded and stored on the mobile device 1708 for later update of the electrically motorized wheel such as via a Bluetooth connection.

The new version of the application module 1702 may be sent from the mobile device 1708 to the boot loader module 1704 via a wireless connection. The boot loader module 1704 may confirm the transfer of the individual packets and the total transfer of the new application module 1702 onto the control system 1700. If the boot loader module 1704 confirms that the new application module 1702 was loaded successfully, the mobile device 1708 may initiate a restart of the electrically motorized wheel and control system 1700. Alternatively the boot loader module 1704 may proceed with updates though a hard-wired interface such as a CAN bus that is made externally available at the User Interface panel or power port.

Figure 17B:
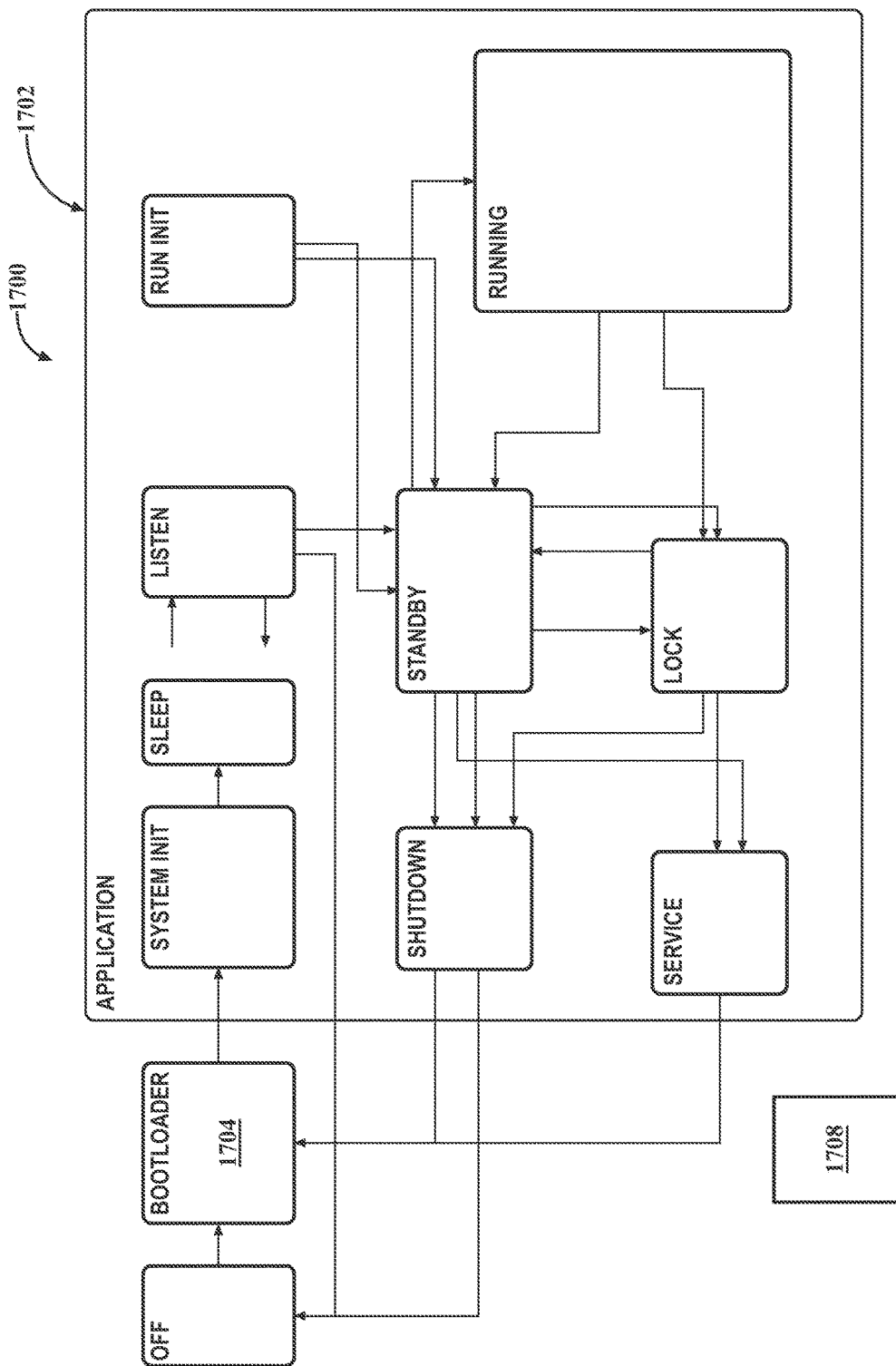
FIG. 17B is a schematic view of a system for the electrically motorized vehicle.

With reference to FIG. 17B, the application module 1702 of the control system 1700 may utilize various control techniques, including algorithms that govern, manage, and/or change operational parameters of the electrically motorized wheel. That is, the operational parameter of the electrically motorized wheel may be changed via the control system that, for example, change the parameter based on various factors, such as the maximum speed of the vehicle on which the electrically motorized wheel is installed, the conditions of the environment (e.g., terrain, weather, and others), input from the user including the force sensed from pedaling effort, data input to the electrically motorized wheel, etc., and parameters that are based on multiple factors (referred to herein in some cases as blended parameters), the energy used (such as by the user, by a battery associated with the electrically motorized wheel, or the like), and/or other control systems that provide various other modes.

In embodiments, levels of gain (such as the level of assistance and/or resistance provided by the electrically motorized wheel in relation to a given user input such as pedaling effort) can be managed in connection with the electrically motorized wheel. In some embodiments, a progression of gains may be utilized to smooth the transition from one operational regime to another regime (e.g., a change in terrain from uphill to downhill conditions, a change in speed of the vehicle on which the electrically motorized wheel is installed, environmental conditions such as wind direction and temperature, etc.) Other embodiments may include a step-wise change between an initial gain one or more new levels of gain. Normally a step-wise change in operational mode of the electrically motorized wheel (e.g., between differing levels of assistance or from assistance to resistance) or a change in gains may result in a discontinuity in the response of the electrically motorized wheel to torque command. Such discontinuities may be smoothed by:

1. recognizing that a change in gains has occurred;
2. taking and optionally storing the value of the command immediately prior to the change;
3. creating an offset that is at least a portion of the difference between the prior command and the new command;
4. subtracting the offset from the new command (this results in a new command that has a value of or in the range of the old command to the new command); and
5. reducing the offset over a period of time until it is zero, at which point the transition to the new command is completed.

This smoothing process beneficially effectuates gain changes and control regime changes because it preserves a degree of continuity in the user experience. The process can handle repeated transitions, as new offsets are generated with each change (e.g., in regime and condition) that results in a new command. This may include offsets from prior transitions, and there may be a variety of ways to reduce the command to give the transition different characteristics (e.g., a finite transition time, a fixed rate of command change, a maximum level of change, etc.)

Figure 18A:
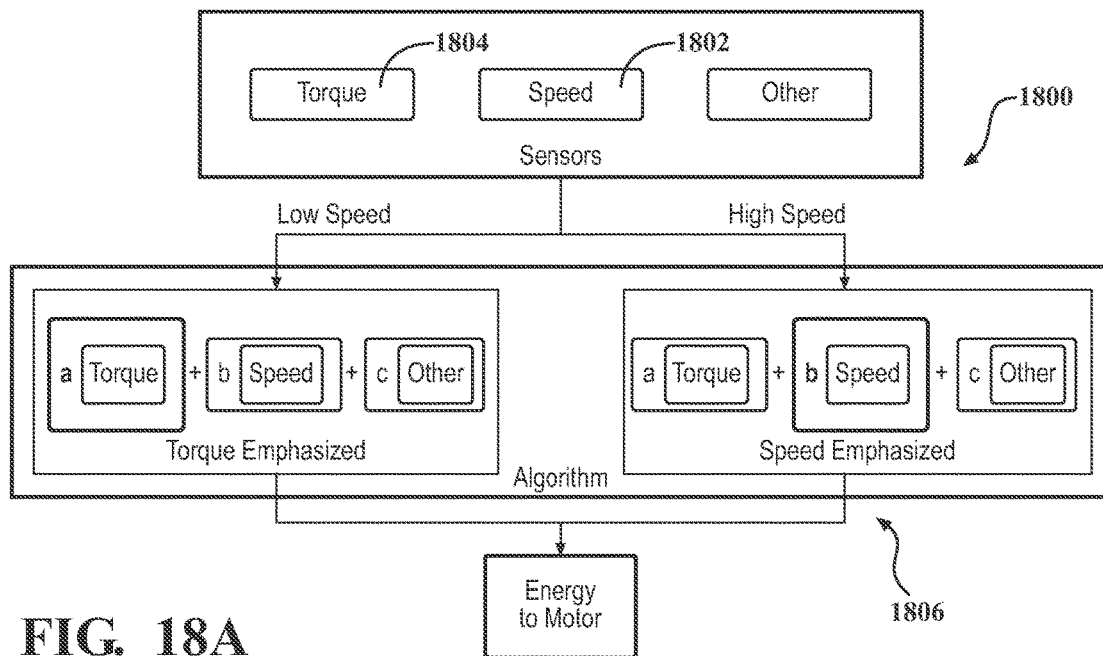
FIG. 18A is an algorithm for operation of the electrically motorized vehicle.

With reference to FIG. 18A, a blending algorithm 1800 for operation of the electrically motorized wheel may also be controlled by blending 1806 inputs relating to different factors that may be sensed in connection with the operation of the electrically motorized wheel. For example, sensor inputs may be considered from both a speed sensor 1802 that senses the speed of rotation of the electrically motorized wheel or displacement of the vehicle, and as a torque sensor 1804 that senses the amount of torque on the electrically motorized wheel.

The control parameters of relevance to the user experience can vary significantly depending on, for example, the speed of the vehicle. In consideration a bicycle pedaling example, at low speeds, responding to pedal torque may be relatively more important to ride quality, as significant effort is required to initiate movement of the vehicle. At higher speeds, maintenance of a consistent cadence or speed may be relatively more important to ride quality. As such, the amount of assistance in response to each user input (in this example torque and cadence) may vary based on the speed of the vehicle. Thus, data from the torque sensor may be used as a primary factor in a control regime at low speeds, while the data from the speed sensor may be used as the primary factor in the control regime at higher speeds. As a result, control may be managed by delivering high responsiveness to the torque sensor at low speeds and by using less responsiveness to the torque sensor at high speeds. Components related to the torque and the speed can be factored into the control algorithm that ultimately determines the quantity of energy, or rate of energy delivery from the battery system to the electric motor.

The blending algorithm 1800 is thereby operable to provide a fluid control scheme that scales the importance of each sensor as a factor in the control scheme based on speed.

Figure 19A:
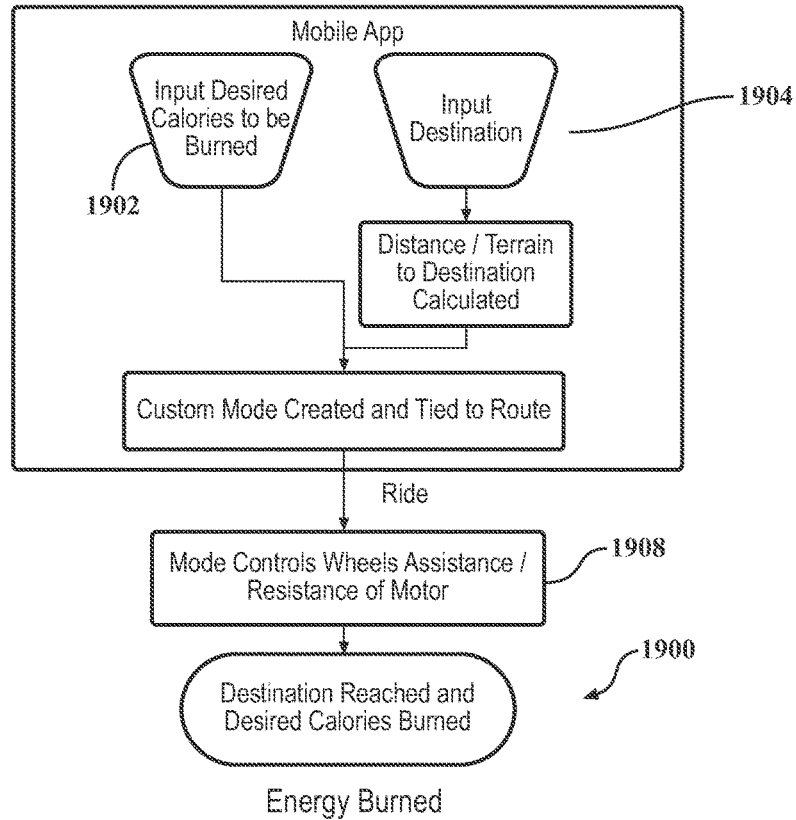
FIG. 19A is an algorithm for operation of the electrically motorized vehicle.

With reference to FIG. 19A, an energy burn control algorithm 1900 permits a user to input the amount of energy (step 1902) the user would like to burn on a particular ride (e.g., how many calories to burn between home and work). The energy burned by the user relates to the amount of work performed in order to move the vehicle from a first point to a second point. This work may be modeled based on various physical factors, including the terrain, friction, the weight of the user such as measured by a sensor of the vehicle or entered by the user, the weight of the bicycle including any accessories and additional loads, e.g., camping equipment, the distance traveled, and others.

A portion of the work may be performed by the user, such as by pedaling, while the remainder may be provided by the electrically motorized wheel. The portion of energy expended by the user may be modeled as the difference between the total work required to move a user of a given weight over the terrain (which may be known based on a GPS model of the terrain or based on measurements (such as altimeter measurements) from past trips) and the amount of assistance provided to the user by the electrically motorized wheel. Thus, as the user indicates an amount of energy desired to be burned, the control system 1700 may control the electrically motorized wheel to provide assistance, such as on hills of the route, to make up any difference between the desired work and the actual work required to cover the distance. If the desired portion of the work performed by the user is higher, the electrically motorized wheel may provide resistance to the user, re-route the user to a longer route, etc. Thus, the algorithm 1900 may utilizes the user input 1902 and data about the route/terrain 1904 to adjust the assistance/resistance of the electric motor 908 so that the user burns the desired amount of calories over the course of the route. Once the goal has been identified, the ride may be previewed and, as the ride progresses, the user interface may transition to a progress screen that highlights progress to the goal such as the destination and specified calorie burn.

Figure 19B:
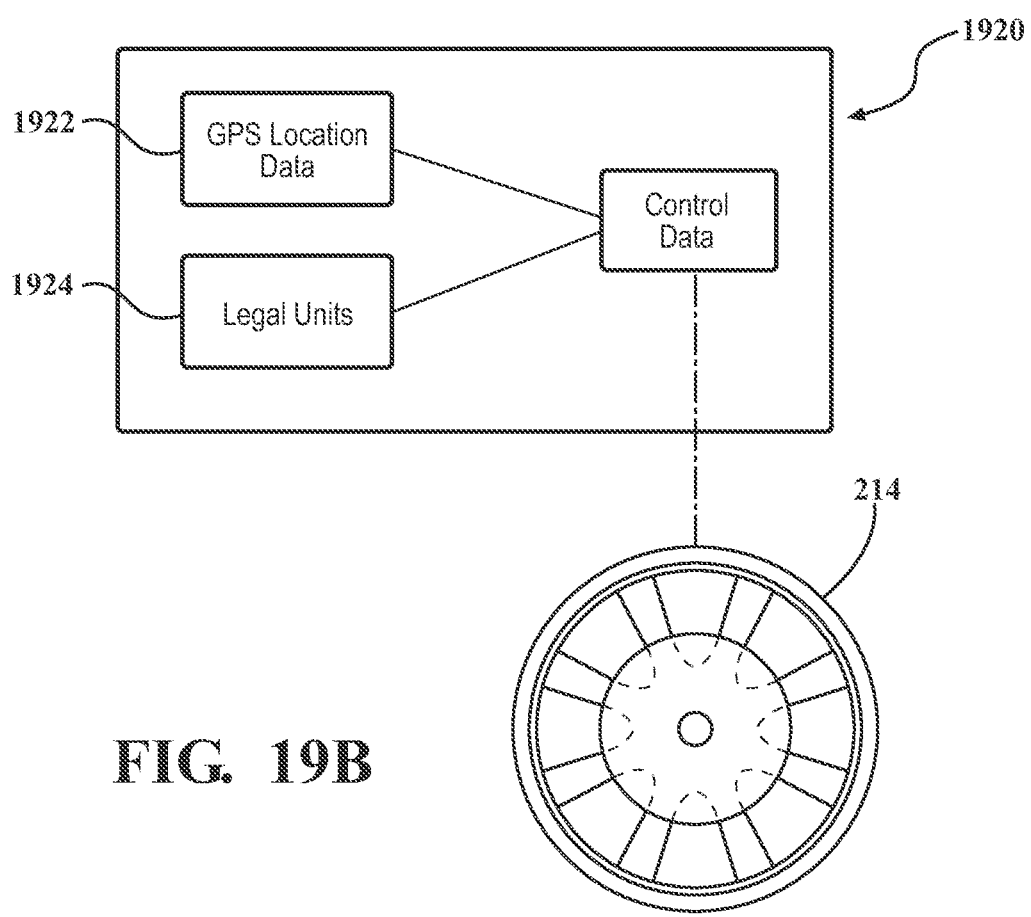
FIG. 19B is an algorithm for operation of the electrically motorized vehicle.

With respect to FIG. 19B, the mobile application 1920 may utilize available GPS location data 1922 and a stored database of data to determine legal limits 1924 as regulations vary geographically with respect to various factors that govern operation of electrically driven or assisted vehicles. These may include regulations of assisted speeds, level of assistance provided, and/or motor output. The mobile application 1920 or other control system may use this data to create a custom mode or set of control parameters that can be sent to electrically motorized wheel, such as to govern maximum assistance, speed, or the like. The mobile device or other control system may recalculate control parameters when the legal limits change and send updated control parameters to the electrically motorized wheel.

In one example, the EU may have a standard regulation of a top-assisted speed of 25 km/h and 250 W of motor assistance, while the US may have a top assisted speed of 32 km/h and 750 W of motor assistance. By using the GPS data available at any given location, it is possible to regulate the assistance cutoff within the electrically motorized wheel to comply automatically with the local regulations, without further intervention.

Further, many of the laws only apply to bicycles when they are riding on roads with other motor vehicles and pedestrians. If the GPS indicates the bicycle to be sufficiently far away from the road, the bicycle may be assumed to be on a trail in which case the local regulations may be different, or nonexistent, in which case limitations on the assistance provided may be removed. In embodiments, a user may be permitted, such as through the mobile application, to override the controls, such as to allow more assistance in an emergency situation.

In embodiments the mobile application 1920 may also utilize available GPS location data 1922 to facilitate control while in operational modes. For example, extremely hilly terrain will result in different battery regeneration calculations than flat terrain.

Figure 20A:
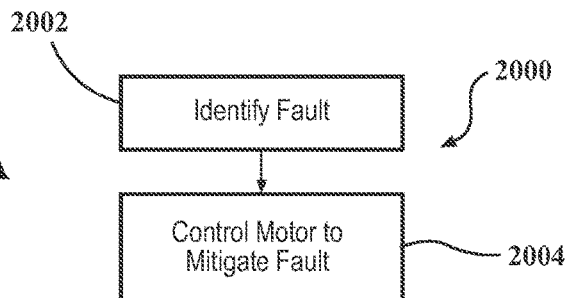
FIG. 20A is an algorithm for operation of the electrically motorized vehicle.

With reference to FIG. 20A, a fault detection and prediction system, referred to herein as a "faultless algorithm"

2000 is operable to sense conditions that have the potential to damage wheel hardware or subsystems as they occur in essentially real time (step 2002) then respond by performing mitigating actions based on the detection of same (step 2004). For example, if the electric motor approaches a predetermined maximum temperature, beyond which damage may occur to the electric motor, the amount of assistance or resistance generated by the electrically motorized wheel to the user of a vehicle on which the electrically motorized wheel is disposed can be reduced to prevent a further rise in temperature of the motor.

Figure 21A:
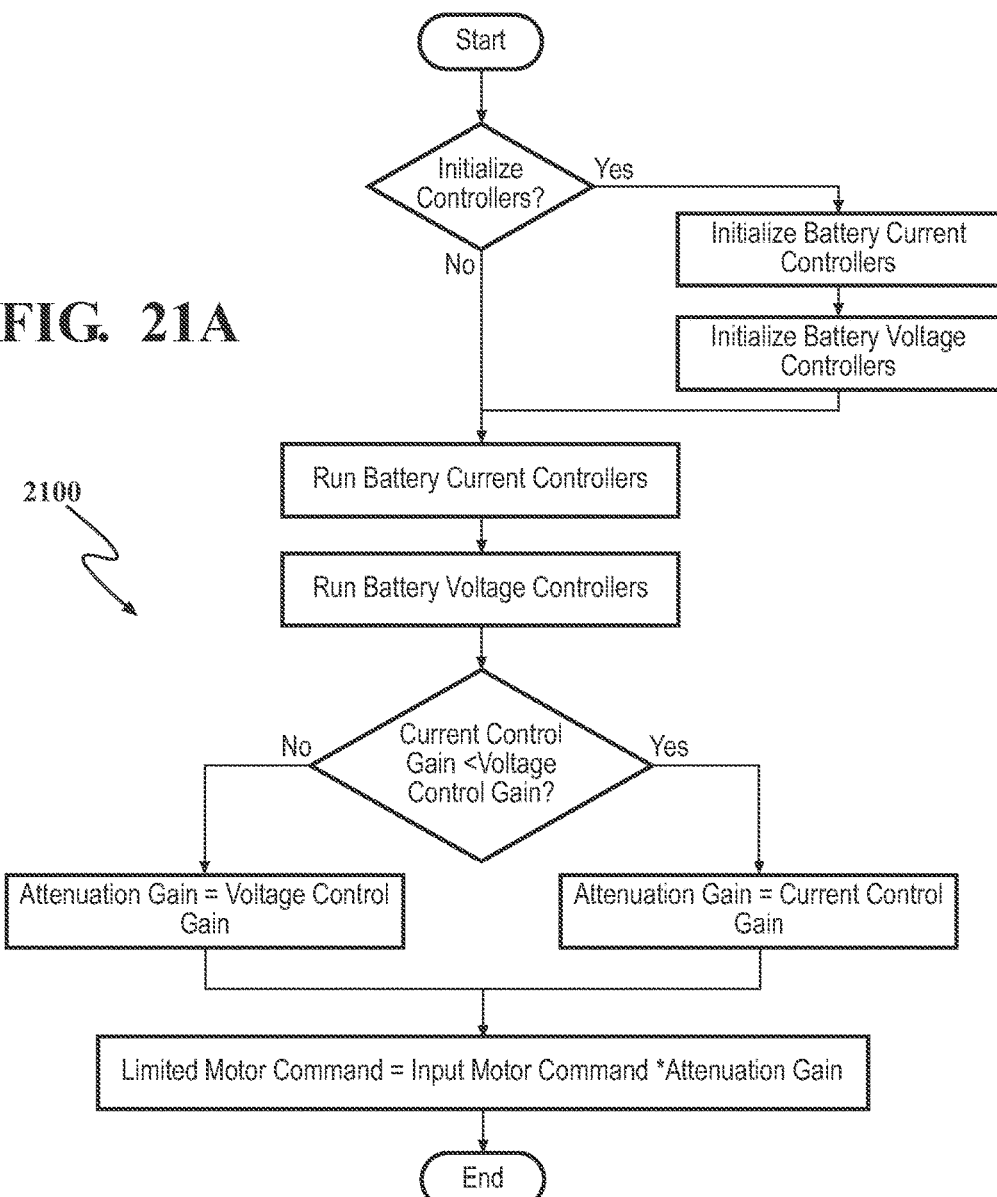
FIG. 21A is an algorithm for operation of the electrically motorized vehicle.

With reference to FIG. 21A, a battery protection algorithm 2100 may provide different and optionally independent command attenuators, including, but not limited to:

1. Protecting the battery from high discharge currents;
2. Protecting the battery from high regeneration currents;
3. Protecting the battery from high voltages that may result from regeneration;
4. Protecting the battery from low voltages that may result from motoring;
5. Protecting the battery from high temperatures due to high loads or heat from other components like the motor; and/or
6. Protecting the battery from regeneration currents at low temperatures.

Each of these command attenuators can utilize automatic controls such as a single-sided, closed loop proportional-integral (PI) control system to generate an attenuated gain ranging from 1.0 (no attenuation) to 0.0 (full attenuation). Alternatively, command limiters may be utilized instead of the command attenuators. The command attenuators provide an immediate and linear smooth response as command limiters are inherently non-linear in nature and can present control challenges, but are nonetheless a valid controllers.

In embodiments, the gain from relevant attenuators can be determined, combined, and applied to the motor command. The algorithm may be based on the minimum gain among all control systems, the maximum gain among all control systems, the sum of gains from all control systems, and various other ways for combining the gains, multiplying them, conditionally selecting, limiting the assistance provided by the motor to the user, etc.

Under some conditions, the electric motor may be driven by the battery system, while under other conditions the battery system may store energy from the motor such as when the motor is used to slow the vehicle in downhill operation. In situations with significant energy generation capability, the battery system may be subjected beyond its normal operational limits for temperature, voltage and/or current. As such, there are limits that may need to be enforced for operation of the battery system. There are at least three general sets of battery limits, i.e., current, voltage, and temperature. As to limits relating to current, there may be maximum discharge current and maximum battery regeneration current. As to voltage limits, there may be a maximum voltage limit and a minimum voltage limit. As to temperature, there may be a maximum temperature limit and a minimum temperature limit.

The battery protection algorithm 2100 may operate to manage the motor drive operation, such as to maintain battery parameters within acceptable operational values for voltage, current and temperature. This may address the electric motor contribution to the load on the battery system. Other sources of load on the battery system may also be managed separately.

In embodiments, single-sided proportional-integral (PI) closed loop limiters, e.g., one for each limit, may be deployed in connection with limiting various operational conditions, such as: battery motoring current; battery regeneration current; battery over voltage; battery under voltage, etc.

The output of each PI closed loop limiter may be an attenuation gain. Each PI closed loop limiter may have its own control system, with its own separate gains, as the dynamics of each limiter may require individual tuning.

The minimum gain of all the limiters may be taken and applied to the motor current control command. As a particular limit is approached, the motor command may be attenuated, such as to reduce the demand on the battery. The voltage limiters may selectively apply the attenuation gain. For the over voltage limiter, the attenuation gain for over voltage may be applied only when commanding regeneration of the battery. This allows motoring to then alleviate or avoid the over voltage condition. For the under voltage limiter the attenuation gain may be applied only when commanding motoring/assistance which allows regeneration to then alleviate or avoid the low voltage condition.

In embodiments, battery power control systems may run at the motor control system frequency, as the battery control systems may need to have similar or higher bandwidth to keep limit excursions short in duration. In other embodiments, battery power control systems may run just prior to the motor control current loop and after motor drive analog data has been collected, such that the battery control systems attenuate the command for the motor control current loop. This sequence may reduce delay in the control response that would occur if the data collection and attenuation occurred at different times.

The control system may be initialized each time the motor drive is enabled, as the motor drive can be enabled and disabled during normal operation. The battery control systems may have data items, such as integrators, that can be reset with every instance of enablement of the motor drive.

The control system can provide dynamic limits, because limits of the battery system may not be static over time and may vary, for example, with state of charge, temperature, etc. Dynamic control system limits may be bounded by predetermined maximum and minimum values, as this provides some protection against potential errors in measuring time-varying gains. Battery current and battery voltage may need to be sampled at the same data rate as other motor control feedback, as these control systems are part of the motor drive control, and because they run at motor control update rates, the sensor data may need to have the same frequency of sampling as other motor control data.

The control system may be single sided, closed loop, PI limiters that attenuate the motor current control loop command as PI limiters beneficially provide steady-state limiting with good bandwidth. An attenuator output, as compared to a limit output, may provide immediate intervention.

Over voltage attenuation gains may be only applied when the sign of the motor current command is negative (e.g. the motor is being commanded to oppose forward momentum, i.e., regenerate), because this allows motoring to alleviate high voltage conditions. Under voltage attenuation gain may be applied only when the sign of the motor current command is positive (e.g., the motor is being commanded to assistance in driving the vehicle), because this allows regeneration to alleviate low voltage conditions.

The PI control systems may have enough control authority to attenuate the motor current control system command to zero, because attenuating the command to zero is the maximum control authority possible, and maintain the battery system within operational limits may have priority over providing assistance to the user.

Sensors used in hardware protection algorithms may include sensing of battery voltage, battery current, motor voltage, motor current, battery temperature, ambient temperature or humidity, etc. Limits may be set statically in accordance with component design specifications or updated over time to account for factors such as component age or environment of usage as determined by GPS or weather data.

Pedal cadence is useful for a user to maintain a desired pace over the course of a ride. Typically, a cyclists may desire to pedal at a specific cadence to make the most efficient use of their effort and provide the most benefit from an exercise physiology standpoint.

In typical bicycle cadence sensors, measurements are performed directly at the crank, however, such direct measurements are not possible, nor desired, if the sensor system is to be contained within the electrically motorized wheel that is separated from the pedals by a drivetrain. Although this embodiment has specific illustrated components in a bicycle embodiment, the embodiments of this disclosure are not limited to those particular combinations and it is possible to use some of the components or features from any of the embodiments in combination with features or components from any of the other embodiments.

Figure 22A:
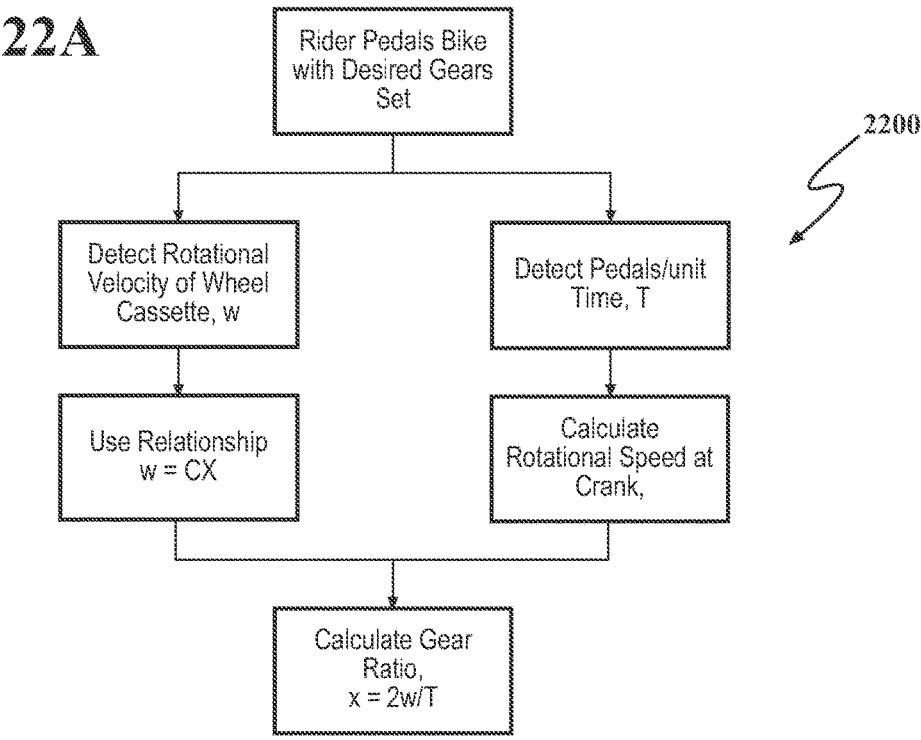
FIG. 22A is an algorithm for operation of the electrically motorized vehicle.

With reference to FIG. 22A, a pedal cadence estimation algorithm 2200 operates to estimate the pedal cadence from the torque input frequency which will have frequency content that is directly related to pedal cadence. Each time the user provides a rotational input, i.e., pushes on the pedal, the user is generating a torque into the system that is detectable. That is, the pedal rotational frequency (or cadence) is detected by the torque sensor system and can be communicated to the control system for use by a gear estimation algorithm 2200. The gear estimation algorithm 2200 is operable to calculate the gear ratio because the rotational velocity of the cassette is known from, for example, a cassette speed sensor, and the pedal cadence is known by estimation. The gear ratio may be determined by a ratio of these two speeds.

In embodiments, there are two speed sensors: one for the electrically motorized wheel and one for the cassette of the mechanical drive system. With knowledge of a rotational velocity of the cassette, and the torque frequency, both pedal cadence (pedal speed), and the gear ratio are readily determined by the gear estimation algorithm 2200. That is, how the pedal frequency relates to the rotational velocity of the electrically motorized wheel is known even if the number of speeds on a particular bicycle, or which gears are set on the rear cassette and the crank, are not known.

For example, the rotational velocity w is known from the cassette speed sensor. The torque frequency, t, is related to cadence, C: C=t/2. C is equal to the number of revolutions of the crank per second. Therefore, $\omega$=CX, or $\omega$=(t/2)X, where X is the gear ratio. Thus in simple forms, X=2 $\omega$/t. Additional sophistication may exist in the estimator to update estimates under conditions where input signals may be small, such as at low speed or low torques. This sophistication may include closed-loop state estimation algorithms for example.

Figure 23A:
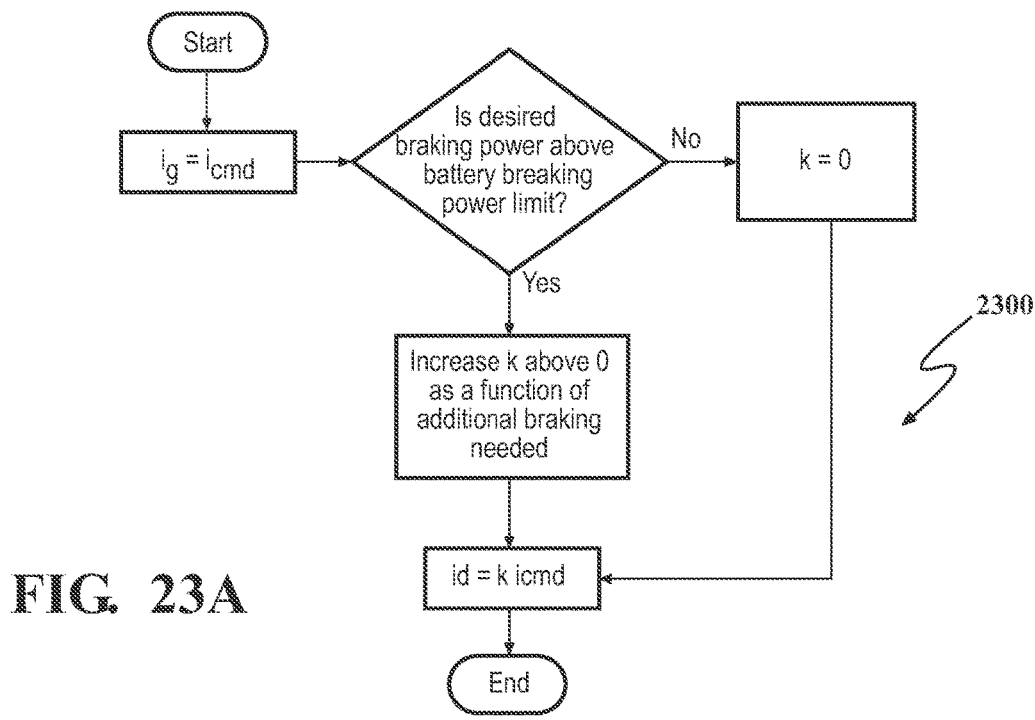
FIG. 23A is an algorithm for operation of the electrically motorized vehicle.

With reference to FIG. 23A, a braking dissipation algorithm 2300 accommodates an architecture in which the battery system 906 may be relatively limited in the amount of energy that can be absorbed during braking (in which energy can be directed to recharge the battery) without damage occurring to the battery. In embodiments, the motor control system of the electrically motorized wheel is field-oriented and controls the magnetic flux generated in the stator 911 as a vector that is precisely aligned with the rotor 913. This vector may be controlled to rotate through the stator 911 in synchronization with the rotor 913 of the motor by segregating the applied current vector into two orthogonal components. One component, Iq, the quadrature component, is at a right angle to the back electromagnetic field (back-EMF) vector generated by the motor. The other, Id, the direct component, is directly aligned with the back-EMF vector.

Maintaining the direct component (which produces no torque in certain embodiments) at zero (Id=0) and the quadrature component at a commanded level (Iq=Icmd) is how a field-oriented control system normally ensures the most efficient use of battery power to produce motor torque. Allowing Id to stray from zero is less efficient and thus dissipates more energy in the motor, which, while normally inefficient in regimes in which the desire is to maximize efficiency of power generation to propel a vehicle, creates an opportunity when other objectives are in play, such as involving braking and/or reducing current flow into the battery during regeneration, to degrade efficiency of motor in transferring power to the battery.

The battery protection algorithm 2100 maintains regenerative charging currents within limits that will not damage the battery, for example, below about 5.5 A of regeneration in certain embodiments. Since the battery protection algorithm limits the quantity of power that can be delivered back into the battery, the braking dissipation algorithm provides another place to send braking power in lieu of the battery without the addition of another dissipative load such as a traditional shunt resistor, thus allowing or causing more braking than would otherwise be allowed. This is effectuated by reducing motor current (used to control power) as needed to maintain the regeneration current directed to the battery in check. Also the braking torque is reduced, in some cases significantly, at higher speeds.

This speed dependence is because at higher speeds, the same amount of braking torque generates proportionally higher power levels. That is, at the battery system 906, since voltage is essentially constant, higher regeneration power translates directly to higher current into the battery system. Since current is limited, capacity for braking thus goes down as speed goes up.

The electric motor 908 in embodiments may have windings with a relatively high resistance. One consequence of this is that during hard braking, when the braking torque is high and thus the motor current is high, the power dissipated in the electric motor 908 is quite high, so the motor absorbs significant braking energy. As the speed drops, the braking power drops and the proportion of the braking power absorbed by the motor increases until it reaches the point where the motor is absorbing all of the braking power. At this point regeneration of power back into the battery system 906 ceases and the available braking torque is at a maximum. This threshold can be reached fairly quickly when slowing down and can cause the braking experienced by the user to rise abruptly. This behavior is likely unexpected by the user and thus is potentially undesirable.

In embodiments, the dynamic braking algorithm 2300 is activated by backpedaling so the user can use just one method of control, i.e., pedaling forward is a control that signals acceleration/assist while pedaling backwards is a control that signals braking—in either case the user need utilize only a single user input that is typical of the vehicle, i.e., pedaling in this example. The relative lack of desired braking at high speed, and the abrupt increase in braking at lower speeds is addressed such that the user mode of control, e.g. pedaling in this example, is seamless. That is, the braking that this technique provides at higher speeds also provides a partial solution to braking abruptness problem when slowing down by narrowing the difference in braking capability at high and low speeds.

In embodiments, the motor control system is field-oriented and controls the magnetic flux generated in the stator 911 as a vector that is precisely aligned with the rotor 913 for generating maximum torque. This vector is controlled to rotate through the stator 911 in synchronization with the rotor 913 of the motor by segregating the applied current vector into two orthogonal components. The quadrature component is thus at a right angle to the back-EMF vector generated by the motor, while the direct component is directly aligned with the back-EMF vector such that each of these components has a control system therefor.

The quadrature component produces torque, while the direct component produces no torque. Thus, for maximum efficiency, a control system is commanded to maintain the direct component at zero (Id=0) while the quadrature component is controlled at the commanded current level (Iq=Icmd). If the control system were to allow the direct component to grow, the overall motor current would increase, but no additional torque would be produced, and energy would be wasted in the resistance of the stator 911 windings.

Embodiments for braking set Iq=Id=Icmd. This locates the current vector out of alignment with the back-EMF vector by 45 degrees. As Icmd increases, both Iq and Id would increase and vice-versa. This has the benefit of allowing higher overall Iq values than when holding Id to zero, because Id is dissipating at least some of the energy regenerated by Iq, rather than it returning it all to the battery. If the motor current is to be attenuated to protect the battery, motor, or electronics, both are attenuated equally. It should be understood, however, that ratios of Id to Iq other than one may alternatively be provided, with different ratios affecting the level of regeneration relative to wasting of mechanical power, and such ratios may be varied, such as accounting for factors like vehicle speed, the level of stored energy in the battery, sensed state (e.g., temperature) of motor components, and others.

In one example, when the motor gets hot, such as while braking during downhill travel in hot weather, the motor may not have the capacity to accept the added power and the supplied braking may fade. Damage to the motor is avoided by having the control systems limit the motor current which is where the sensation of fading brakes originates. In embodiments, this may prompt other actions, such as activating supplemental braking systems, prompting to the user via the mobile device to use manual braking, etc.

In embodiments, a directly connected electric motor is of the permanent magnet type, such that the rotor rotates with the electrically motorized wheel. When the motor drive applies a voltage higher than the generated voltage of the electric motor, the motor assists the user. The faster the electrically motorized wheel rotates, the higher the voltage generated. If the speed is high enough to generate a voltage that is higher than an allowed voltage, the electrically motorized wheel is in an "over-speed" condition. The allowed voltage may be specified for safety, hardware protection, and/or other reasons such as protection from high-back EMF due to high wheel speeds. EMF is present, however, EMF may become a problem when wheel speed is high enough for it to exceed battery voltage.

An inherent function of the power bridge that drives the motor is full wave rectification of the back-EMF voltage from the rotation of the electrically motorized wheel onto the DC bus. Thus, it is possible for the user to pedal the bicycle to speeds that can generate this over-speed condition, especially downhill. In embodiments such as ones involving direct drive motors, the voltage that can be generated is limited only by how fast the vehicle is moving and thus has the potential to damage embedded system electronics.

Electronic braking through regeneration can be used to facilitate automatic control of maximum vehicle speed. However, the battery can only absorb so much energy before its voltage reaches its maximum limit such that a battery protection algorithm may automatically protect itself by disconnecting the battery from the DC bus if the voltage reaches a predetermined value. True, power is related to current, but at lower battery voltages the power limit will be lower (P=1*V) while the current limit is the same.

Further, even when the battery state of charge is low enough to accept regeneration energy, the rate at which the battery can accept the energy is bounded by its charging current limit. At higher speeds, this charging current limit may severely reduce the braking capability of the electrically motorized wheel, making it more likely for the user to overcome any automatic speed regulation the electrically motorized wheel may try to enforce, especially on a steep downhill. To address this condition, a warning may be provided to the user via the mobile device.

Reasonable speeds are allowed, and mitigation of potential damage to the hardware may be provided, such as by placement of a relay to isolate and protect the power-electronics bridge and all other electronics connected to the DC bus from the high voltage generated by back-EMF generated when the motor is mechanically driven to an over-speed condition.

Figure 23B:
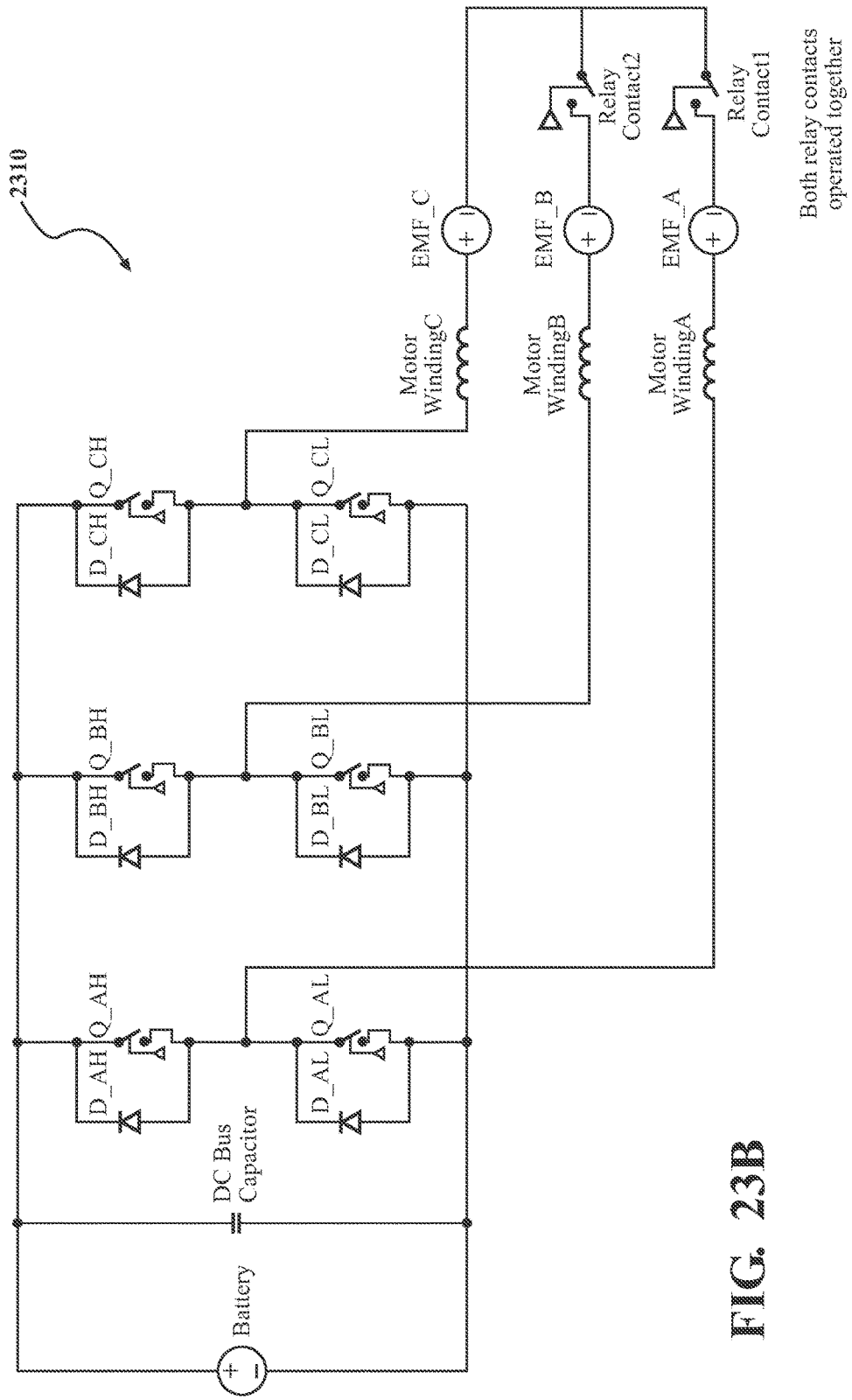
FIG. 23B is a schematic view of a wiring diagram for of the electrically motorized vehicle.

In embodiments, diodes in the bridge 2310 operate as rectifiers if the back-EMF voltage exceeds the DC bus voltage (FIG. 23B). As motor over-speed increases, back-EMF potentially pushes the DC bus voltage to uncontrolled levels. To avoid such an over-voltage condition, relay contacts are opened based upon measured or estimated back-EMF appearing at motor terminals approaching the DC bus voltage. In one embodiment Back-Emf is estimated in accordance with:

$$VEMF = Ke * SpdMot$$

Where:
VEMF is the terminal-to-terminal EMF voltage [V].
Ke is the motor back EMF constant [V/(rad/s)].
SpdMot is the motor speed [rad/s].
SI units are used here with voltages measured line-to-line (vs. line-to-neutral), and 0-to-peak of sine (vs. RMS). So the units on Vemf are [V], on SpdMot are [rad/s], and on Ke are [V/(rad/s)].

With reference to FIG. 23C, a method 2320 of motor over-speed protection includes:
Measuring SpdMot and Vbat (step 2322);
Estimating the VEMF as Ke*SpdMot (step 2324); and
Sensing if VEMF>= to Vbatt−VDisableMargin (step 2326).
If Yes, the Motor Drive is disabled (step 2328).
If No, sensing if VEMF>= to Vbatt−VrelayOpeningMargin (step 2330);
If Yes, the Motor relay contacts are opened (step 2332).
If No, determine if VEMF<= to Vbatt−VrelayCloseMargin (step 2334).

If Yes, close the motor relay contacts and enable the Motor Drive (step 2336).

If No, END (step 2338).

That is, the motor relay contacts are opened as the estimated back EMF of the motor, based for example, on the back EMF constant and the speed of the motor, approaches the measured bus voltage which varies with battery state of charge.

Figure 23D:
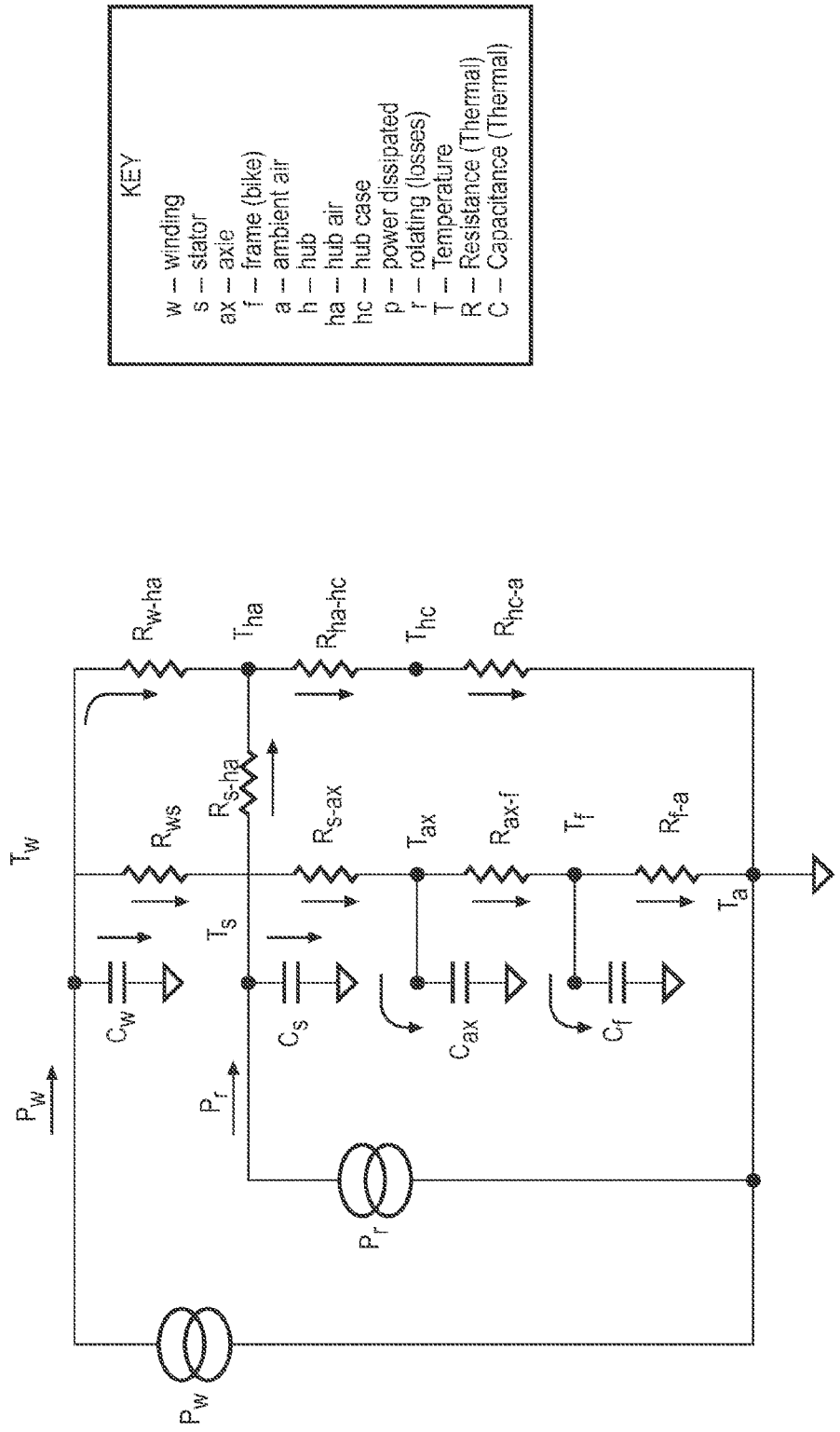
FIG. 23D is an electrical schematic representative of a thermal model for the electrically motorized vehicle.

With reference to FIG. 23D, an example thermal model schematic for the motor utilize capacitors to represent heat-sinking characteristic of the various thermal generating components in the hub shell assembly. They are responsible for the fact that it takes some time for these components to heat up, thus allowing the wheel to have higher performance until those thermal generating components are hot. The resistors represent the paths for heat to spread inside of, then ultimately escape the hub shell assembly.

Figure 23E:
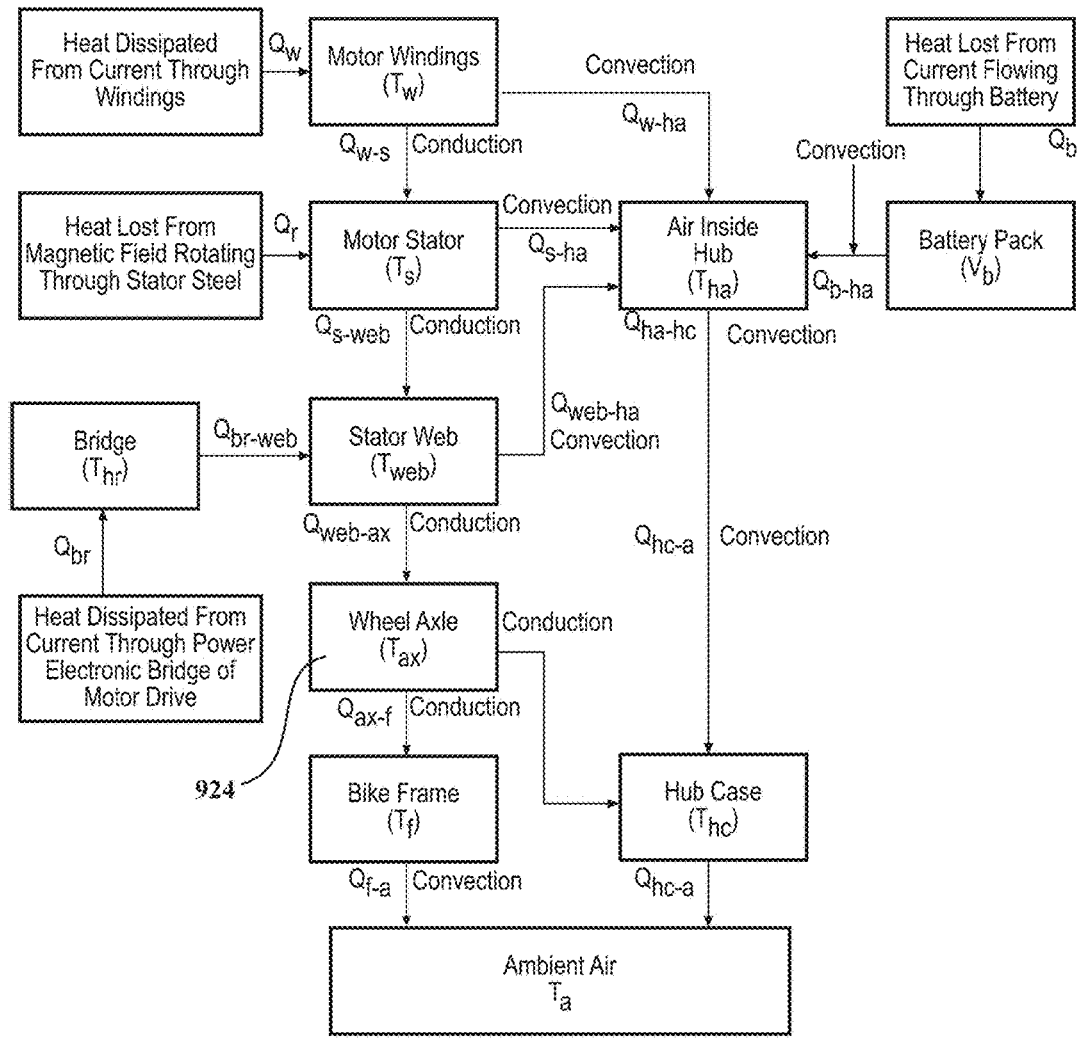
FIG. 23E is a thermal schematic for the electrically motorized vehicle.

With reference to FIG. 23E, a thermal schematic for the electrically motorized wheel includes four major heat sources: winding losses in the motor windings, rotational losses in the motor stator steel, losses in the power electronic bridge of the motor drive, and losses in the battery pack. The heat sources are ultimately communicated to the shaft 924, thence to the bicycle frame along mechanical conductive thermal paths. The bicycle frame thus ultimately operates as a heat sink of significant volume.

Figures 24A, 24B:
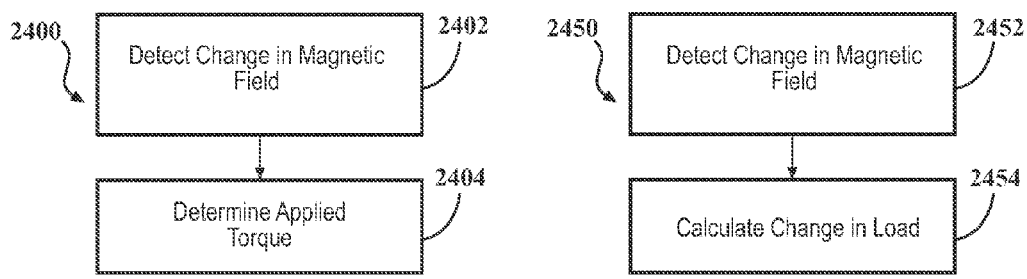
FIG. 24A is an algorithm for operation of the electrically motorized vehicle.
FIG. 24B is an algorithm for operation of the electrically motorized vehicle.

With reference to FIG. 24A, a torque sensing algorithm 2400 may be provided to measure different process parameters related to torque. The torque sensing algorithm 2400 may include non-contact sensor technology that utilizes fundamental mechanical and magnetic properties of the material to measure different process parameters such as magnetoelastic materials. The process involves measuring changes in the properties of remnant magnetic fields as the mechanical characteristics change, such as shear stress, as external forces are applied onto the sensor host (step 2402).

The torque sensor 1204 may include highly sensitive fluxgate sensors located in close proximity to a magnetized member to sense the change in the magnetic-field characteristics that are proportional to the applied force. The mechanical member may be directly magnetized instead of attaching additional elements, such as a ring. The change in the magnetic-field characteristics are linear and repeatable within the elastic limit of the material, and are accurate under normal and extended operating conditions such that an applied force can be readily determined (step 2404).

For example, when the shaft is subjected to a mechanical stress, such as torque from pedaling, the magnetic susceptibility of the magnetoelastic material changes and is detected by the surrounding sensor. The torque sensor 1204 produces a signal proportional to the torque applied by the user then communicated to the control system 914.

With reference to FIG. 24B, a vertical load sensing algorithm 2450 may be provided to measure different process parameters such as vertical load. The vertical load sensing algorithm 2450 may communicate with a magnetic field flux sensor measuring change in magnetic field (step 2452) resulting from an initial mechanical stress applied such as, for example, when the user mounts the bicycle. The change in magnetic field may be generated by the shaft, shell, or other wheel component manufactured or including a magnetoelastic material that is deformed when a load is applied on electrically motorized wheel. The change in the magnetic-field characteristics are linear and repeatable within the elastic limit of the material, and are accurate under normal and extended operating conditions such that an applied force can be readily determined (step 2454).

The measured vertical load may be used as a modifier by the control algorithms. For example, the measured vertical load may contribute to calculations controlling for calories burned due to a weight of the user, identification of a user to unlock the electrically motorized wheel, etc.

In embodiments, various components of the shell, such as the drive side shell 940, the non-drive side ring 942, the removable access door 944, and the like may include a magnetoelastic material. Alternately, a thin coating of magnetoelastic material may be applied to a component. The coating may be applied overall or in a directional pattern and in various thicknesses. Magnetic flux sensors situated in close proximity to the magnetoelastic material enable the detection of changes in the magnetic flux created by the deformation of the component during operation. Insight into the deformation of a component, such as the shell, may be used to understand electrically motorized wheel environment and inform future design modifications.

Figure 25B:
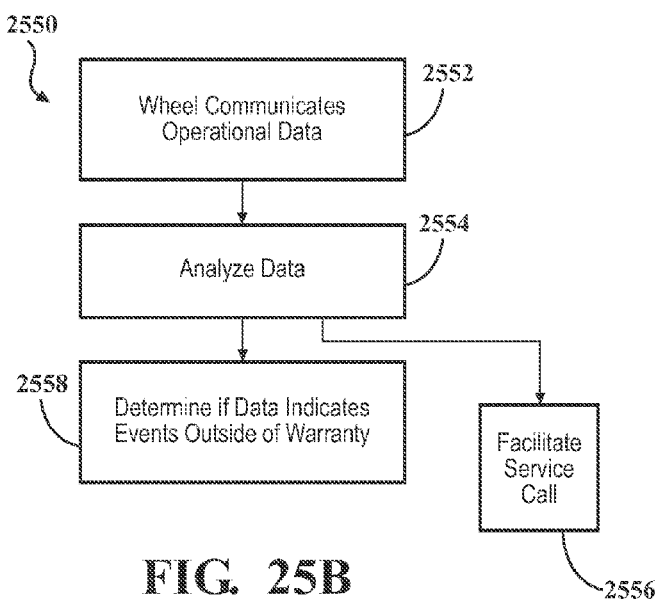
FIG. 25B is an algorithm for operation of the electrically motorized vehicle.
Figure 25A:
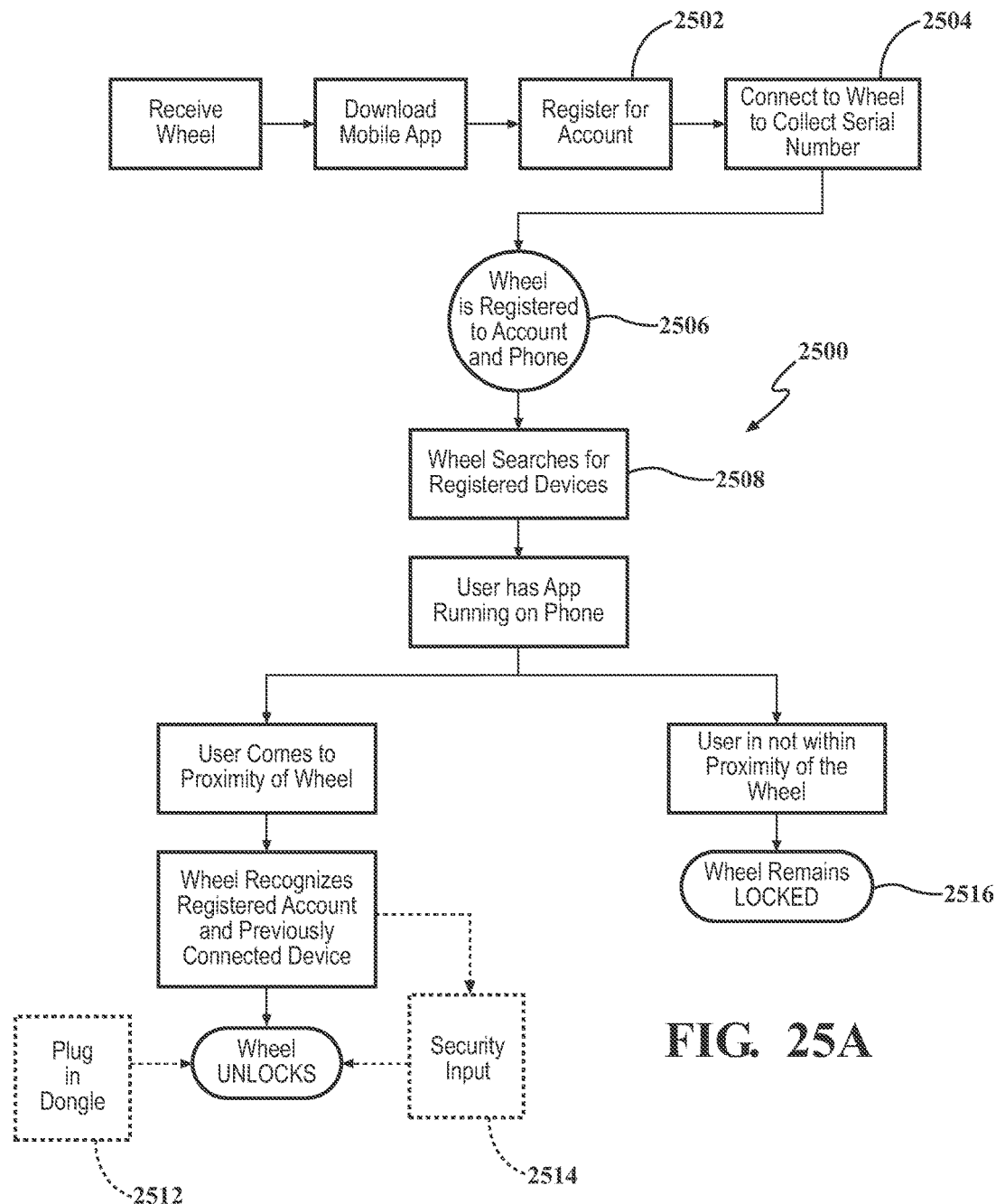
FIG. 25A is an algorithm for operation of the electrically motorized vehicle.

With reference to FIG. 25A, a security algorithm 2500, may be provided for security of the electrically motorized wheel until authentication is performed in an exchange between a mobile device and the electrically motorized wheel. This may be automatic once an initial authentication is performed (step 2502). Initial authentication may be performed when first connecting to the electrically motorized wheel to collect the serial number (step 2504).

Once the electrically motorized wheel is registered to the account and mobile device (step 2506), the electrically motorized wheel will search for registered mobile devices via a relatively short range wireless connection, for example, Bluetooth (BT) (step 2508). The electrically motorized wheel may store previously authenticated mobile devices and reconnect to them automatically when within a predetermined proximity (step 2510). Alternatively, another key such as a wireless car key, or other key is utilized to unlock the electrically motorized wheel (step 2512).

Alternatively, or in addition, a dongle plugs into the electrically motorized wheel to unlock the electrically motorized wheel (step 2512).

When locked, the main control board 1450 can configure motor controller to resist or prevent rotation of the electrically motorized wheel. Alternatively, the lock function could prevent the use of the electrically motorized wheel to provide assist while letting the wheel spin freely. In one example, identification of the authenticated mobile device being within a predetermined proximity is sufficient to unlock the electrically motorized wheel. Alternatively, or in addition, a security input (step 2514) to the mobile device, or directly to the electrically motorized wheel such as entry of a code, entry of a password, facial recognition, fingerprint scan, unlock plug, and others may be utilized to unlock the electrically motorized wheel.

The electrically motorized wheel may be triggered to lock (step 2516) by a combination of criteria, such as the electrically motorized wheel no longer being connected to the mobile device, the mobile device being beyond a predetermined proximity from the vehicle, a user not being seated on the vehicle, the electrically motorized wheel not moving for a prescribed time period, the vehicle not moving for a prescribed time period, a timeout, etc. Further, the electrically motorized wheel may be selectively locked from the mobile device.

The electrically motorized wheel may receive input from various sensors and other data sources for interface with the control system 1700. The support and/or ports provided for additional sensors and other hardware (FIG. 14A) may be used to enhance user safety in a variety of ways such as alerting the user to a danger, alerting other's to the user's presence, enhancing user visibility and others. Data from one or more sensors may be transferred to the main control board and from there to the user's mobile device or to a remote location. In some examples, data may be sent to the user's mobile device and commands sent back to the electrically motorized wheel in response. In some examples, data may be sent to a server then commands sent back to the electrically motorized wheel in response. In other examples, data may be processed directly at the mobile device for the electrically motorized wheel. For example, a proximity sensor may send data to the user's mobile device causing the mobile device to provide an alert to the user using one or more of an audio alert, a visual alert, and a tactile alert. A tactile alert may be delivered by providing commands to the electrically motorized wheel so as to cause a small perturbation in performance of the electrically motorized wheel, such as a vibration, a change in speed, a change in the amount of assistance provided to a pedaling user, a change in resistance and others, which may be felt by a user and understood as a signal indicating a change in performance or the approach to an operational limit of the wheel, such as maximum motor temperature, or maximum regeneration current.

Figure 14C:
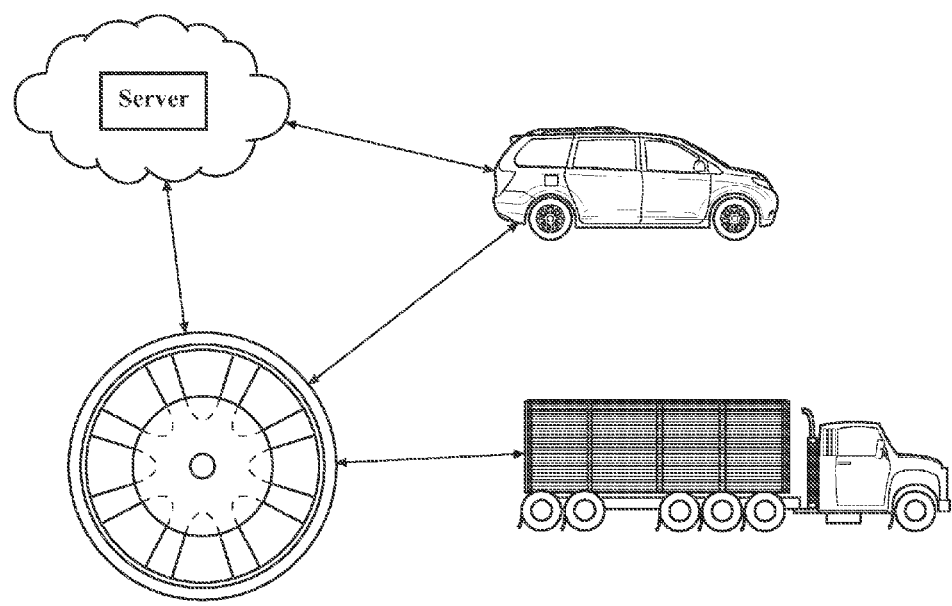
FIG. 14C is a schematic view of an ad hoc local traffic net system for the electrically motorized vehicle.

In embodiments, a proximity sensor may provide data regarding the user's location, such as via a traffic network, for alerting drivers of other vehicles (automobiles, trucks, buses, other electrically motorized vehicles, or the like) of the user's presence. A proximity sensor may be GPS or other global location sensor (or set of sensors, such as used in triangulation to locations of infrastructure elements, such as satellites, cellular towers, or the like), a sensor or sensors associated with a network (e.g., a cellular, Bluetooth, NFS, or other local wireless network), a sensor associated with a transportation infrastructure (e.g., located at a road sign, traffic signal, crossing, or the like), a sensor associated with a mobile device (e.g., a camera of a mobile device), or any other sensor that would provide data about the location of vehicle enabled with an electrically motorized wheel. For example, the electrically motorized wheel may communicate directly with other vehicles, (e.g., a cellular, Bluetooth, NFS, or other wireless network) to form an ad hoc local traffic network (FIG. 14C) that provides relative positional information of the adjacent vehicles to, for example, alert a vehicle to the presence and relative position of the electrically motorized wheel. Alternatively, the electrically motorized wheel may communicate globally with a local server (FIG. 14D), such as that located at an intersection, or a city wide server that then communicates with adjacent vehicles on the traffic net to provide relative positional information of the adjacent vehicles.

In another example, an illumination level sensor may provide data to an application that would cause the bicycle lights to turn on when illumination falls below a set level. Alternatively a data source may provide daylight data based on geological clock, which may be associated with proximity data, such that the electrically motorized wheel sends a signal to turn on illumination when in use at night at the current location of the electrically motorized wheel.

With reference to FIG. 25B, a remote diagnostics algorithm 2500, may be provided for the electrically motorized wheel. The remote diagnostics algorithm 2500 operates to collect operational data from, for example, the various sensors in the sensory system of the electrically motorized wheel (step 2552).

The operational data may include software and hardware version numbers as well as an application state of the electrically motorized wheel to include, but not be limited to, system initialization, sleeping, listening, stand by initiated, standing by, running initiated, running, locked, service mode, shutdown, default, boot loading, and others. The operational data may also include hazard indicators, both critical hazard indicators, which require the cessation of assist functions, such as motor overheated and transient hazard indicators, which allow continued use but with restricted performance, such as motor temperature being close to a limit but not over it.

The operational data may include system response data such as a reduction in motor assistance in response to a motor warm hazard indicator, regenerative braking turned off in response to the battery being full, results of a self test run in response to a torque sensor fault, and others. The operational data may also include any system fault errors generated by the different subsystems such as battery, motor drive, sensors, communications, processing board, peripheral, system, and others. The operational data may further include sensor data that is used for controlling the vehicle such as bicycle velocity, pedal speed, cassette torque, cassette speed, and others.

The operational data may be communicated on a predetermined frequency basis for analysis (step 2554). The data may be communicated either directly to a server via, for example, wireless or cellular technology such as 3 G/4 G, or to the connected mobile device via a wired connection, Bluetooth, or other wireless technologies. Data communicated to the mobile device may then be sent directly to a server or stored on the mobile device to be communicated to the server at a later time according to a set of rules that may include, for example, battery charge on the mobile device, signal strength, the presence of a Wi-Fi connection, and others. Data may also be stored locally on the wheel and sent to the server at a later time, either automatically once a mobile device connects to the wheel, or when connected to service tool through a wireless or a wired connection port 218. Data sent to the server may be associated with the specific wheel that generated the data. This association enables a service representative to view and analyze the operational data when responding to a trouble call, thus facilitating resolution of the issue (step 2556).

The operational data may be analyzed for internal consistency and error detection. For example, if a positive torque is measured at the cassette but there a negative speed measured at the cassette, there is a problem either with the torque or speed measurement. This is because in a bicycle with a freewheel positive torques cannot be sustained with negative pedal speed.

In another example, data, such as cassette speed, may be checked for errors using a variety of sensors such as the speed sensor, the torque frequency measured at the cassette torque sensor. Because the pedals cannot spin faster than the measured wheel speed, if the pedal speed exceeds the motor speed there is a problem either with the cassette or wheel speed measurements.

Additionally, operational data may be collected for understanding the context of usage. For example, temperature data may be reviewed to determine the temperature at which the batteries were charged and discharged and/or accelerometer data may be used to sense crashes, falls, drops and others. The operational data may thus be used to determine the occurrence of user actions and events outside the "normal wear and tear," that might void the warranty (step 2558).

Extensive testing may be performed during manufacturing to verify the robustness of various components prior to final assembly. For example, the shell 1320 and the magnetic ring rotor 913 may be assembled then torque applied to check for slippage of the magnetic ring rotor 913 relative to the shell 1320 prior to full assembly. In another example, torque may be applied to the torque sensor until destruction. In another example, accelerated life testing may be performed and may include environmental and performance testing.

Figure 26A:
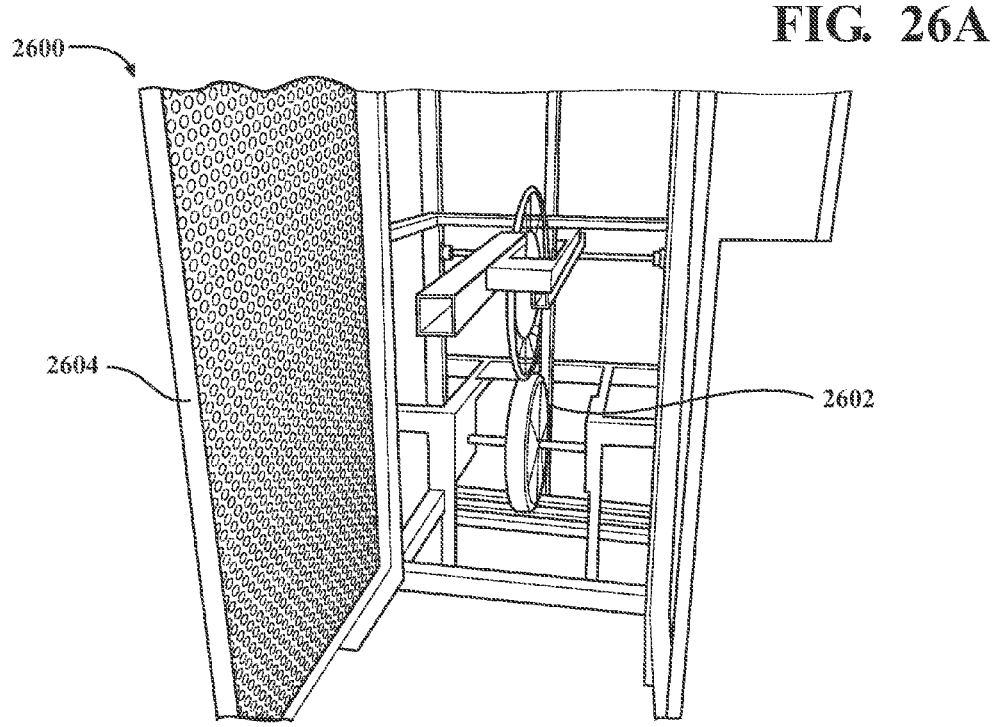
FIG. 26A is a perspective view of a test cell for the electrically motorized vehicle.

With reference to FIG. 26A, an electrically motorized wheel testing apparatus 2600 positions a drive wheel 2602 with a number of "bumps" fixed onto the circumference thereof into driving contact with the electrically motorized wheel to be tested. The bumps may be removable or otherwise configurable to represent various road conditions.

The electrically motorized wheel to be tested rotates the drive wheel 2602 and an outer cage 2604 protects personnel. The electrically motorized wheel may be supplied with external power to run for extended periods. Alternatively, the drive wheel 2602 may be powered to drive the electrically motorized wheel. As the drive wheel 2602 rotates, the electrically motorized wheel is thus subjected to a "bumpy" road. The electrically motorized wheel testing apparatus 2600 thus provides a compact extended life test cell to facilitate testing.

The ability to alter the amount of assistance or resistance provided by the electrically motorized wheel together with the reporting of data therefrom supports the use of electrically motorized wheel in remote rehabilitation therapies. Rehabilitation from an injury or recovery from a surgery may involve a progressive increase in usage time, an increase in resistance weight, and others for the recovering body part. For example, rehabilitation of a knee may involve weight training with the weight increasing a given percentage per week or biking with the distance increasing a given percentage a week.

Figure 27A:
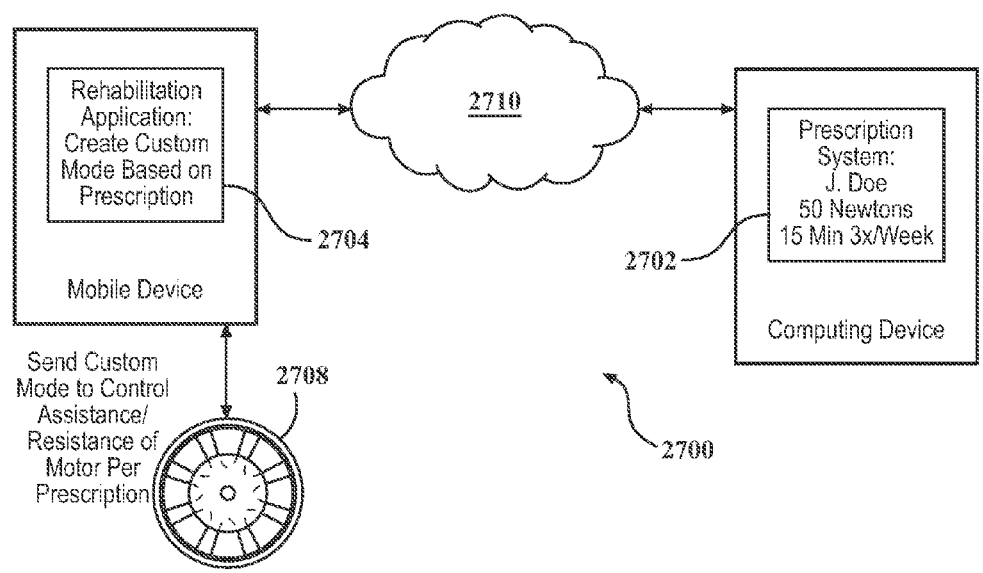
FIG. 27A is a schematic view of a server for the electrically motorized vehicle.

With reference to FIG. 27A, a rehabilitation system 2700 is disclosed in which a rehabilitation provider may prescribe an exercise regime for a patient. The prescription may include a desired a level of exertion, resistance, torque, length of time, frequency and other factors using a prescription system 2702 on a computing device accessible to the rehabilitation provider. The prescription may be communicated via a server 2710 to a corresponding rehabilitation application 2704 resident on a patient's mobile device.

The rehabilitation application 2704 may be utilized to generate a custom mode such that the control parameters sent to the patient's electrically motorized wheel 2708 provides the prescribed assistance and resistance to the user. Alternatively, the rehabilitation application 2704 may calculate the appropriate assistance and resistance to effectuate the prescription. The rehabilitation application 2704 may additionally encourage the patient to use the electrically motorized wheel for the desired time and frequency.

The rehabilitation application 2704, together with the server 2710, provides compliance data and wheel performance data such as speed, distance, time, torque, energy used and others, to the prescription system 2702 where a rehabilitation provider may review patient compliance relative to the prescription, actual torque provided by patient, leg to leg non-uniformity of applied torque, and others. This data may then be used to modify the patient prescription such as altering the level of assistance and resistance, altering recommend training time, notifying the patient of unexpected results, and others.

In embodiments, the mobile device 1502 may be in communication with a wearable sensor such as a heart rate monitor to selectively adjust the operational mode of the wheel in response thereto. Such selection may be utilized in concert with a training mode to maintain a desired heart rate or in rehabilitation mode to assure the user's heart rate does not exceed a predetermined value.

In embodiments, the mobile device 1502 can be utilized to measure a force on the user such as a force applied to a user's knees via one or more sensors in communication therewith. The rehabilitation application 2704 may then be utilized to provide compliance and goal related data during performance of the physical therapy program. This data may then be used to modify the patient prescription such as altering the level of assistance and resistance, so that user may experience optimized levels of assistance and resistance in essentially real time. A feedback loop is thus provided to control the level of assistance and resistance in based on a training or rehabilitation regimen.

Figure 28A:
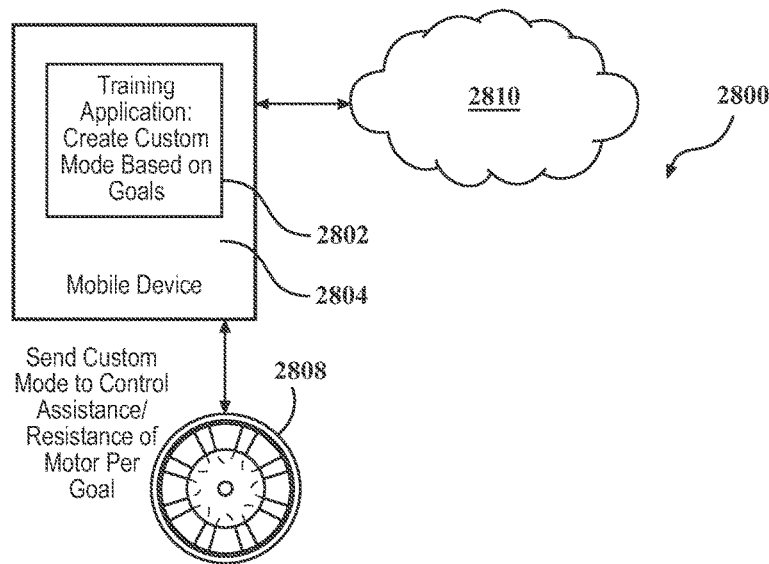
FIG. 28A is a schematic view of a server for the electrically motorized vehicle.

With reference to FIG. 28A, a training system 2800 is disclosed in which a training application 2802 on a mobile device 2804 is in communication with an electrically motorized wheel 2808. The training application 2802 permits the user to specify training goals such as a level of exertion, level of resistance, rate of Calorie expenditure, maximum heart rate, desired Calorie expenditure, percent increase over previous performance, fitness goals (e.g. complete the tour de France).

The training application 2802 may then convert the specified goals to a custom set of control parameters to be transmitted to the electrically motorized wheel and provide the appropriate assistance and resistance to meet the specified goals. The electrically motorized wheel may provide performance data such as levels of assistance and resistance provided, total calories burned, rate of calories burned, torque applied by the user and others to the training application 2802 for review by the user or a trainer.

Bicycle stands for stationary indoor training may be used with the electrically motorized wheel, however, when the electrically motorized wheel provides resistance for the user, electricity is generated. Such generated electricity may be used to drive peripheral devices such as a fan, power or charge mobile devices, and others. The power generated may be used to heat the room, stored to an external battery, or uploaded to the electrical grid. Alternatively, the power generated may simply be dissipated via a resistor or other energy conversion device that for example, plugs into the electrically motorized wheel when operated on a bicycle stand.

In embodiments, the bicycle stands for stationary indoor training may also be particularly tailored to the electrically motorized wheel to provide power output connections, docking for accessory devices, peripheral devices, battery charging stations, etc.

Figure 29A:
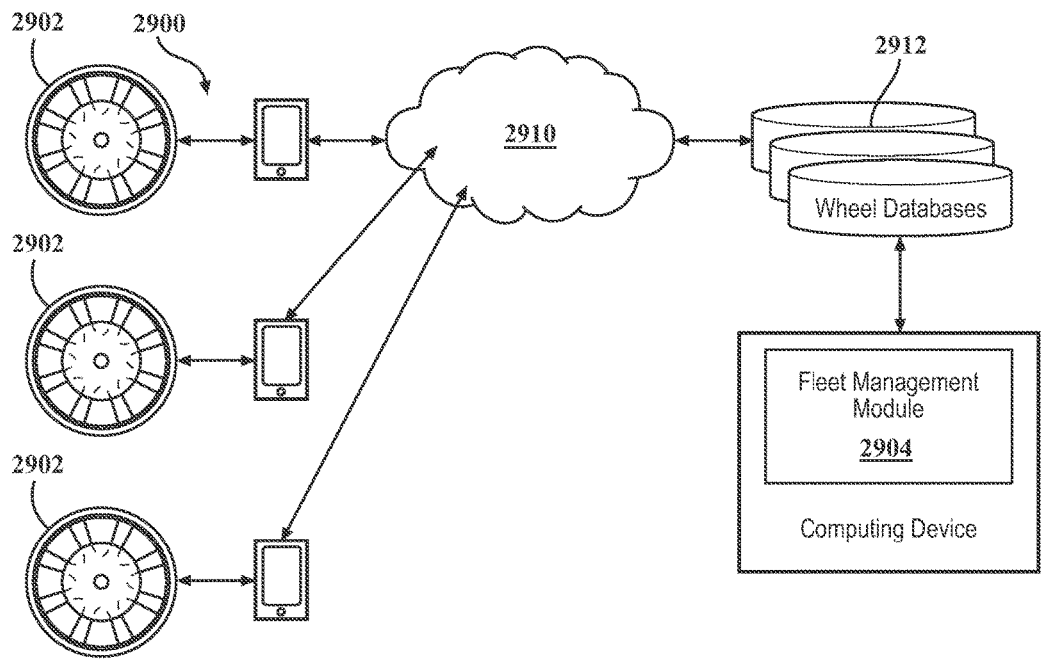
FIG. 29A is a schematic view of a server for the electrically motorized vehicle.

With respect to FIG. 29A, a fleet management system 2900 includes a plurality of electrically motorized wheels 2902 that may be in communication with a server 2910 to receive data for interchange with one or more wheel databases 2912. The data received may include user data such as user mode selections, user route selections and annotations, calories burned during current ride, time riding and others. The plurality of electrically motorized wheels 2902 may belong to a common owner such as a delivery service, a multiple of wheel chairs in a hospital, or a multiple of shopping carts in a store. The data received may also include operating versions, wheel performance data such as speed over time, control parameters, available battery life, accelerations, motor assistance and others. The data received may also include environmental data such as elevation changes, ambient temperature, humidity, and others.

A fleet management module 2904 may utilize the data in the electrically motorized wheel databases 2912 to facilitate coordination of a fleet such as assuring that all vehicles in the fleet have the same software version, have proper battery conditioning and maintenance performed, coordinating routing based on wheel location, meta-analysis of fleet data and other aggregation and correlation of data such that issues with specific electrically motorized wheels may be readily identified.

For example, data regarding current location, routes, available battery life, motor assistance/resistance provided during current ride, Calories burned during current ride, user's average ride statistics such as speed, and others might be used to determine new routings and selection of users for new destinations being added.

In another example, data regarding wheel speed over time, accelerations, motor assistance and resistance provided, wheel sensor data, temperature data over different routes may be used to optimize future routes. In yet another example, data such as speed over time, accelerations motor assistance and resistance, route, and others may be used as input when evaluating overall user performance.

In still another example, the fleet management system 2900 may be utilized to confirm driver activity and metrics to facilitate payment, improved performance, route coordination, etc.

Figure 30A:
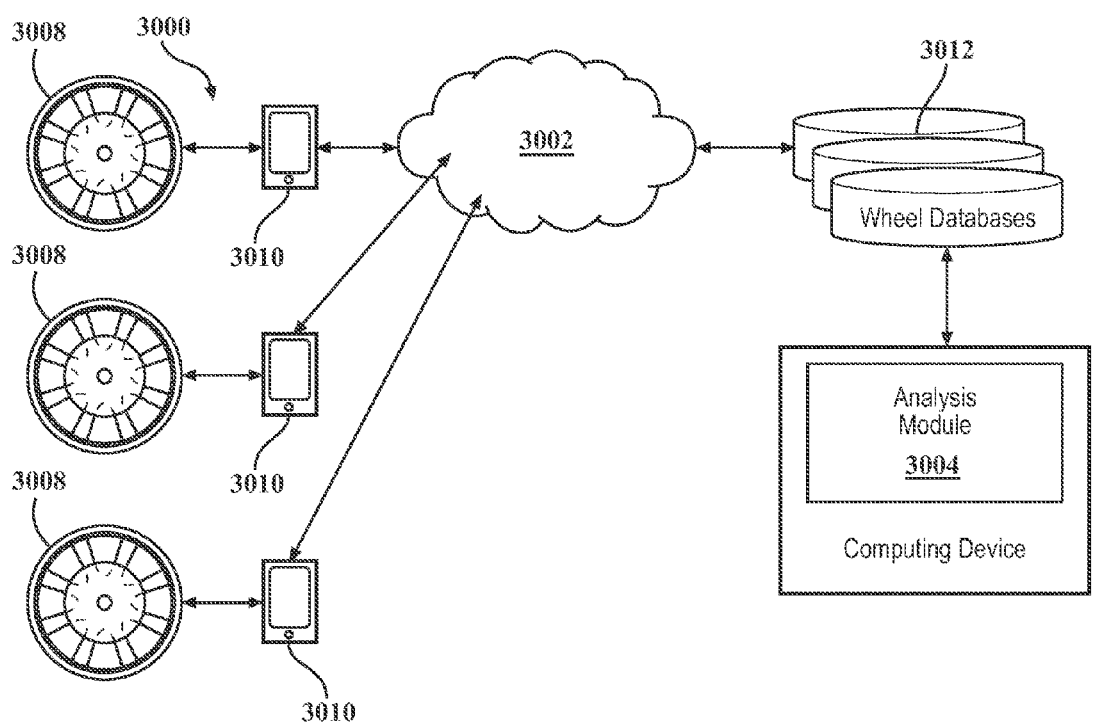
FIG. 30A is a schematic view of a server for the electrically motorized vehicle.

With reference to FIG. 30A, a server 3002 such as cloud-based server/API may receive user data, wheel performance data, environmental data, and geographic data, is in communication with a multiple electrically motorized wheels 3008 to interchange data. The data may originate with the electrically motorized wheel 3008 via the associated mobile device 3010. The data may then be transmitted to the server 3002 from each of the electrically motorized wheels 3008. The data received may include user data such as user mode selections, user route selections, annotations, travelled routes, available battery mode over a trip, and instantaneous battery life at a given location, energy supplied by the user, time required to travel a route, average speed over route, and others. The data received may also include wheel performance data such as speed over time, control parameters, accelerations, motor assistance and others. The data received may still further include location of mobile device 3010.

A computer-based analysis module 3004 may access an electrically motorized wheel database 3012 and analyze the combined wheel data from multiple rides reported by an individual wheel to identify trends in that user's health, fitness level, user preferences, and other such data. The computer-based analysis module 3004 may also analyze the combined data from different users to identify patterns and sense trends in public health and fitness levels, frequently used routes and others.

User annotations may alternatively or additionally be used to rate links in the road network and facilitate identification of where to locate new bicycle paths. The data regarding the differences between location where an electrically motorized wheel stopped and the final location may be used to optimize bicycle paths and bicycle parking.

Alternatively or in addition, aggregated data over common routes may be used for pothole detection, identification of road conditions/road type, whether a street is closed, average number of starts and stops on a route, average energy consumed over links in the road network, elevation gains over links in the road network, and others. This data may be used to optimize control algorithms along a particular route or recommend safer routes to a user, as starts and stops may be indicative of energy consumption and/or user safety. More frequent starts and stops may increase energy consumption. Also, starts and stops may be seen as indicative of intersections and a user's risk of injury typically increases with each intersection.

Alternatively or in addition, aggregated data over may be used to facilitate multi-player games such as geo-caching where the user visits specified geographic locations. The data collection system thereby collects data location and time such that users with access to the computer-based analysis module 3004 can compare locations visited.

The methods and systems described herein may be deployed in part or in whole through a machine that executes computer software, program codes, and/or instructions on a processor. The processor may be part of a server, application data server, client, network infrastructure, mobile computing platform, stationary computing platform, or other computing platform. A processor may be any kind of computational or processing device capable of executing program instructions, codes, binary instructions and others. The processor may be or include a signal processor, digital processor, embedded processor, microprocessor or any variant such as a co-processor (math co-processor, graphic co-processor, communication co-processor and others) and others that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and others described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and others.

A processor may include one or more cores that may enhance speed and performance of a multiprocessor. In embodiments, the process may be a dual core processor, quad core processors, other chip-level multiprocessor and others that combine two or more independent cores (called a die).

The methods and systems described herein may be deployed in part or in whole through a machine that executes computer software on a server, application data server, client, firewall, gateway, hub, router, or other such computer and/or networking hardware. The software program may be associated with a server that may include a file server, print server, domain server, internet server, intranet server and other variants such as secondary server, host server, distributed server and others. The server may include one or more of memories, processors, computer readable media, storage media, ports (physical and virtual), communication devices, and interfaces capable of accessing other servers, clients, machines, and devices through a wired or a wireless medium, and others. The server, as described herein and elsewhere may execute the methods, programs, or codes. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and others. Additionally, this coupling and/or connection may facilitate remote execution of program across the network. The networking of some or all of these devices may facilitate parallel processing of a program or method at one or more location without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and others. The client may include one or more of memories, processors, computer readable media, storage media, ports (physical and virtual), communication devices, and interfaces capable of accessing other clients, servers, machines, and devices through a wired or a wireless medium, and others. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and others. Additionally, this coupling and/or connection may facilitate remote execution of program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and others. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and others. The cell network may be a GSM, GPRS, 3 G, EVDO, mesh, or other networks types.

The methods, programs codes, and instructions described herein and elsewhere may be implemented on or through mobile devices. The mobile devices may include navigation devices, cell mobile devices, mobile devices, mobile personal digital assistants, laptops, palmtops, netbooks, pagers, electronic books readers, music players and others. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and others; other computer memory such as dynamic memory, static memory, read/write storage, mutable storage, read only, random access, sequential access, location addressable, file addressable, content addressable, network attached storage, storage area network, bar codes, magnetic ink, and others.

The methods and systems described herein may transform physical and/or or intangible items from one state to another. The methods and systems described herein may also transform data representing physical and/or intangible items from one state to another, such as from usage data to a normalized usage dataset.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile devices, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and others. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be understood that the various steps identified and described above may be varied, and that the order of steps may be operable to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontroller systems, embedded microcontroller systems, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be understood that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the other embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

All documents referenced herein are hereby incorporated by reference.

It should be understood that relative positional terms such as "forward," "aft," "upper," "lower," "above," "below," "bottom", "top", and others are with reference to the normal operational attitude and should not be considered otherwise limiting.

It should be understood that like reference numerals identify corresponding or similar elements throughout the several drawings. It should also be understood that although a particular component arrangement is disclosed in the illustrated embodiment, other arrangements will benefit herefrom.

Although the different embodiments have specific illustrated components, the embodiments of this disclosure are not limited to those particular combinations. It is possible to use some of the components or features from any of the embodiments in combination with features or components from any of the other embodiments.

Although particular step sequences are shown, described, and claimed, it should be understood that steps may be performed in any order, separated or combined unless otherwise indicated and will still benefit from the present disclosure.

The foregoing description is exemplary rather than defined by the limitations within. Various embodiments are disclosed herein, however, one of ordinary skill in the art would recognize that various modifications and variations in light of the above teachings will fall within the scope of the appended claims. It is therefore to be understood that within the scope of the appended claims, the disclosure may be practiced other than as specifically described. For that reason the appended claims should be studied to determine true scope and content.

What is claimed:

1. A system, comprising:
a server adapted to operate in data communication with a plurality of motorized human-powered vehicles, each motorized human-powered vehicle comprising a motor and a control system; and
a data analysis module in communication with the server, wherein the data analysis module is operable to:
receive and analyze a data set related to one or more of the motorized human-powered vehicles, wherein the data set includes at least one of sensor data related to user inputs to the one or more of the motorized human-powered vehicles and sensor data related to motion of the one or more of the motorized human-powered vehicles;
analyze the data set to determine parameters related to movement of the one or more of the motorized human-powered vehicles through a road network; and
transmit a recommendation based on the analyzed data set to the control system of one of the plurality of motorized human-powered vehicles to be used by the control system of the one of the plurality of motorized human-powered vehicles to control the motor of the one of the plurality of motorized human-powered vehicles.

2. The system as recited in claim 1, wherein the recommendation includes an operational mode.

3. The system as recited in claim 1, wherein the recommendation includes a route.

4. The system as recited in claim 1, wherein the recommendation is based at least in part on demographics.

5. The system as recited in claim 1, wherein the recommendation is based at least in part on fitness.

6. The system as recited in claim 1, wherein the recommendation is based at least in part on a similarity to one or more of a user of an other of the plurality of motorized human-powered vehicles.

7. The system as recited in claim 1, wherein the server is further operable to transmit the recommendation to a mobile device in communication with one of the plurality of motorized human-powered vehicles.

8. The system as recited in claim 1, wherein the server is further operable to create a profile of a user operating one of the plurality of motorized human-powered vehicles from the data set related to the vehicle.

9. The system as recited in claim 8, wherein the server is further operable to identify trends in the profile of the user over time.

10. The system as recited in claim 8, wherein the server is further operable to detect changes in mobility patterns of the user from the profile.

11. The system as recited in claim 8, wherein the server is further operable to detect long-term, slowly developing diseases from the profile.

12. The system as recited in claim 1, wherein the server is further operable to communicate the data into an electronic medical record (EMR) of the user.

13. The system as recited in claim 1, wherein the data analysis module is further operable to provide data sets for public health analysis.

14. The system as recited in claim 1, wherein the parameters include at least one of road quality, a direction of travel, speed, existence of a pothole in the road network, frequency or number of stops and starts, presence of other human-powered vehicles, car traffic, and elevation gain.

15. The system as recited in claim 1, wherein the parameters include energy required to traverse the road network, wherein the energy required includes at least one of user energy expenditure and electrical power output of the one of the plurality of motorized human-powered vehicles.

16. The system as recited in claim 1, wherein the server is operable to use the data set to update a database of data about the road network.

17. The system as recited in claim 16, wherein the server is operable to update the database of data in real time.

* * * * *